(12) United States Patent
Aihara et al.

(10) Patent No.: US 9,090,924 B2
(45) Date of Patent: *Jul. 28, 2015

(54) NUCLEIC ACID CONSTRUCT COMPRISING PYRIPYROPENE BIOSYNTHETIC GENE CLUSTER AND MARKER GENE

(75) Inventors: Sato Aihara, Odawara (JP); Naomi Sumida, Odawara (JP); Koichiro Murashima, Odawara (JP); Kouji Yanai, Odawara (JP); Hiroyuki Anzai, Ibaraki-Ken (JP); Kentaro Yamamoto, Kawasaki (JP)

(73) Assignee: MEIJI SEIKA PHARMA CO., LTD., Tokyo-To (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/575,145

(22) PCT Filed: Jan. 19, 2011

(86) PCT No.: PCT/JP2011/050852
§ 371 (c)(1),
(2), (4) Date: Sep. 19, 2012

(87) PCT Pub. No.: WO2011/093186
PCT Pub. Date: Aug. 4, 2011

(65) Prior Publication Data
US 2013/0017581 A1 Jan. 17, 2013

(30) Foreign Application Priority Data

Jan. 26, 2010 (JP) .................. 2010-014700
Nov. 11, 2010 (JP) .................. 2010-253183

(51) Int. Cl.
*C12P 17/18* (2006.01)
*C12N 9/02* (2006.01)
*C12N 9/10* (2006.01)
*C12N 9/88* (2006.01)
*C12N 9/00* (2006.01)
*C12N 15/52* (2006.01)

(52) U.S. Cl.
CPC ............ *C12P 17/181* (2013.01); *C12N 9/0071* (2013.01); *C12N 9/1025* (2013.01); *C12N 9/1029* (2013.01); *C12N 9/88* (2013.01); *C12N 9/93* (2013.01); *C12N 15/52* (2013.01); *C12Y 114/13008* (2013.01); *C12Y 114/14001* (2013.01); *C12Y 203/00* (2013.01); *C12Y 203/01* (2013.01); *C12Y 205/01* (2013.01); *C12Y 406/01* (2013.01); *C12Y 602/01* (2013.01)

(58) Field of Classification Search
None
See application file for complete search history.

(56) References Cited

U.S. PATENT DOCUMENTS

| 5,807,721 | A | 9/1998 | Omura et al. |
| 7,285,404 | B1 | 10/2007 | Midoh et al. |
| 2003/0068677 | A1* | 4/2003 | Khosla et al. ............... 435/69.1 |
| 2006/0135645 | A1 | 6/2006 | Glassel et al. |
| 2006/0135664 | A1 | 6/2006 | Glassel et al. |
| 2006/0281780 | A1 | 12/2006 | Goto et al. |
| 2009/0182014 | A1 | 7/2009 | Kim et al. |
| 2010/0160640 | A1 | 6/2010 | Goto et al. |
| 2012/0015410 | A1 | 1/2012 | Anzai et al. |

FOREIGN PATENT DOCUMENTS

| EP | 2 107 060 | 10/2009 |
| JP | 4-360895 | 12/1992 |
| JP | 6-184158 | 7/1994 |
| JP | 8-239385 | 9/1996 |
| JP | 8-259569 | 10/1996 |
| JP | 8-269062 | 10/1996 |
| JP | 8-269063 | 10/1996 |
| JP | 8-269064 | 10/1996 |
| JP | 8-269065 | 10/1996 |
| JP | 8-269066 | 10/1996 |
| JP | 8-291164 | 11/1996 |
| WO | 94/09147 | 4/1994 |
| WO | 2004/060065 | 7/2004 |
| WO | 2006/129714 | 12/2006 |
| WO | 2008/066153 | 6/2008 |
| WO | 2009/022702 | 2/2009 |
| WO | 2010/010955 | 1/2010 |

OTHER PUBLICATIONS

International Search Report issued Apr. 12, 2011 in International (PCT) Application No. PCT/JP2011/050852, of which the present application is the national stage.

N. Fedorova et al., "Genomic Islands in the Pathogenic Filamentous Fungus *Aspergillus fumigatus*", PLoS Geneticss, vol. 4, Issue 4, Apr. 2008, pp. 1-13.

W. Nierman et al., "Genomic sequence of the pathogenic and allergenic filamentous fungus *Aspergillus fumigatus*", Nature, vol. 438, No. 7071, Dec. 2005, pp. 1151-1156.

H. Tomoda et al., "Biosynthesis of Pyripyropene A", J. Org. Chem., vol. 61, 1996, pp. 882-886.

(Continued)

*Primary Examiner* — David J Steadman
*Assistant Examiner* — Paul Holland
(74) *Attorney, Agent, or Firm* — Wenderoth, Lind & Ponack, L.L.P.

(57) ABSTRACT

There is provided a nucleic acid construct comprising a pyripyropene biosynthetic gene cluster and a marker gene. The nucleic acid construct according to the present invention provides an inexpensive and highly productive method for producing pyripyropene.

5 Claims, 3 Drawing Sheets

(56) References Cited

OTHER PUBLICATIONS

T. Sunazuka et al., "Total Synthesis of α-Pyrone Meroterpenoids, Novel Bioactive Microbial Metabolites", Chem. Rev., vol. 105, No. 12, 2005, pp. 4559-4580.
G. Tsujiuchi et al., "Novel Microorganism Having Ability to Produce Pyripyropenes", Japan Institute of Invention and Innovation, Journal of Technical Disclosure, Journal No. 2008-500997, Feb. 13, 2008, with English translation.
International Preliminary Report on Patentability and Written Opinion issued Sep. 27, 2012 in International (PCT) Application No. PCT/JP2011/050852.
Frisvad, J.C., et al., "Polyphasic Taxonomy of Subgenus *Penicillium*", Studies in Mycology, vol. 49, 2004, pp. 53-92.
Tsujiuchi, G., et al., "Pyripyropene-rui Seisanno o Yusuru Shinki Biseibutsu", Hatsumei Kyokai Kokai Giho Kogi Bango, 2008-500997 Go, Feb. 13, 2008, with English translation.
Varga, János, et al., "Diversity of polyketide synthase gene sequences in *Aspergillus* species", Research in Microbiology, vol. 154, No. 8, Oct. 1, 2003, pp. 593-600.
Extended European Search Report issued Dec. 17, 2013 in corresponding Application No. 11 736 900.9.
International Preliminary Report on Patentability and Written Opinion issued Sep. 27, 2012 in International (PCT) Application No. PCT/JP2011/050851.
International Search Report issued Oct. 20, 2009 in International (PCT) Application No. PCT/JP2009/063293, with English translation.
Fedorova, Natalie D., et al., "Genomic Islands in the Pathogenic Filamentous Fungus *Aspergillus fumigatus*", PLoS Genetics, vol. 4, No. 4, Apr. 11, 2008, pp. 1-13.
Nierman, William C., et al., "Genomic Sequence of the Pathogenic and Allergenic Filamentous Fungus *Aspergillus fumigatus*", Nature, vol. 438, No. 7071, Dec. 2005, pp. 1151-1156.
Tomoda, Hiroshi, et al., "Biosynthesis of Pyripyropene A", J. Org. Chem., vol. 61, No. 3, 1996, pp. 882-886.
Sunazuka, Toshiaki, et al., "Total Synthesis of α-Pyrone Meroterpenoids, Novel Bioactive Microbial Metabolites", Chem. Rev., vol. 105, No. 12, 2005, pp. 4559-4580.
Tsujiuchi, G., et al., "Pyripyropene-rui Seisanno o Yusuru Shinki Biseibutsu", Hatsumei Kyokai Kokai Giho Kogi Bango, 2008-500997 Go, Feb. 13, 2008, with English translation.
Omura, S., et al., "Pyripyropenes, Highly Potent Inhibitors of Acyl-CoA: Cholesterol Acyltransferase Produced by *Aspergillus fumigatus*", The Journal of Antibiotics, vol. 46, No. 7, Jul. 1993, pp. 1168-1169.
Sunazuka, Toshiaki, et al., "Synthetic Study of α-Pyrone Meroterpenoids, Pyripyropens", Journal of Synthetic Organic Chemistry, Japan, vol. 56, No. 6, 1998, pp. 478-488, with English abstract.
Obata, Rika, et al., "Chemical Modification and Structure-Activity Relationships of Pyripyropenes 3. Synthetic Conversion of Pyridine-Pyrone Moiety", The Journal of Antibiotics, vol. 50, No. 3, Mar. 1997, pp. 229-236.
Wang, Hui-Juan, et al., "Aflavinines and Other Antiisectan Metabolites from the Ascostromata of *Eupenicillium crustaceum* and Related Species", Applied and Environmental Microbiology, vol. 61, No. 12, Dec. 1995, pp. 4429-4435.
Smith, Amos B., et al., "Biomimetic Total Synthesis of the ACAT Inhibitor(+)-Pyripyropene E", Tetrahedron Letters, vol. 37, No. 36, 1996, pp. 6461-6464.
Tomoda, Hiroshi, et al., "Pyripyropenes, Novel ACAT Inhibitors Produced by *Aspergillus fumigates* IV. Structure Elucidation of Pyripyropenes M to R", The Journal of Antibiotics, vol. 49, No. 3, Mar. 1996, pp. 292-298.
Supplementary European Search Report issued Nov. 29, 2011 in corresponding European Application No. 09 80 0469.
Hu, Jie, et al., "Characterization of two cytochrome P450 monooxygenase genes of the pyripyropene biosynthetic gene cluster from *Penicillium coprobium*", The Journal of Antibiotics, vol. 64, No. 3, Jan. 12, 2011, pp. 221-227.
Itoh, Takayuki, et al., "Reconstitution of a fungal meroterpenoid biosynthesis reveals the involvement of a novel family of terpene cyclases", Nature Chemistry, vol. 2, No. 10, published online on Aug. 1, 2010, pp. 858-864.
Cox, Russel J., "Polyketides, proteins and genes in fungi: programmed nano-machines begin to reveal their secrets", Organic and Biomolecular Chemistry, vol. 5, No. 13, Jan. 1, 2007, pp. 2010-2026.
Varga, Janos, et al., "Diversity of polyketide synthase gene sequences in *Aspergillus* species", Research in Microbiology, vol. 154, No. 8, Oct. 1, 2003, pp. 593-600.

* cited by examiner

NUCLEIC ACID CONSTRUCT COMPRISING PYRIPYROPENE BIOSYNTHETIC GENE CLUSTER AND MARKER GENE

CROSS-REFERENCE TO RELATED APPLICATION

This patent application claims priority to Japanese Patent Application No. 14700/2010 that was filed on Jan. 26, 2010 and Japanese Patent Application No. 253183/2010 that was filed on Nov. 11, 2010, and the entire disclosures of all are incorporated herein by reference.

BACKGROUND OF THE INVENTION

1. Field of Invention

The present invention relates to a nucleic acid construct comprising a pyripyropene biosynthetic gene cluster and a marker gene.

2. Background Art

It has been thus far proven that there are 18 types of naturally-occurring analogs from pyripyropene A to pyripyropene R in pyripyropenes, which analogs differ in structures of their side chains (Non-patent Document 1).

It has been disclosed that pyripyropenes have an ACAT inhibitory activity (Patent Document 1). Application thereof to treatment of diseases caused by cholesterol accumulation or the like is expected. Also, it has been disclosed that pyripyropenes have an insecticidal activity against *Helicoverpa armigera* larva (Non-patent Document 2), Diamondback moth larva (Patent Document 2), *Tenebrio molitor* (Patent Document 2) or aphids (Patent Document 3) and application thereof to insecticides is expected.

It has been known that pyripyropenes are produced as secondary metabolites by filamentous fungus. For instance, it has been disclosed that *Penicillium coprobium* PF1169 strain (Patent Document 4), *Aspergillus fumigatus* IFO-1289 strain (Patent Document 5), *Eupenicillium reticulosporum* NRRL-3446 strain (Non-patent Document 2) or *Penicillium griseofulvum* F1959 strain (Patent Document 2) each produces pyripyropenes.

Industrial production of pyripyropenes is carried out by culturing the above-mentioned production bacteria and collecting pyripyropenes. In general, the amount of secondary metabolism products produced by a separated naturally-occurring microorganism is small. In order to use this industrially, productivity of these desired products needs to be improved.

To improve the productivity of the desired products, studies for a method for culturing the desired product-producing microorganisms, studies for components of culture media and modifications of fermentation conditions such as addition of precursors, as well as modifications of bacterial strains using mutation by irradiation with ultraviolet light or mutagens have been carried out. Further, in addition to these methods, the improvement of the productivity using gene recombination has recently been carried out.

A general method in the improvement of the productivity by gene recombination is to enhance expression of a biosynthetic gene. For instance, by this method, a method for improving productivity of PF1022 substance produced by *Agonomycetales* is disclosed (Patent Document 6). In order to apply this method, it is required that the biosynthetic gene of a desired product be isolated and a method for transformation be established in a desired product-producing microorganism.

As for pyripyropenes, there are thus far no reports on isolation of their biosynthetic gene cluster. In addition, a method for transformation of a pyripyropene-producing fungus as a host has not been established. Therefore, it has thus far been difficult to introduce the biosynthetic gene cluster of pyripyropenes into the pyripyropene-producing microorganism and the improvement of the productivity by gene recombination is not able to be attained.

PRIOR ART REFERENCES

Patent Documents

[Patent Document 1] Japanese Patent Laid-Open Publication No. 184158/1994
[Patent Document 2] WO2004/060065
[Patent Document 3] WO2006/129714
[Patent Document 4] Journal of Technical Disclosure No. 500997/2008
[Patent Document 5] Japanese Patent Laid-Open Publication No. 360895/1992
[Patent Document 6] Japanese Patent No. 3961289

Non-Patent Documents

[Non-patent Document 1] Journal of Antibiotics (1996), 49(3), 292-298
[Non-patent Document 2] Applied and Environmental Microbiology (1995), 61 (12), 4429-4435

SUMMARY OF THE INVENTION

The present inventors have now found that, by expressing a nucleic acid construct comprising a pyripyropene biosynthetic gene cluster and marker gene in a host, productivity of pyripyropenes is significantly improved. The present invention has been made based on such finding.

Accordingly, an object of the present invention is to provide a nucleic acid construct comprising a pyripyropene biosynthetic gene cluster and marker gene.

According to one embodiment of the present invention, a nucleic acid construct comprising a pyripyropene biosynthetic gene cluster and marker gene is provided.

Also, according to another embodiment of the present invention, a transformant which is obtainable by introducing the above-mentioned nucleic acid construct into a host is provided.

Further, according to another embodiment of the present invention, a transformant which is obtainable by simultaneously or separately introducing a nucleic acid construct comprising the above-mentioned pyripyropene biosynthetic gene cluster and the nucleic acid construct comprising the above-mentioned marker gene into a host is provided.

In addition, according to another embodiment of the present invention, a method for producing pyripyropenes comprising culturing the above-mentioned transformant and collecting pyripyropenes from a culture is provided.

BRIEF DESCRIPTION OF DRAWINGS

FIG. 2 shows an electrophoresis pattern of PCR products by agarose gel. For the electrophoresis, the PCR products amplified using the following primers were used: M: molecular weight marker (100 bp ladder), lane 1: primers of SEQ ID NOs:253 and 254, lane 2: primers of SEQ ID NOs:257 and 258, lane 3: primers of SEQ ID NOs: 259 and 260, lane 4: primers of SEQ ID NOs:255 and 256, lane 5: primers of SEQ ID NOs:261 and 262.

FIG. 3 shows an electrophoresis pattern of PCR products by agarose gel. For the electrophoresis, the PCR products amplified using the following primers were used: lane 1: molecular weight marker (100 bp ladder), lane 2: primers of SEQ ID NOs:264 and 265 (400 bp amplified fragment).

DETAILED DESCRIPTION OF THE INVENTION

Deposition of Microorganisms

Figure 1:
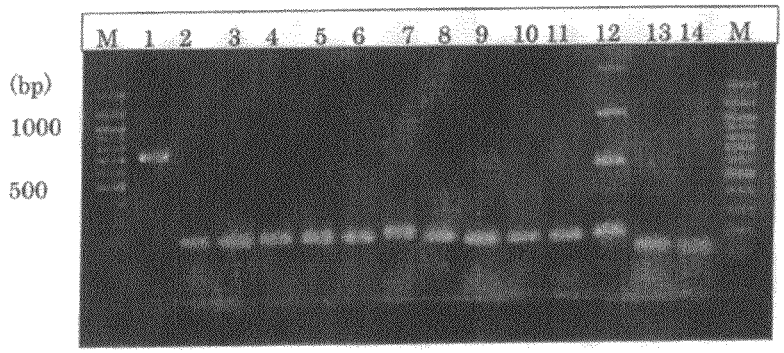
FIG. 1 shows an electrophoresis pattern of PCR products by agarose gel. For the electrophoresis, the PCR products amplified using the following primers were used: M: molecular weight marker (100 bp ladder), lane 1: primers of SEQ ID NOs:1 and 2, lane 2: primers of SEQ ID NOs:239 and 240, lane 3: primers of SEQ ID NOs:237 and 238, lane 4: primers of SEQ ID NOs:241 and 242, lane 5: primers of SEQ ID NOs:247 and 248, lane 6: primers of SEQ ID NOs:251 and 252, lane 7: primers of SEQ ID NOs:245 and 246, lane 8: primers of SEQ ID NOs:243 and 244, lane 9: primers of SEQ ID NOs:249 and 250, lane 10: primers of SEQ ID NOs:235 and 236, lane 11: primers of SEQ ID NOs:233 and 234, lane 12: primers of SEQ ID NOs:227 and 228, lane 13: primers of SEQ ID NOs:229 and 230, lane 14: primers of SEQ ID NOs:231 and 232.

*Escherichia coli* (*Escherichia coli* EPI300™-T1®) transformed with plasmid pCC1-PP1 has been deposited with International Patent Organism Depositary, National Institute of Advanced Industrial Science and Technology (Address: AIST Tsukuba Central 6, 1-1-1 Higashi, Tsukuba, Ibaraki, Japan, 305-8566), under accession No. FERM BP-11133 (converted from domestic deposition under accession No. FERM P-21704) (identification reference by the depositor: *Escherichia coli* EPI300™-T1®/pCC1-PP1) as of Oct. 9, 2008 (original deposition date).

*Escherichia coli* transformed with plasmid pPYRI02 has been deposited with International Patent Organism Depositary, National Institute of Advanced Industrial Science and Technology (Address: AIST Tsukuba Central 6, 1-1-1 Higashi, Tsukuba, Ibaraki, Japan, 305-8566), under accession No. FERM BP-11203 (identification reference by the depositor: XL1-Blue MRA/pPYRI02) as of Dec. 14, 2009.

*Escherichia coli* transformed with cosmid pPYRI07 has been deposited with International Patent Organism Depositary, National Institute of Advanced Industrial Science and Technology (Address: AIST Tsukuba Central 6, 1-1-1 Higashi, Tsukuba, Ibaraki, Japan, 305-8566), under accession No. FERM BP-11316 (identification reference by the depositor: XL1-Blue MRA/pPYRI07) as of Dec. 1, 2010.

Pyripyropene Biosynthetic Gene Cluster

The pyripyropene biosynthetic gene cluster in the present invention is arranged in a nucleic acid construct so as to be able to be expressed with the marker gene described later in a host. As long as it is a gene cluster involved in biosynthesis of pyripyropenes, it is not particularly restricted. Preferably, a construct comprising the full length of at least one nucleotide sequence selected from the nucleotide sequences in (I) to (IV) below or a part thereof is provided:

(I) a nucleotide sequence from 2911 to 27797 in SEQ ID NO:266;

(II) a nucleotide sequence which is capable of hybridizing with a sequence complementary to the nucleotide sequence from 2911 to 27797 in SEQ ID NO:266 under stringent conditions, and which encodes a protein substantially equivalent to a protein encoded by the nucleotide sequence from 2911 to 27797 in SEQ ID NO:266;

(III) a nucleotide sequence of a polynucleotide of the nucleotide sequence from 2911 to 27797 in SEQ ID NO:266 in which one or more nucleotides are deleted, substituted, inserted or added, and which encodes a protein substantially equivalent to a protein encoded by the nucleotide sequence from 2911 to 27797 in SEQ ID NO:266; and (IV) a nucleotide sequence which has at least 90% identity to a polynucleotide of the nucleotide sequence from 2911 to 27797 in SEQ ID NO:266, and which encodes a protein substantially equivalent to a protein encoded by the nucleotide sequence from 2911 to 27797 in SEQ ID NO:266.

According to a further preferred embodiment of the pyripyropene biosynthetic gene cluster in the present invention, it is a gene cluster comprising a gene in interest and an expression regulatory region. Here, the gene in interest is one having one or more genes encoding a protein involved in biosynthesis of pyripyropenes. Also, the expression regulatory region is not restricted as long as it has a nucleotide sequence necessary to regulate expression of the above-mentioned gene in interest in a host. For instance, promoters and terminators which are nucleotide sequences regulating the amount of transcription of the gene in interest in a host are included. In addition, the protein involved in the biosynthesis of pyripyropenes is, for example, a protein involved in any of the biosynthetic pathways shown in the following Scheme 1.

TABLE 1

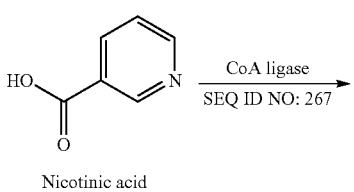

Nicotinic acid

TABLE 1-continued
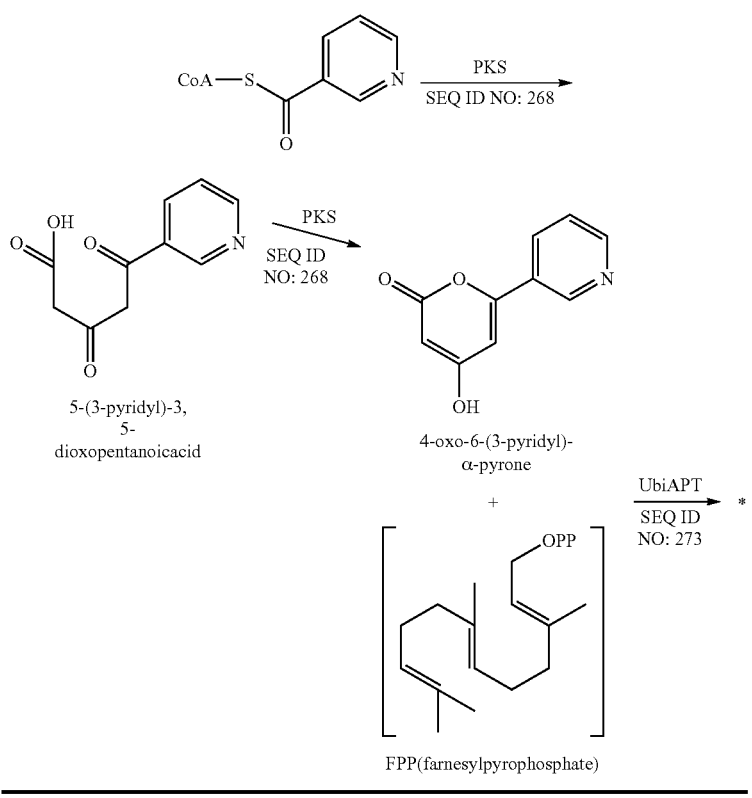
Scheme 1
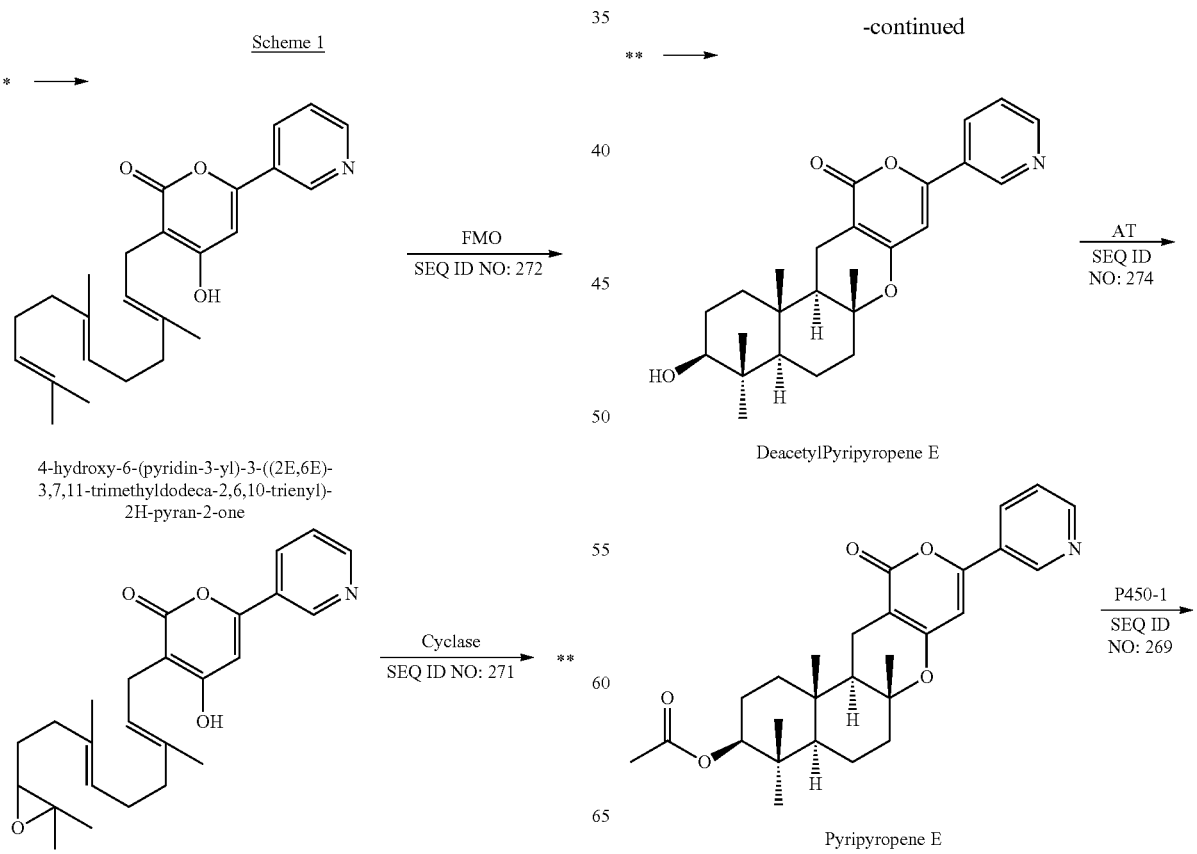

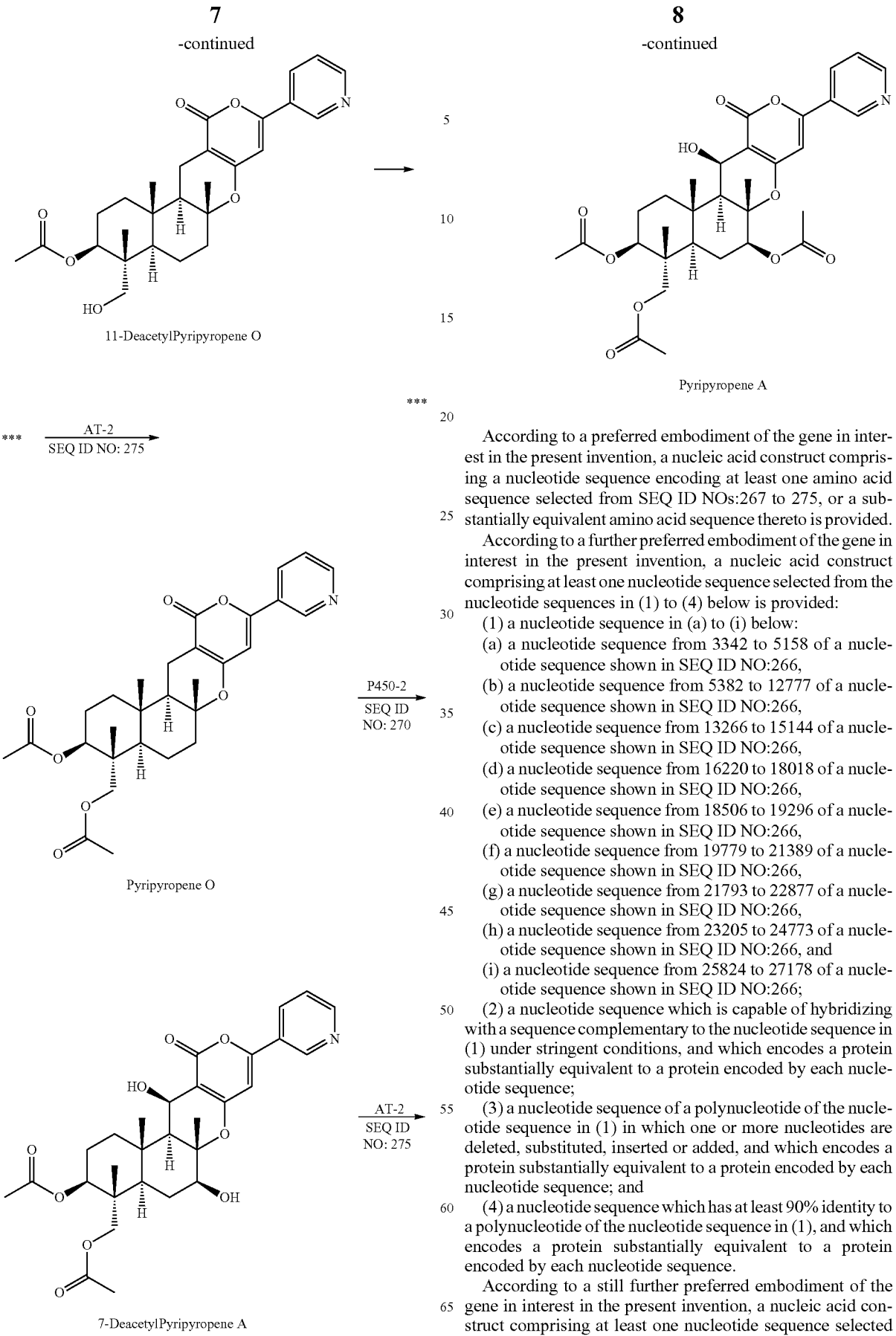

According to a preferred embodiment of the gene in interest in the present invention, a nucleic acid construct comprising a nucleotide sequence encoding at least one amino acid sequence selected from SEQ ID NOs:267 to 275, or a substantially equivalent amino acid sequence thereto is provided.

According to a further preferred embodiment of the gene in interest in the present invention, a nucleic acid construct comprising at least one nucleotide sequence selected from the nucleotide sequences in (1) to (4) below is provided:

(1) a nucleotide sequence in (a) to (i) below:
 (a) a nucleotide sequence from 3342 to 5158 of a nucleotide sequence shown in SEQ ID NO:266,
 (b) a nucleotide sequence from 5382 to 12777 of a nucleotide sequence shown in SEQ ID NO:266,
 (c) a nucleotide sequence from 13266 to 15144 of a nucleotide sequence shown in SEQ ID NO:266,
 (d) a nucleotide sequence from 16220 to 18018 of a nucleotide sequence shown in SEQ ID NO:266,
 (e) a nucleotide sequence from 18506 to 19296 of a nucleotide sequence shown in SEQ ID NO:266,
 (f) a nucleotide sequence from 19779 to 21389 of a nucleotide sequence shown in SEQ ID NO:266,
 (g) a nucleotide sequence from 21793 to 22877 of a nucleotide sequence shown in SEQ ID NO:266,
 (h) a nucleotide sequence from 23205 to 24773 of a nucleotide sequence shown in SEQ ID NO:266, and
 (i) a nucleotide sequence from 25824 to 27178 of a nucleotide sequence shown in SEQ ID NO:266;

(2) a nucleotide sequence which is capable of hybridizing with a sequence complementary to the nucleotide sequence in (1) under stringent conditions, and which encodes a protein substantially equivalent to a protein encoded by each nucleotide sequence;

(3) a nucleotide sequence of a polynucleotide of the nucleotide sequence in (1) in which one or more nucleotides are deleted, substituted, inserted or added, and which encodes a protein substantially equivalent to a protein encoded by each nucleotide sequence; and (4) a nucleotide sequence which has at least 90% identity to a polynucleotide of the nucleotide sequence in (1), and which encodes a protein substantially equivalent to a protein encoded by each nucleotide sequence.

According to a still further preferred embodiment of the gene in interest in the present invention, a nucleic acid construct comprising at least one nucleotide sequence selected from the nucleotide sequences in (1) to (4) below is provided:

(1) a nucleotide sequence comprising all of the full length nucleotide sequences in the above-mentioned (a) to (i) or (a) to (h);

(2) a nucleotide sequence which is capable of hybridizing with a sequence complementary to the nucleotide sequence in (1) under stringent conditions, and which encodes a protein substantially equivalent to a protein encoded by the nucleotide sequence;

(3) a nucleotide sequence of a polynucleotide of the nucleotide sequence in (1) in which one or more nucleotides are deleted, substituted, inserted or added, and which encodes a protein substantially equivalent to a protein encoded by the nucleotide sequence; and (4) a nucleotide sequence which has at least 90% identity to a polynucleotide of the nucleotide sequence in (1), and which encodes a protein substantially equivalent to a protein encoded by the nucleotide sequence.

According to a preferred embodiment of the expression regulatory region in the present invention, a nucleic acid construct comprising at least one nucleotide sequence selected from the nucleotide sequences in (1) to (4) below is provided:

(1) a full length nucleotide sequence in (j) to (s) below, or a part thereof:

(j) a nucleotide sequence from 2911 to 3341 of a nucleotide sequence shown in SEQ ID NO:266, (k) a nucleotide sequence from 5159 to 5381 of a nucleotide sequence shown in SEQ ID NO:266, (l) a nucleotide sequence from 12778 to 13265 of a nucleotide sequence shown in SEQ ID NO:266, (m) a nucleotide sequence from 15145 to 16219 of a nucleotide sequence shown in SEQ ID NO:266, (n) a nucleotide sequence from 18019 to 18505 of a nucleotide sequence shown in SEQ ID NO:266, (o) a nucleotide sequence from 19297 to 19778 of a nucleotide sequence shown in SEQ ID NO:266, (p) a nucleotide sequence from 21390 to 21792 of a nucleotide sequence shown in SEQ ID NO:266, (q) a nucleotide sequence from 22878 to 23204 of a nucleotide sequence shown in SEQ ID NO:266, (r) a nucleotide sequence from 24774 to 25823 of a nucleotide sequence shown in SEQ ID NO:266, and (s) a nucleotide sequence from 27179 to 27797 of a nucleotide sequence shown in SEQ ID NO:266;

(2) a nucleotide sequence which is capable of hybridizing with the nucleotide sequence in (1) under stringent conditions, and which has a function substantially equivalent to each nucleotide sequence;

(3) a nucleotide sequence of a polynucleotide of the nucleotide sequence in (1) in which one or more nucleotides are deleted, substituted, inserted or added, and which has a function substantially equivalent to each nucleotide sequence; and (4) a nucleotide sequence which has at least 90% identity to a polynucleotide of the nucleotide sequence in (1), and which has a function substantially equivalent to each nucleotide sequence.

According to a more preferred embodiment of the expression regulatory region in the present invention, a nucleic acid construct comprising at least one nucleotide sequence selected from the nucleotide sequences in (1) to (4) below is provided:

(1) a nucleotide sequence comprising all of the full length nucleotide sequences in the above-mentioned (j) to (s) or (j) to (r);

(2) a nucleotide sequence which is capable of hybridizing with the nucleotide sequence in (1) under stringent conditions, and which has a function substantially equivalent to each nucleotide sequence;

(3) a nucleotide sequence of a polynucleotide of the nucleotide sequence in (1) in which one or more nucleotides are deleted, substituted, inserted or added, and which has a function substantially equivalent to each nucleotide sequence; and (4) a nucleotide sequence which has at least 90% identity to a polynucleotide of the nucleotide sequence in (1), and which has a function substantially equivalent to each nucleotide sequence.

As the pyripyropene biosynthetic gene cluster in the present invention, the full length or a part of biosynthetic gene cluster derived from a pyripyropene-producing fungus can be isolated to be used, preferably the full length or a part of the pyripyropene biosynthetic gene cluster derived from *Penicillium coprobium* PF1169 strain shown in SEQ ID NO:266 can be used, and further preferably the full length pyripyropene biosynthetic gene cluster derived from *Penicillium coprobium* PF1169 strain shown in SEQ ID NO:266 can be used.

In the present invention, the term "substantially equivalent amino acid sequence" means an amino acid sequence which does not affect an activity of a polypeptide despite the fact that one or more amino acids are altered by substitution, deletion, addition or insertion. Preferably, an amino acid sequence which is altered by amino acid substitution, deletion, addition or insertion has a sequence identity of 70% or more, preferably 80% or more, more preferably 90% or more, still more preferably 95% or more, and still more preferably 98% or more to the amino acid sequence before alteration and the like. Further, the number of the altered amino acid residues is preferably 1 to 40, more preferably 1 to 20, still more preferably 1 to 10, still more preferably 1 to 8, and most preferably 1 to 4.

Further, an example of the alteration which does not affect the activity includes conservative substitution. The term "conservative substitution" means substitution of preferably 1 to 40, more preferably 1 to 20, more preferably 1 to 10, still more preferably 1 to 8, and most preferably 1 to 4 amino acid residues with other chemically similar amino acid residues such that the activity of the polypeptide is not substantially altered. Examples thereof include cases where a certain hydrophobic amino acid residue is substituted with another hydrophobic amino acid residue and cases where a certain polar amino acid residue is substituted with another polar amino acid residue having the same charges. Functionally similar amino acids capable of such a substitution are known in the art for each amino acid. Concretely, examples of non-polar (hydrophobic) amino acids include alanine, valine, isoleucine, leucine, proline, tryptophan, phenylalanine, methionine and the like. Examples of polar (neutral) amino acids include glycine, serine, threonine, tyrosine, glutamine, asparagine, cysteine and the like. Examples of positively charged (basic) amino acids include arginine, histidine, lysine and the like. Examples of negatively charged (acidic) amino acids include aspartic acid, glutamic acid and the like.

The term, "stringent conditions" in the present invention means conditions where a washing operation of membranes after hybridization is carried out at high temperatures in a solution with low salt concentrations, a person skilled in the art would be able to appropriately determine the condition, for example, the condition includes the condition of washing in a solution with 2×SSC (1×SSC: 15 mM trisodium citrate, 150 mM sodium chloride) and 0.5% SDS at 60° C. for 20 minutes, and the condition of washing in a solution with 0.2×SSC (1×SSC: 15 mM trisodium citrate, 150 mM sodium chloride) and 0.1% SDS at 60° C. for 15 minutes.

Hybridization can be carried out in accordance with a known method. Also, in cases where a commercially-available library is used, it can be carried out in accordance with a method described in the attached instructions.

In the present description, the term "identity" (also referred to as homology) for nucleotide sequences means a degree of match of bases constituting each sequence among the sequences to be compared. At that time, the presence of a gap(s) and characteristics of the amino acids are taken into account. Any values of the "identity" shown in the present description may be values calculated using a homology search program known to those skilled in the art. For instance, the value can be readily calculated by using default (initial setting) parameters in FASTA, BLAST or the like.

In the present description, the "identity" for nucleotide sequences is 90% or more, preferably 95% or more, more preferably 98% or more, still more preferably 99% or more.

In the present description, the term, "one or more nucleotides are deleted, substituted, inserted or added in a polynucleotide" means that alteration was made by a known method such as a site specific mutagenesis method, or substitution or the like of a plurality of nucleotides in a degree at which they may naturally occur. The number of the altered nucleotides is one or more nucleotides (for example, one to several nucleotides or 1, 2, 3 or 4 nucleotides).

The term "nucleotide sequence which encodes a protein substantially equivalent to the protein encoded by the (each) nucleotide sequence" means a nucleotide sequence encoding a protein which has an activity equivalent to that of "the protein encoded by the (each) nucleotide sequence."

It is preferred that a protein substantially equivalent to a protein encoded by the nucleotide sequence from 3342 to 5158 of the nucleotide sequence shown in SEQ ID NO:266 have CoA ligase activity.

It is preferred that a protein substantially equivalent to a protein encoded by the nucleotide sequence from 5382 to 12777 of the nucleotide sequence shown in SEQ ID NO:266 have LovB-like polyketide synthase (PKS) activity.

It is preferred that a protein substantially equivalent to a protein encoded by the nucleotide sequence from 13266 to 15144 of the nucleotide sequence shown in SEQ ID NO:266 have Cytochrome P450 monooxygenase (1) (P450-1) activity.

It is preferred that a protein substantially equivalent to a protein encoded by the nucleotide sequence from 16220 to 18018 of the nucleotide sequence shown in SEQ ID NO:266 have Cytochrome P450 monooxygenase (2) (P450-2) activity.

It is preferred that a protein substantially equivalent to a protein encoded by the nucleotide sequence from 18506 to 19296 of the nucleotide sequence shown in SEQ ID NO:266 have Cyclase (IMP: Integral membrane protein) activity.

It is preferred that a protein substantially equivalent to a protein encoded by the nucleotide sequence from 19779 to 21389 of the nucleotide sequence shown in SEQ ID NO:266 have FAD-dependent monooxygenase (FMO) activity.

It is preferred that a protein substantially equivalent to a protein encoded by the nucleotide sequence from 21793 to 22877 of the nucleotide sequence shown in SEQ ID NO:266 have UbiA-like prenyltransferase (UbiAPT) activity.

It is preferred that a protein substantially equivalent to a protein encoded by the nucleotide sequence from 23205 to 24773 of the nucleotide sequence shown in SEQ ID NO:266 have Acetyltransferase (AT) activity.

It is preferred that a protein substantially equivalent to a protein encoded by the nucleotide sequence from 25824 to 27178 of the nucleotide sequence shown in SEQ ID NO:266 have Acetyltransferase-2 (AT-2) activity.

"A nucleotide sequence having a function substantially equivalent to each nucleotide sequence" is not particularly restricted as long as it has the function equivalent to "each nucleotide sequence", and, for example, means that a function to regulate expression of a gene in interest is equivalent, and, more particularly, for example, a function of a promoter activity or terminator activity is equivalent.

The above-mentioned gene in interest and expression regulatory region can be obtained by carrying out DNA amplification by PCR method with the genomic DNA derived from a pyripyropene-producing fungus or the like as a template using appropriate primers synthesized based on the above-mentioned nucleotide sequence, or by carrying out total chemical synthesis.

Pyripyropenes

Pyripyropenes in the present invention include pyripyropene A to pyripyropene R, and are preferably pyripyropene A, E and O with pyripyropene A being further preferred.

Method for Isolating Pyripyropene Biosynthetic Gene Cluster

A pyripyropene biosynthetic gene cluster can be isolated, for example, by the following method. For instance, the genomic DNA of a pyripyropene-producing fungus is extracted and digested with an appropriate restriction enzyme, and thereafter a library composed of the genomic DNA is prepared using a cosmid vector. Subsequently, based on the nucleotide sequence contained in a pyripyropene biosynthetic gene cluster such as cytochrome P450, appropriate primers are synthesized in accordance with the description of Example 12. PCR method is carried out with the genomic DNA derived from a pyripyropene-producing fungus as a template using the primers to amplify a DNA fragment composed of part of the biosynthetic gene cluster. Using this DNA fragment as a probe, the full length or a part of the pyripyropene biosynthetic gene cluster can be isolated by screening the genomic library.

The pyripyropene biosynthetic gene cluster expressed in a host in the present invention can be obtaining by, besides the above-mentioned method, ligating, to a gene in interest, an expression regulatory region which functions in the host. Any manner of ligation between the gene in interest and expression regulatory region may be employed as long as the gene in interest is expressed in the host. For example, there is a method for operatably ligating a promoter upstream of the gene in interest and a terminator downstream of it. The ligation between the gene in interest and expression regulatory region by the present invention can be carried out in accordance with a known method.

Marker Gene

The marker gene according to the present invention is one arranged in a nucleic acid construct in the state wherein it can be expressed with the above-described pyripyropene biosynthetic gene cluster in a host and can appropriately be selected depending on a method for selecting a transformant. For instance, genes encoding drug resistance and genes complementing auxotrophy can be used. Examples of the drug resistant genes include genes against drugs such as destomycin, hygromycin, benomyl, oligomycin, G418, bleomycin, bialaphos, blasticidin S, phleomycin, phosphinothricin, ampicillin or kanamycin, preferably a destomycin resistant gene or hygromycin resistant gene. Examples of the genes complementing auxotrophy include genes such as amdS, pyrG, argB, trpC, niaD, TRP1, LEU2 or URA3.

These marker genes can be isolated, amplified, or synthesized by the same method as, for example, the pyripyropene biosynthetic gene cluster, to be used.

Nucleic Acid Construct

The nucleic acid construct in the present invention may be in any form as long as it can be introduced in a gene of a host, and preferably a form incorporated in a vector when introduced in a host can be used. Therefore, according to a preferred embodiment of the present invention, a recombinant vector comprising the nucleic acid construct by the present invention is provided.

The recombinant vector according to the present invention can be prepared by introducing a pyripyropene biosynthetic gene cluster and marker gene which is expressed in a host in an appropriate vector.

As a procedure and method for constructing a recombinant vector, one commonly employed in the field of genetic engineering can be used.

As a vector which can be used in the present invention, any vector can be used as long as it can be introduced in the host. Examples thereof include cosmids, phage vectors, pUC-based plasmids, pBluescript-based plasmids, pBR322 plasmids and the like.

Host

A host which can be used in the present invention is not particularly restricted as long as it is a host capable of producing pyripyropenes by introducing the nucleic acid construct of the present invention. It is preferred to be a microorganism capable of producing pyripyropenes even in the state wherein the nucleic acid construct of the present invention is not introduced. It is more preferable to be filamentous fungi, still more preferably microorganisms belonging the genus *Penicillium*, the genus *Eupenicillium* or the genus *Aspergillus*, still further more preferably *Penicillium coprobium, Penicillium griseofulvum, Eupenicillium reticulosporum* or *Aspergillus fumigatus*. Among them, *Penicillium coprobium* is preferred with *Penicillium coprobium* PF1169 strain being most preferred.

Making of Transformant

According to the present invention, by transforming the above-mentioned host using the above-mentioned nucleic acid construct, a transformant in which the pyripyropene biosynthetic gene cluster was introduced is provided. A method for introducing the nucleic acid construct in the host is not particularly restricted as long as introduction into the host is achieved. For instance, the nucleic acid construct can be introduced into the host by the following method using a recombinant vector.

Introduction of the nucleic acid construct into the host using the recombinant vector can be carried out in accordance with a conventional method. Examples of the method for introduction include an electroporation method, polyethylene glycol method, *Agrobacterium* method, lithium method, calcium chloride method and the like. A method efficient for host cells is selected. In cases where *Penicillium coprobium* is used as the host, the polyethylene glycol method is preferred.

According to a preferred embodiment of the present invention, a transformant which is obtainable by introducing plasmid pPYRI02 into the host (accession number of *E. coli* transformed with plasmid pPYRI02: FERM BP-11203) or cosmid pPYRI07 into the host (accession number of *E. coli* transformed with cosmid pPYRI07: FERM BP-11316) is provided.

Culturing of Transformant and Production of Pyripyropenes

According to the present invention, a method for producing pyripyropenes comprising culturing the transformant made above and collecting pyripyropenes from the culture, preferably a method for producing pyripyropenes in a large scale is provided.

The culturing of the transformant can be carried out by appropriately selecting a medium, culturing conditions and the like in accordance with a conventional method. As the medium, commonly used components, for example, as carbon sources, glucose, sucrose, cellulose, starch syrup, dextrin, starch, glycerol, molasses, animal and vegetable oils or the like, can be used. Also, as nitrogen sources, soybean flour, wheat germ, pharmamedia, corn steep liquor, cotton seed meal, bouillon, peptone, polypeptone, malto extract, yeast extract, ammonium sulfate, sodium nitrate, urea or the like can be used. Besides, as required, addition of sodium, potassium, calcium, magnesium, cobalt, chlorine, phosphoric acid, sulfuric acid or inorganic salts which can generate other ions, such as potassium chloride, calcium carbonate, dibasic potassium phosphate, magnesium sulfate, potassium dihydrogen phosphate, zinc sulfate, manganese sulfate or copper sulfate is effective. Also, as required, trace nutrients such as various vitamins such as thiamin (thiamine hydrochloride or the like), amino acids such as glutamic acid (sodium glutamate or the like) or asparagine (DL-asparagine or the like), or nucleotides; or selection agents such as antibiotics can be added. Further, organic substances or inorganic substances which help the growth of a fungus and promote the production of pyripyropenes can be appropriately added.

As the method for culturing, shake culturing under aerobic conditions, culturing with bubbling under stirring or deep part aerobic culturing can be employed and, in particular, culturing with bubbling under stirring is most appropriate. The pH of the medium is, for example, about pH 6 to pH 8. The appropriate temperature for the culturing is 15° C. to 40° C. and, in many cases, the growth takes place around 26° C. to 37° C. The production of pyripyropenes varies depending on the medium and culturing conditions, or the used host. In any method for culturing, the accumulation usually reaches its peak in 2 days to 25 days.

The culturing is terminated at the time when the amount of pyripyropenes during the culturing reaches the peak, and pyripyropenes are collected from the culture and, as required, isolated and purified. In cases where a plurality of types of pyripyropenes is produced, a plurality of types of pyripyropenes may be simultaneously collected and, as required, isolated and purified; or a plurality of types of pyripyropenes may be separately collected and, as required, isolated and purified.

EXAMPLES

The present invention will be further illustrated in detail by the following examples, which are not intended to restrict the present invention.

Example 1

Preparation of Genomic DNA of *Penicillium coprobium* PF1169 Strain

Sterilized NB medium (500 ml) was placed in an Erlenmeyer flask (1 L). *Penicillium coprobium* PF1169 strain (Journal of Technical Disclosure No. 500997/2008 (Patent Document 4)) precultured in ½ CMMY agar medium at 28° C. for days was added to the above-mentioned medium and subjected to liquid culture at 28° C. for 4 days. Filtration was carried out with Miracloth to obtain 5 g of fungal cells. From these fungal cells, 30 μg of genomic DNA was obtained in accordance with the manual attached to genomic DNA purification kit Genomic-tip 100/G (manufactured by Qiagen K.K.).

Example 2

Degenerate Primers for Amplification of Polyketide Synthase (PKS) and Amplified Fragment Thereof Based on an amino acid sequence conserved among various filamentous fungus polyketide synthases, the following primers were designed and synthesized as degenerate primers for amplification:

```
                                       (SEQ ID NO: 1)
LC1: GAYCCIMGITTYTTYAAYATG (SEQ ID NO: 2)
LC2c: GTICCIGTICCRTGCATYTC
```

(wherein R = A/G, Y = C/T, M = A/C, I = inosine).

Using these degenerate primers, the genomic DNA prepared in Example 1 and ExTaq polymerase (manufactured by Takara Bio Inc.) were allowed to react in accordance with the attached manual. An amplified fragment of about 700 bp was detected (FIG. 1). Further then, the above-mentioned amplified fragment was analyzed to specify the sequence of its internal 500 bp (SEQ ID NO:3).

Example 3

Large-Scale Sequencing of Genomic DNA and Amino Acid Sequence Homology Search

The genomic DNA of *Penicillium coprobium* PF1169 strain obtained in Example 1 was subjected to large-scale sequencing and homology search for amino acid sequences. Specifically, part of 50 μg of genomic DNA was pretreated and thereafter subjected to Roche 454FLX DNA sequencer to obtain 103 thousands of about 250 bp fragment sequences (sequence of 49 Mb in total).

For theses sequences, as known sequences among polyketide synthases and prenyltransferases, the following five sequences (sequences derived from polyketide synthases: *Aspergillus(A.) fumigatus* PKS 2146 a.a. and *Penicillium(P.) qriseofluvum* 6-methylsalycilic acid synthase 1744 a.a.; as well as prenyltransferases: *Aspergillus (A.) fumigatus* Prenyltransferase, *Aspergillus(A.) fumigatus* Prenyltransferase (4-hydroxybezoate octaprenyltransferase) and *Penicillium(P.) marneffei* Prenyltransferase) were selected and search by homology sequence search software blastx was carried out, thereby obtaining 89, 86, 2, 1 and 3 of homology sequences, respectively (see Table 2). Further, from the homology sequences of *A. fumigatus* PKS 2146 a.a. and *P. griseofluvum* 6-methylsalycilic acid synthase 1744 a.a., 19 and 23 of contig sequences were respectively obtained (the contig sequences of *A. fumigatus* PKS 2146 a.a.: SEQ ID NOs:179 to 197; the contig sequences of *P. griseofluvum* 6-methylsalycilic acid synthase 1744 a.a.: SEQ ID NOs:198 to 220) (see Table 2).

TABLE 2

| Enzyme Name | Origin | Number of Homology Sequences | SEQ ID NO. |
|---|---|---|---|
| Polyketide Synthases | *A. fumigatus* PKS 2146 a.a. | 89 | 4 to 92 |
|  | *P. griseofluvum* 6-methylsalycilic acid synthase 1744 a.a. | 86 | 93 to 178 |
|  | *A. fumigatus* PKS 2146 a.a. | 19 (Contig seqeences) | 179 to 197 |
|  | *P. griseofluvum* 6-methylsalycilic acid synthase 1744 a.a. | 23 (Contig seqeences) | 198 to 220 |
| Prenyltransferases | *A. fumigatus* Prenyltransferase | 2 | 221, 222 |
|  | *A. fumigatus* Prenyltransferase (4-hydroxybezoate octaprenyltransferase | 1 | 223 |
|  | *P. marneffei* Prenyltransferase | 3 | 224 to 226 |

Example 4

PCR Amplification of Genomic DNA

Figure 2:
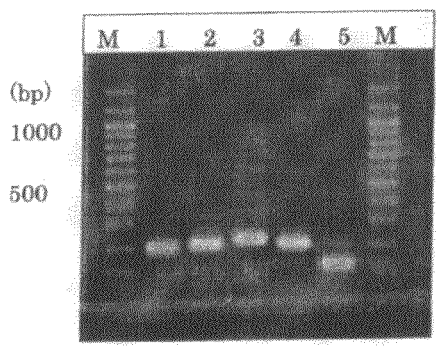
FIG. 2 Similarly to FIG. 1.

From the search results of blastx obtained in Example 3, for polyketide synthases, 13 types of primer pairs shown in SEQ ID NOs:227 to 252 were synthesized. Similarly, for prenyltransferases, 5 types of primer pairs shown in SEQ ID NOs: 253 to 262 were synthesized. When PCR was carried out for the genomic DNA using these primers, amplified fragments with the expected size were seen for all of the primer pairs (see FIG. 1 and FIG. 2).

Example 5

Construction of Phage Genomic Library

A λ phage genomic library of *Penicillium coprobium* PF1169 strain was constructed using λ BlueSTAR Xho I Half-site Arms Kit (manufactured by Takara Bio Inc., Cat. No. 69242-3) in accordance with the attached manual. That is, genomic DNA was partially digested using a restriction enzyme, Sau3A1. The DNA fragment with about 20 kb (0.5 μg) was ligated to 0.5 μg of λ BlueSTAR DNA attached to the kit. This ligation solution was subjected to in vitro packaging using Lambda INN Packaging kit (manufactured by Nippon Gene Co., Ltd.) based on the manual attached to the kit to obtain 1 ml of a solution. This solution with packaged phages (10 μl) was infected into 100 μl of *E. coli* ER1647 strain and cultured on a plaque-forming medium at 37° C. overnight, thereby obtaining about 500 clones of plaques. Thus, the genomic library composed of about 50000 clones of phages in which 10 to 20 kb genomic DNA of *Penicillium coprobium* PF1169 strain were introduced by clone infection was constructed.

Example 6

Screening from Phage Library

For 10000 clones of the phage library prepared in Example 5, the primary screening was carried out by plaque hybridization using, as a probe, the PCR product amplified by LC1-LC2c primer pair prepared above. For labeling and detection of the probe, AlkPhos Direct Labelling and Detection System with CDP-Star (manufactured by GE Healthcare, Cat. No.

RPN3690) was used. The above-mentioned hybridization was carried out in accordance with the attached manual.

By the primary screening, 6 clones remained as candidates. Further, as the result of the secondary screening by plaque hybridization, 4 clones were obtained. These positive clones were infected into *E. coli* BM25.8 strain and the phages were converted to plasmids in accordance with the attached manual, thereby obtaining 4 types of plasmids comprising the desired region.

Example 7

Preparation of Fosmid Genome Library

A genomic library of *Penicillium coprobium* PF1169 strain was constructed in accordance with the manual attached to CopyControl Fosmid Library Production Kit (manufactured by EPICENTRE, Cat. No. CCFOS110). That is, 0.25 μg of DNA fragment of about 40 kb genomic DNA was blunt-ended and then incorporated in fosmid vector pCCFOS (manufactured by Epicentre). This ligation solution was subjected to in vitro packaging using MaxPlax Lambda Packaging Extract attached to the kit based on the manual attached to the kit. This solution with packaged viruses (10 μl) was infected into 100 μl of *E. coli* EPI300™-T1® strain and cultured on a medium containing chloramphenicol at 37° C. overnight and selected, thereby obtaining about 300 clones of colonies. Thus, about 30000 clones of the fosmids in which 40 kb the genomic DNA of *Penicillium coprobium* PF1169 strain were introduced by infection were obtained. They were aliquoted in a 96 well plate so as to be about 50 clones per well. Thus, the genomic library composed of 96 pools, about 4800 clones was constructed.

Example 8

Fosmid Library Screening

In accordance with the manual attached to the fosmid, plasmid DNAs were individually prepared from 96 pools of the library prepared in Example 7. Using the degenerate primers for polyketide synthase amplification synthesized in Example 2, PCR was carried out for 96 pools of these plasmid DNA samples. As a result, DNA fragments of about 700 bp were amplified from 9 pools. Further, a petri dish containing colonies of about 300 clones or more was prepared from the positive pool and re-screening was carried out by colony hybridization. As a result, using by LC1-LC2c primer pair, 9 types of fosmids were obtained from about 4800 clones.

Example 9

Large-Scale Sequencing of Genomic DNA and Amino Acid Sequence Homology Search

Genomic DNA of *Penicillium coprobium* PF1169 strain obtained in Example 1 was subjected to large-scale sequencing and homology search for amino acid sequences. Specifically, part of 50 μg of genomic DNA was pretreated and then subjected to Roche 454FLX DNA sequencer to obtain 1405 fragment sequences with an average contig length of 19.621 kb (sequence of a total base length of 27.568160 Mb).

For these sequences, as known sequences among polyketide synthases and prenyltransferases, the following five sequences (sequences derived from polyketide synthases: *Penicillium*(*P.*) *griseofluvum* 6-methylsalyciIic acid synthase 1744 a.a. (P22367) and *Aspergillus*(*A.*) *fumigatus* PKS 2146 a.a. (Q4WZA8); as well as prenyltransferases: *Penicillium*(*P.*) *marneffei* Prenyltransferase (Q0MRO8), *Aspergillus* (*A.*) *fumigatus* Prenyltransferase (Q4WBI5) and *Aspergillus*(*A.*) *fumigatus* Prenyltransferase (4-hydroxybezoate octaprenyltransferase) (Q4WLD0)) were selected and search by homology sequence search software blastx was carried out, thereby obtaining 22 (P22367), 21 (Q4WZA8), 2 (Q0MRO8), 3 (Q4WBI5) and 3 (Q4WLD0) of the homologous sequences, respectively.

Example 10

Fosmid Library Screening and Sequence Analysis of Cluster Genes

Figure 3:
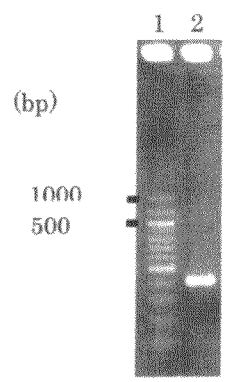
FIG. 3 Similarly to FIG. 1.

In accordance with the manual attached to a fosmid kit (manufactured by EPICENTRE, CopyControl Fosmid Library Production Kit), plasmid DNAs were individually prepared from 96 pools of the library prepared in Example 7. Based on base sequences determined by Roche 454FLX DNA sequencer, homology search for amino acid sequences was carried out to search regions adjacent to polyketide synthase and prenyltransferase. Based on the base sequence of prenyltransferase of the region obtained, a primer pair (No. 27) capable of amplifying 400 bp DNA fragment was synthesized. Using the primers, PCR was carried out for these 48 pools of plasmid DNA samples. As a result, expected DNA fragments of about 400 bp (SEQ ID NO:263) were amplified from 11 pools (see FIG. 3). Further, a petri dish containing colonies of about 300 clones or more was prepared from 6 pools of the positive pool and re-screening was carried out by colony hybridization. As a result, using by 27F+27R primer pair (27F primer: SEQ ID NO:264), 27R primer: SEQ ID NO:265)), 4 types of fosmids were obtained from about 4800 clones. One of them was named pCC1-PP1 and the entire sequence of the inserted fragment was determined (SEQ ID NO:266)).

The pCC1-PP1 obtained was transformed into *Escherichia coli* EPI300™-T1® strain (attached to the fosmid kit), thereby obtaining *Escherichia coli* EPI300™-T1® strain/pCC1-PP1 (Accession No. FERM BP-11133).

When a homology search was carried out between the above-mentioned sequence of SEQ ID NO:266 and each of CoA ligase; LovB-like polyketide synthase (PKS); Cytochrome P450 monooxygenase, Cyclase, FAD-dependent monooxygenase (FMO), which are hydroxylases; UbiA-like prenyltransferase (UbiAPT); Acetyltransferase (AT), Acetyltransferase-2 (AT-2), which are acetyltransferases; and Cation transporting ATPase (the above-mentioned enzymes are all derived from *Aspergillus fumigatus* Af293 strain), a high homology of 70% or more was seen in any search.

The nucleotides 3342 to 5158 of SEQ ID NO:266 encode CoA ligase and the corresponding polypeptide is shown with the amino acid sequence depicted in SEQ ID NO:267; the nucleotides 5382 to 12777 of SEQ ID NO:266 encode LovB-like polyketide synthase (PKS) and the corresponding polypeptide is shown with the amino acid sequence depicted in SEQ ID NO:268; the nucleotides 13266 to 15144 of SEQ ID NO:266 (hereinafter, a protein encoded by this nucleotide sequence (P450-1) is referred to as Cytochrome P450 monooxygenase (1)) and the nucleotides 16220 to 18018 (hereinafter, a protein encoded by this nucleotide sequence (P450-2) is referred to as Cytochrome P450 monooxygenase (2)) encode Cytochrome P450 monooxygenases and the corresponding polypeptides are shown with the amino acid sequences depicted in SEQ ID NOs:269 and 270, respectively; the nucleotides 18506 to 19296 of SEQ ID NO:266 encode Cyclase and the corresponding polypeptide is shown with the amino acid sequence depicted in SEQ ID NO:271; the nucleotides 19779 to 21389 of SEQ ID NO:266 encode FAD-dependent monooxygenase (FMO) and the corresponding polypeptide is shown with the amino acid sequence depicted in SEQ ID NO:272; the nucleotides 21793 to 22877 of SEQ ID NO:266 encode UbiA-like prenyltransferase (Ubi-APT) and the corresponding polypeptide is shown with the amino acid sequence depicted in SEQ ID NO:273; the nucleotides 23205 to 24773 of SEQ ID NO:266 encode Acetyltransferase (AT) and the corresponding polypeptide is shown with the amino acid sequence depicted in SEQ ID NO:274; the nucleotides 25824 to 27178 of SEQ ID NO:266 encode Acetyltransferase-2 (AT-2) and the corresponding polypeptide is shown with the amino acid sequence depicted in SEQ ID NO:275; and the nucleotides 27798 to 31855 of SEQ ID NO:266 encode Cation transporting ATPase and the corresponding polypeptide is shown with the amino acid sequence depicted in SEQ ID NO:276.

Example 11

Preparation of Genomic DNA Library

Cosmid vector pMFCOS1 which is capable of transformation of fungi was constructed as follows. From plasmid pMKD01 (Japanese Patent No. 3593134), an about 3.0 kb XbaI fragment containing a destomycin resistant gene, which is a marker gene for fungus transformation, was prepared and blunt-ended using T4 polymerase. This fragment was ligated to a commercially-available cosmid vector, Super Cosi. (Stratagene) which was double digested with restriction enzymes SmaI and StuI, thereby obtaining cosmid vector pMFCOS1.

Next, *Penicillium coprobium* PF1169 strain (Journal of Technical Disclosure No. 500997/2008 (Patent Document 4)) which is a pyripyropene A-producing fungus was inoculated in a liquid medium (3% glycerin, 0.8% nutrient broth, 0.3% malt extract, 0.2% yeast extract, 0.1% sodium glutamate, pH 7.0) and cultured at 26° C. for 48 hours. After completion of the culturing, fungal cells were collected by centrifugation and the chromosomal DNA was prepared from these fungal cells. After the chromosomal DNA was partially digested with a restriction enzyme, Sau3AI, alkaline phosphatase treatment was carried out to dephosphorylate the ends of DNA. This DNA fragment was ligated to cosmid vector pMFCOS1 which was in advance digested with a restriction enzyme XbaI, dephosphorylated by the alkaline phosphatase treatment, and further digested with a restriction enzyme BamHI, to obtain a recombinant cosmid vector. This recombinant cosmid vector was subjected to in vitro packaging using MAXPLAX Lambda Packaging Extract manufactured by Epicentre and infected into *E. coli* XLI-Blue MRA, thereby obtaining the genomic DNA library.

Example 12

Screening of Genomic DNA Library

As a probe to screen the genomic DNA library prepared in Example 1, it was determined that cytochrome P450 gene which was one of the pyripyropene A biosynthetic genes was used. Further, the probe was prepared by PCR as shown below.

PCR was carried out with the genomic DNA shown in Example 1 as a template using oligo DNAs of 5'-ATGATCGAGCTCAAAGATGC-3' (SEQ ID NO:277) and 5'-CT-TCTTTCCAGTCAATACCT-3' (SEQ ID NO:278) as primers. PCR was carried out with Prime STAR HS DNA polymerase (Takara Bio Inc.) as DNA polymerase using PERKIN ELMER GeneAmp PCR System 9700. The reaction solution contained 0.5 µl (an amount equivalent to 0.5 µg) of genomic DNA, 25 µl of 2-fold concentrated reaction buffer attached to the enzyme, 4 µl of 2.5 mM dNTP solution, 0.5 µl each of the above-mentioned primers adjusted to a concentration of 100 pmol/µl, 0.5 µl of the enzyme and 19 µl of sterilized water was added to attain a final volume of 50 µl. The reaction was carried out by, after pretreatment at 94° C. for 5 minutes, repeating an incubation of 98° C. for 10 seconds, 50° C. for 5 seconds and 72° C. for 2 minutes 25 cycles. After the completion of the reaction, part of the reaction mixture was subjected to agarose gel electrophoresis, it was, as a result, confirmed that about 1.8 kbp DNA fragment was specifically amplified. Thus, the remaining reaction solution was extracted with phenol:chloroform:isoamyl alcohol (25:24:1), followed by ethanol precipitation. The precipitate was redissolved in sterilized water and subjected to agarose gel electrophoresis. About 1.8 kbp band was excised in accordance with a conventional method to recover the DNA fragment.

Colony hybridization was carried out with the above-mentioned DNA fragment as a probe by using ECL Direct DNA/RNA Labeling and Detection System (manufactured by Amersham Pharmacia Biotech Inc.) and about 5000 colonies were screened. A plurality of positive clones was obtained. From one clone of these, plasmid pPYRI02 was isolated. Also, the base sequence of the end of the inserted fragment of this plasmid pPYRI02 was analyzed and it was, as a result, confirmed that it contained 1 to 25000 of SEQ ID NO:266 and the upstream region thereof.

Example 13

Making of Transformant

*Penicillium coprobium* PF1169 strain which is a pyripyropene-producing fungus was inoculated in a liquid medium (3% glycerin, 0.8% nutrient broth, 0.3% malt extract, 0.2% yeast extract, 0.1% sodium glutamate, 2% glycine, pH 7.0) and cultured at 26° C. for 24 hours and thereafter fungal cells were collected by centrifugation. The fungal cells obtained were washed with 1.0 M KCl and suspended in 10 mL of protoplast formation enzyme solution (3 mg/mL β-glucuronidase, 1 mg/mL Chitinase, 3 mg/mL Lysing enzyme, 1.0 M KCl) filtered with 0.45 µm filter. The suspension was shaken at 30° C. for 60 to 90 minutes and hyphae were transformed into protoplasts. This suspension was filtered and centrifuged to collect the protoplasts, which were washed with SUTC buffer solution (0.5 mol/L sucrose, 10 mM calcium chloride, 10 mM tris hydrochloric acid [pH7.5]).

The protoplasts prepared were suspended in 1 mL of the SUTC buffer solution. For 100 µL of this, 10 µg of pPYRI02 DNA solution (20 µL) was added and the mixture was left to stand in ice for 5 minutes. Next, 400 µL of PEG solution (60% PEG4000, 10 mM calcium chloride, 10 mM tris hydrochloric acid [pH7.5]) was added, mixed and left to stand in ice for 20 minutes. Further, 10 mL of the SUTC buffer solution was added and centrifuged to collect fungal cells transformed into protoplasts. The fungal cells obtained was suspended in 1 mL of the SUTC buffer solution and then centrifuged at 4000 rpm for 5 minutes, and finally suspended in 100 µL of the SUTC buffer solution.

The fungal cells subjected to the above treatment were overlaid on potato dextrose agar containing 200 µg/mL hygromycin B and 1.0 M sucrose together with soft potato dextrose agar medium containing 1.0 M sucrose. After the culturing at 26° C. for 4 days, formed colonies were used as transformants.

Example 14

Culture of Transformant and Quantification of Pyripyropenes in Culture Medium

For culturing the transformant, as a seed culture medium, a medium (pH 7.0 before sterilization) having the composition of 2.0% starch, 1.0% glucose, 0.5% polypeptone, 0.6% wheat germ, 0.3% yeast extract, 0.2% soybean cake and 0.2% calcium carbonate was used. Also, as a production medium, a medium (pH 7.0 before sterilization) having the composition of 10.0% glucose, 1.3% defatted soybean, 0.3% sodium glutamate, 0.8% wheat germ, 0.125% sodium chloride, 0.15% calcium carbonate and 0.2% nicotinamide was used.

The above-mentioned seed culture medium (40 ml) was aliquoted in a 250 ml-Erlenmeyer flask, which was sterilized at 122° C. for 20 minutes. To this, the transformant described in Example 13 was collected with a platinum loop and seeded, and cultured with shaking at 26° C. for 3 days. The production medium (20 ml) was aliquoted in a 250 ml-Erlenmeyer flask, which was sterilized at 122° C. for 20 minutes. To this, 0.5 ml of the above seed culture solution was aseptically seeded and cultured with shaking at 26° C. for 8 days. To 0.5 ml of the culture solution obtained, 9.5 ml of methanol was added to extract pyripyropenes. The resultant was filtered, thereby obtaining an extract solution. 10 μl of this was subjected to HPLC analysis. HPLC analysis was carried out using HPLC system LC-2010C (Shimadzu Corporation). Conditions for the analysis were as follows: column: Inertsil ODS-3 4.6×250 mm, mobile phase: acetonitrile:water=60:40, flow rate: 1.0 ml/min, column temperature: 40° C. and UV wave length: 320 nm. The pattern obtained was compared with pyripyropene standards. Peaks derived from pyripyropenes were specified. From area thereof, pyripyropenes was quantified. The pyripyropene analogues quantified were pyripyropene A, E and O which were produced in the present fungus.

At the same time, for *Penicillium coprobium* PF1169 strain which was the parent strain of the transformant, culturing and quantification of pyripyropenes in the culture medium were similarly carried out.

As a result, as shown in Table 3 blow, it has been found that the productivity of pyripyropenes of the transformant is about 2.6 fold higher than that of the parent strain, and that the transformant transformed with pPYRI02 which does not contains the full-length pyripyropene biosynthetic gene cluster still improves the productivity of pyripyropenes.

TABLE 3

| Strain | Production in Culture Medium (μg/mL) | | | | |
| --- | --- | --- | --- | --- | --- |
| | Pyripyropene A | Pyripyropene E | Pyripyropene O | Total | Relative Productivity |
| Parent | 812 | 171 | 72 | 1055 | 1 |
| Transformant | 1876 | 724 | 113 | 2713 | 2.6 |

Example 15

Transformation of *Penicillium coprobium* Using *Agrobacterium tumefaciens*

*Penicillium coprobium* strain PF1169 was cultured in ½ CMMY agar medium at 28° C. for 3 days, and the condia were recovered by scraping. The spores were obtained by filtration through sterile miracloth (manufactured by Carbiochem, Cat No. 475855), and diluted with IM liquid medium (1.74 g/L $K_2HPO_4$, 1.36 g/L $KH_2PO_4$, 0.14 g/L NaCl, 0.49 g/L $MgSO_4 \cdot 7H_2O$, 0.10 g/L $CaCl_2 \cdot 2H_2O$, 100μ/L 9 mM $FeSO_4$, 0.53 g/L $(NH_4)2SO_2$, 1.8 g/L glucose, 8.53 g/L MES (2-Morpholinoethanesulfonic acid), 5 mL/L glycerin, pH 5.3) to $10^3$/ml to obtain suspension of the *Penicillium coprobium* spores.

Figure 4:
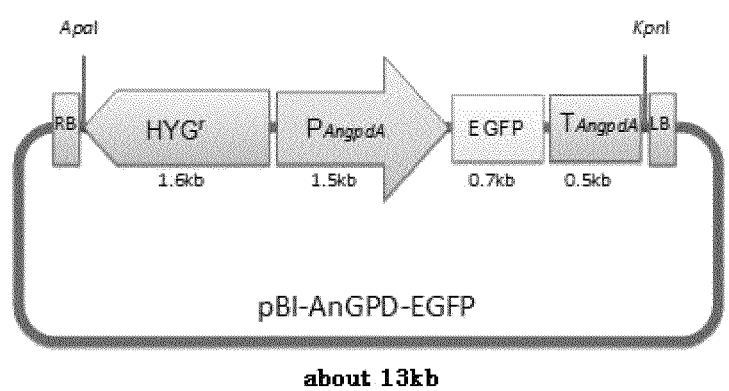
FIG. 4 shows the map of plasmid vector pBI-AnGPD-EGFP for the filamentous fungus used. In this figure, RB refers to the right border, HYG$^r$ refers to the Hygromycin resistance coding region, PAngpdA refers to the *Aspergillus nidulans* glyceraldehyde-3-phosphate dehydrogenase promoter, EGFP refers to the enhanced green fluorescent protein coding region, TAngpdA refers to the *Aspergillus nidulans* glyceraldehyde-3-phosphate dehydrogenase terminater, and LB refers to the left border.
Figure 5A:
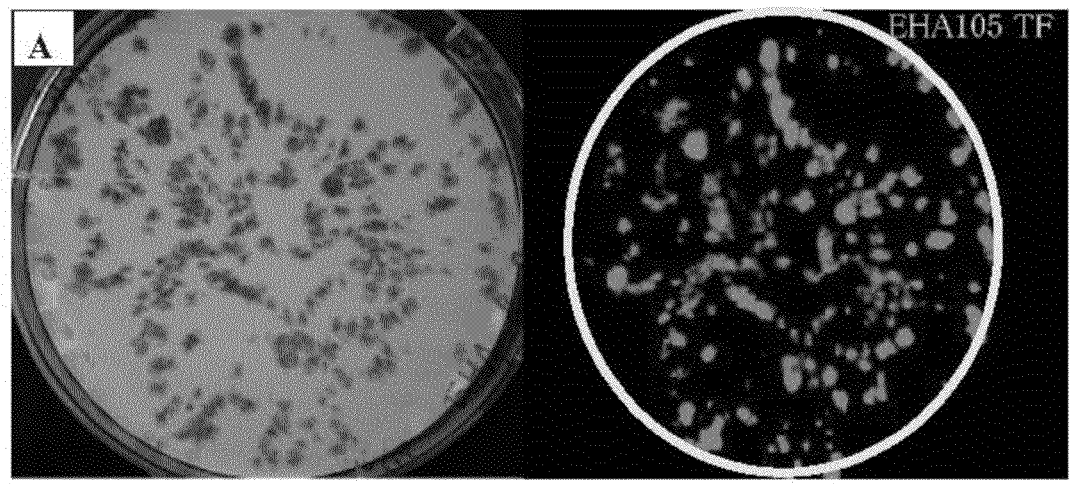
In FIG. 5A, the left panel shows hygromycin-resistant colonies formed with *Agrobacterium* infection, and the right panel shows the results of the observation of the GFP fluorescence.
Figure 5B:
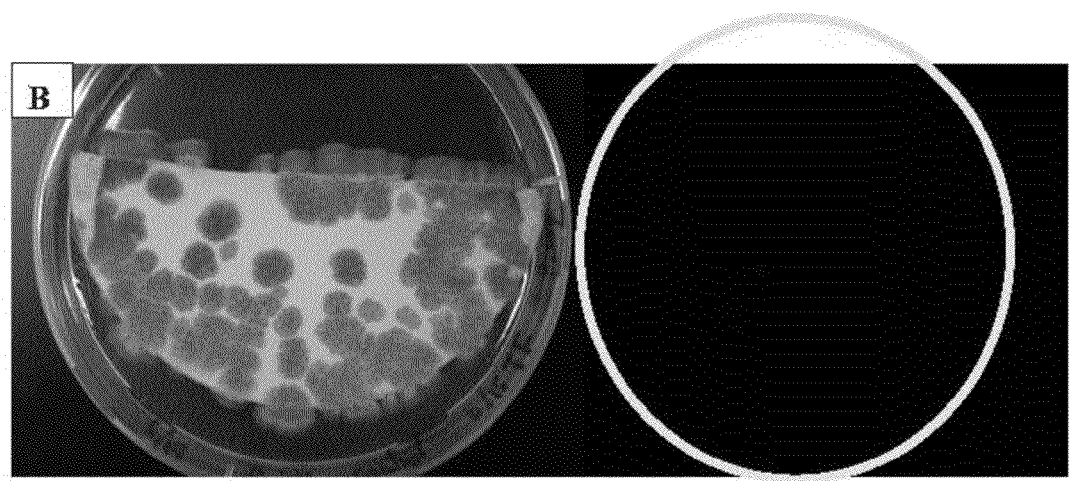
In FIG. 5B, the left panel shows the colonies of *Penicillium coprobium* strain PF1169 without *Agrobacterium* infection, the colonies being formed in medium containing no hygromycin, and the right panel shows the results of the observation of the GFP fluorescence.

*Agrobacterium tumefaciens* strain EHA105 into which pBI-AnGPD-EGFP (RIKEN) shown in FIG. 4 has been introduced was inoculated into IM liquid medium containing 50 ppm kanamycin (Km), and cultured at 28° C. overnight. The resultant was diluted with IM liquid medium containing 50 ppm Km so that the absorption of the transmitted light at 660 nm ranges from 0.3 to 0.45. Acetosyringone (AS) was added at a final concentration of 500 μm, and the resultant was cultured at 28° C. for 6 hours to give *Agrobacterium* culture medium. Hybond-N+ (manufactured by GE Health Science, 82 mm in diameter, Cat No. RPN82B) was laid on co-cultivation agar medium (1.74 g/L $K_2HPO_4$, 1.36 g/L $KH_2PO_4$, 0.14 g/L NaCl, 0.49 g/L $MgSO_4 \cdot 7H_2O$, 0.10 g/L $CaCl_2 \cdot 2H_2O$, 100 μL/L 9 mM $FeSO_4$, 0.53 g/L $(NH_4)_2SO_2$, 0.9 g/L glucose, 8.53 g/L MES (2-Morpholinoethanesulfonic acid), 5 mL/L glycerin, 15 g/L agar, pH 5.3) containing 50 ppm Km and 500 μM AS. And the mixture of 100 μL of the suspension of the *Penicillium coprobium* spores and 100 μL of the *Agrobacterium* culture medium, both of which were obtained through the above methods, was evenly spread on the Hybond-N+. After co-culturing at 25° C. for 2 days, the resultant was transferred to MM agar medium (1.74 g/L $K_2HPO_4$, 1.36 g/L $KH_2PO_4$, 0.14 g/L NaCl, 0.49 g/L $MgSO_4 \cdot 7H_2O$, 0.10 g/L $CaCl_2 \cdot 2H_2O$, 100 μL/L 9 mM $FeSO_4$, 0.53 g/L $(NH_4)_2SO_2$, 1.8 g/L glucose, 15 g/L agar) containing 50 ppm hygromycin and 25 ppm meropenem (manufactured by Sumitomo Pharmaceuticals) and cultured for 4 days. The resultant colonies were transferred to ½ CMMY agar medium containing 25 ppm hygromycin and 25 ppm meropenem, and the grown transformants were obtained. As seen from FIG. 5A which shows the obtained hygromycin-resistant colonies and the results of the observation of the GFP fluorescence, the fluorescence was detected on the most of the obtained hygromycin-resistant colonies. On the other hand, as shown in FIG. 5B, no fluorescence was detected on the control, *Penicillium coprobium* strain PF1169 without *Agrobacterium* infection. And the introduction of a hygromycin-resistant gene and a GFP gene was confirmed by genomic PCR of the hygromycin-resistant colonies, whose data is not shown.

Example 16

Screening 2 of Genome DNA Library

The base sequence of the end of the inserted fragment of plasmid pPYRI02 obtained in Example 12 is the sequence of the region from 1 to 25000 of SEQ ID NO:266 and the upstream region thereof. In order to obtain a full-length pyripyropene biosynthetic gene cluster, where the downstream region of the pyripyropene biosynthetic gene cluster is further added, the full-length biosynthetic gene cluster is constructed by ligating the downstream region of the pyripyropene biosynthetic gene cluster which was separately cloned to the inserted fragment of pPYI02 as described above.

In the method for constructing the full-length biosynthetic gene cluster, the downstream region of the cluster was cloned from the genome DNA library produced in Example 11, using as a probe the O-acetyltransferase gene, which is a pyripyropene A biosynthetic gene not contained in pPYRI02.

PCR was carried out in the same conditions as in Example 12 except that the genome DNA described in Example was used as a template, and that 5'-ATGGATTCCCTATTGAC-GAG-3' (SEQ ID NO:279) and 5'-TTAAATCTCCCCAC-CAACCG-3' (SEQ ID NO:280) were used as primers for amplifying the DNA fragment for use as a probe.

Colony hybridization was carried out using the above-mentioned DNA fragment as a probe by using ECL Direct DNA/RNA Labeling and Detection System to screen the about 5000 colonies. A plurality of positive clones was obtained. From one of these clones, plasmid pPYRI03 was isolated. PCR analysis of the clone has confirmed that it sufficiently has the downstream region of the biosynthetic gene cluster and that with regard to the upstream region, it has the region for Cytochrome P450 monooxygenase and it does not contain the region for Adenylate forming enzyme (CoA ligase).

Cosmids which have the full-length biosynthetic gene cluster were constructed by using the inserted fragment of pPYRI02 obtained in Example 12 and the inserted fragment of pPYRI03 as described above. Analysis of the base sequence of each of the cosmids could reveal the restriction enzyme sites on the cluster. Further, it has been found that the full-length biosynthetic gene cluster can be constructed by ligating the BsiWI fragment (about 20.2 kb) of pPYRI02, which is used as the upstream region of the biosynthetic gene cluster, to the BsiWI-AflII fragment (about 4.9 kb) of pPYRI03, which is used as the downstream region.

Plasmid pSET152 for the conjugal transfer in *Actinomyces* described in [Bierman, M. et al. "Gene", (Netherlands) 1992, 116, p 43-49] was digested with SphI, blunt-ended with T4 DNA polymerase, and ligated to the HindIII linker (5'-CCCAAGCTTGGG-3' (SEQ ID NO:281), manufactured by Takara Shuzo) to construct plasmid pSET153. In order to change a multicloning site of pSET153 into HindIII-NotI-BsiWI-AflII-NotI-EcoRI, synthetic oligonucleotides Hin-Not-Bsi-Afl-Not-Eco-1 (5'-AGCTTGCGGCCGCG-TACGCTTAAGGCGGCCGCG-3') (SEQ ID NO:282) and Hin-Not-Bsi-Afl-Not-Eco-2 (5'-AATTCGCGGCCGCCT-TAAGCGTACGCGGCCGCA-3') (SEQ ID NO:283) were annealed, and then ligated to pSET153 which was double digested with HindIII and EcoRI to construct plasmid pSET201. The BsiWI-AflII fragment of about 4.9 kb derived from pPYRI03 was inserted into the BsiWI-AflII site of pSET201 to obtain plasmid pPYRI05. The BsiWI fragment of about 20.2 kb derived from pPYRI02 was inserted into the BsiWI site of pPYRI05, and the clones in which the BsiWI fragment was inserted in the same direction as in the natural biosynthetic gene cluster were selected to obtain plasmid pPYRI06. Because pPYRI06, which is a plasmic containing the full-length biosynthetic gene cluster, has no marker for fungus transformation, the inserted fragment was inserted to cosmid vector pMFCOS1. More specifically, the NotI fragment of the cosmid vector region of about 8.5 kb derived from pPYRI02 and the NotI fragment of about 25.1 kb derived from pPYRI06 were ligated to obtain cosmid pPYRI07 (the translation region: SEQ ID NO:284, the untranslated region: SEQ ID NO:285). pPYRI07 is a cosmid which has the full-length biosynthetic gene cluster, and which also has a marker gene for fungus transformation.

Analysis of the base sequence of the end of the inserted fragment of pPYRI07 has confirmed that pPYRI07 contains the region from the 2446th to 27505th of SEQ ID NO:266 and the upstream region thereof which has the base sequence of the vector region, and that pPYRI07 contains the full-length of pyripyropene biosynthetic gene cluster.

Example 17

Making of Transformant Using pPYRI07

A transformant was made in the same conditions as in Example 13 except that pPYRI07 obtained in Example 16 was used.

Example 18

Culturing of Transformant and Quantification of Pyripyropenes in Culture Medium

The methods for culturing the transformant obtained in Example 17 and for quantifying pyripyropenes in the culture medium were the same as those described in Example 14. The pyripyropene analogues quantified were pyripyropene A, E and O, which were produced by the present fungus. At the same time, *Penicillium coprobium* strain PF1169, which is the parent strain of the transformant, was cultured and the pyripyropenes in the culture medium were quantified in the same manner.

As a result, as shown in Table 4 below, the productivity of pyripyropenes of the transformant was 3.6 fold higher than that of the parent strain. The result has shown that the introduction of the full-length pyripyropene biosynthetic gene cluster improves the productivity of *Penicillium coprobium* strain PF1169.

TABLE 4

| | Production in Culture Medium (µg/mL) | | | | |
|---|---|---|---|---|---|
| Strain | Pyripyro-pene A | Pyripyro-pene E | Pyripyro-pene O | Total | Relative Productivity |
| Parent | 987 | 196 | 48 | 1231 | 1 |
| Transformant | 3821 | 255 | 340 | 4416 | 3.6 |

Example 19

Making of Transformant Using *Penicillium coprobium*

In order to confirm that the introduction of the full-length pyripyropene biosynthetic gene cluster also improves the productivity of *Penicillium coprobium* strains other than *Penicillium coprobium* strain PF1169, *Penicillium coprobium* strain ATCC58615 (see Studies in Mycology (2004), 49, p 84-85) was transformed.

The transformant was made in the same manner as in Example 13 except that pPYRI07 obtained in Example 16 was used.

Example 20

Culturing of Transformant and Quantification of Pyripyropenes in Culture Medium

The methods for culturing the transformant obtained in Example 19 and for quantifying pyripyropenes in the culture medium were the same as those described in Example 14 except that the culture time was 4 days. The pyripyropene analogues quantified were pyripyropene A, E, and O, which were produced by the present fungus. At the same time, *Penicillium coprobium* strain ATCC58615, which is the parent strain of the transformant, was cultured, and the pyripyropenes in the culture medium were quantified in the same manner.

As a result, as shown in Table 5 below, the productivity of pyripyropenes of the transformant was 2.5 fold higher than that of the parent strain. The result has shown that the introduction of the full-length pyripyropene biosynthetic gene cluster also improves the productivity of *Penicillium coprobium* strains other than the *Penicillium coprobium* strain PF1169. It has also been found that *Penicillium coprobium* strain PF1169 improves the productivity more than *Penicillium coprobium* strain ATCC58615.

TABLE 5

| Strain | Production in Culture Medium (μg/mL) | | | | Relative Productivity |
|---|---|---|---|---|---|
| | Pyripyropene A | Pyripyropene E | Pyripyropene O | Total | |
| Parent | 15 | 10 | 1 | 26 | 1 |
| Transformant | 32 | 23 | 9 | 64 | 2.5 |

ACCESSION NUMBERS

FERM BP-11133
FERM BP-11203
FERM BP-11316

The invention claimed is:

1. A method for producing pyripyropenes comprising culturing a transformed host cell obtained by transforming a heterologous host cell with a heterologous nucleic acid construct and collecting pyripyropenes from the culture, wherein said heterologous nucleic acid construct comprises a pyripyropene biosynthetic gene cluster and a marker gene simultaneously or separately, and wherein said pyripyropene biosynthetic gene cluster comprises at least one nucleotide sequence selected from (I) to (IV) below:

(I) the nucleotide sequence of positions 2911 to 27797 in the nucleotide sequence set forth in SEQ ID NO: 266;

(II) a nucleotide sequence which is capable of hybridizing with every nucleotide in the full length complementary sequence of positions 2911 to 27797 in SEQ ID NO: 266 under stringent conditions wherein said stringent conditions comprise washing with 2× saline-sodium citrate (SSC) buffer and 0.5% sodium dodecyl sulfate (SDS) at 60° C. for 20 minutes, and then washing with 0.2×SSC and 0.1% SDS at 60° C. for 15 minutes, wherein positions of the nucleotide sequence corresponding to positions 3342 to 5158 in SEQ ID NO: 266 encode a protein having CoA ligase activity, positions of the nucleotide sequence corresponding to positions 5382 to 12777 in SEQ ID NO: 266 encode a protein having LovB-like polyketide synthase activity, positions of the nucleotide sequence corresponding to positions 13266 to 15144 in SEQ ID NO: 266 encode a protein having Cytochrome P450 monooxygenase-1 activity, positions of the nucleotide sequence corresponding to positions 16220 to 18018 in SEQ ID NO: 266 encode a protein having Cytochrome P450 monooxygenase-2 activity, positions of the nucleotide sequence corresponding to positions 18506 to 19296 in SEQ ID NO: 266 encode a protein having Cyclase activity, positions of the nucleotide sequence corresponding to positions 19779 to 21389 in SEQ ID NO: 266 encode a protein having FAD-dependent monooxygenase activity, positions of the nucleotide sequence corresponding to positions 21793 to 22877 in SEQ ID NO: 266 encode a protein having UbiA-like prenyltransferase activity, positions of the nucleotide sequence corresponding to positions 23205 to 24773 in SEQ ID NO: 266 encode a protein having Acetyltransferase activity, and positions of the nucleotide sequence corresponding to positions 25824 to 27178 in SEQ ID NO: 266 encode a protein having Acetyltransferase-2 activity;

III) a nucleotide sequence comprising positions 2911 to 27797 of the nucleotide sequence set forth in SEQ ID NO: 266 having no more than 10 nucleotides deleted, substituted, inserted, or added in each of the nucleotide sequences corresponding to positions 3342 to 5158, 5382 to 12777, 13266 to 15144, 16220 to 18018, 18506 to 19296, 19779 to 21389, 21793 to 22877, 23205 to 24773, and 258124 to 27178 of the nucleotide sequence set forth in SEQ ID NO: 266, wherein positions of the nucleotide sequence having no more than 10 nucleotides deleted, substituted, inserted, or added and corresponding to positions 3342 to 5158 in SEQ ID NO: 266 encode a protein having CoA ligase activity, positions of the nucleotide sequence having no more than 10 nucleotides deleted, substituted, inserted, or added and corresponding to positions 5382 to 12777 in SEQ ID NO: 266 encode a protein having LovB-like polyketide synthase activity, positions of the nucleotide sequence having no more than 10 nucleotides deleted, substituted, inserted, or added and corresponding to positions 13266 to 15144 in SEQ ID NO: 266 encode a protein having Cytochrome P450 monooxygenase-1 activity, positions of the nucleotide sequence having no more than 10 nucleotides deleted, substituted, inserted, or added and corresponding to positions 16220 to 18018 in SEQ ID NO: 266 encode a protein having Cytochrome P450 monooxygenase-2 activity, positions of the nucleotide sequence having no more than 10 nucleotides deleted, substituted, inserted, or added and corresponding to positions 18506 to 19296 in SEQ ID NO: 266 encode a protein having Cyclase activity, positions of the nucleotide sequence having no more than 10 nucleotides deleted, substituted, inserted, or added and corresponding to positions 19779 to 21389 in SEQ ID NO: 266 encode a protein having FAD-dependent monooxygenase activity, positions of the nucleotide sequence having no more than 10 nucleotides deleted, substituted, inserted, or added and corresponding to positions 21793 to 22877 in SEQ ID NO: 266 encode a protein having UbiA-like prenyltransferase activity, positions of the nucleotide sequence having no more than 10 nucleotides deleted, substituted, inserted, or added and corresponding to positions 23205 to 24773 in SEQ ID NO: 266 encode a protein having Acetyltransferase activity, and positions of the nucleotide sequence having no more than 10 nucleotides deleted, substituted, inserted, or added and corresponding to positions 25824 to 27178 in SEQ ID NO: 266 encode a protein having Acetyltransferase-2 activity; and IV) a nucleotide sequence comprising at least 95% identity to each of the nucleotide sequences corresponding to positions 3342 to 5158, 5382 to 12777, 13266 to 15144, 16220 to 18018, 18506 to 19296, 19779 to 21389, 21793 to 22877, 23205 to 24773, and 258124 to 27178 of the nucleotide sequence set forth in SEQ ID NO: 266 wherein positions of the nucleotide sequence corresponding to positions 3342 to 5158 in SEQ ID NO: 266 encode a protein having CoA ligase activity, positions of the nucleotide sequence corresponding to positions 5382 to 12777 in SEQ ID NO: 266 encode a protein having LovB-like polyketide synthase activity, positions of the nucleotide sequence corresponding to positions 13266 to 15144 in SEQ ID NO: 266 encode a protein having Cytochrome P450 monooxygenase-1 activity, positions of the nucleotide sequence corresponding to positions 16220 to 18018 in SEQ ID NO: 266 encode a protein having Cytochrome P450 monooxygenase-2 activity, positions of the nucleotide sequence corresponding to positions 18506 to 19296 in SEQ ID NO: 266 encode a protein having Cyclase activity, positions of the nucleotide sequence corresponding to positions 19779 to 21389 in SEQ ID NO: 266 encode a protein having FAD-dependent monooxygenase activity, positions of the nucleotide sequence corresponding to positions 21793 to 22877 in SEQ ID NO: 266 encode a protein having UbiA-like prenyltransferase activity, positions of the nucleotide sequence corresponding to positions 23205 to 24773 in SEQ ID NO: 266 encode a protein having Acetyltransferase activity, and positions of the nucleotide sequence corresponding to positions 25824 to 27178 in SEQ ID NO: 266 encode a protein having Acetyltransferase-2 activity.

2. The method of claim 1, comprising culturing a transformant, wherein said gene cluster and said marker gene are on the same heterologous nucleic acid.

3. A method for producing pyripyropenes comprising culturing a transformed host cell obtained by transforming a heterologous host cell with a heterologous nucleic acid construct and collecting pyripyropenes from the culture, wherein said heterologous nucleic acid construct comprises a pyripyropene biosynthetic gene cluster and a marker gene, and wherein said pyripyropene biosynthetic gene cluster comprises the nucleotide sequence of positions 1 to 25000 of the nucleotide sequence set forth in SEQ ID NO: 266.

4. The method of claim 1, wherein said pyripyropene biosynthetic gene cluster comprises the nucleotide sequence of part (I).

5. The method of claim 1, wherein said pyripyropene biosynthetic gene cluster comprises the nucleotide sequence of part (III).

* * * * *

SEQUENCE LISTING

```
<160> NUMBER OF SEQ ID NOS: 285

<210> SEQ ID NO 1
<211> LENGTH: 21
<212> TYPE: DNA
<213> ORGANISM: unknown
<220> FEATURE:
<223> OTHER INFORMATION: Filamentous fungi
<220> FEATURE:
<221> NAME/KEY: modified_base
<222> LOCATION: (6)..(6)
<223> OTHER INFORMATION: I
<220> FEATURE:
<221> NAME/KEY: modified_base
<222> LOCATION: (9)..(9)
<223> OTHER INFORMATION: I

<400> SEQUENCE: 1
gayccnmgnt tyttyaayat g                                            21

<210> SEQ ID NO 2
<211> LENGTH: 20
<212> TYPE: DNA
<213> ORGANISM: unknown
<220> FEATURE:
<223> OTHER INFORMATION: Filamentous fungi
<220> FEATURE:
<221> NAME/KEY: modified_base
<222> LOCATION: (3)..(3)
<223> OTHER INFORMATION: I
<220> FEATURE:
<221> NAME/KEY: modified_base
<222> LOCATION: (6)..(6)
<223> OTHER INFORMATION: I
<220> FEATURE:
<221> NAME/KEY: modified_base
<222> LOCATION: (9)..(9)
<223> OTHER INFORMATION: I

<400> SEQUENCE: 2
gtnccngtnc crtgcatytc                                              20

<210> SEQ ID NO 3
<211> LENGTH: 500
<212> TYPE: DNA
<213> ORGANISM: unknown
<220> FEATURE:
<223> OTHER INFORMATION: Filamentous fungi

<400> SEQUENCE: 3
cattaccgag tgagggccct ctgggtccaa cctcccaccc gtgtttattt accttgttgc      60
ttcggcgggc ccgccttaac tggccgccgg ggggcttacg ccccgggcc cgcgcccgcc     120
```

-continued

```
gaagacaccc tcgaactctg tctgaagatt gtagtctgag tataaatata aattatttaa    180
aactttcaac aacggatctc ttggttccgg catcgatgaa gaacgcagcg aaatgcgata    240
cgtaatgtga attgcaaatt cagtgaatca tcgagtcttt gaacgcacat tgcgccccct    300
ggtattccgg ggggcatgcc tgtccgagcg tcattgctgc cctcaagccc ggcttgtgtg    360
ttgggccccg tcctccgatt ccgggggacg ggcccgaaag gcagcggcgg caccgcgtcc    420
ggtcctcgag cgtatggggc tttgtcaccc gctctgtagg cccggccggc gcttgccgat    480
caacccaaat ttttatccag                                                500
```

```
<210> SEQ ID NO 4
<211> LENGTH: 28
<212> TYPE: PRT
<213> ORGANISM: Penicillium coprobium PF1169

<400> SEQUENCE: 4

Gln Pro Trp Lys Asp Ser Ile Trp Ala Gly Asp Val Tyr Met Phe Glu
1               5                   10                  15

Gly Asp Asp Ile Val Ala Val Tyr Gly Gly Val Lys
            20                  25

<210> SEQ ID NO 5
<211> LENGTH: 36
<212> TYPE: PRT
<213> ORGANISM: Penicillium coprobium PF1169

<400> SEQUENCE: 5

His Asn Ser Ile Phe Gln Ala Leu Ala Arg Lys Ile Leu Asp Met Ala
1               5                   10                  15

Leu Pro Pro Gly Gly Gly Ala Pro Ala Pro Ala Pro Ala Ala Lys Arg
            20                  25                  30

Pro Ala Pro Ile
        35

<210> SEQ ID NO 6
<211> LENGTH: 70
<212> TYPE: PRT
<213> ORGANISM: Penicillium coprobium PF1169

<400> SEQUENCE: 6

Gly Arg Phe Leu Ser Ser Asp Gly Arg Cys His Thr Phe Asp Glu Lys
1               5                   10                  15

Ala Asn Gly Tyr Ala Arg Gly Glu Ala Val Gly Cys Leu Ile Leu Lys
            20                  25                  30

Pro Leu Ala Lys Ala Leu His Asp Gln Asn Lys Ile Arg Ala Val Ile
        35                  40                  45

Arg Gly Thr Gly Ser Asn Gln Asp Gly Arg Thr Ala Gly Ile Thr Val
    50                  55                  60

Pro Asn Gly Ala Ala Gln
65                  70

<210> SEQ ID NO 7
<211> LENGTH: 74
<212> TYPE: PRT
<213> ORGANISM: Penicillium coprobium PF1169

<400> SEQUENCE: 7

Arg Ile Ser Tyr Tyr Phe Asp Trp Gln Gly Pro Ser Met Ala Val Asp
1               5                   10                  15
```

```
Thr Gly Cys Ser Ser Leu Leu Ala Val His Leu Gly Val Glu Ala
            20                  25                  30

Leu Gln Asn Asp Asp Cys Ser Met Ala Val Ala Val Gly Ser Asn Leu
                35                  40                  45

Ile Leu Ser Pro Asn Ala Tyr Ile Ala Asp Ser Lys Thr Arg Met Leu
 50                  55                  60

Ser Pro Thr Gly Arg Ser Arg Met Trp Asp
 65                  70

<210> SEQ ID NO 8
<211> LENGTH: 51
<212> TYPE: PRT
<213> ORGANISM: Penicillium coprobium PF1169

<400> SEQUENCE: 8

Ser Ser Phe Leu Thr Ser Thr Val Gln Gln Ile Val Glu Glu Thr Ile
 1               5                  10                  15

Gln Gly Gly Thr Gly Gln Val Val Met Glu Ser Asp Leu Met Gln Thr
            20                  25                  30

Glu Phe Leu Glu Ala Ala Asn Gly His Arg Met Asn Asp Cys Gly Val
        35                  40                  45

Val Thr Ser
     50

<210> SEQ ID NO 9
<211> LENGTH: 79
<212> TYPE: PRT
<213> ORGANISM: Penicillium coprobium PF1169

<400> SEQUENCE: 9

Phe Asn Ala Ala His Arg Val Leu Pro Leu Pro Ser Tyr Lys Trp Asp
 1               5                  10                  15

Leu Lys Asn Tyr Trp Ile Pro Tyr Thr Asn Asn Phe Cys Leu Leu Lys
            20                  25                  30

Gly Ala Pro Ala Ala Pro Val Ala Glu Ala Thr Pro Ile Ser Val Phe
        35                  40                  45

Leu Ser Ser Ala Ala Gln Arg Val Leu Glu Thr Ser Gly Asp Asn Ser
     50                  55                  60

Ser Ala Phe Ile Val Ile Glu Asn Asp Ile Ala Asp Pro Asp Leu
 65                  70                  75

<210> SEQ ID NO 10
<211> LENGTH: 84
<212> TYPE: PRT
<213> ORGANISM: Penicillium coprobium PF1169

<400> SEQUENCE: 10

Val Ile Arg Gly Thr Gly Ser Asn Gln Asp Gly Arg Thr Ala Gly Ile
 1               5                  10                  15

Thr Val Pro Asn Gly Ala Ala Gln Glu Ser Leu Ile Arg Ser Val Tyr
            20                  25                  30

Ala Gln Ala Asp Leu Asp Pro Ser Glu Thr Asp Phe Val Glu Ala His
        35                  40                  45

Gly Thr Gly Thr Leu Ala Gly Asp Pro Val Glu Thr Gly Ala Ile Ala
     50                  55                  60

Arg Val Phe Gly Thr Asp Arg Pro Pro Gly Asp Pro Val Arg Ile Gly
 65                  70                  75                  80

Ser Ile Lys Thr
```

<210> SEQ ID NO 11
<211> LENGTH: 81
<212> TYPE: PRT
<213> ORGANISM: Penicillium coprobium PF1169

<400> SEQUENCE: 11

```
Gln Glu Ala Lys Ala Met Asp Pro Gln Gln Arg Met Leu Leu Glu Cys
1               5                   10                  15

Thr Tyr Glu Ala Leu Glu Asn Gly Gly Ile Ser Lys Gly Ser Leu Lys
            20                  25                  30

Gly Gln Asn Val Gly Val Phe Val Gly Ser Ala Phe Pro Asp Tyr Glu
        35                  40                  45

Met Tyr Asn Arg Arg Asp Leu Glu Thr Ala Pro Met His Gln Ser Thr
    50                  55                  60

Gly Asn Ala Leu Ala Leu Gln Ser Asn Arg Ile Ser Tyr Tyr Phe Asp
65                  70                  75                  80

Phe
```

<210> SEQ ID NO 12
<211> LENGTH: 66
<212> TYPE: PRT
<213> ORGANISM: Penicillium coprobium PF1169

<400> SEQUENCE: 12

```
Asn His Thr Gly Arg Ala Glu Gln Ser Lys Ile Ala Ile Gly Leu
1               5                   10                  15

Ser Gly Arg Phe Pro Glu Ala Pro Asp Thr Glu Ala Phe Trp Asp Leu
            20                  25                  30

Leu Lys Lys Gly Leu Asp Val His Arg Glu Val Pro Pro Glu Arg Trp
        35                  40                  45

Asp Val Lys Ala His Val Asp Pro Glu Gly Lys Lys Arg Thr Pro Ala
    50                  55                  60

Lys Leu
65
```

<210> SEQ ID NO 13
<211> LENGTH: 14
<212> TYPE: PRT
<213> ORGANISM: Penicillium coprobium PF1169

<400> SEQUENCE: 13

```
Glu Lys Asn Thr Ser Gln Val Glu Tyr Gly Cys Trp Tyr Asn
1               5                   10
```

<210> SEQ ID NO 14
<211> LENGTH: 71
<212> TYPE: PRT
<213> ORGANISM: Penicillium coprobium PF1169

<400> SEQUENCE: 14

```
Ala Gly Gly Asn Thr Thr Val Ala Leu Glu Asp Ala Pro Ile Arg Thr
1               5                   10                  15

Arg Ser Gly Ser Asp Pro Arg Ser Leu His Pro Ile Ala Ile Ser Ala
            20                  25                  30

Lys Ser Lys Val Ser Leu Arg Gly Asn Leu Glu Asn Leu Leu Ala Tyr
        35                  40                  45

Leu Asp Thr His Pro Asp Val Ser Leu Ser Asp Leu Ser Tyr Thr Thr
    50                  55                  60
```

Thr Ala Arg Arg His His His
65                  70

<210> SEQ ID NO 15
<211> LENGTH: 77
<212> TYPE: PRT
<213> ORGANISM: Penicillium coprobium PF1169

<400> SEQUENCE: 15

Ala Thr Asp Thr Glu Lys Phe Trp Asp Leu Leu Ala Ser Gly Val Asp
1               5                   10                  15

Val His Arg Lys Ile Pro Ala Asp Arg Phe Asp Val Glu Thr His Tyr
            20                  25                  30

Asp Pro Asn Gly Lys Arg Met Asn Ala Ser His Thr Pro Tyr Gly Cys
        35                  40                  45

Phe Ile Asp Glu Pro Gly Leu Phe Asp Ala Ala Phe Phe Asn Met Ser
    50                  55                  60

Pro Arg Glu Ala Gln Gln Thr Asp Pro Met Gln Arg Leu
65                  70                  75

<210> SEQ ID NO 16
<211> LENGTH: 39
<212> TYPE: PRT
<213> ORGANISM: Penicillium coprobium PF1169

<400> SEQUENCE: 16

Pro Glu Tyr Ser Gln Pro Leu Cys Thr Ala Ile Gln Ile Ala Leu Val
1               5                   10                  15

Glu Leu Leu Glu Ser Phe Gly Val Val Pro Lys Ala Val Val Gly His
            20                  25                  30

Ser Ser Gly Glu Ile Ala Ala
            35

<210> SEQ ID NO 17
<211> LENGTH: 71
<212> TYPE: PRT
<213> ORGANISM: Penicillium coprobium PF1169

<400> SEQUENCE: 17

Arg Arg Thr Phe Leu Pro Trp Arg Leu Thr Ser Ser Ala Leu Ser Gly
1               5                   10                  15

Gln Glu Leu Thr Gln Ser Leu Ala Ile Asp Ala Val Pro Ile Arg Ser
            20                  25                  30

Ser Lys Glu Pro Thr Val Gly Phe Val Phe Thr Gly Gln Gly Ala Gln
        35                  40                  45

Trp His Gly Met Gly Lys Glu Leu Leu Ser Thr Tyr Pro Ile Phe Arg
    50                  55                  60

Gln Thr Met Gln Asp Val Asp
65                  70

<210> SEQ ID NO 18
<211> LENGTH: 75
<212> TYPE: PRT
<213> ORGANISM: Penicillium coprobium PF1169

<400> SEQUENCE: 18

Leu Arg Arg Leu Leu His Ala Lys Asn Asp Ser Leu Val Ala Ala Phe
1               5                   10                  15

Phe Gln Lys Thr Tyr Cys Ala Leu Arg Lys Glu Ile Thr Ser Leu Pro

```
                        20                  25                  30

Pro Ser Glu Arg Gln Val Phe Pro Arg Phe Thr Ser Ile Val Asp Leu
            35                  40                  45

Leu Ala Arg Phe Lys Glu Phe Gly Pro Asn Pro Ala Leu Glu Ser Ala
    50                  55                  60

Leu Thr Thr Ile Tyr Gln Leu Gly Cys Phe Ile
65                  70                  75

<210> SEQ ID NO 19
<211> LENGTH: 81
<212> TYPE: PRT
<213> ORGANISM: Penicillium coprobium PF1169

<400> SEQUENCE: 19

Phe Asp Ala Ala Phe Asn Met Ser Pro Arg Glu Ala Gln Gln Thr
1               5                   10                  15

Asp Pro Met Gln Arg Leu Ala Ile Val Thr Ala Tyr Glu Ala Leu Glu
            20                  25                  30

Arg Ala Gly Tyr Val Ala Asn Arg Thr Ala Ala Thr Asn Leu His Arg
        35                  40                  45

Ile Gly Thr Phe Tyr Gly Gln Ala Ser Asp Asp Tyr Arg Glu Val Asn
    50                  55                  60

Thr Ala Gln Glu Ile Ser Thr Tyr Phe Ile Pro Gly Gly Cys Arg Ala
65                  70                  75                  80

Phe

<210> SEQ ID NO 20
<211> LENGTH: 38
<212> TYPE: PRT
<213> ORGANISM: Penicillium coprobium PF1169

<400> SEQUENCE: 20

Asp Thr Ala Cys Ser Ser Ser Leu Val Ala Leu His Tyr Ala Val Gln
1               5                   10                  15

Ser Leu Arg Asn Gly Glu Ser Thr Glu Ala Leu Ile Ala Gly Cys His
            20                  25                  30

Leu Asn Ile Val Pro Asp
        35

<210> SEQ ID NO 21
<211> LENGTH: 75
<212> TYPE: PRT
<213> ORGANISM: Penicillium coprobium PF1169

<400> SEQUENCE: 21

Ala Lys His Pro Pro Ala Thr Ser Ile Leu Leu Gln Gly Asn Pro Lys
1               5                   10                  15

Thr Ala Thr Gln Ser Leu Phe Leu Phe Pro Asp Gly Ser Gly Ser Ala
            20                  25                  30

Thr Ser Tyr Ala Thr Ile Pro Gly Ile Ser Pro Asp Val Cys Val Tyr
        35                  40                  45

Gly Leu Asn Cys Pro Tyr Met Arg Thr Pro Glu Lys Leu Lys Phe Ser
    50                  55                  60

Leu Asp Glu Leu Thr Ala Pro Tyr Val Ala Glu
65                  70                  75

<210> SEQ ID NO 22
<211> LENGTH: 38
```

```
<212> TYPE: PRT
<213> ORGANISM: Penicillium coprobium PF1169

<400> SEQUENCE: 22

Gly Asn Gly Ser Ala Met Ile Ser Asn Arg Ile Ser Trp Phe Phe Asp
1               5                   10                  15

Leu Lys Gly Pro Ser Leu Ser Leu Asp Thr Ala Cys Ser Ser Ser Leu
            20                  25                  30

Val Ala Leu His Leu Ala
        35

<210> SEQ ID NO 23
<211> LENGTH: 57
<212> TYPE: PRT
<213> ORGANISM: Penicillium coprobium PF1169

<400> SEQUENCE: 23

Ala Ile Arg Asp Glu Val Arg Gln Leu Pro Thr Pro Leu Arg Ala Leu
1               5                   10                  15

Val Pro Ala Phe Glu Asn Val Leu Glu Leu Ala Asn Tyr Thr Asp Leu
            20                  25                  30

Arg Lys Gly Pro Leu Ser Gly Ser Ile Asp Gly Val Leu Leu Cys Val
        35                  40                  45

Val Gln Leu Ser Ser Leu Ile Gly Tyr
    50                  55

<210> SEQ ID NO 24
<211> LENGTH: 74
<212> TYPE: PRT
<213> ORGANISM: Penicillium coprobium PF1169

<400> SEQUENCE: 24

Ala Val Ala Trp Asp Pro Gln Gln Arg Ile Leu Leu Glu Val Val Tyr
1               5                   10                  15

Glu Ala Leu Glu Ser Ala Gly Tyr Phe Arg Ala Gly Ile Lys Pro Glu
            20                  25                  30

Leu Asp Asp Tyr Gly Cys Tyr Ile Gly Ala Val Met Asn Asn Tyr Tyr
        35                  40                  45

Asp Asn Met Ser Cys Gln Pro Thr Thr Ala Tyr Ala Thr Val Gly Thr
    50                  55                  60

Ser Arg Cys Phe Leu Ser Gly Cys Val Ser
65                  70

<210> SEQ ID NO 25
<211> LENGTH: 52
<212> TYPE: PRT
<213> ORGANISM: Penicillium coprobium PF1169

<400> SEQUENCE: 25

Gly Val Ile Val Gly Ser Ala Ala Asn Gln Asn Leu Asn Leu Ser His
1               5                   10                  15

Ile Thr Val Pro His Ser Gly Ser Gln Val Lys Leu Tyr Gln Asn Val
            20                  25                  30

Met Ser Gln Ala Gly Val His Pro His Ser Val Thr Tyr Val Glu Ala
        35                  40                  45

His Gly Thr Gly
    50

<210> SEQ ID NO 26
```

```
-continued

<211> LENGTH: 57
<212> TYPE: PRT
<213> ORGANISM: Penicillium coprobium PF1169

<400> SEQUENCE: 26

Trp Arg Ile Thr Val Ala Ile Val Gly Gly Val Asn Ala Leu Cys Gly
1               5                   10                  15

Pro Gly Leu Thr Arg Val Leu Asp Lys Ala Gly Ala Ile Ser Ser Asp
            20                  25                  30

Gly Ser Cys Lys Ser Phe Asp Asp Ala His Gly Tyr Ala Arg Gly
        35                  40                  45

Glu Gly Ala Gly Ala Leu Val Leu Lys
    50                  55

<210> SEQ ID NO 27
<211> LENGTH: 78
<212> TYPE: PRT
<213> ORGANISM: Penicillium coprobium PF1169

<400> SEQUENCE: 27

Leu Ile Asp Asp Thr Thr Val Trp Ile Glu Ile Gly Pro His Pro Val
1               5                   10                  15

Cys Leu Gly Phe Val Lys Ala Thr Leu Glu Ser Val Ala Val Ala Val
            20                  25                  30

Pro Ser Leu Arg Arg Gly Glu Asn Ala Trp Cys Thr Leu Ala Gln Ser
        35                  40                  45

Leu Thr Thr Leu His Asn Ala Gly Val Pro Val Gly Trp Ser Glu Phe
    50                  55                  60

His Arg Pro Phe Glu Arg Ala Leu Cys Leu Leu Asp Leu Pro
65                  70                  75

<210> SEQ ID NO 28
<211> LENGTH: 65
<212> TYPE: PRT
<213> ORGANISM: Penicillium coprobium PF1169

<400> SEQUENCE: 28

Val Trp Ile Glu Ile Gly Pro His Pro Val Cys Leu Gly Phe Val Lys
1               5                   10                  15

Ala Thr Leu Glu Ser Val Ala Val Ala Val Pro Ser Leu Arg Arg Gly
            20                  25                  30

Glu Asn Ala Trp Cys Thr Leu Ala Gln Ser Leu Thr Thr Leu His Asn
        35                  40                  45

Ala Gly Val Pro Val Gly Trp Ser Glu Phe His Arg Pro Phe Glu Arg
    50                  55                  60

Ala
65

<210> SEQ ID NO 29
<211> LENGTH: 83
<212> TYPE: PRT
<213> ORGANISM: Penicillium coprobium PF1169

<400> SEQUENCE: 29

Thr Ser Asp Asp Tyr Arg Glu Val Asn Ser Gly Gln Asp Ile Asp Thr
1               5                   10                  15

Tyr Phe Ile Pro Gly Gly Asn Arg Ala Phe Thr Pro Gly Arg Ile Asn
            20                  25                  30

Tyr Tyr Phe Lys Phe Ser Gly Pro Ser Val Ser Val Asp Thr Ala Cys
```

```
            35                  40                  45
Ser Ser Ser Leu Ala Ile His Val Ala Cys Asn Ser Leu Trp Arg
        50                  55                  60

Asn Glu Ser Asp Ser Ala Val Ala Gly Gly Val Asn Ile Leu Thr Asn
 65                  70                  75                  80

Pro Asp Asn
```

<210> SEQ ID NO 30
<211> LENGTH: 54
<212> TYPE: PRT
<213> ORGANISM: Penicillium coprobium PF1169

<400> SEQUENCE: 30

```
Gly Arg Phe Leu Ser Ser Asp Gly Arg Cys His Thr Phe Asp Glu Lys
 1               5                  10                  15

Ala Asn Gly Tyr Ala Arg Gly Glu Ala Val Gly Cys Leu Ile Leu Lys
                20                  25                  30

Pro Leu Ala Lys Ala Leu His Asp Gln Asn Lys Ile Arg Ala Val Ile
        35                  40                  45

Arg Gly Thr Gly Ser Asn
    50
```

<210> SEQ ID NO 31
<211> LENGTH: 63
<212> TYPE: PRT
<213> ORGANISM: Penicillium coprobium PF1169

<400> SEQUENCE: 31

```
Asp Thr Ala Cys Ser Ser Ser Leu Tyr Ala Leu His Ser Ala Cys Leu
 1               5                  10                  15

Ala Leu Asp Ser Arg Asp Cys Asp Gly Ala Val Val Ala Ala Ala Asn
                20                  25                  30

Leu Ile Gln Ser Pro Glu Gln Gln Met Ile Ala Val Lys Ala Gly Ile
        35                  40                  45

Leu Ser Pro Asp Ser Met Cys His Thr Phe Asp Glu Ser Ala Asn
    50                  55                  60
```

<210> SEQ ID NO 32
<211> LENGTH: 55
<212> TYPE: PRT
<213> ORGANISM: Penicillium coprobium PF1169

<400> SEQUENCE: 32

```
Lys Gln Thr Thr Ser Arg Gly Tyr Phe Leu Asp His Leu Glu Asp Phe
 1               5                  10                  15

Asp Cys Gln Phe Phe Gly Ile Ser Pro Lys Glu Ala Glu Gln Met Asp
                20                  25                  30

Pro Gln Gln Arg Val Ser Leu Glu Val Ala Ser Glu Ala Leu Glu Asp
        35                  40                  45

Ala Gly Ile Pro Ala Lys Ser
    50                  55
```

<210> SEQ ID NO 33
<211> LENGTH: 38
<212> TYPE: PRT
<213> ORGANISM: Penicillium coprobium PF1169

<400> SEQUENCE: 33

```
Pro Val Gly Cys Arg Ala Phe Gly Pro Gly Arg Ile Asn Tyr Phe Phe
```

```
1               5                   10                  15
Lys Phe Ser Gly Pro Ser Phe Ser Ile Asp Thr Ala Cys Ser Ser
                20                  25                  30

Leu Ala Thr Ile Gln Val
            35
```

<210> SEQ ID NO 34
<211> LENGTH: 18
<212> TYPE: PRT
<213> ORGANISM: Penicillium coprobium PF1169

<400> SEQUENCE: 34

```
Ala Cys Thr Ser Leu Trp Asn Gly Glu Thr Asp Thr Val Val Ala Gly
1               5                   10                  15

Gly Met
```

<210> SEQ ID NO 35
<211> LENGTH: 12
<212> TYPE: PRT
<213> ORGANISM: Penicillium coprobium PF1169

<400> SEQUENCE: 35

```
Thr Ala Gln Glu Ile Ser Thr Tyr Phe Ile Pro Gly
1               5                   10
```

<210> SEQ ID NO 36
<211> LENGTH: 39
<212> TYPE: PRT
<213> ORGANISM: Penicillium coprobium PF1169

<400> SEQUENCE: 36

```
Pro Glu Tyr Ser Gln Pro Leu Cys Thr Ala Ile Gln Ile Ala Leu Val
1               5                   10                  15

Glu Leu Leu Glu Ser Phe Gly Val Val Pro Lys Ala Val Val Gly His
                20                  25                  30

Ser Ser Gly Glu Ile Ala Ala
            35
```

<210> SEQ ID NO 37
<211> LENGTH: 36
<212> TYPE: PRT
<213> ORGANISM: Penicillium coprobium PF1169

<400> SEQUENCE: 37

```
Ile Ser Gln Pro Ala Cys Thr Ala Leu Gln Ile Ala Leu Val Asp Leu
1               5                   10                  15

Leu Ala Glu Trp Ser Ile Thr Pro Ser Val Val Val Gly His Ser Ser
                20                  25                  30

Gly Glu Ile Ala
            35
```

<210> SEQ ID NO 38
<211> LENGTH: 39
<212> TYPE: PRT
<213> ORGANISM: Penicillium coprobium PF1169

<400> SEQUENCE: 38

```
Pro Glu Tyr Ser Gln Pro Leu Cys Thr Ala Ile Gln Ile Ala Leu Val
1               5                   10                  15

Glu Leu Leu Glu Ser Phe Gly Val Val Pro Lys Ala Val Val Gly His
                20                  25                  30
```

Ser Ser Gly Glu Ile Ala Ala
        35

<210> SEQ ID NO 39
<211> LENGTH: 76
<212> TYPE: PRT
<213> ORGANISM: Penicillium coprobium PF1169

<400> SEQUENCE: 39

Glu Glu Phe Trp Asp Leu Cys Ser Arg Gly Arg Gly Ala Trp Ser Pro
1               5                   10                  15

Val Pro Lys Asp Arg Phe Asn Ala Gly Ser Phe Tyr His Pro Asn Ala
            20                  25                  30

Asp Arg Pro Gly Ser Phe Asn Ala Ala Gly Ala His Phe Leu Thr Glu
        35                  40                  45

Asp Ile Gly Leu Phe Asp Ala Pro Phe Phe Asn Ile Thr Leu Gln Glu
    50                  55                  60

Ala Gln Thr Met Asp Pro Gln Gln Arg Ile Phe Leu
65                  70                  75

<210> SEQ ID NO 40
<211> LENGTH: 77
<212> TYPE: PRT
<213> ORGANISM: Penicillium coprobium PF1169

<400> SEQUENCE: 40

Ile Asn Glu Pro Arg Asp Arg Pro Gln Phe Phe His Ala His Gly Thr
1               5                   10                  15

Gly Thr Gln Ala Gly Asp Pro Gln Glu Ala Glu Ala Val Ser Thr Ala
            20                  25                  30

Leu Phe Pro Asp Gly Ser Asn Ile Glu Thr Lys Leu Phe Val Gly Ser
        35                  40                  45

Ile Lys Thr Val Ile Gly His Thr Glu Gly Ser Ala Gly Leu Ala Ser
    50                  55                  60

Leu Ile Gly Ser Ser Leu Ala Met Lys His Gly Val Ile
65                  70                  75

<210> SEQ ID NO 41
<211> LENGTH: 43
<212> TYPE: PRT
<213> ORGANISM: Penicillium coprobium PF1169

<400> SEQUENCE: 41

Lys Leu Ala Phe Val Phe Thr Gly Gln Gly Gly Gln Trp Ala Gly Met
1               5                   10                  15

Gly Arg Glu Leu Leu Ser Ile Ser Thr Phe Arg Glu Ser Met Ala Arg
            20                  25                  30

Ser Gln Glu Ile Leu Ala Ser Leu Gly Cys Pro
        35                  40

<210> SEQ ID NO 42
<211> LENGTH: 71
<212> TYPE: PRT
<213> ORGANISM: Penicillium coprobium PF1169

<400> SEQUENCE: 42

Lys Ser Phe Leu Asp Asp Leu Ala Phe Thr Val Asn Glu Arg Arg Ser
1               5                   10                  15

Ile Phe Pro Trp Lys Ala Ala Val Val Gly Asp Thr Met Glu Gly Leu

```
                    20                  25                  30

Ala Ala Ser Leu Ala Gln Asn Ile Lys Pro Arg Ser Val Leu Arg Met
            35                  40                  45

Pro Thr Leu Gly Phe Val Phe Thr Gly Gln Gly Ala Gln Trp Pro Gly
        50                  55                  60

Met Gly Lys Glu Leu Leu Gln
65                  70

<210> SEQ ID NO 43
<211> LENGTH: 55
<212> TYPE: PRT
<213> ORGANISM: Penicillium coprobium PF1169

<400> SEQUENCE: 43

Ser Val Ala Cys Ile Asn Ser Pro Phe Asn Cys Thr Leu Ser Gly Pro
1               5                  10                  15

Glu Glu Asp Ile Asp Ala Val Lys Ala Gln Ala Asp Gln Asp Gly Leu
                20                  25                  30

Phe Ala Gln Lys Leu Lys Thr Gly Val Ala Tyr His Ser Thr Ala Met
            35                  40                  45

Ser Ala Ile Ala Asn Asp Tyr
        50                  55

<210> SEQ ID NO 44
<211> LENGTH: 68
<212> TYPE: PRT
<213> ORGANISM: Penicillium coprobium PF1169

<400> SEQUENCE: 44

Met Leu Ala Val Gly Ala Ser Ala Ser Asp Ile Gln Gln Ile Leu Asp
1               5                  10                  15

Ala Met Arg Gly Asn Lys Ala Val Ile Ala Cys Val Asn Ser Glu Ser
                20                  25                  30

Ser Val Thr Leu Ser Gly Asp Leu Asp Val Ile Ala Asn Leu Gln Thr
            35                  40                  45

Ala Leu Asp Lys Glu Gly Ile Phe Thr Arg Lys Leu Lys Val Asp Val
        50                  55                  60

Ala Tyr His Ser
65

<210> SEQ ID NO 45
<211> LENGTH: 38
<212> TYPE: PRT
<213> ORGANISM: Penicillium coprobium PF1169

<400> SEQUENCE: 45

Gly Asn Gly Ser Ala Met Ile Ser Asn Arg Ile Ser Trp Phe Phe Asp
1               5                  10                  15

Leu Lys Gly Pro Ser Leu Ser Leu Asp Thr Ala Cys Ser Ser Ser Leu
                20                  25                  30

Val Ala Leu His Leu Ala
            35

<210> SEQ ID NO 46
<211> LENGTH: 77
<212> TYPE: PRT
<213> ORGANISM: Penicillium coprobium PF1169

<400> SEQUENCE: 46
```

```
Gly Pro Ser Met Thr Ile Asp Thr Ala Cys Ser Ser Leu Ile Ala
1               5                   10                  15

Leu His Gln Ala Val Gln Ser Leu Arg Ser Gly Glu Thr Asp Val Ala
            20                  25                  30

Val Ala Ala Gly Thr Asn Leu Leu Gly Pro Glu Gln Tyr Ile Ala
            35                  40                  45

Glu Ser Lys Leu Lys Met Leu Ser Pro Asn Gly Arg Ser Arg Met Trp
50                  55                  60

Asp Lys Asp Ala Asp Gly Tyr Ala Arg Gly Asp Gly Ile
65                  70                  75

<210> SEQ ID NO 47
<211> LENGTH: 61
<212> TYPE: PRT
<213> ORGANISM: Penicillium coprobium PF1169

<400> SEQUENCE: 47

Ile Gly Ser Ile Lys Pro Asn Ile Gly His Leu Glu Ala Gly Ala Gly
1               5                   10                  15

Val Met Gly Phe Ile Lys Ala Ile Leu Ser Ile Gln Lys Gly Val Leu
            20                  25                  30

Ala Pro Gln Ala Asn Leu Thr Lys Leu Asn Ser Arg Ile Asp Trp Lys
            35                  40                  45

Thr Ala Gly Val Lys Val Val Gln Glu Ala Thr Pro Trp
50                  55                  60

<210> SEQ ID NO 48
<211> LENGTH: 37
<212> TYPE: PRT
<213> ORGANISM: Penicillium coprobium PF1169

<400> SEQUENCE: 48

Gly Leu Phe Asp Ala Pro Phe Phe Asn Ile Thr Leu Gln Glu Ala Gln
1               5                   10                  15

Thr Met Asp Pro Gln Gln Arg Ile Phe Leu Glu Cys Val Tyr Glu Ala
            20                  25                  30

Leu Glu Asn Gly Gly
            35

<210> SEQ ID NO 49
<211> LENGTH: 70
<212> TYPE: PRT
<213> ORGANISM: Penicillium coprobium PF1169

<400> SEQUENCE: 49

Gly Arg Phe Leu Ser Ser Asp Gly Arg Cys His Thr Phe Asp Glu Lys
1               5                   10                  15

Ala Asn Gly Tyr Ala Arg Gly Glu Ala Val Gly Cys Leu Ile Leu Lys
            20                  25                  30

Pro Leu Ala Lys Ala Leu His Asp Gln Asn Lys Ile Arg Ala Val Ile
            35                  40                  45

Arg Gly Thr Gly Ser Asn Gln Asp Gly Arg Thr Ala Gly Ile Thr Val
50                  55                  60

Pro Asn Gly Ala Ala Gln
65                  70

<210> SEQ ID NO 50
<211> LENGTH: 37
<212> TYPE: PRT
```

<213> ORGANISM: Penicillium coprobium PF1169

<400> SEQUENCE: 50

Ser Phe Asp Ser Arg Ala Glu Gly Tyr Ala Arg Gly Glu Gly Val Gly
1               5                   10                  15

Thr Val Val Lys Pro Leu Ser Thr Ala Ile Arg Asp Gly Asp Thr
            20                  25                  30

Ile Arg Ala Val Ile
        35

<210> SEQ ID NO 51
<211> LENGTH: 83
<212> TYPE: PRT
<213> ORGANISM: Penicillium coprobium PF1169

<400> SEQUENCE: 51

Trp Pro Arg Leu Pro Glu Arg Arg Ile Ala Val Val Asn Asn Phe
1               5                   10                  15

Ser Ala Ala Gly Gly Asn Thr Thr Val Ala Leu Glu Asp Ala Pro Ile
            20                  25                  30

Arg Thr Arg Ser Gly Ser Asp Pro Arg Ser Leu His Pro Ile Ala Ile
        35                  40                  45

Ser Ala Lys Ser Lys Val Ser Leu Arg Gly Asn Leu Glu Asn Leu Leu
    50                  55                  60

Ala Tyr Leu Asp Thr His Pro Asp Val Ser Leu Ser Asp Leu Ser Tyr
65                  70                  75                  80

Thr Thr Thr

<210> SEQ ID NO 52
<211> LENGTH: 59
<212> TYPE: PRT
<213> ORGANISM: Penicillium coprobium PF1169

<400> SEQUENCE: 52

Val Tyr Ser Gly Ser Met Thr Asn Asp Tyr Glu Leu Leu Ser Thr Arg
1               5                   10                  15

Asp Ile Tyr Asp Met Pro His Asn Ser Ala Thr Gly Asn Gly Arg Thr
            20                  25                  30

Met Leu Ala Asn Arg Leu Ser Trp Phe Phe Asp Leu Gln Gly Pro Ser
        35                  40                  45

Ile Met Met Asp Thr Ala Cys Ser Ser Ser Leu
    50                  55

<210> SEQ ID NO 53
<211> LENGTH: 67
<212> TYPE: PRT
<213> ORGANISM: Penicillium coprobium PF1169

<400> SEQUENCE: 53

Leu Ser Pro Gln Asn Asn Pro Glu Asp Arg Cys Gln Tyr Phe Glu Ala
1               5                   10                  15

His Gly Thr Gly Thr Gln Ala Gly Asp Pro Gln Glu Ala Ala Ala Ile
            20                  25                  30

Asn Ser Ser Phe Phe Gly Pro Glu Ser Val Pro Asp Ser Thr Asp Arg
        35                  40                  45

Leu Tyr Val Gly Ser Ile Lys Thr Ile Ile Gly His Thr Glu Ala Thr
    50                  55                  60

Ala Gly Leu

<210> SEQ ID NO 54
<211> LENGTH: 83
<212> TYPE: PRT
<213> ORGANISM: Penicillium coprobium PF1169

<400> SEQUENCE: 54

Asp Gly Tyr Gly Arg Gly Glu Gly Val Ala Ser Val Val Leu Lys Arg
1               5                   10                  15

Leu Gln Asp Ala Ile Asn Asp Gly Asp Pro Ile Glu Cys Val Ile Arg
            20                  25                  30

Ala Ser Gly Ala Asn Ser Asp Gly Arg Thr Met Gly Ile Thr Met Pro
        35                  40                  45

Asn Pro Lys Ala Gln Gln Ser Leu Ile Leu Ala Thr Tyr Ala Arg Ala
    50                  55                  60

Gly Leu Ser Pro Gln Asn Asn Pro Glu Asp Arg Cys Gln Tyr Phe Glu
65                  70                  75                  80

Ala His Gly

<210> SEQ ID NO 55
<211> LENGTH: 38
<212> TYPE: PRT
<213> ORGANISM: Penicillium coprobium PF1169

<400> SEQUENCE: 55

Met Leu Ala Val Gly Ala Ser Ala Ser Asp Ile Gln Gln Ile Leu Asp
1               5                   10                  15

Ala Met Arg Gly Asn Lys Ala Val Ile Ala Cys Val Asn Ser Glu Ser
            20                  25                  30

Ser Val Thr Leu Ser Gly
        35

<210> SEQ ID NO 56
<211> LENGTH: 29
<212> TYPE: PRT
<213> ORGANISM: Penicillium coprobium PF1169

<400> SEQUENCE: 56

Ser Gly Cys Tyr Arg Glu Leu Ala Asp Cys Pro Gly Gln Arg Gly Ile
1               5                   10                  15

Phe Thr Arg Lys Leu Lys Val Asp Val Ala Tyr His Ser
            20                  25

<210> SEQ ID NO 57
<211> LENGTH: 38
<212> TYPE: PRT
<213> ORGANISM: Penicillium coprobium PF1169

<400> SEQUENCE: 57

Gly Asn Gly Ser Ala Met Ile Ser Asn Arg Ile Ser Trp Phe Phe Asp
1               5                   10                  15

Leu Lys Gly Pro Ser Leu Ser Leu Asp Thr Ala Cys Ser Ser Ser Leu
            20                  25                  30

Val Ala Leu His Leu Ala
        35

<210> SEQ ID NO 58
<211> LENGTH: 59
<212> TYPE: PRT

<213> ORGANISM: Penicillium coprobium PF1169

<400> SEQUENCE: 58

Ile Ser Glu Cys Val Thr Val Tyr Trp Lys Ala Ile Lys Ser Ala Gln
1               5                   10                  15

Pro Asp Gly Pro Tyr Ala Leu Ala Gly Tyr Ser Tyr Gly Ser Met Leu
            20                  25                  30

Ala Phe Glu Val Ala Lys Leu Leu Ile Lys Asn Gly Asp Lys Val Asp
        35                  40                  45

Phe Leu Gly Cys Phe Asn Leu Pro Pro His Ile
    50                  55

<210> SEQ ID NO 59
<211> LENGTH: 72
<212> TYPE: PRT
<213> ORGANISM: Penicillium coprobium PF1169

<400> SEQUENCE: 59

Gly Ala Ala Val Gln Leu Val Ile Glu Gly Gly Asn Gln Pro Lys Gly
1               5                   10                  15

Ala Met Met Ala Val Gly Ala Asn Ala Ser Thr Val Gln Pro Leu Leu
            20                  25                  30

Asp Ala Met Lys Asp Lys His Ala Val Val Ala Cys Ile Asn Ser Asp
        35                  40                  45

Ser Ser Ile Thr Val Ser Gly Asp Glu Thr Ala Ile Glu Asp Leu Glu
    50                  55                  60

Ser Val Leu Lys Arg Gln Asp Ile
65                  70

<210> SEQ ID NO 60
<211> LENGTH: 79
<212> TYPE: PRT
<213> ORGANISM: Penicillium coprobium PF1169

<400> SEQUENCE: 60

Ser Val Pro Ile Glu Glu His Ser Pro Val Val Thr Gln Leu Gly Thr
1               5                   10                  15

Thr Cys Val Gln Met Ala Leu Thr Lys Tyr Trp Thr Ser Leu Gly Val
            20                  25                  30

Thr Pro Ser Phe Val Met Gly His Ser Leu Gly Glu Phe Ala Ala Leu
        35                  40                  45

Asn Ala Ala Gly Val Leu Thr Ile Ser Asp Thr Ile Tyr Leu Ala Gly
    50                  55                  60

Arg Arg Ala Gln Leu Leu Thr Glu Gln Ile Lys Val Gly Thr His
65                  70                  75

<210> SEQ ID NO 61
<211> LENGTH: 67
<212> TYPE: PRT
<213> ORGANISM: Penicillium coprobium PF1169

<400> SEQUENCE: 61

Phe Ile Glu Asp Ser Ile Ser Lys Glu His Lys Pro Thr Arg Val Pro
1               5                   10                  15

Ile His Gly Pro Tyr His Ala Ser His Leu Tyr Asn Asp Arg Asp Ile
            20                  25                  30

Asp Arg Ile Met Glu Ser Trp Pro Thr Glu Gln Leu Trp Ala Tyr Val
        35                  40                  45

```
Pro Gln Ile Pro Val Leu Ser Thr Gln Thr Gly Lys Ala Phe Gln Ala
        50                  55                  60

Asp Ser Leu
65

<210> SEQ ID NO 62
<211> LENGTH: 76
<212> TYPE: PRT
<213> ORGANISM: Penicillium coprobium PF1169

<400> SEQUENCE: 62

Gly Pro Ser Met Thr Ile Asp Thr Ala Cys Ser Ser Ser Leu Ile Ala
1               5                   10                  15

Leu His Gln Ala Val Gln Ser Leu Arg Ser Gly Glu Thr Asp Val Ala
            20                  25                  30

Val Ala Ala Gly Thr Asn Leu Leu Leu Gly Pro Glu Gln Tyr Ile Ala
        35                  40                  45

Glu Ser Lys Leu Lys Met Leu Ser Pro Asn Gly Arg Ser Arg Met Trp
    50                  55                  60

Asp Lys Asp Ala Asp Gly Tyr Ala Arg Gly Asp Gly
65                  70                  75

<210> SEQ ID NO 63
<211> LENGTH: 31
<212> TYPE: PRT
<213> ORGANISM: Penicillium coprobium PF1169

<400> SEQUENCE: 63

Leu Phe Leu Phe Pro Asp Gly Ser Gly Ser Ala Thr Ser Tyr Ala Thr
1               5                   10                  15

Ile Pro Gly Ile Ser Pro Asp Val Cys Val Tyr Gly Leu Asn Cys
            20                  25                  30

<210> SEQ ID NO 64
<211> LENGTH: 26
<212> TYPE: PRT
<213> ORGANISM: Penicillium coprobium PF1169

<400> SEQUENCE: 64

Ala Lys His Pro Pro Ala Thr Ser Ile Leu Leu Gln Gly Asn Pro Lys
1               5                   10                  15

Thr Ala Thr Gln Ser Phe Ile Phe Val Pro
            20                  25

<210> SEQ ID NO 65
<211> LENGTH: 46
<212> TYPE: PRT
<213> ORGANISM: Penicillium coprobium PF1169

<400> SEQUENCE: 65

Tyr Gln Ala Thr Gly Cys Ala Ala Ser Leu Gln Ser Asn Arg Ile Ser
1               5                   10                  15

Tyr Phe Phe Asp Leu Arg Gly Pro Ser Ile Thr Ile Asp Thr Ala Cys
            20                  25                  30

Ser Ser Ser Leu Val Ala Leu His Tyr Ala Val Gln Ser Leu
        35                  40                  45

<210> SEQ ID NO 66
<211> LENGTH: 66
<212> TYPE: PRT
<213> ORGANISM: Penicillium coprobium PF1169
```

<400> SEQUENCE: 66

Tyr Ser Ala Thr Gly Ser Gly Leu Thr Val Leu Ala Asn Arg Ile Thr
1               5                   10                  15

His Cys Phe Asp Leu Arg Gly Pro Ser His Val Val Asp Thr Ala Cys
            20                  25                  30

Ser Ser Ser Leu Tyr Ala Leu His Ser Ala Cys Leu Ala Leu Asp Ser
        35                  40                  45

Arg Asp Cys Asp Gly Ala Val Val Ala Ala Asn Leu Ile Gln Ser
    50                  55                  60

Pro Glu
65

<210> SEQ ID NO 67
<211> LENGTH: 76
<212> TYPE: PRT
<213> ORGANISM: Penicillium coprobium PF1169

<400> SEQUENCE: 67

Ser Val Pro Ile Glu Glu His Ser Pro Val Val Thr Gln Leu Gly Thr
1               5                   10                  15

Thr Cys Val Gln Met Ala Leu Thr Lys Tyr Trp Thr Ser Leu Gly Val
            20                  25                  30

Thr Pro Ser Phe Val Met Gly His Ser Leu Gly Glu Phe Ala Ala Leu
        35                  40                  45

Asn Ala Ala Gly Val Leu Thr Ile Ser Asp Thr Ile Tyr Leu Ala Gly
    50                  55                  60

Arg Arg Ala Gln Leu Leu Thr Glu Gln Ile Lys Val
65                  70                  75

<210> SEQ ID NO 68
<211> LENGTH: 71
<212> TYPE: PRT
<213> ORGANISM: Penicillium coprobium PF1169

<400> SEQUENCE: 68

His Leu Asn Leu Met Gly Pro Ser Thr Ala Val Asp Ala Ala Cys Ala
1               5                   10                  15

Ser Ser Leu Val Ala Ile His His Gly Val Gln Ala Ile Lys Leu Gly
            20                  25                  30

Glu Ser Arg Val Ala Ile Val Gly Gly Val Asn Ala Leu Cys Gly Pro
        35                  40                  45

Gly Leu Thr Arg Val Leu Asp Lys Ala Gly Ser Ile Ser Ser Asp Gly
    50                  55                  60

Ser Cys Lys Ser Phe Asp Asp
65                  70

<210> SEQ ID NO 69
<211> LENGTH: 84
<212> TYPE: PRT
<213> ORGANISM: Penicillium coprobium PF1169

<400> SEQUENCE: 69

Ser Phe Arg Arg Gln Glu Asp Thr Trp Lys Val Leu Ser Asn Ala Thr
1               5                   10                  15

Ser Thr Leu Tyr Leu Ala Gly Ile Glu Ile Lys Trp Lys Glu Tyr His
            20                  25                  30

Gln Asp Phe Asn Ala Ala His Arg Val Leu Pro Leu Pro Ser Tyr Lys

```
                35                  40                  45

Trp Asp Leu Lys Asn Tyr Trp Ile Pro Tyr Thr Asn Asn Phe Cys Leu
 50                  55                  60

Leu Lys Gly Ala Pro Ala Ala Pro Val Ala Glu Ala Thr Pro Ile Ser
 65                  70                  75                  80

Val Phe Leu Ser

<210> SEQ ID NO 70
<211> LENGTH: 78
<212> TYPE: PRT
<213> ORGANISM: Penicillium coprobium PF1169

<400> SEQUENCE: 70

Lys Thr Ser Cys Phe Val Gly Ser Phe Ser Ala Asp Tyr Thr Asp Leu
 1               5                  10                  15

Leu Leu Arg Asp Pro Glu Cys Val Pro Met Tyr Gln Cys Thr Asn Ala
                20                  25                  30

Gly Gln Ser Arg Ala Met Thr Ala Asn Arg Leu Ser Tyr Phe Phe Asp
                35                  40                  45

Leu Lys Gly Pro Ser Val Thr Val Asp Thr Ala Cys Ser Gly Ser Leu
 50                  55                  60

Val Ala Leu His Leu Ala Cys Gln Ser Leu Arg Thr Gly Asp
 65                  70                  75

<210> SEQ ID NO 71
<211> LENGTH: 67
<212> TYPE: PRT
<213> ORGANISM: Penicillium coprobium PF1169

<400> SEQUENCE: 71

Tyr Ser Ala Thr Gly Ser Gly Leu Thr Val Leu Ala Asn Arg Ile Thr
 1               5                  10                  15

His Cys Phe Asp Leu Arg Gly Pro Ser His Val Val Asp Thr Ala Cys
                20                  25                  30

Ser Ser Ser Leu Tyr Ala Leu His Ser Ala Cys Phe Gly Pro Leu Asn
                35                  40                  45

Ser Arg Asp Cys Asp Gly Ala Val Val Ala Ala Asn Leu Ile Gln
 50                  55                  60

Ser Pro Glu
 65

<210> SEQ ID NO 72
<211> LENGTH: 79
<212> TYPE: PRT
<213> ORGANISM: Penicillium coprobium PF1169

<400> SEQUENCE: 72

Ser Val Pro Ile Glu Glu His Ser Pro Val Val Thr Gln Leu Gly Thr
 1               5                  10                  15

Thr Cys Val Gln Met Ala Leu Thr Lys Tyr Trp Thr Ser Leu Gly Val
                20                  25                  30

Thr Pro Ser Phe Val Met Gly His Ser Leu Gly Glu Phe Ala Ala Leu
                35                  40                  45

Asn Ala Ala Gly Val Leu Thr Ile Ser Asp Thr Ile Tyr Leu Ala Gly
 50                  55                  60

Arg Arg Ala Gln Leu Leu Thr Glu Gln Ile Glu Gly Gly Thr His
 65                  70                  75
```

<210> SEQ ID NO 73
<211> LENGTH: 40
<212> TYPE: PRT
<213> ORGANISM: Penicillium coprobium PF1169

<400> SEQUENCE: 73

Glu Ala Asn Leu His Val Pro Leu Glu Pro Thr Pro Trp Pro Ala Gly
1               5                   10                  15

Arg Pro Glu Arg Ile Ser Val Asn Ser Phe Gly Ile Gly Gly Ser Asn
            20                  25                  30

Ala His Ala Ile Leu Glu Ser Ala
        35                  40

<210> SEQ ID NO 74
<211> LENGTH: 70
<212> TYPE: PRT
<213> ORGANISM: Penicillium coprobium PF1169
<220> FEATURE:
<221> NAME/KEY: misc_feature
<222> LOCATION: (5)..(5)
<223> OTHER INFORMATION: Xaa can be any naturally occurring amino acid

<400> SEQUENCE: 74

Ile Gly His Thr Xaa Gly Ser Ala Gly Leu Ala Ser Leu Ile Gly Ser
1               5                   10                  15

Ser Leu Ala Met Lys His Gly Val Ile Pro Pro Asn Leu His Phe Gly
            20                  25                  30

Gln Leu Ser Glu Lys Val Ala Pro Phe Tyr Thr His Leu Asn Ile Pro
        35                  40                  45

Thr Glu Pro Val Pro Trp Pro Asn Ser Thr Ser Ser Gln Val Lys Arg
    50                  55                  60

Ala Ser Ile Asn Ser Phe
65                  70

<210> SEQ ID NO 75
<211> LENGTH: 45
<212> TYPE: PRT
<213> ORGANISM: Penicillium coprobium PF1169

<400> SEQUENCE: 75

Pro Val Cys Ser Gly Met Val Lys Ala Thr Phe Gly Pro Gln Ala Thr
1               5                   10                  15

Thr Val Ala Ser Phe Arg Arg Gln Glu Asp Thr Trp Lys Val Leu Ser
            20                  25                  30

Asn Ala Thr Ser Thr Leu Tyr Leu Ala Gly Ile Glu Ile
        35                  40                  45

<210> SEQ ID NO 76
<211> LENGTH: 19
<212> TYPE: PRT
<213> ORGANISM: Penicillium coprobium PF1169
<220> FEATURE:
<221> NAME/KEY: misc_feature
<222> LOCATION: (13)..(13)
<223> OTHER INFORMATION: Xaa can be any naturally occurring amino acid

<400> SEQUENCE: 76

Leu Leu Gly Leu Arg Leu Lys Trp Lys Glu Tyr His Xaa Asp Phe Asn
1               5                   10                  15

Ala Ala His

<210> SEQ ID NO 77
<211> LENGTH: 69
<212> TYPE: PRT
<213> ORGANISM: Penicillium coprobium PF1169

<400> SEQUENCE: 77

Val Tyr Ser Gly Ser Met Thr Asn Asp Tyr Glu Leu Leu Ser Thr Arg
1               5                   10                  15

Asp Ile Tyr Asp Met Pro His Asn Ser Ala Thr Gly Asn Gly Arg Thr
            20                  25                  30

Met Leu Ala Asn Arg Leu Ser Trp Phe Phe Asp Leu Gln Gly Pro Ser
        35                  40                  45

Ile Met Met Asp Thr Ala Cys Ser Ser Ser Leu Thr Ala Val His Leu
50                  55                  60

Ala Ala Gln Ser Leu
65

<210> SEQ ID NO 78
<211> LENGTH: 85
<212> TYPE: PRT
<213> ORGANISM: Penicillium coprobium PF1169

<400> SEQUENCE: 78

Asp Ala Gln Phe Phe Gly Thr Lys Pro Val Glu Ala Asn Ser Ile Asp
1               5                   10                  15

Pro Gln Gln Arg Leu Leu Leu Glu Thr Val Tyr Glu Gly Leu Glu Thr
            20                  25                  30

Ser Gly Ile Pro Met Glu Arg Leu Gln Gly Ser Asn Thr Ala Val Tyr
        35                  40                  45

Val Gly Leu Met Thr Asn Asp Tyr Ala Asp Met Leu Gly Arg Asp Met
50                  55                  60

Gln Asn Phe Pro Thr Tyr Phe Ala Ser Gly Thr Ala Arg Ser Ile Leu
65                  70                  75                  80

Ser Asn Arg Val Ser
                85

<210> SEQ ID NO 79
<211> LENGTH: 28
<212> TYPE: PRT
<213> ORGANISM: Penicillium coprobium PF1169

<400> SEQUENCE: 79

Asp Pro Ala Tyr Phe Asp Ser Ser Phe Phe Asn Ile Thr Lys Thr Glu
1               5                   10                  15

Leu Leu Thr Leu Asp Pro Gln Gln Arg Leu Val Leu
            20                  25

<210> SEQ ID NO 80
<211> LENGTH: 51
<212> TYPE: PRT
<213> ORGANISM: Penicillium coprobium PF1169

<400> SEQUENCE: 80

Val Ala Cys Val Asn Ser Pro Ala Ser Thr Thr Leu Ser Gly Asp Val
1               5                   10                  15

Asp Tyr Ile Asn Gln Leu Glu Ala Arg Leu Gln Gln Asp Gly His Phe
            20                  25                  30

Ala Arg Lys Leu Arg Ile Asp Thr Ala Tyr His Ser Pro His Met Glu
        35                  40                  45

```
Glu Leu Val
    50

<210> SEQ ID NO 81
<211> LENGTH: 24
<212> TYPE: PRT
<213> ORGANISM: Penicillium coprobium PF1169

<400> SEQUENCE: 81

Leu Lys Ser Ile Ser Pro Val Val Thr Gln Leu Gly Thr Thr Cys Val
1               5                   10                  15

Gln Met Ala Leu Thr Lys Tyr Trp
            20

<210> SEQ ID NO 82
<211> LENGTH: 59
<212> TYPE: PRT
<213> ORGANISM: Penicillium coprobium PF1169

<400> SEQUENCE: 82

Gly Cys Phe Tyr Gly Met Thr Ser Asp Asp Tyr Arg Glu Val Asn Ser
1               5                   10                  15

Gly Gln Asp Ile Asp Thr Tyr Phe Ile Pro Gly Gly Asn Arg Ala Phe
            20                  25                  30

Thr Pro Gly Arg Ile Asn Tyr Tyr Phe Lys Phe Ser Gly Pro Ser Val
        35                  40                  45

Ser Val Asp Thr Ala Cys Ser Ser Leu Ala
    50                  55

<210> SEQ ID NO 83
<211> LENGTH: 16
<212> TYPE: PRT
<213> ORGANISM: Penicillium coprobium PF1169

<400> SEQUENCE: 83

Leu Glu Met Ala Gly Phe Ile Pro Asp Ser Ile Pro Leu Arg Arg Arg
1               5                   10                  15

<210> SEQ ID NO 84
<211> LENGTH: 53
<212> TYPE: PRT
<213> ORGANISM: Penicillium coprobium PF1169

<400> SEQUENCE: 84

Ala Ile Val Gly Gly Val Asn Ala Leu Cys Gly Pro Gly Leu Thr Arg
1               5                   10                  15

Val Leu Asp Lys Ala Gly Ala Ile Ser Ser Asp Gly Ser Cys Lys Ser
            20                  25                  30

Phe Asp Asp Asp Ala His Gly Tyr Ala Arg Gly Glu Gly Ala Gly Ala
        35                  40                  45

Leu Val Thr Lys Lys
    50

<210> SEQ ID NO 85
<211> LENGTH: 60
<212> TYPE: PRT
<213> ORGANISM: Penicillium coprobium PF1169

<400> SEQUENCE: 85

Ile Ala Ile Val Gly Ile Gly Gly Arg Phe Pro Gly Glu Ala Thr Asn
1               5                   10                  15
```

Pro Asn Arg Leu Trp Asp Met Val Ser Asn Gly Arg Ser Ala Leu Thr
                20                  25                  30

Glu Val Pro Lys Asp Arg Phe Asn Ile Asp Ala Phe Tyr His Pro His
            35                  40                  45

Ala Glu Arg Gln Gly Thr Met Asn Val Arg Arg Gly
        50                  55                  60

<210> SEQ ID NO 86
<211> LENGTH: 53
<212> TYPE: PRT
<213> ORGANISM: Penicillium coprobium PF1169

<400> SEQUENCE: 86

Ser Val Pro Ile Glu Glu His Ser Pro Val Val Thr Gln Leu Gly Thr
1               5                   10                  15

Thr Cys Val Gln Met Ala Leu Thr Lys Tyr Trp Thr Ser Leu Gly Val
                20                  25                  30

Thr Pro Ser Phe Val Met Gly His Ser Leu Gly Glu Phe Ala Ala Leu
            35                  40                  45

Asn Ala Ala Gly Val
        50

<210> SEQ ID NO 87
<211> LENGTH: 18
<212> TYPE: PRT
<213> ORGANISM: Penicillium coprobium PF1169

<400> SEQUENCE: 87

Ser Val Pro Ile Glu Glu His Ser Pro Val Val Thr Gln Leu Gly Thr
1               5                   10                  15

Thr Cys

<210> SEQ ID NO 88
<211> LENGTH: 62
<212> TYPE: PRT
<213> ORGANISM: Penicillium coprobium PF1169

<400> SEQUENCE: 88

Phe Leu Asp Asp Leu Ala Phe Thr Val Asn Glu Arg Arg Ser Ile Phe
1               5                   10                  15

Pro Trp Lys Ala Ala Val Val Gly Asp Thr Met Glu Gly Leu Ala Ala
                20                  25                  30

Ser Leu Ala Gln Asn Ile Lys Pro Arg Ser Val Leu Arg Met Pro Thr
            35                  40                  45

Leu Gly Phe Val Phe Thr Gly Gln Gly Ala Gln Trp Pro Gly
        50                  55                  60

<210> SEQ ID NO 89
<211> LENGTH: 51
<212> TYPE: PRT
<213> ORGANISM: Penicillium coprobium PF1169

<400> SEQUENCE: 89

Ser Ser Phe Leu Thr Ser Thr Val Gln Gln Ile Val Glu Glu Thr Ile
1               5                   10                  15

Gln Gly Gly Thr Gly Gln Val Val Met Glu Ser Asp Leu Met Gln Thr
                20                  25                  30

Glu Phe Leu Glu Ala Ala Asn Gly His Arg Met Asn Asp Cys Gly Val
            35                  40                  45

-continued

Val Thr Ser
    50

<210> SEQ ID NO 90
<211> LENGTH: 77
<212> TYPE: PRT
<213> ORGANISM: Penicillium coprobium PF1169

<400> SEQUENCE: 90

Glu Cys Gly Phe Val Glu Met His Gly Thr Gly Thr Lys Ala Gly Asp
1               5                   10                  15

Pro Val Glu Ala Ala Ala Val His Ala Ala Leu Gly Lys Asn Arg Thr
            20                  25                  30

Leu Arg Asn Pro Leu Tyr Ile Gly Ser Val Lys Ser Asn Ile Gly His
        35                  40                  45

Leu Glu Gly Ala Ser Gly Ile Val Ala Val Ile Lys Ala Ala Met Met
    50                  55                  60

Leu Asp Arg Asp Leu Met Leu Pro Asn Ala Glu Phe Lys
65                  70                  75

<210> SEQ ID NO 91
<211> LENGTH: 78
<212> TYPE: PRT
<213> ORGANISM: Penicillium coprobium PF1169
<220> FEATURE:
<221> NAME/KEY: misc_feature
<222> LOCATION: (4)..(4)
<223> OTHER INFORMATION: Xaa can be any naturally occurring amino acid

<400> SEQUENCE: 91

Phe Phe Lys Xaa Ser Gly Pro Ser Phe Ser Ile Asp Thr Ala Cys Ser
1               5                   10                  15

Ser Ser Leu Ala Thr Ile Gln Val Cys Thr His Leu Phe His Val His
            20                  25                  30

Leu Asn Arg Gln Leu Thr Ile Ala Ala Cys Thr Ser Leu Trp Asn Gly
        35                  40                  45

Glu Thr Asp Thr Val Val Ala Gly Gly Met Asn Ile Leu Thr Asn Ser
    50                  55                  60

Asp Ala Phe Ala Gly Leu Ser His Gly His Phe Leu Thr Lys
65                  70                  75

<210> SEQ ID NO 92
<211> LENGTH: 79
<212> TYPE: PRT
<213> ORGANISM: Penicillium coprobium PF1169

<400> SEQUENCE: 92

Ser Val Pro Ile Glu Glu His Ser Pro Val Val Thr Gln Leu Gly Thr
1               5                   10                  15

Thr Cys Val Gln Met Ala Leu Thr Lys Tyr Trp Thr Ser Leu Gly Val
            20                  25                  30

Thr Pro Ser Phe Val Met Gly His Ser Leu Gly Glu Phe Ala Ala Leu
        35                  40                  45

Asn Ala Ala Gly Val Leu Thr Ile Ser Asp Thr Ile Tyr Leu Ala Gly
    50                  55                  60

Arg Arg Ala Gln Leu Leu Thr Glu Gln Ile Glu Gly Gly Thr His
65                  70                  75

<210> SEQ ID NO 93
<211> LENGTH: 68

```
<212> TYPE: PRT
<213> ORGANISM: Penicillium coprobium PF1169

<400> SEQUENCE: 93

Leu Ser Ser Asp Gly Arg Cys His Thr Phe Asp Glu Lys Ala Asn Gly
1               5                   10                  15

Tyr Ala Arg Gly Glu Ala Val Gly Cys Leu Ile Leu Lys Pro Leu Ala
            20                  25                  30

Lys Ala Leu His Asp Gln Asn Lys Ile Arg Ala Val Ile Arg Gly Thr
        35                  40                  45

Gly Ser Asn Gln Asp Gly Arg Thr Ala Gly Ile Thr Val Pro Asn Gly
    50                  55                  60

Ala Ala Gln Glu
65

<210> SEQ ID NO 94
<211> LENGTH: 80
<212> TYPE: PRT
<213> ORGANISM: Penicillium coprobium PF1169

<400> SEQUENCE: 94

Ser Pro Leu Phe Gly Leu Ala Arg Ile Ile Ala Ser Glu His Pro Asp
1               5                   10                  15

Leu Gly Ser Leu Ile Asp Ile Glu Glu Pro Ile Ile Pro Leu Ser Thr
            20                  25                  30

Met Arg Tyr Ile Gln Gly Ala Asp Ile Val Arg Ile Ser Asp Gly Ile
        35                  40                  45

Ala Arg Thr Ser Arg Phe Arg Ser Leu Pro Arg Thr Lys Leu Arg Pro
    50                  55                  60

Val Ser Asp Gly Pro Arg Leu Leu Pro Arg Pro Glu Gly Thr Tyr Leu
65                  70                  75                  80

<210> SEQ ID NO 95
<211> LENGTH: 75
<212> TYPE: PRT
<213> ORGANISM: Penicillium coprobium PF1169

<400> SEQUENCE: 95

Asn Arg Ile Ser Tyr Tyr Phe Asp Trp Gln Gly Pro Ser Met Ala Val
1               5                   10                  15

Asp Thr Gly Cys Ser Ser Ser Leu Leu Ala Val His Leu Gly Val Glu
            20                  25                  30

Ala Leu Gln Asn Asp Asp Cys Ser Met Ala Val Ala Val Gly Ser Asn
        35                  40                  45

Leu Ile Leu Ser Pro Asn Ala Tyr Ile Ala Asp Ser Lys Thr Arg Met
    50                  55                  60

Leu Ser Pro Thr Gly Arg Ser Arg Met Trp Asp
65                  70                  75

<210> SEQ ID NO 96
<211> LENGTH: 81
<212> TYPE: PRT
<213> ORGANISM: Penicillium coprobium PF1169

<400> SEQUENCE: 96

Val Asp Val Asn Pro Ala Val Leu Lys Asp Ala Pro Leu Pro Trp Asp
1               5                   10                  15

Pro Ser Ser Trp Ala Pro Ile Leu Asp Ala Ala Thr Ser Val Gly Ser
            20                  25                  30
```

```
Thr Ile Phe Gln Thr Ala Ala Leu Arg Met Pro Ala Gln Ile Glu Arg
        35                  40                  45

Val Glu Ile Phe Thr Ser Glu Asn Pro Pro Lys Thr Ser Trp Leu Tyr
 50                  55                  60

Val Gln Glu Ala Ser Asp Ala Val Pro Thr Ser His Val Ser Val Val
 65                  70                  75                  80

Ser

<210> SEQ ID NO 97
<211> LENGTH: 37
<212> TYPE: PRT
<213> ORGANISM: Penicillium coprobium PF1169

<400> SEQUENCE: 97

Pro Leu Phe Gly Leu Ala Arg Ile Ile Ala Ser Glu His Pro Asp Leu
 1               5                  10                  15

Gly Ser Leu Ile Asp Ile Glu Glu Pro Ile Ile Pro Leu Ser Thr Met
                20                  25                  30

Arg Tyr Ile Arg Gly
         35

<210> SEQ ID NO 98
<211> LENGTH: 84
<212> TYPE: PRT
<213> ORGANISM: Penicillium coprobium PF1169

<400> SEQUENCE: 98

Ala Val Ile Arg Gly Thr Gly Ser Asn Gln Asp Gly Arg Thr Ala Gly
 1               5                  10                  15

Ile Thr Val Pro Asn Gly Ala Ala Gln Glu Ser Leu Ile Arg Ser Val
                20                  25                  30

Tyr Ala Gln Ala Asp Leu Asp Pro Ser Glu Thr Asp Phe Val Glu Ala
            35                  40                  45

His Gly Thr Gly Thr Leu Ala Gly Asp Pro Val Glu Thr Gly Ala Ile
        50                  55                  60

Ala Arg Val Phe Gly Thr Asp Arg Pro Pro Gly Asp Pro Val Arg Ile
 65                  70                  75                  80

Gly Ser Ile Lys

<210> SEQ ID NO 99
<211> LENGTH: 69
<212> TYPE: PRT
<213> ORGANISM: Penicillium coprobium PF1169

<400> SEQUENCE: 99

Leu Glu Val Val Trp Glu Cys Leu Glu Asn Ser Gly Glu Thr Gln Trp
 1               5                  10                  15

Arg Gly Lys Glu Ile Gly Cys Phe Val Gly Val Phe Gly Glu Asp Trp
                20                  25                  30

Leu Glu Met Ser His Lys Asp Pro Gln His Leu Asn Gln Met Phe Pro
            35                  40                  45

Ile Ala Thr Gly Gly Phe Ala Leu Ala Asn Gln Val Ser Tyr Arg Phe
        50                  55                  60

Asp Leu Thr Gly Pro
 65

<210> SEQ ID NO 100
```

```
<211> LENGTH: 79
<212> TYPE: PRT
<213> ORGANISM: Penicillium coprobium PF1169

<400> SEQUENCE: 100

Gly Gly Ala Thr Asp Thr Glu Lys Phe Trp Asp Leu Leu Ala Ser Gly
1               5                   10                  15

Val Asp Val His Arg Lys Ile Pro Ala Asp Arg Phe Asp Val Glu Thr
            20                  25                  30

His Tyr Asp Pro Asn Gly Lys Arg Met Asn Ala Ser His Thr Pro Tyr
        35                  40                  45

Gly Cys Phe Ile Asp Glu Pro Gly Leu Phe Asp Ala Ala Phe Phe Asn
    50                  55                  60

Met Ser Pro Arg Glu Ala Gln Gln Thr Asp Pro Met Gln Arg Leu
65                  70                  75

<210> SEQ ID NO 101
<211> LENGTH: 52
<212> TYPE: PRT
<213> ORGANISM: Penicillium coprobium PF1169

<400> SEQUENCE: 101

Glu Leu Arg His Gly Lys Asn Ile Asp Lys Pro Glu Tyr Ser Gln Pro
1               5                   10                  15

Leu Cys Thr Ala Ile Gln Ile Ala Leu Val Glu Leu Leu Glu Ser Phe
            20                  25                  30

Gly Val Val Pro Lys Ala Val Val Gly His Ser Ser Gly Glu Ile Ala
        35                  40                  45

Ala Ala Tyr Val
    50

<210> SEQ ID NO 102
<211> LENGTH: 34
<212> TYPE: PRT
<213> ORGANISM: Penicillium coprobium PF1169

<400> SEQUENCE: 102

Val Gly Phe Val Phe Thr Gly Gln Gly Ala Gln Trp His Gly Met Gly
1               5                   10                  15

Lys Glu Leu Leu Ser Thr Tyr Pro Ile Phe Arg Gln Thr Met Gln Asp
            20                  25                  30

Val Asp

<210> SEQ ID NO 103
<211> LENGTH: 63
<212> TYPE: PRT
<213> ORGANISM: Penicillium coprobium PF1169

<400> SEQUENCE: 103

Phe Asp Ala Ala Phe Phe Asn Met Ser Pro Arg Glu Ala Gln Gln Thr
1               5                   10                  15

Asp Pro Met Gln Arg Leu Ala Ile Val Thr Ala Tyr Glu Ala Leu Glu
            20                  25                  30

Arg Ala Gly Tyr Val Ala Asn Arg Thr Ala Ala Thr Asn Leu His Arg
        35                  40                  45

Ile Gly Thr Phe Tyr Gly Gln Ala Ser Asp Asp Tyr Arg Glu Val
    50                  55                  60

<210> SEQ ID NO 104
```

```
<211> LENGTH: 43
<212> TYPE: PRT
<213> ORGANISM: Penicillium coprobium PF1169

<400> SEQUENCE: 104

Ala Val Val Ser Gly Val Ser Ile Leu Glu Asn Pro Val Thr Ile
1               5                   10                  15

Gly Met Ser His His Gly Leu Leu Gly Pro Gln Gly Arg Ser Phe Ser
            20                  25                  30

Phe Asp Ser Arg Ala Glu Gly Tyr Ala Arg Gly
        35                  40

<210> SEQ ID NO 105
<211> LENGTH: 71
<212> TYPE: PRT
<213> ORGANISM: Penicillium coprobium PF1169

<400> SEQUENCE: 105

Lys Ala Ser Leu Ser Leu Gln His Gly Met Ile Ala Pro Asn Leu Leu
1               5                   10                  15

Met Gln His Leu Asn Pro Lys Ile Lys Pro Phe Ala Ala Lys Leu Ser
            20                  25                  30

Val Pro Thr Glu Cys Ile Pro Trp Pro Ala Val Pro Asp Gly Cys Pro
        35                  40                  45

Arg Arg Ala Ser Val Asn Ser Phe Gly Phe Gly Gly Ala Asn Val His
    50                  55                  60

Val Val Leu Glu Ser Tyr Thr
65                  70

<210> SEQ ID NO 106
<211> LENGTH: 28
<212> TYPE: PRT
<213> ORGANISM: Penicillium coprobium PF1169

<400> SEQUENCE: 106

Pro Trp Pro Thr Thr Gly Leu Arg Arg Ala Ser Val Asn Ser Phe Gly
1               5                   10                  15

Tyr Gly Gly Thr Asn Ala His Cys Val Leu Asp Asp
            20                  25

<210> SEQ ID NO 107
<211> LENGTH: 71
<212> TYPE: PRT
<213> ORGANISM: Penicillium coprobium PF1169

<400> SEQUENCE: 107

Lys Ala Ser Leu Ser Leu Gln His Gly Met Ile Ala Pro Asn Leu Leu
1               5                   10                  15

Met Gln His Leu Asn Pro Lys Ile Lys Pro Phe Ala Ala Lys Leu Ser
            20                  25                  30

Val Pro Thr Glu Cys Ile Pro Trp Pro Ala Val Pro Asp Gly Cys Pro
        35                  40                  45

Arg Arg Ala Ser Val Asn Ser Phe Gly Phe Gly Gly Ala Asn Val His
    50                  55                  60

Val Val Leu Glu Ser Tyr Thr
65                  70

<210> SEQ ID NO 108
<211> LENGTH: 50
<212> TYPE: PRT
```

<213> ORGANISM: Penicillium coprobium PF1169

<400> SEQUENCE: 108

Asp Arg Leu Phe Leu Gln Met Ser His Glu Glu Trp Glu Ala Ala Leu
1               5                   10                  15

Ala Pro Lys Val Thr Gly Thr Trp Asn Leu His His Ala Thr Ala Gln
            20                  25                  30

His Ser Leu Asp Phe Phe Val Val Phe Gly Ser Ile Ala Gly Val Cys
        35                  40                  45

Gly Asn
    50

<210> SEQ ID NO 109
<211> LENGTH: 82
<212> TYPE: PRT
<213> ORGANISM: Penicillium coprobium PF1169

<400> SEQUENCE: 109

Thr Phe Leu Lys Gly Thr Gly Gly Gln Met Leu Gln Asn Val Val Leu
1               5                   10                  15

Arg Val Pro Val Ala Ile Asn Ala Pro Arg Ser Val Gln Val Val Val
            20                  25                  30

Gln Gln Asp Gln Val Lys Val Val Ser Arg Leu Ile Pro Ser Glu Ala
        35                  40                  45

Ser Val Leu Asp Asp Asp Ala Ser Trp Val Thr His Thr Thr Ala Tyr
    50                  55                  60

Trp Asp Arg Arg Val Leu Gly Ser Glu Asp Arg Ile Asp Leu Ala Ala
65                  70                  75                  80

Val Lys

<210> SEQ ID NO 110
<211> LENGTH: 30
<212> TYPE: PRT
<213> ORGANISM: Penicillium coprobium PF1169

<400> SEQUENCE: 110

Asp Thr Ala Cys Ser Ser Ser Leu Val Ala Leu His Tyr Ala Val Gln
1               5                   10                  15

Ser Leu Arg Asn Gly Glu Ser Thr Glu Ala Leu Ile Ala Gly
            20                  25                  30

<210> SEQ ID NO 111
<211> LENGTH: 38
<212> TYPE: PRT
<213> ORGANISM: Penicillium coprobium PF1169

<400> SEQUENCE: 111

Gly Thr Gly Asn Gly Ser Ala Met Ile Ser Asn Arg Ile Ser Trp Phe
1               5                   10                  15

Phe Asp Leu Lys Gly Pro Ser Leu Ser Leu Asp Thr Ala Cys Ser Ser
            20                  25                  30

Ser Leu Val Ala Leu His
        35

<210> SEQ ID NO 112
<211> LENGTH: 72
<212> TYPE: PRT
<213> ORGANISM: Penicillium coprobium PF1169

<400> SEQUENCE: 112

```
Thr Ser Thr Gln Leu Asn Asp Leu Asn Glu Thr Asn Ala Ile Lys Lys
1               5                   10                  15

Val Phe Gly Lys Gln Ala Tyr Asn Ile Pro Ile Ser Ser Thr Lys Ser
            20                  25                  30

Tyr Thr Gly His Leu Ile Gly Ala Ala Gly Thr Met Glu Thr Ile Phe
            35                  40                  45

Cys Ile Lys Thr Met Gln Glu Lys Ile Ala Pro Ala Thr Thr Asn Leu
    50                  55                  60

Lys Glu Arg Asp Ser Asn Cys Asp
65              70
```

<210> SEQ ID NO 113
<211> LENGTH: 50
<212> TYPE: PRT
<213> ORGANISM: Penicillium coprobium PF1169

<400> SEQUENCE: 113

```
Val Ile Val Gly Ser Ala Ala Asn Gln Asn Leu Asn Leu Ser His Ile
1               5                   10                  15

Thr Val Pro His Ser Gly Ser Gln Val Lys Leu Tyr Gln Asn Val Met
            20                  25                  30

Ser Gln Ala Gly Val His Pro His Ser Val Thr Tyr Val Glu Ala His
            35                  40                  45

Gly Thr
    50
```

<210> SEQ ID NO 114
<211> LENGTH: 48
<212> TYPE: PRT
<213> ORGANISM: Penicillium coprobium PF1169

<400> SEQUENCE: 114

```
Leu Pro Thr Ala Ile Gln Pro Leu Phe Arg Ala Asn Val Ser Tyr Leu
1               5                   10                  15

Leu Val Gly Gly Leu Gly Gly Ile Gly Lys Glu Val Ala Leu Trp Met
            20                  25                  30

Val Gln Asn Gly Ala Lys Ser Leu Ile Phe Val Asn Arg Ser Gly Leu
            35                  40                  45
```

<210> SEQ ID NO 115
<211> LENGTH: 53
<212> TYPE: PRT
<213> ORGANISM: Penicillium coprobium PF1169

<400> SEQUENCE: 115

```
Val Ala Ile Val Gly Gly Val Asn Ala Leu Cys Gly Pro Gly Leu Thr
1               5                   10                  15

Arg Val Leu Asp Lys Ala Gly Ala Ile Ser Ser Asp Gly Ser Cys Lys
            20                  25                  30

Ser Phe Asp Asp Asp Ala His Gly Tyr Ala Arg Gly Glu Gly Ala Gly
            35                  40                  45

Ala Leu Val Leu Lys
    50
```

<210> SEQ ID NO 116
<211> LENGTH: 28
<212> TYPE: PRT
<213> ORGANISM: Penicillium coprobium PF1169

<400> SEQUENCE: 116

Pro Trp Glu Ser Pro Gly Ala Arg Arg Val Ser Val Asn Ser Phe Gly
1               5                   10                  15

Tyr Gly Gly Ser Asn Ala His Val Ile Ile Glu Asp
            20                  25

<210> SEQ ID NO 117
<211> LENGTH: 72
<212> TYPE: PRT
<213> ORGANISM: Penicillium coprobium PF1169

<400> SEQUENCE: 117

Lys Thr Leu Arg Glu Trp Met Thr Ala Glu Gly Lys Asp His Asn Leu
1               5                   10                  15

Ser Asp Ile Leu Thr Thr Leu Ala Thr Arg Arg Asp His His Asp Tyr
            20                  25                  30

Arg Ala Ala Leu Val Val Asp Asp Asn Arg Asp Ala Glu Leu Ala Leu
        35                  40                  45

Gln Ala Leu Glu His Gly Val Asp Gln Thr Phe Thr Thr Gln Ser Arg
    50                  55                  60

Val Phe Gly Ala Asp Ile Ser Lys
65                  70

<210> SEQ ID NO 118
<211> LENGTH: 80
<212> TYPE: PRT
<213> ORGANISM: Penicillium coprobium PF1169

<400> SEQUENCE: 118

Ser Asp Asp Tyr Arg Glu Val Asn Ser Gly Gln Asp Ile Asp Thr Tyr
1               5                   10                  15

Phe Ile Pro Gly Gly Asn Arg Ala Phe Thr Pro Gly Arg Ile Asn Tyr
            20                  25                  30

Tyr Phe Lys Phe Ser Gly Pro Ser Val Ser Val Asp Thr Ala Cys Ser
        35                  40                  45

Ser Ser Leu Ala Ala Ile His Val Ala Cys Asn Ser Leu Trp Arg Asn
    50                  55                  60

Glu Ser Asp Ser Ala Val Ala Gly Gly Val Asn Ile Leu Thr Asn Pro
65                  70                  75                  80

<210> SEQ ID NO 119
<211> LENGTH: 56
<212> TYPE: PRT
<213> ORGANISM: Penicillium coprobium PF1169

<400> SEQUENCE: 119

Leu Ser Ser Asp Gly Arg Cys His Thr Phe Asp Glu Lys Ala Asn Gly
1               5                   10                  15

Tyr Ala Arg Gly Glu Ala Val Gly Cys Leu Ile Leu Lys Pro Leu Ala
            20                  25                  30

Lys Ala Leu His Asp Gln Asn Lys Ile Arg Ala Val Ile Arg Gly Thr
        35                  40                  45

Gly Ser Asn Gln Gly Arg Ala Asn
    50                  55

<210> SEQ ID NO 120
<211> LENGTH: 63
<212> TYPE: PRT
<213> ORGANISM: Penicillium coprobium PF1169

-continued

<400> SEQUENCE: 120

Asp Thr Ala Cys Ser Ser Leu Tyr Ala Leu His Ser Ala Cys Leu
1               5                   10                  15

Ala Leu Asp Ser Arg Asp Cys Asp Gly Ala Val Val Ala Ala Asn
            20                  25                  30

Leu Ile Gln Ser Pro Glu Gln Gln Met Ile Ala Val Lys Ala Gly Ile
        35                  40                  45

Leu Ser Pro Asp Ser Met Cys His Thr Phe Asp Glu Ser Ala Asn
    50                  55                  60

<210> SEQ ID NO 121
<211> LENGTH: 28
<212> TYPE: PRT
<213> ORGANISM: Penicillium coprobium PF1169

<400> SEQUENCE: 121

Pro Trp Pro Thr Thr Gly Leu Arg Arg Ala Ser Val Asn Ser Phe Gly
1               5                   10                  15

Tyr Gly Gly Thr Asn Ala His Cys Val Leu Asp Asp
            20                  25

<210> SEQ ID NO 122
<211> LENGTH: 62
<212> TYPE: PRT
<213> ORGANISM: Penicillium coprobium PF1169

<400> SEQUENCE: 122

Ala Gly Ile Pro Leu Ala Asn Ile Met Gly Thr Lys Thr Ser Cys Phe
1               5                   10                  15

Val Gly Ser Phe Ser Ala Asp Tyr Thr Asp Leu Leu Leu Arg Asp Pro
            20                  25                  30

Glu Cys Val Pro Met Tyr Gln Cys Thr Asn Ala Gly Gln Ser Arg Ala
        35                  40                  45

Met Thr Ala Asn Arg Leu Ser Tyr Phe Leu Ile Lys Gly Pro
    50                  55                  60

<210> SEQ ID NO 123
<211> LENGTH: 80
<212> TYPE: PRT
<213> ORGANISM: Penicillium coprobium PF1169

<400> SEQUENCE: 123

Arg Trp Glu Pro Tyr Tyr Arg Arg Asp Pro Arg Asn Glu Lys Phe Leu
1               5                   10                  15

Lys Gln Thr Thr Ser Arg Gly Tyr Phe Leu Asp His Leu Glu Asp Phe
            20                  25                  30

Asp Cys Gln Phe Phe Gly Ile Ser Pro Lys Glu Ala Glu Gln Met Asp
        35                  40                  45

Pro Gln Gln Arg Val Ser Leu Glu Val Ala Ser Glu Ala Leu Glu Asp
    50                  55                  60

Ala Gly Ile Pro Ala Lys Ser Leu Ser Gly Ser Asp Thr Ala Val Phe
65                  70                  75                  80

<210> SEQ ID NO 124
<211> LENGTH: 28
<212> TYPE: PRT
<213> ORGANISM: Penicillium coprobium PF1169

<400> SEQUENCE: 124

```
Pro Gly Arg Ile Asn Tyr Phe Phe Lys Phe Ser Gly Pro Ser Phe Ser
1               5                   10                  15

Ile Asp Thr Ala Cys Ser Ser Ser Leu Ala Thr Ile
            20                  25
```

<210> SEQ ID NO 125
<211> LENGTH: 64
<212> TYPE: PRT
<213> ORGANISM: Penicillium coprobium PF1169

<400> SEQUENCE: 125

```
Ala Gly Ile Pro Leu Ala Asn Ile Met Gly Thr Lys Thr Ser Cys Phe
1               5                   10                  15

Val Gly Ser Phe Ser Ala Asp Tyr Thr Asp Leu Leu Leu Arg Asp Pro
                20                  25                  30

Glu Cys Val Pro Met Tyr Gln Cys Thr Asn Ala Gly Gln Ser Arg Ala
            35                  40                  45

Met Thr Ala Asn Arg Leu Ser Tyr Phe Phe Asp Leu Lys Gly Pro Ser
    50                  55                  60
```

<210> SEQ ID NO 126
<211> LENGTH: 52
<212> TYPE: PRT
<213> ORGANISM: Penicillium coprobium PF1169

<400> SEQUENCE: 126

```
Glu Leu Arg His Gly Lys Asn Ile Asp Lys Pro Glu Tyr Ser Gln Pro
1               5                   10                  15

Leu Cys Thr Ala Ile Gln Ile Ala Leu Val Glu Leu Glu Ser Phe
                20                  25                  30

Gly Val Val Pro Lys Ala Val Gly His Ser Ser Gly Glu Ile Ala
            35                  40                  45

Ala Ala Tyr Val
    50
```

<210> SEQ ID NO 127
<211> LENGTH: 38
<212> TYPE: PRT
<213> ORGANISM: Penicillium coprobium PF1169

<400> SEQUENCE: 127

```
Gln Pro Leu Cys Thr Ala Ile Gln Ile Ala Leu Val Glu Leu Leu Glu
1               5                   10                  15

Ser Phe Gly Val Val Pro Lys Ala Val Val Gly His Ser Ser Gly Glu
                20                  25                  30

Ile Ala Ala Ala Tyr Val
        35
```

<210> SEQ ID NO 128
<211> LENGTH: 86
<212> TYPE: PRT
<213> ORGANISM: Penicillium coprobium PF1169

<400> SEQUENCE: 128

```
Arg Leu Pro Gly Asp Val Ser Thr Pro Glu Glu Phe Trp Asp Leu Cys
1               5                   10                  15

Ser Arg Gly Arg Gly Ala Trp Ser Pro Val Pro Lys Asp Arg Phe Asn
                20                  25                  30

Ala Gly Ser Phe Tyr His Pro Asn Ala Asp Arg Pro Gly Ser Phe Asn
```

```
            35                  40                  45
Ala Ala Gly Ala His Phe Leu Thr Glu Asp Ile Gly Leu Phe Asp Ala
 50                  55                  60
Pro Phe Phe Asn Ile Thr Leu Gln Glu Ala Gln Thr Met Asp Pro Gln
65                  70                  75                  80
Gln Arg Ile Phe Leu Glu
                85

<210> SEQ ID NO 129
<211> LENGTH: 69
<212> TYPE: PRT
<213> ORGANISM: Penicillium coprobium PF1169

<400> SEQUENCE: 129

Gln Phe Phe His Ala His Gly Thr Gly Thr Gln Ala Gly Asp Pro Gln
 1               5                  10                  15
Glu Ala Glu Ala Val Ser Thr Ala Leu Phe Pro Asp Gly Ser Asn Ile
                20                  25                  30
Glu Thr Lys Leu Phe Val Gly Ser Ile Lys Thr Val Ile Gly His Thr
            35                  40                  45
Glu Gly Ser Ala Gly Leu Ala Ser Leu Ile Gly Ser Ser Leu Ala Met
 50                  55                  60
Lys His Gly Val Ile
65

<210> SEQ ID NO 130
<211> LENGTH: 64
<212> TYPE: PRT
<213> ORGANISM: Penicillium coprobium PF1169

<400> SEQUENCE: 130

Ala Gly Ile Pro Leu Ala Asn Ile Met Gly Thr Lys Thr Ser Cys Phe
 1               5                  10                  15
Val Gly Ser Phe Ser Ala Asp Tyr Thr Asp Leu Leu Arg Asp Pro
                20                  25                  30
Glu Cys Val Pro Met Tyr Gln Cys Thr Asn Ala Gly Gln Ser Arg Ala
            35                  40                  45
Met Thr Ala Asn Arg Leu Ser Tyr Phe Phe Asp Leu Lys Gly Pro Ser
 50                  55                  60

<210> SEQ ID NO 131
<211> LENGTH: 67
<212> TYPE: PRT
<213> ORGANISM: Penicillium coprobium PF1169

<400> SEQUENCE: 131

Leu Asp Asp Leu Ala Phe Thr Val Asn Glu Arg Ser Ile Phe Pro
 1               5                  10                  15
Trp Lys Ala Ala Val Val Gly Asp Thr Met Glu Gly Leu Ala Ala Ser
                20                  25                  30
Leu Ala Gln Asn Ile Lys Pro Arg Ser Val Leu Arg Met Pro Thr Leu
            35                  40                  45
Gly Phe Val Phe Thr Gly Gln Gly Ala Gln Trp Pro Gly Met Gly Lys
 50                  55                  60
Glu Leu Leu
65

<210> SEQ ID NO 132
```

```
<211> LENGTH: 21
<212> TYPE: PRT
<213> ORGANISM: Penicillium coprobium PF1169

<400> SEQUENCE: 132

Ala His Gly Thr Gly Thr Lys Val Gly Asp Pro Met Glu Val Glu Ala
1               5                   10                  15

Ile Ala Asp Val Phe
            20

<210> SEQ ID NO 133
<211> LENGTH: 71
<212> TYPE: PRT
<213> ORGANISM: Penicillium coprobium PF1169

<400> SEQUENCE: 133

Lys Gly Gly Met Leu Ala Val Gly Ala Ser Ala Ser Asp Ile Gln Gln
1               5                   10                  15

Ile Leu Asp Ala Met Arg Gly Asn Lys Ala Val Ile Ala Cys Val Asn
            20                  25                  30

Ser Glu Ser Ser Val Thr Leu Ser Gly Asp Leu Asp Val Ile Ala Asn
        35                  40                  45

Leu Gln Thr Ala Leu Asp Lys Glu Gly Ile Phe Thr Arg Lys Leu Lys
    50                  55                  60

Val Asp Val Ala Tyr His Ser
65                  70

<210> SEQ ID NO 134
<211> LENGTH: 75
<212> TYPE: PRT
<213> ORGANISM: Penicillium coprobium PF1169

<400> SEQUENCE: 134

Leu Glu Asn Leu Glu Thr Ala Leu Ala Arg Asn Ala Pro Ile Tyr Ala
1               5                   10                  15

Glu Val Thr Gly Tyr Ala Asn Tyr Ser Asp Ala Tyr Asp Ile Thr Ala
            20                  25                  30

Pro Ala Asp Asp Leu Met Gly Arg Tyr Met Ser Ile Thr Lys Ala Ile
        35                  40                  45

Glu Gln Ala Gln Leu Asn Ile Asn Glu Ile Asp Tyr Ile Asn Ala His
    50                  55                  60

Gly Thr Ser Thr Gln Leu Asn Asp Leu Asn Glu
65                  70                  75

<210> SEQ ID NO 135
<211> LENGTH: 53
<212> TYPE: PRT
<213> ORGANISM: Penicillium coprobium PF1169

<400> SEQUENCE: 135

Met Ala Met Lys Lys Ala Leu Lys Gln Ala Gln Leu Arg Pro Ser Ala
1               5                   10                  15

Val Asp Tyr Val Asn Ala His Ala Thr Ser Thr Ile Val Gly Asp Ala
            20                  25                  30

Ala Glu Asn Ala Ala Ile Lys Ala Leu Leu Leu Gly Ala Asp Gly Lys
        35                  40                  45

Asp Lys Ala Ala Asp
    50
```

```
<210> SEQ ID NO 136
<211> LENGTH: 38
<212> TYPE: PRT
<213> ORGANISM: Penicillium coprobium PF1169

<400> SEQUENCE: 136

Gly Thr Gly Asn Gly Ser Ala Met Ile Ser Asn Arg Ile Ser Trp Phe
1               5                   10                  15

Phe Asp Leu Lys Gly Pro Ser Leu Ser Leu Asp Thr Ala Cys Ser Ser
                20                  25                  30

Ser Leu Val Ala Leu His
            35

<210> SEQ ID NO 137
<211> LENGTH: 76
<212> TYPE: PRT
<213> ORGANISM: Penicillium coprobium PF1169

<400> SEQUENCE: 137

Gly Pro Ser Met Thr Ile Asp Thr Ala Cys Ser Ser Leu Ile Ala
1               5                   10                  15

Leu His Gln Ala Val Gln Ser Leu Arg Ser Gly Glu Thr Asp Val Ala
                20                  25                  30

Val Ala Ala Gly Thr Asn Leu Leu Leu Gly Pro Glu Gln Tyr Ile Ala
            35                  40                  45

Glu Ser Lys Leu Lys Met Leu Ser Pro Asn Gly Arg Ser Arg Met Trp
        50                  55                  60

Asp Lys Asp Ala Asp Gly Tyr Ala Arg Gly Asp Gly
65                  70                  75

<210> SEQ ID NO 138
<211> LENGTH: 85
<212> TYPE: PRT
<213> ORGANISM: Penicillium coprobium PF1169

<400> SEQUENCE: 138

Ile Gly Ser Ile Lys Pro Asn Ile Gly His Leu Glu Ala Gly Ala Gly
1               5                   10                  15

Val Met Gly Phe Ile Lys Ala Ile Leu Ser Ile Gln Lys Gly Val Leu
                20                  25                  30

Ala Pro Gln Ala Asn Leu Thr Lys Leu Asn Ser Arg Ile Asp Trp Lys
            35                  40                  45

Thr Ala Gly Val Lys Val Val Gln Glu Ala Thr Pro Trp Pro Ser Ser
        50                  55                  60

Asp Ser Ile Arg Arg Ala Gly Val Cys Ser Tyr Gly Tyr Gly Gly Thr
65                  70                  75                  80

Val Ser His Ala Val
            85

<210> SEQ ID NO 139
<211> LENGTH: 57
<212> TYPE: PRT
<213> ORGANISM: Penicillium coprobium PF1169

<400> SEQUENCE: 139

Asn Ala Ala Gly Ala His Phe Leu Thr Glu Asp Ile Gly Leu Phe Asp
1               5                   10                  15

Ala Pro Phe Phe Asn Ile Thr Leu Gln Glu Ala Gln Thr Met Asp Pro
                20                  25                  30
```

Gln Gln Arg Ile Phe Leu Glu Cys Val Tyr Glu Ala Leu Glu Asn Gly
            35                  40                  45

Gly Ile Pro Thr His Glu Ile Thr Gly
 50                  55

<210> SEQ ID NO 140
<211> LENGTH: 68
<212> TYPE: PRT
<213> ORGANISM: Penicillium coprobium PF1169

<400> SEQUENCE: 140

Leu Ser Ser Asp Gly Arg Cys His Thr Phe Asp Glu Lys Ala Asn Gly
1               5                   10                  15

Tyr Ala Arg Gly Glu Ala Val Gly Cys Leu Ile Leu Lys Pro Leu Ala
            20                  25                  30

Lys Ala Leu His Asp Gln Asn Lys Ile Arg Ala Val Ile Arg Gly Thr
        35                  40                  45

Gly Ser Asn Gln Asp Gly Arg Thr Ala Gly Ile Thr Val Pro Asn Gly
 50                  55                  60

Ala Ala Gln Glu
65

<210> SEQ ID NO 141
<211> LENGTH: 37
<212> TYPE: PRT
<213> ORGANISM: Penicillium coprobium PF1169

<400> SEQUENCE: 141

Ser Phe Asp Ser Arg Ala Glu Gly Tyr Ala Arg Gly Glu Gly Val Gly
1               5                   10                  15

Thr Val Val Lys Pro Leu Ser Thr Ala Ile Arg Asp Gly Asp Thr
            20                  25                  30

Ile Arg Ala Val Ile
        35

<210> SEQ ID NO 142
<211> LENGTH: 72
<212> TYPE: PRT
<213> ORGANISM: Penicillium coprobium PF1169

<400> SEQUENCE: 142

Gly Ile Pro Ile Asp Thr Leu Pro Gly Ser Asn Thr Ala Val Tyr Ser
1               5                   10                  15

Gly Ser Met Thr Asn Asp Tyr Glu Leu Leu Ser Thr Arg Asp Ile Tyr
            20                  25                  30

Asp Met Pro His Asn Ser Ala Thr Gly Asn Gly Arg Thr Met Leu Ala
        35                  40                  45

Asn Arg Leu Ser Trp Phe Phe Asp Leu Gln Gly Pro Ser Ile Met Met
 50                  55                  60

Asp Thr Ala Cys Ser Ser Ser Leu
65                  70

<210> SEQ ID NO 143
<211> LENGTH: 83
<212> TYPE: PRT
<213> ORGANISM: Penicillium coprobium PF1169

<400> SEQUENCE: 143

Ala Gln Gln Ser Leu Ile Leu Ala Thr Tyr Ala Arg Ala Gly Leu Ser
1               5                   10                  15

Pro Gln Asn Asn Pro Glu Asp Arg Cys Gln Tyr Phe Glu Ala His Gly
            20                  25                  30

Thr Gly Thr Gln Ala Gly Asp Pro Gln Glu Ala Ala Ile Asn Ser
        35                  40                  45

Ser Phe Phe Gly Pro Glu Ser Val Pro Asp Ser Thr Asp Arg Leu Tyr
50                  55                  60

Val Gly Ser Ile Lys Thr Ile Ile Gly His Thr Glu Ala Thr Ala Gly
65                  70                  75                  80

Leu Ala Gly

<210> SEQ ID NO 144
<211> LENGTH: 69
<212> TYPE: PRT
<213> ORGANISM: Penicillium coprobium PF1169

<400> SEQUENCE: 144

Pro Leu Trp Arg Lys Ile Glu Thr Ala Pro Leu Asn Thr Gly Leu Thr
1               5                   10                  15

His Asp Val Glu Lys His Thr Leu Leu Gly Gln Arg Ile Pro Val Ala
            20                  25                  30

Gly Thr Asp Thr Phe Val Tyr Thr Thr Arg Leu Asp Asn Glu Thr Lys
        35                  40                  45

Pro Phe Pro Gly Ser His Pro Leu His Gly Thr Glu Ile Val Pro Ala
50                  55                  60

Ala Gly Leu Ile Asn
65

<210> SEQ ID NO 145
<211> LENGTH: 64
<212> TYPE: PRT
<213> ORGANISM: Penicillium coprobium PF1169

<400> SEQUENCE: 145

Ala Gly Ile Pro Leu Ala Asn Ile Met Gly Thr Lys Thr Ser Cys Phe
1               5                   10                  15

Val Gly Ser Phe Ser Ala Asp Tyr Thr Asp Leu Leu Leu Arg Asp Pro
            20                  25                  30

Glu Cys Val Pro Met Tyr Gln Cys Thr Asn Ala Gly Gln Ser Arg Ala
        35                  40                  45

Met Thr Ala Asn Arg Leu Ser Tyr Phe Phe Asp Leu Lys Gly Pro Ser
50                  55                  60

<210> SEQ ID NO 146
<211> LENGTH: 81
<212> TYPE: PRT
<213> ORGANISM: Penicillium coprobium PF1169

<400> SEQUENCE: 146

Gly Tyr Gly Arg Gly Glu Gly Val Ala Ser Val Val Leu Lys Arg Leu
1               5                   10                  15

Gln Asp Ala Ile Asn Asp Gly Asp Pro Ile Glu Cys Val Ile Arg Ala
            20                  25                  30

Ser Gly Ala Asn Ser Asp Gly Arg Thr Met Gly Ile Thr Met Pro Asn
        35                  40                  45

Pro Lys Ala Gln Gln Ser Leu Ile Leu Ala Thr Tyr Ala Arg Ala Gly
50                  55                  60

Leu Ser Pro Gln Asn Asn Pro Glu Asp Arg Cys Gln Tyr Phe Glu Ala

```
             65                  70                  75                  80
His

<210> SEQ ID NO 147
<211> LENGTH: 38
<212> TYPE: PRT
<213> ORGANISM: Penicillium coprobium PF1169

<400> SEQUENCE: 147

Gly Thr Gly Asn Gly Ser Ala Met Ile Ser Asn Arg Ile Ser Trp Phe
1               5                   10                  15

Phe Asp Leu Lys Gly Pro Ser Leu Ser Leu Asp Thr Ala Cys Ser Ser
            20                  25                  30

Ser Leu Val Ala Leu His
        35

<210> SEQ ID NO 148
<211> LENGTH: 53
<212> TYPE: PRT
<213> ORGANISM: Penicillium coprobium PF1169

<400> SEQUENCE: 148

Glu Ala Thr Ser Met Asp Ala Gln Gln Arg Lys Leu Leu Glu Val Thr
1               5                   10                  15

Tyr Glu Ala Leu Glu Asn Ala Gly Val Pro Leu Glu Thr Ile Gln Gly
            20                  25                  30

Ser Asn Thr Gly Val Tyr Val Gly Asn Phe Thr Asn Asp Phe Leu Asn
        35                  40                  45

Met Gln Tyr Lys Asp
        50

<210> SEQ ID NO 149
<211> LENGTH: 82
<212> TYPE: PRT
<213> ORGANISM: Penicillium coprobium PF1169

<400> SEQUENCE: 149

Gly Ser Leu Ile Asp Ile Glu Glu Pro Ile Ile Pro Leu Ser Thr Met
1               5                   10                  15

Arg Tyr Ile Gln Gly Ala Asp Ile Val Arg Ile Ser Asp Gly Ile Ala
            20                  25                  30

Arg Thr Ser Arg Phe Arg Ser Leu Pro Arg Thr Lys Leu Arg Pro Val
        35                  40                  45

Ser Asp Gly Pro Arg Leu Leu Pro Arg Pro Glu Gly Thr Tyr Leu Ile
        50                  55                  60

Thr Gly Gly Leu Gly Ile Leu Gly Leu Glu Val Ala Asp Phe Leu Val
65                  70                  75                  80

Glu Lys

<210> SEQ ID NO 150
<211> LENGTH: 65
<212> TYPE: PRT
<213> ORGANISM: Penicillium coprobium PF1169

<400> SEQUENCE: 150

Gln Leu Gly Thr Thr Cys Val Gln Met Ala Leu Thr Lys Tyr Trp Thr
1               5                   10                  15

Ser Leu Gly Val Thr Pro Ser Phe Val Met Gly His Ser Leu Gly Glu
            20                  25                  30
```

```
Phe Ala Ala Leu Asn Ala Ala Gly Val Leu Thr Ile Ser Asp Thr Ile
        35                  40                  45

Tyr Leu Ala Gly Arg Arg Ala Gln Leu Leu Thr Glu Gln Ile Lys Val
50                  55                  60

Gly
65
```

<210> SEQ ID NO 151
<211> LENGTH: 78
<212> TYPE: PRT
<213> ORGANISM: Penicillium coprobium PF1169
<220> FEATURE:
<221> NAME/KEY: misc_feature
<222> LOCATION: (45)..(45)
<223> OTHER INFORMATION: Xaa can be any naturally occurring amino acid

<400> SEQUENCE: 151

```
Gly Pro Arg Leu Leu Pro Arg Pro Glu Gly Thr Tyr Leu Ile Thr Gly
1               5                   10                  15

Gly Leu Gly Ile Leu Gly Leu Glu Val Ala Asp Phe Leu Val Glu Lys
            20                  25                  30

Gly Ala Arg Arg Val Leu Leu Ile Ser Arg Arg Ala Xaa Pro Pro Arg
        35                  40                  45

Arg Thr Trp Asp Gln Val Ala Thr Glu Phe Gln Pro Ala Ile Thr Lys
50                  55                  60

Ile Arg Leu Leu Glu Ser Arg Gly Ala Ser Val Tyr Val Leu
65                  70                  75
```

<210> SEQ ID NO 152
<211> LENGTH: 76
<212> TYPE: PRT
<213> ORGANISM: Penicillium coprobium PF1169

<400> SEQUENCE: 152

```
Gly Pro Ser Met Thr Ile Asp Thr Ala Cys Ser Ser Ser Leu Ile Ala
1               5                   10                  15

Leu His Gln Ala Val Gln Ser Leu Arg Ser Gly Glu Thr Asp Val Ala
            20                  25                  30

Val Ala Ala Gly Thr Asn Leu Leu Leu Gly Pro Glu Gln Tyr Ile Ala
        35                  40                  45

Glu Ser Lys Leu Lys Met Leu Ser Pro Asn Gly Arg Ser Arg Met Trp
50                  55                  60

Asp Lys Asp Ala Asp Gly Tyr Ala Arg Gly Asp Gly
65                  70                  75
```

<210> SEQ ID NO 153
<211> LENGTH: 38
<212> TYPE: PRT
<213> ORGANISM: Penicillium coprobium PF1169

<400> SEQUENCE: 153

```
Asn Arg Ile Ser Tyr Phe Phe Asp Leu Arg Gly Pro Ser Ile Thr Ile
1               5                   10                  15

Asp Thr Ala Cys Ser Ser Ser Leu Val Ala Leu His Tyr Ala Val Gln
            20                  25                  30

Ser Leu Arg Asn Gly Glu
        35
```

<210> SEQ ID NO 154

<211> LENGTH: 74
<212> TYPE: PRT
<213> ORGANISM: Penicillium coprobium PF1169

<400> SEQUENCE: 154

Gly Ser Gly Leu Thr Val Leu Ala Asn Arg Ile Thr His Cys Phe Asp
1               5                   10                  15

Leu Arg Gly Pro Ser His Val Val Asp Thr Ala Cys Ser Ser Ser Leu
            20                  25                  30

Tyr Ala Leu His Ser Ala Cys Leu Ala Leu Asp Ser Arg Asp Cys Asp
        35                  40                  45

Gly Ala Val Val Ala Ala Asn Leu Ile Gln Ser Pro Glu Gln Gln
    50                  55                  60

Met Ile Ala Val Lys Ala Gly Ile Leu Ser
65                  70

<210> SEQ ID NO 155
<211> LENGTH: 57
<212> TYPE: PRT
<213> ORGANISM: Penicillium coprobium PF1169

<400> SEQUENCE: 155

Gln Leu Gly Thr Thr Cys Val Gln Met Ala Leu Thr Lys Tyr Trp Thr
1               5                   10                  15

Ser Leu Gly Val Thr Pro Ser Phe Val Met Gly His Ser Leu Gly Glu
            20                  25                  30

Phe Ala Ala Leu Asn Ala Ala Gly Val Leu Thr Ile Ser Asp Thr Ile
        35                  40                  45

Tyr Leu Ala Gly Arg Arg Ala Gln Leu
    50                  55

<210> SEQ ID NO 156
<211> LENGTH: 72
<212> TYPE: PRT
<213> ORGANISM: Penicillium coprobium PF1169

<400> SEQUENCE: 156

His Leu Asn Leu Met Gly Pro Ser Thr Ala Val Asp Ala Ala Cys Ala
1               5                   10                  15

Ser Ser Leu Val Ala Ile His His Gly Val Gln Ala Ile Lys Leu Gly
            20                  25                  30

Glu Ser Arg Val Ala Ile Val Gly Gly Val Asn Ala Leu Cys Gly Pro
        35                  40                  45

Gly Leu Thr Arg Val Leu Asp Lys Ala Gly Ser Ile Ser Ser Asp Gly
    50                  55                  60

Ser Cys Lys Ser Phe Asp Asp Asp
65                  70

<210> SEQ ID NO 157
<211> LENGTH: 81
<212> TYPE: PRT
<213> ORGANISM: Penicillium coprobium PF1169

<400> SEQUENCE: 157

Leu Lys Gly Thr Gly Gly Gln Met Leu Gln Asn Val Val Leu Arg Val
1               5                   10                  15

Pro Val Ala Ile Asn Ala Pro Arg Ser Val Gln Val Val Gln Gln
            20                  25                  30

Asp Gln Val Lys Val Val Ser Arg Leu Ile Pro Ser Glu Ala Ser Val

```
              35                  40                  45

Leu Asp Asp Ala Ser Trp Val Thr His Thr Thr Ala Tyr Trp Asp
 50                  55                  60

Arg Arg Val Leu Gly Ser Glu Asp Arg Ile Asp Leu Ala Ala Val Lys
 65                  70                  75                  80

Ser

<210> SEQ ID NO 158
<211> LENGTH: 82
<212> TYPE: PRT
<213> ORGANISM: Penicillium coprobium PF1169

<400> SEQUENCE: 158

Ile Met Gly Thr Lys Thr Ser Cys Phe Val Gly Ser Phe Ser Ala Asp
 1               5                  10                  15

Tyr Thr Asp Leu Leu Arg Asp Pro Glu Cys Val Pro Met Tyr Gln
                 20                  25                  30

Cys Thr Asn Ala Gly Gln Ser Arg Ala Met Thr Ala Asn Arg Leu Ser
                 35                  40                  45

Tyr Phe Phe Asp Leu Lys Gly Pro Ser Val Thr Val Asp Thr Ala Cys
 50                  55                  60

Ser Gly Ser Leu Val Ala Leu His Leu Ala Cys Gln Ser Leu Arg Thr
 65                  70                  75                  80

Gly Asp

<210> SEQ ID NO 159
<211> LENGTH: 75
<212> TYPE: PRT
<213> ORGANISM: Penicillium coprobium PF1169

<400> SEQUENCE: 159

Gly Ser Gly Leu Thr Val Leu Ala Asn Arg Ile Thr His Cys Phe Asp
 1               5                  10                  15

Leu Arg Gly Pro Ser His Val Val Asp Thr Ala Cys Ser Ser Ser Leu
                 20                  25                  30

Tyr Ala Leu His Ser Ala Cys Phe Gly Pro Leu Asn Ser Arg Asp Cys
                 35                  40                  45

Asp Gly Ala Val Val Ala Ala Asn Leu Ile Gln Ser Pro Glu Gln
 50                  55                  60

Gln Met Ile Ala Val Lys Arg Asp Ser Ile Ala
 65                  70                  75

<210> SEQ ID NO 160
<211> LENGTH: 28
<212> TYPE: PRT
<213> ORGANISM: Penicillium coprobium PF1169

<400> SEQUENCE: 160

Pro Trp Pro Thr Thr Gly Leu Arg Arg Ala Ser Val Asn Ser Phe Gly
 1               5                  10                  15

Tyr Gly Gly Thr Asn Ala His Cys Val Leu Asp Asp
                 20                  25

<210> SEQ ID NO 161
<211> LENGTH: 64
<212> TYPE: PRT
<213> ORGANISM: Penicillium coprobium PF1169

<400> SEQUENCE: 161
```

```
Gln Leu Gly Thr Thr Cys Val Gln Met Ala Leu Thr Lys Tyr Trp Thr
1               5                   10                  15

Ser Leu Gly Val Thr Pro Ser Phe Val Met Gly His Ser Leu Gly Glu
            20                  25                  30

Phe Ala Ala Leu Asn Ala Ala Gly Val Leu Thr Ile Ser Asp Thr Ile
        35                  40                  45

Tyr Leu Ala Gly Arg Arg Ala Gln Leu Leu Thr Glu Gln Ile Glu Gly
50                  55                  60
```

<210> SEQ ID NO 162
<211> LENGTH: 60
<212> TYPE: PRT
<213> ORGANISM: Penicillium coprobium PF1169

<400> SEQUENCE: 162

```
Ile Ala Pro Asn Ile His Phe Lys Met Pro Asn Pro Gln Ile Pro Phe
1               5                   10                  15

Asn Glu Ala Asn Leu His Val Pro Leu Glu Pro Thr Pro Trp Pro Ala
            20                  25                  30

Gly Arg Pro Glu Arg Ile Ser Val Asn Ser Phe Gly Ile Gly Gly Ser
        35                  40                  45

Asn Ala His Ala Ile Leu Glu Ser Ala Ser Thr Val
50                  55                  60
```

<210> SEQ ID NO 163
<211> LENGTH: 34
<212> TYPE: PRT
<213> ORGANISM: Penicillium coprobium PF1169

<400> SEQUENCE: 163

```
Gly Leu Val Asn Ile Leu Arg Ser Trp Gly Ile Glu Pro Ser Thr Val
1               5                   10                  15

Val Gly His Ser Ser Gly Glu Ile Val Ala Ala Tyr Thr Ala Arg Ala
            20                  25                  30

Ile Ser
```

<210> SEQ ID NO 164
<211> LENGTH: 51
<212> TYPE: PRT
<213> ORGANISM: Penicillium coprobium PF1169

<400> SEQUENCE: 164

```
Pro Trp Pro Ser Glu Gly Leu Arg Arg Ile Ser Val Asn Ser Phe Gly
1               5                   10                  15

Phe Gly Gly Ser Asn Thr His Val Ile Leu Asp Asp Ala Leu His Tyr
            20                  25                  30

Met Gln Gln Arg Gly Leu Thr Gly Asn His Cys Thr Ala Arg Leu Pro
        35                  40                  45

Gly Ile Leu
        50
```

<210> SEQ ID NO 165
<211> LENGTH: 71
<212> TYPE: PRT
<213> ORGANISM: Penicillium coprobium PF1169
<220> FEATURE:
<221> NAME/KEY: misc_feature
<222> LOCATION: (5)..(5)
<223> OTHER INFORMATION: Xaa can be any naturally occurring amino acid

<400> SEQUENCE: 165

Ile Gly His Thr Xaa Gly Ser Ala Gly Leu Ala Ser Leu Ile Gly Ser
1               5                   10                  15

Ser Leu Ala Met Lys His Gly Val Ile Pro Pro Asn Leu His Phe Gly
                20                  25                  30

Gln Leu Ser Glu Lys Val Ala Pro Phe Tyr Thr His Leu Asn Ile Pro
            35                  40                  45

Thr Glu Pro Val Pro Trp Pro Asn Ser Thr Ser Ser Gln Val Lys Arg
        50                  55                  60

Ala Ser Ile Asn Ser Phe Gly
65                  70

<210> SEQ ID NO 166
<211> LENGTH: 74
<212> TYPE: PRT
<213> ORGANISM: Penicillium coprobium PF1169

<400> SEQUENCE: 166

Gly Ser Asn Thr Ala Val Tyr Ser Gly Ser Met Thr Asn Asp Tyr Glu
1               5                   10                  15

Leu Leu Ser Thr Arg Asp Ile Tyr Asp Met Pro His Asn Ser Ala Thr
                20                  25                  30

Gly Asn Gly Arg Thr Met Leu Ala Asn Arg Leu Ser Trp Phe Phe Asp
            35                  40                  45

Leu Gln Gly Pro Ser Ile Met Met Asp Thr Ala Cys Ser Ser Ser Leu
        50                  55                  60

Thr Ala Val His Leu Ala Ala Gln Ser Leu
65                  70

<210> SEQ ID NO 167
<211> LENGTH: 85
<212> TYPE: PRT
<213> ORGANISM: Penicillium coprobium PF1169

<400> SEQUENCE: 167

Asp Ala Gln Phe Phe Gly Thr Lys Pro Val Glu Ala Asn Ser Ile Asp
1               5                   10                  15

Pro Gln Gln Arg Leu Leu Leu Glu Thr Val Tyr Glu Gly Leu Glu Thr
                20                  25                  30

Ser Gly Ile Pro Met Glu Arg Leu Gln Gly Ser Asn Thr Ala Val Tyr
            35                  40                  45

Val Gly Leu Met Thr Asn Asp Tyr Ala Asp Met Leu Gly Arg Asp Met
        50                  55                  60

Gln Asn Phe Pro Thr Tyr Phe Ala Ser Gly Thr Ala Arg Ser Ile Leu
65                  70                  75                  80

Ser Asn Arg Val Ser
                85

<210> SEQ ID NO 168
<211> LENGTH: 60
<212> TYPE: PRT
<213> ORGANISM: Penicillium coprobium PF1169

<400> SEQUENCE: 168

Val Val Ala Cys Val Asn Ser Pro Ala Ser Thr Thr Leu Ser Gly Asp
1               5                   10                  15

Val Asp Tyr Ile Asn Gln Leu Glu Ala Arg Leu Gln Gln Asp Gly His
                20                  25                  30

Phe Ala Arg Lys Leu Arg Ile Asp Thr Ala Tyr His Ser Pro His Met
            35                  40                  45

Glu Glu Leu Val Gly Val Val Gly Asp Ala Ile Ser
 50                  55                  60

<210> SEQ ID NO 169
<211> LENGTH: 56
<212> TYPE: PRT
<213> ORGANISM: Penicillium coprobium PF1169

<400> SEQUENCE: 169

Phe Tyr Gly Met Thr Ser Asp Asp Tyr Arg Glu Val Asn Ser Gly Gln
 1               5                  10                  15

Asp Ile Asp Thr Tyr Phe Ile Pro Gly Gly Asn Arg Ala Phe Thr Pro
            20                  25                  30

Gly Arg Ile Asn Tyr Tyr Phe Lys Phe Ser Gly Pro Ser Val Ser Val
        35                  40                  45

Asp Thr Ala Cys Ser Ser Ser Leu
 50                  55

<210> SEQ ID NO 170
<211> LENGTH: 53
<212> TYPE: PRT
<213> ORGANISM: Penicillium coprobium PF1169

<400> SEQUENCE: 170

Val Ala Ile Val Gly Gly Val Asn Ala Leu Cys Gly Pro Gly Leu Thr
 1               5                  10                  15

Arg Val Leu Asp Lys Ala Gly Ala Ile Ser Ser Asp Gly Ser Cys Lys
            20                  25                  30

Ser Phe Asp Asp Asp Ala His Gly Tyr Ala Arg Gly Glu Gly Ala Gly
        35                  40                  45

Ala Leu Val Thr Lys
 50

<210> SEQ ID NO 171
<211> LENGTH: 40
<212> TYPE: PRT
<213> ORGANISM: Penicillium coprobium PF1169

<400> SEQUENCE: 171

Gln Leu Gly Thr Thr Cys Val Gln Met Ala Leu Thr Lys Tyr Trp Thr
 1               5                  10                  15

Ser Leu Gly Val Thr Pro Ser Phe Val Met Gly His Ser Leu Gly Glu
            20                  25                  30

Phe Ala Ala Leu Asn Ala Ala Gly
        35                  40

<210> SEQ ID NO 172
<211> LENGTH: 69
<212> TYPE: PRT
<213> ORGANISM: Penicillium coprobium PF1169

<400> SEQUENCE: 172

Arg Glu Trp Met Thr Ala Glu Gly Lys Asp His Asn Leu Ser Asp Ile
 1               5                  10                  15

Leu Thr Thr Leu Ala Thr Arg Arg Asp His His Asp Tyr Arg Ala Ala
            20                  25                  30

Leu Val Val Asp Asp Asn Arg Asp Ala Glu Leu Ala Leu Gln Ala Leu 35                  40                  45

Glu His Gly Val Asp Gln Thr Phe Thr Thr Gln Ser Arg Val Phe Gly
                50                  55                  60

Ala Asp Ile Ser Lys
65

<210> SEQ ID NO 173
<211> LENGTH: 51
<212> TYPE: PRT
<213> ORGANISM: Penicillium coprobium PF1169

<400> SEQUENCE: 173

Pro Trp Pro Ser Glu Gly Leu Arg Arg Ile Ser Val Asn Ser Phe Gly
1               5                   10                  15

Phe Gly Gly Ser Asn Thr His Val Ile Leu Asp Asp Ala Leu His Tyr
                20                  25                  30

Met Gln Gln Arg Gly Leu Thr Gly Asn His Cys Thr Ala Arg Leu Pro
            35                  40                  45

Gly Ile Leu
    50

<210> SEQ ID NO 174
<211> LENGTH: 71
<212> TYPE: PRT
<213> ORGANISM: Penicillium coprobium PF1169

<400> SEQUENCE: 174

Phe Val Glu Met His Gly Thr Gly Thr Lys Ala Gly Asp Pro Val Glu
1               5                   10                  15

Ala Ala Ala Val His Ala Ala Leu Gly Lys Asn Arg Thr Leu Arg Asn
                20                  25                  30

Pro Leu Tyr Ile Gly Ser Val Lys Ser Asn Ile Gly His Leu Glu Gly
            35                  40                  45

Ala Ser Gly Ile Val Ala Val Ile Lys Ala Ala Met Met Leu Asp Arg
        50                  55                  60

Asp Leu Met Leu Pro Asn Ala
65                  70

<210> SEQ ID NO 175
<211> LENGTH: 41
<212> TYPE: PRT
<213> ORGANISM: Penicillium coprobium PF1169

<400> SEQUENCE: 175

Leu Ala Ile Val Gly Met Ala Cys Arg Leu Pro Gly Gln Ile Thr Thr
1               5                   10                  15

Pro Gln Glu Leu Trp Glu Leu Cys Ser Arg Gly Arg Ser Ala Trp Ser
                20                  25                  30

Glu Ile Pro Pro Glu Arg Phe Asn Pro
            35                  40

<210> SEQ ID NO 176
<211> LENGTH: 64
<212> TYPE: PRT
<213> ORGANISM: Penicillium coprobium PF1169

<400> SEQUENCE: 176

Gln Leu Gly Thr Thr Cys Val Gln Met Ala Leu Thr Lys Tyr Trp Thr
1               5                   10                  15

```
Ser Leu Gly Val Thr Pro Ser Phe Val Met Gly His Ser Leu Gly Glu
            20                  25                  30

Phe Ala Ala Leu Asn Ala Ala Gly Val Leu Thr Ile Ser Asp Thr Ile
        35                  40                  45

Tyr Leu Ala Gly Arg Arg Ala Gln Leu Leu Thr Glu Gln Ile Glu Gly
    50                  55                  60

<210> SEQ ID NO 177
<211> LENGTH: 74
<212> TYPE: PRT
<213> ORGANISM: Penicillium coprobium PF1169

<400> SEQUENCE: 177

Gly Ala Ser Val Tyr Val Leu Ala Leu Asp Ile Thr Lys Pro Asp Ala
1               5                   10                  15

Val Glu Gln Leu Ser Thr Ala Leu Asp Arg Leu Ala Leu Pro Ser Val
            20                  25                  30

Gln Gly Val Val His Ala Ala Gly Val Leu Asp Asn Glu Leu Val Met
        35                  40                  45

Gln Thr Thr Gln Glu Ala Phe Asn Arg Val Leu Ala Pro Lys Ile Ala
    50                  55                  60

Gly Ala Leu Ala Leu His Glu Pro Phe Pro
65                  70

<210> SEQ ID NO 178
<211> LENGTH: 72
<212> TYPE: PRT
<213> ORGANISM: Penicillium coprobium PF1169

<400> SEQUENCE: 178

Gly Leu Val Asn Ile Leu Arg Ser Trp Gly Ile Glu Pro Ser Thr Val
1               5                   10                  15

Val Gly His Ser Ser Gly Glu Ile Val Ala Ala Tyr Thr Ala Arg Ala
            20                  25                  30

Ile Ser Met Arg Thr Ala Ile Ile Leu Ala Tyr Tyr Arg Gly Lys Val
        35                  40                  45

Ala Gln Pro Leu Glu Gly Leu Gly Ala Met Val Ala Val Gly Leu Ser
    50                  55                  60

Pro Asp Glu Val Ala Gln Tyr Met
65                  70

<210> SEQ ID NO 179
<211> LENGTH: 70
<212> TYPE: PRT
<213> ORGANISM: Penicillium coprobium PF1169

<400> SEQUENCE: 179

Gly Arg Phe Leu Ser Ser Asp Gly Arg Cys His Thr Phe Asp Glu Lys
1               5                   10                  15

Ala Asn Gly Tyr Ala Arg Gly Glu Ala Val Gly Cys Leu Ile Leu Lys
            20                  25                  30

Pro Leu Ala Lys Ala Leu His Asp Gln Asn Lys Ile Arg Ala Val Ile
        35                  40                  45

Arg Gly Thr Gly Ser Asn Gln Asp Gly Arg Thr Ala Gly Ile Thr Val
    50                  55                  60

Pro Asn Gly Ala Ala Gln
65                  70
```

```
<210> SEQ ID NO 180
<211> LENGTH: 51
<212> TYPE: PRT
<213> ORGANISM: Penicillium coprobium PF1169

<400> SEQUENCE: 180
```

Ser Ser Phe Leu Thr Ser Thr Val Gln Gln Ile Val Glu Glu Thr Ile
1               5                   10                  15

Gln Gly Gly Thr Gly Gln Val Val Met Glu Ser Asp Leu Met Gln Thr
            20                  25                  30

Glu Phe Leu Glu Ala Ala Asn Gly His Arg Met Asn Asp Cys Gly Val
        35                  40                  45

Val Thr Ser
    50

```
<210> SEQ ID NO 181
<211> LENGTH: 64
<212> TYPE: PRT
<213> ORGANISM: Penicillium coprobium PF1169

<400> SEQUENCE: 181
```

Leu Leu Gly Leu Arg Leu Lys Trp Lys Glu Tyr His Gln Asp Phe Asn
1               5                   10                  15

Ala Ala His Arg Val Leu Pro Leu Pro Ser Tyr Lys Trp Asp Leu Lys
            20                  25                  30

Asn Tyr Trp Ile Pro Tyr Thr Asn Asn Phe Cys Leu Leu Lys Gly Ala
        35                  40                  45

Pro Ala Ala Pro Val Ala Glu Ala Thr Pro Ile Ser Val Phe Leu Ser
    50                  55                  60

```
<210> SEQ ID NO 182
<211> LENGTH: 26
<212> TYPE: PRT
<213> ORGANISM: Penicillium coprobium PF1169

<400> SEQUENCE: 182
```

Ser Phe Arg Arg Gln Glu Asp Thr Trp Lys Val Leu Ser Asn Ala Thr
1               5                   10                  15

Ser Thr Leu Tyr Leu Ala Gly Ile Glu Ile
            20                  25

```
<210> SEQ ID NO 183
<211> LENGTH: 65
<212> TYPE: PRT
<213> ORGANISM: Penicillium coprobium PF1169

<400> SEQUENCE: 183
```

Ala Gly Gly Asn Thr Thr Val Ala Leu Glu Asp Ala Pro Ile Arg Thr
1               5                   10                  15

Arg Ser Gly Ser Asp Pro Arg Ser Leu His Pro Ile Ala Ile Ser Ala
            20                  25                  30

Lys Ser Lys Val Ser Leu Arg Gly Asn Leu Glu Asn Leu Leu Ala Tyr
        35                  40                  45

Leu Asp Thr His Pro Asp Val Ser Leu Ser Asp Leu Ser Tyr Thr Thr
    50                  55                  60

Thr
65

```
<210> SEQ ID NO 184
<211> LENGTH: 96
```

```
<212> TYPE: PRT
<213> ORGANISM: Penicillium coprobium PF1169

<400> SEQUENCE: 184

Phe Asp Ala Ala Phe Asn Met Ser Pro Arg Glu Ala Gln Gln Thr
1               5                   10                  15

Asp Pro Met Gln Arg Leu Ala Ile Val Thr Ala Tyr Glu Ala Leu Glu
            20                  25                  30

Arg Ala Gly Tyr Val Ala Asn Arg Thr Ala Ala Thr Asn Leu His Arg
        35                  40                  45

Ile Gly Thr Phe Tyr Gly Gln Ala Ser Asp Asp Tyr Arg Glu Val Asn
    50                  55                  60

Thr Ala Gln Glu Ile Ser Thr Tyr Phe Ile Pro Gly Gly Cys Arg Ala
65                  70                  75                  80

Phe Gly Pro Gly Arg Ile Asn Tyr Phe Lys Phe Leu Gly Pro Ala
                85                  90                  95

<210> SEQ ID NO 185
<211> LENGTH: 58
<212> TYPE: PRT
<213> ORGANISM: Penicillium coprobium PF1169

<400> SEQUENCE: 185

Phe Leu Gln Ile Ser Gly Pro Ser Phe Ser Ile Asp Thr Ala Cys Ser
1               5                   10                  15

Ser Ser Leu Ala Thr Ile Gln Val Cys Thr His Leu Phe His Val His
            20                  25                  30

Leu Asn Arg Gln Leu Thr Ile Ala Ala Cys Thr Ser Leu Trp Asn Gly
        35                  40                  45

Glu Thr Asp Thr Val Val Ala Gly Gly Met
    50                  55

<210> SEQ ID NO 186
<211> LENGTH: 59
<212> TYPE: PRT
<213> ORGANISM: Penicillium coprobium PF1169

<400> SEQUENCE: 186

Val Tyr Ser Gly Ser Met Thr Asn Asp Tyr Glu Leu Leu Ser Thr Arg
1               5                   10                  15

Asp Ile Tyr Asp Met Pro His Asn Ser Ala Thr Gly Asn Gly Arg Thr
            20                  25                  30

Met Leu Ala Asn Arg Leu Ser Trp Phe Phe Asp Leu Gln Gly Pro Ser
        35                  40                  45

Ile Met Met Asp Thr Ala Cys Ser Ser Ser Leu
    50                  55

<210> SEQ ID NO 187
<211> LENGTH: 31
<212> TYPE: PRT
<213> ORGANISM: Penicillium coprobium PF1169

<400> SEQUENCE: 187

Leu Phe Leu Phe Pro Asp Gly Ser Gly Ser Ala Thr Ser Tyr Ala Thr
1               5                   10                  15

Ile Pro Gly Ile Ser Pro Asp Val Cys Val Tyr Gly Leu Asn Cys
            20                  25                  30

<210> SEQ ID NO 188
```

<211> LENGTH: 26
<212> TYPE: PRT
<213> ORGANISM: Penicillium coprobium PF1169

<400> SEQUENCE: 188

Ala Lys His Pro Pro Ala Thr Ser Ile Leu Leu Gln Gly Asn Pro Lys
1               5                   10                  15

Thr Ala Thr Gln Ser Phe Ile Phe Val Pro
            20                  25

<210> SEQ ID NO 189
<211> LENGTH: 38
<212> TYPE: PRT
<213> ORGANISM: Penicillium coprobium PF1169

<400> SEQUENCE: 189

Gly Asn Gly Ser Ala Met Ile Ser Asn Arg Ile Ser Trp Phe Phe Asp
1               5                   10                  15

Leu Lys Gly Pro Ser Leu Ser Leu Asp Thr Ala Cys Ser Ser Ser Leu
            20                  25                  30

Val Ala Leu His Leu Ala
            35

<210> SEQ ID NO 190
<211> LENGTH: 76
<212> TYPE: PRT
<213> ORGANISM: Penicillium coprobium PF1169

<400> SEQUENCE: 190

Ala Ile His His Gly Val Gln Ala Ile Lys Leu Gly Glu Ser Arg Val
1               5                   10                  15

Ala Ile Val Gly Gly Val Asn Ala Leu Cys Gly Pro Gly Leu Thr Arg
            20                  25                  30

Val Leu Asp Lys Ala Gly Ala Ile Ser Ser Asp Gly Ser Cys Lys Ser
        35                  40                  45

Phe Asp Asp Asp Ala His Gly Tyr Ala Arg Gly Glu Gly Ala Gly Ala
    50                  55                  60

Leu Val Leu Lys Ser Leu His Gln Ala Leu Leu Asp
65                  70                  75

<210> SEQ ID NO 191
<211> LENGTH: 65
<212> TYPE: PRT
<213> ORGANISM: Penicillium coprobium PF1169

<400> SEQUENCE: 191

Val Trp Ile Glu Ile Gly Pro His Pro Val Cys Leu Gly Phe Val Lys
1               5                   10                  15

Ala Thr Leu Glu Ser Val Ala Val Ala Val Pro Ser Leu Arg Arg Gly
            20                  25                  30

Glu Asn Ala Trp Cys Thr Leu Ala Gln Ser Leu Thr Thr Leu His Asn
        35                  40                  45

Ala Gly Val Pro Val Gly Trp Ser Glu Phe His Arg Pro Phe Glu Arg
    50                  55                  60

Ala
65

<210> SEQ ID NO 192
<211> LENGTH: 53
<212> TYPE: PRT

<213> ORGANISM: Penicillium coprobium PF1169

<400> SEQUENCE: 192

Thr Ser Asp Asp Tyr Arg Glu Val Asn Ser Gly Gln Asp Ile Asp Thr
1               5                   10                  15
Tyr Phe Ile Pro Gly Gly Asn Arg Ala Phe Thr Pro Gly Arg Ile Asn
            20                  25                  30
Tyr Tyr Phe Lys Phe Ser Gly Pro Ser Val Ser Val Asp Thr Ala Cys
        35                  40                  45
Ser Ser Ser Leu Ala
        50

<210> SEQ ID NO 193
<211> LENGTH: 40
<212> TYPE: PRT
<213> ORGANISM: Penicillium coprobium PF1169

<400> SEQUENCE: 193

Val Asp Thr Ala Cys Ser Ser Leu Tyr Ala Leu His Ser Ala Cys
1               5                   10                  15
Phe Gly Pro Leu Asn Ser Arg Asp Cys Asp Gly Ala Val Val Ala Ala
            20                  25                  30
Ala Asn Leu Ile Gln Ser Pro Glu
        35                  40

<210> SEQ ID NO 194
<211> LENGTH: 68
<212> TYPE: PRT
<213> ORGANISM: Penicillium coprobium PF1169

<400> SEQUENCE: 194

Met Leu Ala Val Gly Ala Ser Ala Ser Asp Ile Gln Gln Ile Leu Asp
1               5                   10                  15
Ala Met Arg Gly Asn Lys Ala Val Ile Ala Cys Val Asn Ser Glu Ser
            20                  25                  30
Ser Val Thr Leu Ser Gly Asp Leu Asp Val Ile Ala Asn Leu Gln Thr
        35                  40                  45
Ala Leu Asp Lys Glu Gly Ile Phe Thr Arg Lys Leu Lys Val Asp Val
    50                  55                  60
Ala Tyr His Ser
65

<210> SEQ ID NO 195
<211> LENGTH: 62
<212> TYPE: PRT
<213> ORGANISM: Penicillium coprobium PF1169

<400> SEQUENCE: 195

Phe Leu Asp Asp Leu Ala Phe Thr Val Asn Glu Arg Arg Ser Ile Phe
1               5                   10                  15
Pro Trp Lys Ala Ala Val Val Gly Asp Thr Met Glu Gly Leu Ala Ala
            20                  25                  30
Ser Leu Ala Gln Asn Ile Lys Pro Arg Ser Val Leu Arg Met Pro Thr
        35                  40                  45
Leu Gly Phe Val Phe Thr Gly Gln Gly Ala Gln Trp Pro Gly
    50                  55                  60

<210> SEQ ID NO 196
<211> LENGTH: 76

<212> TYPE: PRT
<213> ORGANISM: Penicillium coprobium PF1169

<400> SEQUENCE: 196

Gly Pro Ser Met Thr Ile Asp Thr Ala Cys Ser Ser Ser Leu Ile Ala
1               5                   10                  15

Leu His Gln Ala Val Gln Ser Leu Arg Ser Gly Glu Thr Asp Val Ala
            20                  25                  30

Val Ala Ala Gly Thr Asn Leu Leu Leu Gly Pro Glu Gln Tyr Ile Ala
        35                  40                  45

Glu Ser Lys Leu Lys Met Leu Ser Pro Asn Gly Arg Ser Arg Met Trp
    50                  55                  60

Asp Lys Asp Ala Asp Gly Tyr Ala Arg Gly Asp Gly
65                  70                  75

<210> SEQ ID NO 197
<211> LENGTH: 79
<212> TYPE: PRT
<213> ORGANISM: Penicillium coprobium PF1169

<400> SEQUENCE: 197

Ser Val Pro Ile Glu Glu His Ser Pro Val Val Thr Gln Leu Gly Thr
1               5                   10                  15

Thr Cys Val Gln Met Ala Leu Thr Lys Tyr Trp Thr Ser Leu Gly Val
            20                  25                  30

Thr Pro Ser Phe Val Met Gly His Ser Leu Gly Glu Phe Ala Ala Leu
        35                  40                  45

Asn Ala Ala Gly Val Leu Thr Ile Ser Asp Thr Ile Tyr Leu Ala Gly
    50                  55                  60

Arg Arg Ala Gln Leu Leu Thr Glu Gln Ile Glu Gly Gly Thr His
65                  70                  75

<210> SEQ ID NO 198
<211> LENGTH: 40
<212> TYPE: PRT
<213> ORGANISM: Penicillium coprobium PF1169

<400> SEQUENCE: 198

Phe Asn Leu Lys Gly Ile Ser Gln Ser Ile Ala Ser Ala Cys Ala Thr
1               5                   10                  15

Ser Ala Asp Ala Ile Gly Tyr Ala Phe His Leu Ile Ala Ala Gly Lys
            20                  25                  30

Gln Asp Leu Met Leu Ala Gly Gly
        35                  40

<210> SEQ ID NO 199
<211> LENGTH: 70
<212> TYPE: PRT
<213> ORGANISM: Penicillium coprobium PF1169

<400> SEQUENCE: 199

Gly Arg Phe Leu Ser Ser Asp Gly Arg Cys His Thr Phe Asp Glu Lys
1               5                   10                  15

Ala Asn Gly Tyr Ala Arg Gly Glu Ala Val Gly Cys Leu Ile Leu Lys
            20                  25                  30

Pro Leu Ala Lys Ala Leu His Asp Gln Asn Lys Ile Arg Ala Val Ile
        35                  40                  45

Arg Gly Thr Gly Ser Asn Gln Asp Gly Arg Thr Ala Gly Ile Thr Val
    50                  55                  60

Pro Asn Gly Ala Ala Gln
65                  70

<210> SEQ ID NO 200
<211> LENGTH: 284
<212> TYPE: PRT
<213> ORGANISM: Penicillium coprobium PF1169

<400> SEQUENCE: 200

Leu Ser Val Lys Arg Val Gly Ile His Asp Asp Phe Phe Glu Leu Gly
1               5                   10                  15

Gly His Ser Leu Leu Ala Val Lys Leu Val Asn His Leu Lys Lys Val
            20                  25                  30

Phe Gly Thr Glu Leu Ser Val Ala Leu Leu Ala Gln Tyr Ser Thr Val
        35                  40                  45

Glu Ser Leu Gly Glu Ile Ile Arg Glu Asn Lys Glu Ile Lys Pro Ser
    50                  55                  60

Ile Val Ile Glu Leu Arg Ser Gly Thr Tyr Gln Pro Leu Trp Leu
65                  70                  75                  80

Phe His Pro Ile Gly Gly Ser Thr Phe Cys Tyr Met Glu Leu Ser Arg
                85                  90                  95

His Leu Asn Pro Asn Arg Thr Leu Arg Ala Ile Gln Ser Pro Gly Leu
            100                 105                 110

Ile Glu Ala Asp Ala Ala Glu Val Ala Ile Glu Met Ala Thr Leu
        115                 120                 125

Tyr Ile Ala Glu Met Gln Lys Met Gln Pro Gln Gly Pro Tyr Phe Leu
130                 135                 140

Gly Gly Trp Cys Phe Gly Gly Ala Ile Ala Tyr Glu Ile Ser Arg Gln
145                 150                 155                 160

Leu Arg Gln Met Gly Gln Gln Val Thr Gly Ile Val Met Ile Asp Thr
                165                 170                 175

Arg Ala Pro Ile Pro Glu Asn Val Pro Glu Asp Ala Asp Asp Ala Met
            180                 185                 190

Leu Leu Ser Trp Phe Ala Arg Asp Leu Ala Val Pro Tyr Gly Lys Lys
        195                 200                 205

Leu Thr Ile Ser Ala Gln Tyr Leu Arg Glu Leu Ser Pro Asp His Met
    210                 215                 220

Phe Asp His Val Leu Lys Glu Ala Lys Ala Ile Asn Val Ile Pro Leu
225                 230                 235                 240

Asp Ala Asn Pro Ser Asp Phe Arg Leu Tyr Phe Asp Thr Tyr Leu Ala
                245                 250                 255

Asn Gly Val Ala Leu Gln Thr Tyr Phe Pro Glu Pro Glu Asp Phe Pro
            260                 265                 270

Ile Leu Leu Val Lys Ala Lys Asp Glu Ser Glu Asp
        275                 280

<210> SEQ ID NO 201
<211> LENGTH: 73
<212> TYPE: PRT
<213> ORGANISM: Penicillium coprobium PF1169

<400> SEQUENCE: 201

Pro Met Asn Lys Asp Lys Val Tyr Trp Ser Ala Ile Ile Arg Thr Leu
1               5                   10                  15

Val Ala Lys Glu Met Arg Val Glu Pro Glu Thr Ile Asp Pro Glu Gln
            20                  25                  30

```
Lys Phe Thr Thr Tyr Gly Leu Asp Ser Ile Val Ala Leu Ser Val Ser
            35                  40                  45

Gly Asp Leu Glu Asp Leu Thr Lys Leu Glu Leu Glu Pro Thr Leu Leu
 50                  55                  60

Trp Asp Tyr Pro Thr Ile Asn Ala Leu
 65                  70

<210> SEQ ID NO 202
<211> LENGTH: 63
<212> TYPE: PRT
<213> ORGANISM: Penicillium coprobium PF1169

<400> SEQUENCE: 202

Gly Ser Leu Ile Asp Ile Glu Glu Pro Ile Ile Pro Leu Ser Thr Met
 1               5                  10                  15

Arg Tyr Ile Gln Gly Ala Asp Ile Val Arg Ile Ser Asp Gly Ile Ala
            20                  25                  30

Arg Thr Ser Arg Phe Arg Ser Leu Pro Arg Thr Lys Leu Arg Pro Val
        35                  40                  45

Ser Asp Gly Pro Arg Leu Leu Pro Arg Pro Glu Gly Thr Tyr Leu
 50                  55                  60

<210> SEQ ID NO 203
<211> LENGTH: 69
<212> TYPE: PRT
<213> ORGANISM: Penicillium coprobium PF1169

<400> SEQUENCE: 203

Leu Glu Val Val Trp Glu Cys Leu Glu Asn Ser Gly Glu Thr Gln Trp
 1               5                  10                  15

Arg Gly Lys Glu Ile Gly Cys Phe Val Gly Val Phe Gly Glu Asp Trp
            20                  25                  30

Leu Glu Met Ser His Lys Asp Pro Gln His Leu Asn Gln Met Phe Pro
        35                  40                  45

Ile Ala Thr Gly Gly Phe Ala Leu Ala Asn Gln Val Ser Tyr Arg Phe
 50                  55                  60

Asp Leu Thr Gly Pro
 65

<210> SEQ ID NO 204
<211> LENGTH: 96
<212> TYPE: PRT
<213> ORGANISM: Penicillium coprobium PF1169

<400> SEQUENCE: 204

Phe Asp Ala Ala Phe Phe Asn Met Ser Pro Arg Glu Ala Gln Gln Thr
 1               5                  10                  15

Asp Pro Met Gln Arg Leu Ala Ile Val Thr Ala Tyr Glu Ala Leu Glu
            20                  25                  30

Arg Ala Gly Tyr Val Ala Asn Arg Thr Ala Ala Thr Asn Leu His Arg
        35                  40                  45

Ile Gly Thr Phe Tyr Gly Gln Ala Ser Asp Asp Tyr Arg Glu Val Asn
 50                  55                  60

Thr Ala Gln Glu Ile Ser Thr Tyr Phe Ile Pro Gly Gly Cys Arg Ala
 65                  70                  75                  80

Phe Gly Pro Gly Arg Ile Asn Tyr Phe Phe Lys Phe Leu Gly Pro Ala
                85                  90                  95
```

<210> SEQ ID NO 205
<211> LENGTH: 58
<212> TYPE: PRT
<213> ORGANISM: Penicillium coprobium PF1169

<400> SEQUENCE: 205

Phe Leu Gln Ile Ser Gly Pro Ser Phe Ser Ile Asp Thr Ala Cys Ser
1               5                   10                  15

Ser Ser Leu Ala Thr Ile Gln Val Cys Thr His Leu Phe His Val His
            20                  25                  30

Leu Asn Arg Gln Leu Thr Ile Ala Ala Cys Thr Ser Leu Trp Asn Gly
        35                  40                  45

Glu Thr Asp Thr Val Val Ala Gly Gly Met
    50                  55

<210> SEQ ID NO 206
<211> LENGTH: 52
<212> TYPE: PRT
<213> ORGANISM: Penicillium coprobium PF1169

<400> SEQUENCE: 206

Glu Leu Arg His Gly Lys Asn Ile Asp Lys Pro Glu Tyr Ser Gln Pro
1               5                   10                  15

Leu Cys Thr Ala Ile Gln Ile Ala Leu Val Glu Leu Leu Glu Ser Phe
            20                  25                  30

Gly Val Val Pro Lys Ala Val Val Gly His Ser Ser Gly Glu Ile Ala
        35                  40                  45

Ala Ala Tyr Val
    50

<210> SEQ ID NO 207
<211> LENGTH: 59
<212> TYPE: PRT
<213> ORGANISM: Penicillium coprobium PF1169

<400> SEQUENCE: 207

Val Tyr Ser Gly Ser Met Thr Asn Asp Tyr Glu Leu Leu Ser Thr Arg
1               5                   10                  15

Asp Ile Tyr Asp Met Pro His Asn Ser Ala Thr Gly Asn Gly Arg Thr
            20                  25                  30

Met Leu Ala Asn Arg Leu Ser Trp Phe Phe Asp Leu Gln Gly Pro Ser
        35                  40                  45

Ile Met Met Asp Thr Ala Cys Ser Ser Ser Leu
    50                  55

<210> SEQ ID NO 208
<211> LENGTH: 28
<212> TYPE: PRT
<213> ORGANISM: Penicillium coprobium PF1169

<400> SEQUENCE: 208

Pro Trp Pro Thr Thr Gly Leu Arg Arg Ala Ser Val Asn Ser Phe Gly
1               5                   10                  15

Tyr Gly Gly Thr Asn Ala His Cys Val Leu Asp Asp
            20                  25

<210> SEQ ID NO 209
<211> LENGTH: 71
<212> TYPE: PRT
<213> ORGANISM: Penicillium coprobium PF1169

<400> SEQUENCE: 209

Lys Ala Ser Leu Ser Leu Gln His Gly Met Ile Ala Pro Asn Leu Leu
1               5                   10                  15

Met Gln His Leu Asn Pro Lys Ile Lys Pro Phe Ala Ala Lys Leu Ser
            20                  25                  30

Val Pro Thr Glu Cys Ile Pro Trp Pro Ala Val Pro Asp Gly Cys Pro
        35                  40                  45

Arg Arg Ala Ser Val Asn Ser Phe Gly Phe Gly Ala Asn Val His
    50                  55                  60

Val Val Leu Glu Ser Tyr Thr
65                  70

<210> SEQ ID NO 210
<211> LENGTH: 80
<212> TYPE: PRT
<213> ORGANISM: Penicillium coprobium PF1169

<400> SEQUENCE: 210

Leu Lys Gly Thr Gly Gly Gln Met Leu Gln Asn Val Val Leu Arg Val
1               5                   10                  15

Pro Val Ala Ile Asn Ala Pro Arg Ser Val Gln Val Val Gln Gln
            20                  25                  30

Asp Gln Val Lys Val Val Ser Arg Leu Ile Pro Ser Glu Ala Ser Val
        35                  40                  45

Leu Asp Asp Asp Ala Ser Trp Val Thr His Thr Thr Ala Tyr Trp Asp
    50                  55                  60

Arg Arg Val Leu Gly Ser Glu Asp Arg Ile Asp Leu Ala Ala Val Lys
65                  70                  75                  80

<210> SEQ ID NO 211
<211> LENGTH: 38
<212> TYPE: PRT
<213> ORGANISM: Penicillium coprobium PF1169

<400> SEQUENCE: 211

Gly Asn Gly Ser Ala Met Ile Ser Asn Arg Ile Ser Trp Phe Phe Asp
1               5                   10                  15

Leu Lys Gly Pro Ser Leu Ser Leu Asp Thr Ala Cys Ser Ser Ser Leu
            20                  25                  30

Val Ala Leu His Leu Ala
        35

<210> SEQ ID NO 212
<211> LENGTH: 76
<212> TYPE: PRT
<213> ORGANISM: Penicillium coprobium PF1169

<400> SEQUENCE: 212

Ala Ile His His Gly Val Gln Ala Ile Lys Leu Gly Glu Ser Arg Val
1               5                   10                  15

Ala Ile Val Gly Gly Val Asn Ala Leu Cys Gly Pro Gly Leu Thr Arg
            20                  25                  30

Val Leu Asp Lys Ala Gly Ala Ile Ser Ser Asp Gly Ser Cys Lys Ser
        35                  40                  45

Phe Asp Asp Asp Ala His Gly Tyr Ala Arg Gly Glu Gly Ala Gly Ala
    50                  55                  60

Leu Val Leu Lys Ser Leu His Gln Ala Leu Leu Asp

```
                65                  70                  75
```

<210> SEQ ID NO 213
<211> LENGTH: 69
<212> TYPE: PRT
<213> ORGANISM: Penicillium coprobium PF1169

<400> SEQUENCE: 213

```
Arg Glu Trp Met Thr Ala Glu Gly Lys Asp His Asn Leu Ser Asp Ile
1               5                   10                  15

Leu Thr Thr Leu Ala Thr Arg Arg Asp His His Asp Tyr Arg Ala Ala
            20                  25                  30

Leu Val Val Asp Asp Asn Arg Asp Ala Glu Leu Ala Leu Gln Ala Leu
        35                  40                  45

Glu His Gly Val Asp Gln Thr Phe Thr Thr Gln Ser Arg Val Phe Gly
    50                  55                  60

Ala Asp Ile Ser Lys
65
```

<210> SEQ ID NO 214
<211> LENGTH: 53
<212> TYPE: PRT
<213> ORGANISM: Penicillium coprobium PF1169

<400> SEQUENCE: 214

```
Thr Ser Asp Asp Tyr Arg Glu Val Asn Ser Gly Gln Asp Ile Asp Thr
1               5                   10                  15

Tyr Phe Ile Pro Gly Gly Asn Arg Ala Phe Thr Pro Gly Arg Ile Asn
            20                  25                  30

Tyr Tyr Phe Lys Phe Ser Gly Pro Ser Val Ser Val Asp Thr Ala Cys
        35                  40                  45

Ser Ser Ser Leu Ala
    50
```

<210> SEQ ID NO 215
<211> LENGTH: 63
<212> TYPE: PRT
<213> ORGANISM: Penicillium coprobium PF1169

<400> SEQUENCE: 215

```
Ala Gly Ile Pro Leu Ala Asn Ile Met Gly Thr Lys Thr Ser Cys Phe
1               5                   10                  15

Val Gly Ser Phe Ser Ala Asp Tyr Thr Asp Leu Leu Leu Arg Asp Pro
            20                  25                  30

Glu Cys Val Pro Met Tyr Gln Cys Thr Asn Ala Gly Gln Ser Arg Ala
        35                  40                  45

Met Thr Ala Asn Arg Leu Ser Tyr Phe Phe Asp Leu Lys Gly Pro
    50                  55                  60
```

<210> SEQ ID NO 216
<211> LENGTH: 68
<212> TYPE: PRT
<213> ORGANISM: Penicillium coprobium PF1169

<400> SEQUENCE: 216

```
Met Leu Ala Val Gly Ala Ser Ala Ser Asp Ile Gln Gln Ile Leu Asp
1               5                   10                  15

Ala Met Arg Gly Asn Lys Ala Val Ile Ala Cys Val Asn Ser Glu Ser
            20                  25                  30
```

Ser Val Thr Leu Ser Gly Asp Leu Asp Val Ile Ala Asn Leu Gln Thr
         35                  40                  45

Ala Leu Asp Lys Glu Gly Ile Phe Thr Arg Lys Leu Lys Val Asp Val
 50                  55                  60

Ala Tyr His Ser
 65

<210> SEQ ID NO 217
<211> LENGTH: 39
<212> TYPE: PRT
<213> ORGANISM: Penicillium coprobium PF1169

<400> SEQUENCE: 217

Asn Ala Ala Gly Ala His Phe Leu Thr Glu Asp Ile Gly Leu Phe Asp
 1               5                  10                  15

Ala Pro Phe Phe Asn Ile Thr Leu Gln Glu Ala Gln Thr Met Asp Pro
             20                  25                  30

Gln Gln Arg Ile Phe Leu Glu
         35

<210> SEQ ID NO 218
<211> LENGTH: 76
<212> TYPE: PRT
<213> ORGANISM: Penicillium coprobium PF1169

<400> SEQUENCE: 218

Gly Pro Ser Met Thr Ile Asp Thr Ala Cys Ser Ser Ser Leu Ile Ala
 1               5                  10                  15

Leu His Gln Ala Val Gln Ser Leu Arg Ser Gly Glu Thr Asp Val Ala
             20                  25                  30

Val Ala Ala Gly Thr Asn Leu Leu Leu Gly Pro Glu Gln Tyr Ile Ala
         35                  40                  45

Glu Ser Lys Leu Lys Met Leu Ser Pro Asn Gly Arg Ser Arg Met Trp
 50                  55                  60

Asp Lys Asp Ala Asp Gly Tyr Ala Arg Gly Asp Gly
 65                  70                  75

<210> SEQ ID NO 219
<211> LENGTH: 61
<212> TYPE: PRT
<213> ORGANISM: Penicillium coprobium PF1169

<400> SEQUENCE: 219

Gly Leu Val Asn Ile Leu Arg Ser Trp Gly Ile Glu Pro Ser Thr Val
 1               5                  10                  15

Val Gly His Ser Ser Gly Glu Ile Val Ala Ala Tyr Thr Ala Arg Ala
             20                  25                  30

Ile Ser Met Arg Thr Ala Ile Ile Leu Ala Tyr Tyr Arg Gly Lys Val
         35                  40                  45

Ala Gln Pro Leu Glu Gly Leu Gly Ala Met Val Ala Val
 50                  55                  60

<210> SEQ ID NO 220
<211> LENGTH: 79
<212> TYPE: PRT
<213> ORGANISM: Penicillium coprobium PF1169

<400> SEQUENCE: 220

Ser Val Pro Ile Glu Glu His Ser Pro Val Val Thr Gln Leu Gly Thr
 1               5                  10                  15

```
Thr Cys Val Gln Met Ala Leu Thr Lys Tyr Trp Thr Ser Leu Gly Val
         20                  25                  30

Thr Pro Ser Phe Val Met Gly His Ser Leu Gly Glu Phe Ala Ala Leu
         35                  40                  45

Asn Ala Ala Gly Val Leu Thr Ile Ser Asp Thr Ile Tyr Leu Ala Gly
 50                  55                  60

Arg Arg Ala Gln Leu Leu Thr Glu Gln Ile Glu Gly Gly Thr His
 65                  70                  75

<210> SEQ ID NO 221
<211> LENGTH: 81
<212> TYPE: PRT
<213> ORGANISM: Penicillium coprobium PF1169

<400> SEQUENCE: 221

Val Tyr Thr Gly Arg Ile Ser Leu Lys Asp Leu Gly Met Arg Cys Leu
  1               5                  10                  15

Pro Leu Cys Leu Phe Leu Phe Leu Trp Thr Ile Tyr Phe Asn Thr Ala
             20                  25                  30

Tyr Ser Tyr Gln Asp Ile Lys Asp Asp Cys Lys Leu Asn Val Asn Ser
         35                  40                  45

Ser Tyr Val Leu Ala Gly Ser His Val Arg Gly Met Leu Leu Leu Gln
 50                  55                  60

Ala Ile Ala Val Val Leu Val Ile Pro Trp Ile Leu Tyr Thr Ser Ala
 65                  70                  75                  80

Ser

<210> SEQ ID NO 222
<211> LENGTH: 82
<212> TYPE: PRT
<213> ORGANISM: Penicillium coprobium PF1169

<400> SEQUENCE: 222

Arg His Phe Gly Leu Trp Asp Glu Pro Arg Glu Leu Glu Asp Val Glu
  1               5                  10                  15

Phe Leu Leu Lys Ala Asp Val Arg Asn Asn Ser Ala Trp Asn His Arg
             20                  25                  30

Tyr Met Leu Arg Phe Gly Pro Arg Asp Thr Ser Leu Pro Asp Ala Gly
         35                  40                  45

Met Val Asn Ala Gly Asp Leu Ser Thr Ala Pro Ala Glu Lys Gly Arg
 50                  55                  60

Leu Ser Val Val Asp Glu Asp Met Val Asp Gly Glu Leu Lys Phe Ala
 65                  70                  75                  80

Gln Glu

<210> SEQ ID NO 223
<211> LENGTH: 35
<212> TYPE: PRT
<213> ORGANISM: Penicillium coprobium PF1169

<400> SEQUENCE: 223

Ile Met Arg Gly Ala Gly Cys Ala Ile Asn Asp Leu Trp Asp Arg Asn
  1               5                  10                  15

Leu Asp Pro His Val Glu Arg Thr Lys Phe Arg Pro Ile Ala Arg Gly
             20                  25                  30

Ala Leu Ser
         35
```

<210> SEQ ID NO 224
<211> LENGTH: 86
<212> TYPE: PRT
<213> ORGANISM: Penicillium coprobium PF1169

<400> SEQUENCE: 224

Phe Pro Thr Phe Pro Pro Lys Glu Ala Asp Phe Leu Met Glu Met Phe
1               5                   10                  15

Ala Gln Asp Ser Lys Asn Tyr His Val Trp Thr Tyr Arg His Trp Leu
            20                  25                  30

Val Arg His Phe Gly Leu Trp Asp Glu Pro Arg Glu Leu Glu Asp Val
        35                  40                  45

Glu Phe Leu Leu Lys Ala Asp Val Arg Asn Asn Ser Ala Trp Asn His
50                  55                  60

Arg Tyr Met Leu Arg Phe Gly Pro Arg Asp Thr Ser Leu Pro Asp Ala
65                  70                  75                  80

Gly Met Val Asn Ala Gly
                85

<210> SEQ ID NO 225
<211> LENGTH: 82
<212> TYPE: PRT
<213> ORGANISM: Penicillium coprobium PF1169

<400> SEQUENCE: 225

Asn His Arg Tyr Met Leu Arg Phe Gly Pro Arg Asp Thr Ser Leu Pro
1               5                   10                  15

Asp Ala Gly Met Val Asn Ala Gly Asp Leu Ser Thr Ala Pro Ala Glu
            20                  25                  30

Lys Gly Arg Leu Ser Val Val Asp Glu Asp Met Val Asp Gly Glu Leu
        35                  40                  45

Lys Phe Ala Gln Glu Ala Ile Leu Arg Ala Pro Glu Asn Arg Ser Pro
50                  55                  60

Trp Trp Tyr Ala Arg Gly Val Leu Arg Ala Ala Gly Arg Gly Leu Gly
65                  70                  75                  80

Glu Trp

<210> SEQ ID NO 226
<211> LENGTH: 45
<212> TYPE: PRT
<213> ORGANISM: Penicillium coprobium PF1169

<400> SEQUENCE: 226

Arg Pro Thr Ser Arg Lys Leu Gly Val Tyr Pro Gln Tyr Ile Leu Gly
1               5                   10                  15

Ala Ser Ser Ala Leu Thr Ile Leu Pro Ala Trp Ala Ser Val Tyr Thr
            20                  25                  30

Gly Arg Ile Ser Leu Lys Asp Leu Gly Met Arg Cys Leu
        35                  40                  45

<210> SEQ ID NO 227
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 227

```
tacaggcggc ctaaattgtc                                             20

<210> SEQ ID NO 228
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 228
gaacacagcg caagagatca                                             20

<210> SEQ ID NO 229
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 229
cgcaagactt gaggaacaag                                             20

<210> SEQ ID NO 230
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 230
tgaggtcaac agtggacagg                                             20

<210> SEQ ID NO 231
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 231
cgcttttacg gcaatcatct                                             20

<210> SEQ ID NO 232
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 232
tgttcgtcgt ccttgtatgc                                             20

<210> SEQ ID NO 233
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 233
cagacgctgc ataggatcag                                             20

<210> SEQ ID NO 234
<211> LENGTH: 20
<212> TYPE: DNA
<213> ORGANISM: Artificial Sequence
```

```
<220> FEATURE:
<223> OTHER INFORMATION: a primer sequence for PCR

<400> SEQUENCE: 234
ttactagcct ctggggtgga                                              20

<210> SEQ ID NO 235
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 235
tctcttgcgc tgtgttcact                                              20

<210> SEQ ID NO 236
<211> LENGTH: 19
<212> TYPE: DNA
<213> ORGANISM: Artificial Sequence
<220> FEATURE:
<223> OTHER INFORMATION: a primer sequence for PCR

<400> SEQUENCE: 236
atgcggcctt tttcaacat                                               19

<210> SEQ ID NO 237
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 237
cgacgtaagg agctgtgagc                                              20

<210> SEQ ID NO 238
<211> LENGTH: 18
<212> TYPE: DNA
<213> ORGANISM: Artificial Sequence
<220> FEATURE:
<223> OTHER INFORMATION: a primer sequence for PCR

<400> SEQUENCE: 238
acctcgatcc tgctgcaa                                                18

<210> SEQ ID NO 239
<211> LENGTH: 21
<212> TYPE: DNA
<213> ORGANISM: Artificial Sequence
<220> FEATURE:
<223> OTHER INFORMATION: a primer sequence for PCR

<400> SEQUENCE: 239
ggttgtcagg atttgtcaga a                                            21

<210> SEQ ID NO 240
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 240
ttacttcatc cccggtggta                                              20
```

```
<210> SEQ ID NO 241
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 241
agagcatagc ccggttgtta                                              20

<210> SEQ ID NO 242
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 242
cccaccttga tttgctcagt                                              20

<210> SEQ ID NO 243
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 243
agagcatagc ccggttgtta                                              20

<210> SEQ ID NO 244
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 244
gccaccttga tttgctcagt                                              20

<210> SEQ ID NO 245
<211> LENGTH: 22
<212> TYPE: DNA
<213> ORGANISM: Artificial Sequence
<220> FEATURE:
<223> OTHER INFORMATION: a primer sequence for PCR

<400> SEQUENCE: 245
aagaacacag agattggtgt gg                                           22

<210> SEQ ID NO 246
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 246
ccaggaagac acttggaagg                                              20

<210> SEQ ID NO 247
<211> LENGTH: 20
<212> TYPE: DNA
<213> ORGANISM: Artificial Sequence
<220> FEATURE:
<223> OTHER INFORMATION: a primer sequence for PCR
```

-continued

<400> SEQUENCE: 247
agagcatagc ccggttgtta                                          20

<210> SEQ ID NO 248
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 248
ccaccttcga tttgctcagt                                          20

<210> SEQ ID NO 249
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 249
cgcaagactt gaggaacaag                                          20

<210> SEQ ID NO 250
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 250
tccctctacg cagaagaacc                                          20

<210> SEQ ID NO 251
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 251
agagcatagc ccggttgtta                                          20

<210> SEQ ID NO 252
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 252
ccaccttcga tttgctcagt                                          20

<210> SEQ ID NO 253
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 253
gaggcgctgg tgtagagaat                                          20

<210> SEQ ID NO 254

```
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 254
tgtctcccgc tttgtctctt                                              20

<210> SEQ ID NO 255
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 255
agacgtggag ttcctcctga                                              20

<210> SEQ ID NO 256
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 256
caaacttcag ttcgccatca                                              20

<210> SEQ ID NO 257
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 257
caactttccc acccaaagaa                                              20

<210> SEQ ID NO 258
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 258
aagcatgtat cggtggttcc                                              20

<210> SEQ ID NO 259
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 259
cgatacatgc ttcgttttgg                                              20

<210> SEQ ID NO 260
<211> LENGTH: 18
<212> TYPE: DNA
<213> ORGANISM: Artificial Sequence
<220> FEATURE:
<223> OTHER INFORMATION: a primer sequence for PCR

<400> SEQUENCE: 260
```

```
cagcagccct cagcacac                                                    18

<210> SEQ ID NO 261
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 261
ggcgtctatc cgcaatacat                                                  20

<210> SEQ ID NO 262
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 262
gagacaccgc atacccagat                                                  20

<210> SEQ ID NO 263
<211> LENGTH: 406
<212> TYPE: DNA
<213> ORGANISM: Penicillium coprobium PF1169

<400> SEQUENCE: 263
cccagcccaa gacttgagta gactatattt attctctttg atatccatct cagcatcaag      60
ttttttgacgt tgtattacta tcctcgtttg gaattctcct cccaggtctt gcttcattgc    120
ttatagcatt ctaccaaaaa cgtcactgtc atggacgggt ggtcagacat atcatcagcg    180
cctgccggat acaaggatgt tgtttggata gcagatcggg ctctgctagc ccaaggattg    240
ggatggtcaa tcaactacct ggccatgata taccaatcgc gcaaagaccg cacatacggc    300
atggccattt tgccactatg ttgcaacttt gcgtgggaat tcgtctacac tgtcatctat    360
ccttctcaaa atcccttcga gagagctgtc ctcacaacat ggatgg                   406

<210> SEQ ID NO 264
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 264
cccagcccaa gacttgagta                                                  20

<210> SEQ ID NO 265
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 265
ccatccatgt tgtgaggaca                                                  20

<210> SEQ ID NO 266
<211> LENGTH: 39008
<212> TYPE: DNA
<213> ORGANISM: Penicillium coprobium PF1169
```

```
<400> SEQUENCE: 266
gccagccaat gtctcgacga gactctcggt gtcaagctgc ttgaggaggc cattgtgaag      60
atcgaagagc gtatcaggtc gcacggcggt agctgcaccg tgaagatggc acccaaggcc     120
gtcaccgagc aggacgatgc gatcctgcag gagcttatgg agaagcgcga acgtgagaac     180
acccaggtca gcggagatga ggactctgaa agtgatgagg gtgttcccga gtaagcgacg     240
ggctacaaat tcgagtcgag gggcatacag cggtcaccag cgctaaaatt caaagctggt     300
atcaccgcta gagggagtt ggtgaaagat ggatagaaaa aacttgcaca tatcggaaaa     360
aaggctcgat gggccagtgt gctgatgggc aggattacag tcagaactcg cccaggtaag     420
tcgcctggac ttcggggtct ggatatgaca tattcacacc tgtgtatgcg gtattcccat     480
tgcggtcgaa atcctcgttc ccggcatcaa atacactggg tccgcacagg gtgcaagttc     540
tgatgcacat aatgtttgat gcaaccgata cgttcaatgc cagtcatgct tttagatgca     600
attatccctg tagaggccat gtagcaatgt atgtagcaat gtatgtagca atgtatatag     660
caatgtatgt agcaatgtat gtaagatatc ataacaatcg agctcatgaa atggcgggga     720
gagctgaagc ttatctaccg ccgccgatca ttggtgccct caaagccatc gagaacttcc     780 cttttcggcac ttctctttt ccaccaactt tcattctacg cgatatggga cattgggcaa     840
agatctttac cgccgatcgt ggcaggaccc ggcatcgggt cgaggtggaa cgtcgtcggc     900
gtacgtcatt ttccaaacat gcggaacact actgacaagc gcagtgcta ccggcctatg     960 cggccgatga gtctgacgcc tcggatgctt caaaggaaat tgcaaaggtt gctcttcggt    1020
tgaaatatca aattgagcag gttgtctcct gtgaagtgga ggagaacgtc ttgaccgacc    1080
caaacagccg tatcatcacg gatgatgtgg ttgcgactgc taagcaggcc ggtggagatg    1140
aatacaaagc atgcattgtt tatttgtctcc tggtttgtct gcgatggttc aaaatccaat    1200
catccgtcga gctttgggat tccgatctcc atgagattcg agctgtggct gcgaggtca    1260 tcgccaagcg catgtaatgc cccttttca ttccatgttc tcggccattt cctgacccaa    1320
acagtatcga atccgagcag aaccaagaat acgtgctaaa agacattta ctcaagcgat    1380 actcaatctt cagtgaaggt gtggagactg atcccgccaa tgtcattgaa cgatcggtag    1440
atctccatgc tttaaggatc atcagctgtg ctgcgtacca gaagtgtatc cagtatctct    1500
ggagaggttg gatctgccag gaagaaggca acccaactaa cttttgtcgaa tacagtgaga    1560 agtcaaaccc caattattgg gttcatttcc atcctgatcg gatgcggact cctctgtatc    1620
agaatgtctg ccaaatttttg ttttccttga tttaccttgc gacttatacc gcagttatca    1680
ataccgtgaa tcccaccggt gacctggatg tagctgaagc catactgtat gttatgactc    1740
tcgcgttcat ctgcgacgag gcggtcaaat tctggaaggt tggatggaat tatctcgaat    1800
tctggaatgc gttcaactca acgctctact ctatcctggc agtgtctctt gtcttgcgct    1860
ttattgcctt ggcacactca tcatctacgc acgatgaaac aaggcaggca tacaatgaac    1920
tcagctacaa cttcctcgcc tttgcgggcc ctatgttctg gatgcggatg atgctatatc    1980
ttgactcgtt ccgcttcttc ggtgccatgt tcgtggtcct tcgagtgatg atgaaagaaa    2040
gcttgatatt ctttgctctt ctattcgtgg ttatggctgg tttcttccag ggcttcgtcg    2100
gcatggccca agtggatgct gatatcccca tccaccgaaa tattctccag ggaatgatca    2160
atagtatcat gcaaagccct gagtttgaca cttttcagga atttgcattt cccttttggta    2220 tcatcctcta ttatgtgttc aacttcattg ttatgactgg taagtctgta ttacatttgt    2280 ttgggggtgtc gctaaacatt tttagttctg ttgaatattc tcattgcctt gtacaacagc    2340
```

```
gcatatgaag atatctctgg caatgccacg gacgagttca tggccatctt cgcgcagaaa    2400
accatgcagt tcgtccgcgc cccagatgaa aatgtcttca tcccacgtac gtgtttactc    2460
aattctgata tagcatacgt atgactaact ttggtctggg taatagcctt caatctcatc    2520
gagattctct gtttgatagc tccattcgaa tggtggcttt cgcgggagac ttacgccaag    2580
gtgaatgaca ttgtaatggc cgtgatatat tctccgctgc ttgtcgttgc agcctgggtt    2640
gagacccgtc aggcgcataa gattcgatgg aatcgccgtc atggcgaaga agacgatgac    2700
tgcgctcagg aatgggagca tgtggccaag gaggtcaatt ttgatcttga cgatacctgg    2760
aaacagcacg taattgagtc cacgccggat atcaaggttg atagttgtac atatgaactc    2820
cgagagctga gggagcaggt taaaatgttg acggggatgg tgaaggaatt gactcaggag    2880
atggaaaaga aggcggatgg agcaagctag gaagtcctgt tgaattgtac agcaagaata    2940
ctacactgag catgggacat cgcaaaggtg atttgctact gcagtttcac caatattaca    3000
ttgcgaaaac tgtatattct cttaatgtct aatagcagca atcagcccag tggcacggag    3060
gaaagtcacc gtcctgtaag gcaaatactt gtgcttcaaa tgaattttga ctattttca    3120
tgcgataact ggcaaagggc agggggagaa aaaatgatca ttattcaacc caagcaaact    3180
gtccagaaag tgacatgccc actttgcaag taaagaagat atgtgacaat ctaacagtct    3240
caggtagaca ttcgctcttc attaaaatcc atgcgttgct cgccgtagcc caattcgaag    3300
cactgggcaa cccacatcga gaccttaaaa tcgggtgatc atcacacagc aacaggctca    3360
gcaagaatgg aggcaatcgt ctcccttga tgatccagct gtgagagctt cgctcgatgg    3420
tgcttgccaa tacctatccg aggaatgtca tccacaaata caacacctcc atctagggct    3480
ttatagctgg ccagttggct ttgaatcaga cctgccactt gatcggccgt cgtctccggg    3540
gacgtatcat tgcggacgac ataagctcga ggaacctcgc tgctgccatc tgggagcatg    3600
actccgatca cggctgcgtc cttgatactc gggtccttgc gtaggatccc ttcaatctct    3660
gcgggagcga cggagtatct aaatcaagca cgatatgtta gtctatcatc tgctgcatcg    3720
gatgtcatat ggagaggaaa gaaagcgaag gatgtgaagg atgaagccta gaggactggg    3780
taacttgccc tcgaactttg atgagatctt tggtccgtcc gatgacatgg tagtttccgt    3840
cttccacatg gaacatgtct ccagtccgga accatccttg ctcatctttg gcatcagttc    3900
gtcctttgta tgctagaagg agtcccggtc cacggacata caactctcca ggggagtctg    3960
gtgtcccggc gacatcttcg cccgtgtcgg gattgacaaa gcgcagctca tatctgggca    4020
aaagagtccc tacactgcca aattgtggtt gtatcccgta gcgattctgg aaaaccactc    4080
caacctcaga catgccccac agatttcccg ctatagcgtc cggtgatagc aggctctgga    4140
attgctgcat agagtacccg tctatgggag cacccgaaat accgatatag cgcagagaag    4200
acaagctctc ggctacattc aaggaggacc tattgagaat gtggatcatg caggaaccca    4260
tgtacgtttc cgtgatgtgg tgctggcgga tgccgtcgag caaagcggtg atttcgaagc    4320
gcgggataat gtacagaggc tggccgtacc gaatggggaa gatgttgccc cagaagtcgc    4380
caaaagaatg gtacagtggc agtgccatca acgaacgac ggggtatggc acttcatagt    4440
agacgctcag atggtgggaa atgatcgtgt ggtgggttcg aattgcggct ttggggagac    4500
cgctggtgcc actggttagg aacatagccg ccggcgtgat cttgctctcc tcgctatctt    4560
cgaaacgaag ccaatccaac tcgccatact ggagcagact ctccaggcgg ataggttggt    4620
ccactgtctg ggtgtcgaga tcctccgtct gctccgcctg gccatgtgca aattggacta    4680
```

```
cactttcgat agacttctca tccatcagaa ggacttggtt tgaggacatt ccttgattat    4740
tgcaaacttc caggactctg gtcagcgcac tcggagcagt aataatcaac cgaggctcgg    4800
cgacacgaag cagatgagcc acttcatggg ggcgactagc gacatcaaac cccatataca    4860
ctccgcccgc accaacgatg gcaaagaaaa gagcagagtg tagaacctag gctgatgtta    4920
gcagcatatc attgttatgg ggtagtgtga ttacactgtt ctccagttgc acgagtacac    4980
aatcgcctcg ttccacaccc cgggctttga ggcccgcaat gagtgatcgc accagccgtc    5040
ggaattggat ggcattgaaa gcacgcgaag ggttgcgggc atcaatatag atgggcttag    5100
attggtcaaa gcaggaccca ctaaaagcaa agctgactag gtctgtctcg tgctccatat    5160
cgatgcttat attgtacagt tctcgtgtgc tattgacatg cagaacttga tgcaggattt    5220
gtgctcactt taagtagtag tacatggaat gctcagacct cccatatcac tttgatcgac    5280
actgcacggg acaagtatca tgcagaagac tattgagaag aatgccacgc caccaattcg    5340
tattatacta atctagccta agccaataca tgtaaagagt actatttagg acccacactg    5400
tcattgcaga gctttgaagc agctgcatgc gctaattcac ccacagatac gccactaaga    5460
atcaaaatta ccccgatgtc gacgctcagc tctttcgtaa accattgact cagcccaatg    5520
gcgataagcg agtcaatccc gagctcagga atcagcgtgt cagcagagag cggtgcatcc    5580
tcggccaagt tcaagctggc ccgaattttc tccattagtg gtctcacgac tgcttcggct    5640
ttttcttcca agcttgtcgc tgcagtgaca agatctttgg tcgaccgggt ctcaatcaat    5700
gcaagtattt gatcttgaga cgccgtggcc gtataggagt agaatggcca taacttcggt    5760
atcgggcact cgccatagcc acacttcaaa ctctggtgtc ggagtccccc gattaactca    5820
gcgttggaat tggaatctga gcgcccgcag aggattgcct cggcgagtat ctcgtcgaca    5880
tcccgctggg atacagctac cgggccacac caaagaggct gactgggaga aggactagaa    5940
atgccgtgga tctcgcccag atgtactaga cttgctggtc tgccctgggc tcgacggtgg    6000
cggaccagca gggccatttt ctcggacatc gctgcagtca ttgcctggtc cgcatggcct    6060
aacactcctg caatagatcc gatgagcacc caaaagtcca gagttggggt cttgtagagc    6120
tcatctagct gctgcagccc cttcaagacc ggatgcagat ggttccggag ggaatctatc    6180
gtgagctggg acaaggaaca gtcaggtaga ggcggaggct gaattagaac tcctcccact    6240
accgggggga acgcataggg aatagtttga tgcaaactgg tggcagaaat gccatcgatc    6300
aggtttctgg cattgattag cttgtgcatt tgaattcatg ggtacgtaag taacttacat    6360
tttcgagacc gctatgcgcg ttccccgtcg agaaacttct tccaaccacc acgcatctga    6420
gtcaagtcta gagccagcaa ggaggatcca ttttgccccg tgtgttgcta gccaaagaca    6480
gatagcatgg gctagttcac tgcctagacc tacaagtatg taggtttttt tctctgacag    6540
ctgcacctgg gaaccagcag tcggtatctg ggcgagcacc ggagttgtag agtcccaatc    6600
taccacggca tcctgggagt caaggattgg gtactcggaa atcctgctga ttggtaacga    6660
gtccacagaa tttggtggga gcccctcgcg gccggtgtac gccactaagc aggcggttag    6720
gaaagccttg gctatgagtg acgaatcatc cgcgttgatc ggccctgtcg atgcagaggt    6780
aaggtagaaa tcctgcaaat ggattcgtgt cgcgttgtca ggcaagagcg atagcatgcg    6840
atcatagaca ccctgtccac gacgatgtag aatcgctatg gccgacacat ctgagggaag    6900
tacctgagac aattgccgcg cagtgctatg ctcgtgcaaa agcaacatcg gtctttcttt    6960
gtctgggttg cttttgctag tgctgaagat aaccttacca tcccgccggg tcagcatttg    7020
gtggaaaaca gactgaagga ccccatcagc ctcgtgcact acaagcgtgc ctgattgtgg    7080
```

```
gacttgttcg accaggtatc ctgccaacag agcagccgct gtggcgcgga gataagactg   7140
ctcgtgggct tccaacaccg tgtctggcac tgaccacgcc caggagtctg aacgataac    7200 atgagatgca atgtgggacg acagagcgat cattctcttg ttgctcttaa cgtccagccc   7260
tatgaccagc cgcagaaata tggcccctgc aacccgcacg gctgctatac tggaatgtcg   7320
aactcgcaga tgaagggttg ggccataact tgcggttatc ggcggatcag ccatcgaaag   7380
aaggcggaac ccttcacaag tcttgtcggt cgtagcagga aggatttgta caactccctt   7440
gtcgaggtcc acgcagtctg tcactttttg ccgcctggct agatggcgca gcccagtagc   7500
atggtcgtga tattgccgag gaacacggaa catagagccg tcgtattgaa tttcgggctc   7560
gatgttggtg agtccgcacg aatgaggatt tcttgagct gcactagctt gaacaaagtg    7620
tccaagagct gtcgccaata tttccgttgt aactccaacc ggatctgtga tatgtagcag   7680
ttgtagcaga gaagacgatc gttcagaagc caggaaggtg gaaggagac ctttcaccag    7740 tccggcatca gggtggtcga ccttctcaca ggtcaccact aacattcgct tactgactgt   7800
catcagtctg cacaactcgc tcaaggtagc gtttgtcaga tctcgatcat cgacgaggta   7860
cagaacagtc aatttagata aatcgcgatc ttcaatgaga tctaggtctg gcgcatgagc   7920
aaccttgacg aagtcatcct gtaccaattc aaaaagctct gaggtaagac aatctgcctc   7980
ctcagcgtca ccgccaagca acagcaggtc tccgcggctc tgtggttccg caggactgtc   8040
tggagtgcga cagagaagga gtgaaaagtc cccaaggctt tcactctctt gggacgcatc   8100
gaacgaatcc aagccataga atccgccgtt agacagtagc tcaacccagt ccctcctggt   8160
agtaattggc tcaccagagc agtagccttt cccggtctct gtgcatctca ttggaggacc   8220
gaatagaaga ttcaaaatatg tagtgctggg attcgttcgt actagtagga ccaagaatcc   8280
accaggcttg agcaagcgac gaacatgagc caccgcgacc tcttgcagaa ataccgcggc   8340
tgtgatcagc accatatcgt agaattgctc gcggcagccc tgctcgacag gatcctcatt   8400
gatgtccaac gttttgtgcg acacctcgcc aggttgctca aggtcttcct caatcgcttg   8460
taggccagaa acggagagtc cagcataagt aaatgaccga taagtccgac ccatcttctt   8520
cagtccagag tgaacatggc ctccaaattg gccgatctga aggatattca tttgtggaaa   8580
gcggaaacac gcctggctga cgacagatac gagctcgtct tctagatcca agacttgcaa   8640
gtcctccttc agatattgac tttcctcatc gatggccggc caggcctcta tttgaagacc   8700
agaatcacgc agaacgcgag gtagccgctg gcctaccgca gcaatggccg tgagaccagg   8760
gtcattcaag agtgacgggc tcactccagc tgtgaagtcc tcaatcttct ggtccaagca   8820
ctcggattcc ccgacagggt ctggctcttg gctagcattt gcaatgcatt ggttcatcca   8880
tgcaagcaga cgagcaccat cgaaatccaa tccgcttcgc tccaagtccg tcagtccatt   8940
gcgagcctgc ttgagataca gtagcgcaag ctcctctcgg agagagtgta gctgtagcat   9000
ggtagctggc aacttccgtg atcccttctt cagagtgggc tcaagcggtc cccacgcggt   9060
ctgggaaaga acctgcaagt tgtttggtgc agttccagat ggctggcata tgagagaaac   9120
accttcgagc tggacagcct ttccccatt catggtgaag atgtcaatat caccgcgaat    9180
tcgatctcca ttaacgcagg tcagatagct tgctaccgtc aattccttgc cttgccaatc   9240
tgaagcacat aacaccggat ttatccaggt actgtcaaca tttctcgata agaatggtcc   9300
cgtcagcagc gtctcttcaa gcccaccaat tgcagcaatc attgtttgaa caccaaggtc   9360
caaaatagcc gggtgaagag ccatgggctc atccgaatca tttgagggaa cgggcacact   9420
```

```
cccagtggct agatcacgcc tttttgcggag tcccgtcaag gtagagaatg ggccagtaca   9480
gtggtagtca gcgcggcgca ggctgtcata gaattcagtg ctgtccacgg gctccaaggc   9540
ctgaggtagc tgtccctgtg ggggtaggag agcacggtca gaatcccctg gatgcatgat   9600
catcttggct gttgcacact gaacgagctc tccggataca acagcttcgc agcagaacca   9660
agcagtaatg gctccatcat gcgagtgaat actacccacg gtgacaagca cttcagtgcc   9720
gatgggatca ttctgaatcg ggagctgagt gtggatggtc aagtccttga cattcaacaa   9780
gcgtaggcct tgtgtctgtg ccattatcat acctgcctcc agtgccatcg atatgtatcc   9840
tgtctcaggg aagacagatc ccgaatcggc acgacggtcg gccaaccagg gcagctcctc   9900
tggtcgtaga tagtttcgcc aacggaactt ttctgctccg gtctctggac tgagagaacc   9960
gagaagtgcg ttaggagatg tagcacgatg gttatggttc gaagacattc gcgactgtgt  10020
ccagtatgtc tgagtatggt cgaaggggta gaatggtagc gattctacca acacaggcca  10080
atgatttgga tcaaagagtg agacatagtc tgtgaggcgg acgacatttg ggccgaggtg  10140
tgcccaggaa gatcctaggg ccgttgccca tgtatcgagg ccgggctttc ctcgctcagc  10200
aagagcaagg taaggaattg ccgagtgggc cgagtgcatt ttggagaggg tctgtaggac  10260
aggccctctc agtgtcggat ggggcccgat ctcaatgatg agatctggtg gcccagcgtc  10320
tcgtgccgcg gcctctaggg cttgggaaaa ctgaacagga cgcagcatat tctcaaccca  10380
gtactcccct gtcaattcct gctggtcata cccagtcatg acctcccctg ggtagacact  10440
cgagtaccag cgcgaggcag aagctgacag ggcgacagga tacgctttca ttgcgtcacg  10500
atatggatct gcacaaggct tcatatgcgg agagtgatat gcggtgtcca ctcgaagcat  10560
acgcggagtg aggcccaggc tcttcagcag ccactccagc tcccgcaggc actctgcgtc  10620
gccggataac gtgacgctgg atggcgagtt ggcggcagca acgcttatac gtccggagta  10680
ggcttctaaa gcacagatat tctgcgcctg ctgccatgtc aaattcacgg ccatcatccg  10740
acctgtcgga tcgcgtgact tatcaatggt catcccccta aggtacgcga tgcggattgc  10800
atccgaggcc gtcagcacac ccgcagcata ggctgctaca atctcgccgg aagagtgacc  10860
gaccacaatg gtaagctcaa tccctaccgc acgagcatg ttgacttgca tgatttgcaa  10920
cgctgtccgt agggggagag aaaggaggcc ctcgtttacg cgcgaggacg atgccggctg  10980
tgacaactcg tcgagaagag aaaactgtgg acgaaggtct agtggaagct catccaaagc  11040
ttcctccaga ttcataatcc attttcgaat tgagggactt gcctcaatca gatcaagtcc  11100
catttgtggc cattggactc cttggcccgt gaagatgccc atgacgcgtc tgggccgagt  11160
gttggatctg gagacgacag aggctggttt acccgtgacc cttcgactta tttctgtatt  11220
gatctggtct ttcaactctt gtattgagtg tgccattagc gtcaaccggt ggcgatgagt  11280
ggaacgtcga tcccacaaag agagcgccag accaacgaga ctgactgttg cgtgttcctg  11340
gaggaatgtt gcgtatgatt ccatcacaca agtgagggtc cgctcagacg cagcagaaaa  11400
gacaaagggc agactggagg gtatgttgtt ggacggactg agctccgagc gagtgtagct  11460
ttctaggacg acatgcacat tggcaccccc gaatccaaag gagttcaccg aggctcgacg  11520
aggacagcca tctgggactg caggccacgg gatgcattct gtggggacag aaagcttggc  11580
ggcaaacggt ttaatttttg gattgagatg ctgcatcagg agattaggag caatcatccc  11640
gtgttgcagc gagagggatg ccttgatcaa tcccgctagt ccagcagtgg cctctgtatg  11700
tccaattatt gtcttaattg acccaacata cagccgatcg gtcgaatctg gaacggattc  11760
gggcccaaag aagcttgagt tgattgcggc tgcttcctgc ggatctccgg cctgggttcc  11820
```

```
cgtgccatga gcctcgaagt actggcaccg atcttccggg ttgttttgag gagagagccc    11880
cgcgcgtgca taggttgcga ggatcaatga ttgttgtgcc tttggattag gcatcgtgat    11940
ccccatagtt cgcccatccg agtttgcccc tgaggcacgg atcacgcatt cgataggatc    12000
tccatcatta atcgcgtcct gcagacgttt tagtacaacc gaagccacac cctcgccacg    12060
tccgtagccg tcggccttgc tgtcccacat tctactccgg ccggtagggg acagcatccg    12120
tgttttagaa tccgcaatat aggcattggg agacaggatc aggttgcttc ctactgccac    12180
tgccatggaa cagtcatcgt tctgcagagc ctcgactccc agatgaacag ccaagagact    12240
cgaagaacat ccggtgtcaa cggccataga aggaccttgc cagtcaaagt agtaagagat    12300
acgattggcc atgattgacg gtgagtttcc cgtaaccaca tacgcgggga acgcctgagg    12360
atccatggcc tggatttgat tgtaatcgtt gcgaagtgta ccgcagaaca ccccggtctt    12420
tgagcgctgc agcgcatcca tccgtaaccc ggccgcatcg agcgattcgt cacggtctc    12480
taggagcaat cgctgttgtg gatccattgc taccgcttca gttggcgaga tattgaagaa    12540
ggccgcatca aaggctttga tgtcctcgtc caagaagtat gactctttga cgtttgttgt    12600
gccatggtgg tctccatctg gatgataaaa ggcatctata ttgaatctgt cggccggaac    12660
tttgcgcgcg atatcccgag ggcttttgaag aagctcccac agtttcgaag gagaggaagc    12720
gccaccggga aagcggcatc ctgtaccaat aatagcaaca ggctctgttg ctttcattgt    12780
gagattataa gagaggtgta aaacctgaga tcaaataat ttgcagttgg gtggctgtag    12840
ctctactgag agtacgttca tagatataag caatgcagtg ttgccttact tacttccacg    12900
atcttgtcag catatctatc gaacgaatag caaaactgga cctatagagc aatttccggc    12960
catcgataga tcattggata gctgtcctat ttgggaagta tgatctacaa tttatgcagc    13020
cacaaactat acaaagtggt ccatcgccag atttggcgat gagcagcggt gtggaatagt    13080
gactttgatg aacatgtcag gtcctgcatc tacatgtgca ggtgtccaag gatgctcctt    13140
gcgcgaagaa gtggagtagg gacattcagc tacctcctta tcttttccct tcttttaatg    13200
ctcactctgt gcataataat agtggcgaat atcgaagcat cgaaatccaa cgacattgag    13260
acaacatgga taacatggac aacatgaaca acacaccttt aggtttcaac tgggcctggg    13320
cagtcatcat ctcttttcctg ggtctgctga ctttttcctt tgtctcgcca cacctctttc    13380
cttcaagatt gacggtgatt aatggtggaa gagcctggga tatctttcgt accaaggcca    13440
aaaagcgatt tcgctcggac gcagcacgtc ttataaagaa cggcttcgag gaggtgagta    13500
tggaaaaact gcatcattta ggataaagtg ctaaacgttc cttcttactc cagtctcctg    13560
atgcctttcg cattatcacg gataacggtc ctttgctggt cttgtcacct caatacgctc    13620
gtgaggttcg cagcgatgat agactcagcc ttgaccattt cattgcctcg gtttgtcttg    13680
cttcatgtcc aacgtttttc tagttggcgt cgctaagctt ctactgttta ggaatttcac    13740
cccaacatcc caggtttcga gccgttcaaa ttgatcttgg atccaaagaa cccgttgaac    13800
acgatcctca agtccaatct cacacaagca ctgggtactg acatcgtcct ctccgctctt    13860
atgcagccca ttacatagct aacattgttt acctggatag cttatctgac agaggacttg    13920
tctgcggagg taacagaggc actatctgca acctgtaccg atgaccctgg taagctataa    13980
aacatggttt tccaaaggtt ctggtatcaa tactaacttt cttctttctc ttaatcaaag    14040
agtggcacga ggtcagcgtt agtcaaacgg ctctcaaaat tatcgcacaa atggcgtcca    14100
aagccttcat tggacaagaa agatgcccggg atgccaagtg gcataacatt atcatcacgt    14160
```

```
acacgcacaa cgtctatgga gcagcacagg cactccactt ttggcccagt ttcctacgac   14220
ccatagtggc acagttttg ccagcatgcc gaactttgca ggctcagatt gctgaagcgc   14280
gagagatctt ggagccattg gtagcccaga gacgagccga gagagccacc cgagccgctc   14340
aggagaagcc tcatccgtct ggtggggata tcattgactg gctggaacag ttttatgggg   14400
accaaccgta tgatcccgtg gccgcacagc tactgctctc atttgctgct atccatggaa   14460
cttccaatct cctggcgcaa gcgctcatag atctctgtgg ccaaccggag ctagtacagg   14520
atctccggga agaagctgtg tccgtgctgg gtaaagaggg atggaccagg gccgccttgt   14580
accaactcaa actaatggac agcgccctga agaaagcca gcggttggcg ccaaacagat   14640
tgtgtgagtg ggcccttcct cttgcccccc aatttgacca ttcaactggc cattagagac   14700
taattcaggt gtgcttttac agtatcgatg ggacgcattg cgcaaggcga tatggacctg   14760
tctgatggtc tccgtatcca ccggggcacg accctcatgg tgtctgccca acacatgtgg   14820
gatcctgaaa tctaccctga tccccgaaaa tacgatggct accgattcca taagttgcga   14880
caaacatcag ggcaagaggg ccagcaccaa ctcgtatcct cgacgccgga tcacatggga   14940
ttcggatacg gaaagcatgc ttgcccggga cggttttcg ccgcagccca gatcaaagtt   15000
gcattgtgca atatcctcct caagtatgat attgaataca ggggtggcaa gtccccaggt   15060
gtgtggggtc agggcataca tctgtttccc gatccgacgt ctaggatcca cgtccgtcgt   15120
cggaaagagg agattaactt gtgatactat tgtctaacta tgcggatgtg gttgaatgca   15180
aggactctct ctctctctct gtctgattga tatttgagtt ttctatggtg atcgagcaag   15240 attttgcaa tgtggagccc atgcatgctc atgaggccta ttgggccgat ctcttcgaga   15300
tcgtgatcga gagcaaattt gagaacctca gaccttgttt atttgaaagt agcagatgaa   15360
caatagaatt gttttactt ttggaatggt tccacaataa tcctagtcta gatttaagat   15420
accaatattg aagtgttatg tttgcatgta tcttcagctg ctccaccgc gtggagtgat   15480 tattagctta ttagcgcctt ctcattaata cgccctccag ttccagcctc tcaaaagtaa   15540
tatgctggaa tgatagaggt aattggctaa tggcctcaag gcaaccctgc agatagtgaa   15600
gcaaaagcaa taaatattca atattcacac ataatttgac atacggagta ctccgtactc   15660
cgtttaagat cgggcatagt attggatgat gttagaatat atcttggcaa ggtgacatat   15720
acaatgtact ccgtatgttg tacagtgtca atggctttgt ggagctgaag atgcggtgat   15780
ttcttttcct gatgcatcat caagtccgga aaattgatga aaatctacga gtacctcgag   15840
ggatgaactt ccctgcacag atcatgacat acatataaac tattgatcca cttgcattag   15900
cgggagtcta gcaagagcaa gtctatgtat tccctacatg gtcgaggagg taagttcggg   15960
ctgaaaaata cgatgcagca tacactaccc ttacaactag ctgtttaatc agaaaaagca   16020
aatagaaatt agggcacaat ttactcttta ctgccaaccc cccgtcgtaa cccttgctgc   16080
tagcattgat tggctgtcag tcgtacaacg aagaaacgac actgtctgtg attatattct   16140
attccatcac aaacgtagcc cggagtgccc ttcccagagt ccttgtcttg tacaccgtgc   16200
ttgtcttagc attttcatta tgatcgagct caaagatgct tcgatggggg ctgtattgct   16260
gacatgcgtc cttgtgcttg caggcctata tctcattcga ttgacgttat caagcgacca   16320
attggacaag tttcctagca tcaatcctcg gaagccctgg gaaatcgtca atgtcttcgc   16380
ccaaagaaga tttcaacagg atgggcctag gtatctggaa gctgggtatg caaaggtgtg   16440
ttccataagc aactgctcca aaaggcgaat aaggctgaaa gttactacag tcccccatct   16500
ttagcgtggt caccgacctg ggccaaaaat tagtggtttc gggtgcattc atcgaggaat   16560
```

```
tcaaggatga aaagctgttg gaccattatc ggtcaatgat cgaggtttgt acgacgttag   16620
tgattatgaa agagcaagcg cttacttgtg caaggacttc atggcagagg tacctggttt   16680
tgagtcgatg ttcctgggga atctacacaa tacggtactt cgcgatgtga tttctgtcat   16740
cactcgcgaa ctaggtaaat attctttcct tttgactgtc cggttatccg ctgagttcta   16800
attttataga acaactgcta gcacctctct cggatgaagt atcagcggct ctggtagata   16860
cttggacgga ctcaccaggt gggtcaaagc acacttccca atagaaatca ggaggaaata   16920
aaaactaata tcaatataga ctggcatgag gtagcactgc ttccaagcat gctgggcttg   16980
atcgcaaagg tttcatctct cgtcttcgtg ggtgaaccgt tgtgccgcca cccagtctgg   17040
ttggagacag tgatcaactt caccctcatt cgacacaacg caatcttagc cctccaccag   17100
tgccctgctg tacttcggcc cgtccttcac tgggttcttc caccatgcca gaaactccga   17160
cgagagatca gaactgcacg gacactgatc gactctgctc tggaaaaatc aagaaagaat   17220
ccgcagaccg agaaattttc cagcgttgcc tgggttgatg cttttgccaa aggcaacaag   17280
tataatgcag ccatggtgca gttaagactg gcaaatgcgt ccatccactc cagcgccgat   17340
ctcctggtca agattcttat caatctatgc gagcagccag aattgattcg ggacctccgg   17400
gacgagatta tctctgttct tggggagaat ggatggcgat cctcgacact gaaccaatta   17460
aagctccttg atagtgttct gaaggagagc cagcggttgc atccagtcac aaccggtatg   17520
catcgtcggc tgttcaaact gcgtgcccag tgcatatgct gaccatttac tttaggagca   17580
ttttcgcgct ttactcggca agatatcaag ttgaccaatg gcactgagat tccttcagga   17640
acacccatta tggtcactaa tgatgtcgcc ggggatgcca gtatctatga tgatcccgat   17700
gtcttcgatg ggtatcggta cttcagaatg cgtgaaggag ccgataaggc ccgggcacca   17760
ttcacaacga cgggccaaaa tcaccttggg tttgggtacg ggaagtatgc ttgtcctggt   17820
cgattctttg ctgctaccga gattaagata gcgctctgcc atatgttgtt gaagtatgaa   17880
tggaggctag taaaggacag gccgcatggg atagttacaa gcgggttcgc agcattccgt   17940
gacccacgag caagcataga agtccgcaga cgcgcggtgg cgggagaaga gctcgaggta   18000
ttgactggaa agaagtgatc tagggaaaat tacgaactca tagtatgagc aaccataccc   18060
aaaacaaaga gacttaccaa ccccatcatc aaggtagact ggggattttg actatgtcga   18120
tgtaaatcgg tcaacagcct tattaggata tataaattat acgcttctca ggctttaaag   18180
catcacccag cacgataatt tctctggatt attgcaaaac caagaaattc tctgatccac   18240
agctgtatac tccgtactcc gttcatcatc ttacagtcat gcagagggtg aaaggggtca   18300
gtgtgtgacg gtatttcggt atctcgcctc gtaatttgac agatccagcg ttaaacccag   18360
cccaagactt gagtagacta tatttattct ctttgatatc catctcagca tcaagttttt   18420
gacgttgtat tactatcctc gtttggaatt ctcctcccag gtcttgcttc attgcttata   18480
gcattctacc aaaaacgtca ctgtcatgga cgggtggtca gacatatcat cagcgcctgc   18540
cggatacaag gatgttgttt ggatagcaga tcgggctctg ctagcccaag gattgggatg   18600
gtcaatcaac tacctggcca tgatatacca atcgcgcaaa gaccgcacat acggcatggc   18660
cattttgcca ctatgttgca actttgcgtg ggaattcgtc tacactgtca tctatccttc   18720
tcaaaatccc ttcgagagag ctgtcctcac aacatggatg gtcctgaacc tctacctcat   18780
gtacactacc atcaaattcg ctcccaacga atggcagcac gccccgctcg tccagcgaat   18840
tcttccagtg atattccctg tggcaatcgc ggcatttacg gcggggcatc tcgccttggc   18900
```

```
tgcgacagtg ggagtggcca aggcagtcaa ctggagcgcc tttctgtgct ttgagctatt    18960
gactgccggt gccgtgtgcc agctcatgag tcggggatct agcagagggg cgtcgtatac    19020
aatctggtat gttcttttg ccttgtggat cttgcttggg tttattggct aatgtgaatt     19080
gtggttggca gggtctcaag atttctgggc tcgtatatcg gtagtatctt tatgcatgtt    19140
cgagagaccc actggccgca ggagtttgac tggatcagct acccttcgt ggcgtggcat     19200
ggcatcatgt gcttctcgct ggatatttct tatgtgggct tactgtggta cattcgtcgg    19260
caggagcgcc agggccaatt gaagaaagct atgtgatcga caggaccatg catgatggag    19320
gtccgcacta acctcaactg tactttgtac aggtctgagt gctatatgac gatagtcaca    19380
aaacagagtt ggaggttatt tgcgcacatt gactaaaaat gggagagctg atggatatat    19440
gcaagggga tcaggtctcg atctgatcgt gccgatcgac aagaacaatg ctttgtctgg     19500
gcgggtccaa ttgtctagcc tagaagtcta aatttcaatt ttcttcggac tttttacata    19560
gtaactactg cctaggactc gggatatgaa gtataatggc gagaaatggc tggctgcagg    19620
ggacatacag gtgataattt gccctcgatc tggcagctag ttacgtcaat atcttgttag    19680
taaacaccag ttgtagatct ttgcgtatat atgaaactca aaagcatttg tgtctactcc    19740
gtaattacct tcccaacccc tccagtgcca ttgaaaccat gaaggtcatc attgtcggag    19800
ggtccatcgc gggtctcgcc ctcgcccatt gcttggacaa ggccaacatt gactatgtca    19860
ttctagaaaa gaagaaagaa attgcccccc aggaaggtgc ttccattggt atcatgccta    19920
atggtggtcg gatcctggaa cagcttgggt tatacgacca gatcgaggag ctgatcgagc    19980
ctttggtgag ggcgcatgta acttaccccg acggcttcaa ctatacaagt cgataccctg    20040
cactcataca gcagcggtgc gtcaatataa gctttctact ttctgatttg aaactaatgc    20100
gagaggtctt aggtttggct atccacttgc attcttggat cgacagaagt tactgcaaat    20160
tctggcaact cagccggtcc aatccagccg agtgaaacta gaccacaagg ttgagagcat    20220
tgaggtctcc ccatgtggcg tcacggtgat aacaagcaac ggacacacct atcagggcga    20280
tcttgtcgtc ggggctgatg gagtgcatag tcgggtacga gcggagatgt ggcgactggc    20340
agatgcctcg caggggaacg tatgtggaaa tggagacaaa ggtaacatta ttcctactgt    20400
tttgtcctat cctcgctttt tttttcttg gccaagtgtt ttgactttga gctggaaagc     20460
taatatattg atttatagca tttacgatca actatgcctg catctttgga atttcgtcac    20520
acgtcgatca attggaccct ggcgagcaaa taacctgtta caatgatggg tggagtatcc    20580
ttagtgtgat cggacagaat ggcaggatct actggttcct ctttatcaag ctggaaaaag    20640
aattcgttta tgatggatca cacaaaaccc agctccactt tagccgtgaa gacgcccgag    20700
ctcattgcga gaggctggcg caggagcctc tctggaaaga tgtgacattt ggtcaggtct    20760
gggctcgatg tgaggtcttt caaatgacac ccttggaaga aggggtgctt ggcaaatggc    20820
actggagaaa cattatctgc atcggagaca gcatgcataa ggtcagcagc tcattatcac    20880
tcctggctta ctgactttg taattaattg acattctcat gcagttcgca ccgcatattg     20940
gacagggtgc taattgcgct atcgaggatg cagctcagct cagcaatagt ttgcacactt    21000
ggctgagcga atctggaaag gagcatcaac taaaaaccga tgatttgaca gagattctgg    21060
ctcaatttgc acaaactcgc ctccagaggc taggtccgac ggccatggcc gctcgatctg    21120
ctatgcgtct gcatgcgcgg gaagggctca aaaactggat actgggacgc tacttcttgc    21180
cctacgctgg tgacaagccg gccgactggg cctcccgagg aatcgcaggt gggaatactt    21240
tggacttcgt agagcctccc acgcgggctg gtcctggctg gattcagttc agccagtcgg    21300
```

```
gtaaaaggac ttcgtttccc atggcagtgg caggtctgtg cctagtgagc attgtggccc    21360
gaatcatgta tttgaaatta gttgcataga gaggcccacc atatctggag tacttcatac    21420
agagtgtttt atgggacaat ataaacttta gggcaattta gcgctttgat atagatcatc    21480
tgcatactag taaggcaacc ctgaaggtga tcgacacgat ctgcaaaaat caatatcgtg    21540
cttcgttacg gagtattgtt ttctacatgt catagtgcgc gctgcccag tggggctatg    21600 cagaaagtga tttcgatgta ttgctactta cagtgatgtg gtccagcatg tcagccattg    21660
ctctagtgcg tgcgtgtact gaccacatcg cggccattgc catttatcta gggtcctgtc    21720
gcctcaaaag cttgtggtca caaatcgttt gatccttcga gatcatactg aattttgtt    21780 caatctgtca tcatggctgg ctctcagtct acggcgcagt tggctcgcct tctcattgat    21840
atctcccgat ttgacaaata caactgttta tttgctatat tccctggagg tacgagtag    21900 tgcagaccac ttcaacatta taccaccgcg ctcacaattt catatagtct ggtctatctt    21960
ccttgcagca gcctcacgac acgctgatgg cgacccgtc cctctggact ttgtattggg    22020
ccgcgcagga ctggccttca tgtacacgta tatgctgagc ggcgcaggaa tggtatggaa    22080
cgactggatc gaccgcgata tcgatgccca ggtggcccgt accaagaatc ggcccctcgc    22140
ctccggtcgg cttttccacca gagctgccct catttggatg cttgtccagt acgcagcctc    22200
ggtctggctg atggaccgca tggtgagcgg gcaggatgtg tacgtctttt ttcctcctcg    22260
taccccaaac aattattctg ttgattgaaa actgacccta atcattctcc agatggacat    22320
acatgcttcc tctcacaacc gggattatct tgtatccctt cggcaagcga ccgacaagtc    22380
gcaagctggg cgtctatccg caatacatcc tcggtgcaag cagcgccctt actatcctcc    22440
cagcctgggc ctccgtctac acaggccgta tatctttgaa ggatctgggt atgcggtgtc    22500
tcccgctttg tctcttcctg tttctgtgga ccatctactt caacaccgcc tacagctatc    22560
aggatattaa ggatgactgt aagctgaatg tgaattcgtc gtacgtcctc gcggggagcc    22620
atgtgcgtgg aatgcttctg ttacaggcta ttgctgtggt gctggtgatc ccctggattc    22680
tctacaccag cgcctccact tggctctggg tctcatggct gggggtatgg acggcatctc    22740
tcggcgagca gctttatctc tttgatgtga aggatccgag tagcggtgga aaggttcatc    22800
ggcggaattt cgcactgggg atttggaatg tgctggcctg ctttgttgag ctgctatatg    22860
cttcaggctc tctgtgaatg atgttaatac gatgtggtcc ggatgagact tggggagtag    22920
agtctgagag gcttaaaatg ggtaaatggt gcgatgttgg cacagtgtga actattcata    22980
aatctttgct acgaagttgg gcttcacctt tcaattgaga agttgttact ggaattttc    23040 gacactcaaa attcgaagag acttgtatta ttagagggat atagcctatg tcttccaatt    23100
ggtgtagaat cccaactacg agaccgcttc agaacgttgg agcacaagga tagaaagttc    23160
acctattcga aattctctac tgtcgtacat atgctatgta catgttactc ctttgcttgc    23220
gcacctatag cccagcaaaa caagggatcc tttgctaaca ggagctgatc atcacggttc    23280
agagtcagat gcaaatccca cggctccgta ctcgccacat catcctgacc ctttggaagg    23340
ataaagcaca tccccctaa acaggcaaa tgtagttgga accctcgagg ttgcgctcca    23400
aggctctccc caaagtccag tccgaagatt tcaaaattcc taaagctgct cagagggata    23460
ggaactcccc gaaatccgat atccgcccag tcaggctgcg agtggagatg ggatagagcg    23520
tcttgaatat attctgcgtc aaccgccaaa agactctggc gtatacgagc tgcaatttgt    23580
gtgagatcct ccagacactc ctggcgcaat tccaccgaag gatctgtgcc atcaactagg    23640
```

```
gcctcgtttc tcccagcttg aattggcgta tatgtcaata gcaccatgtt tcccagatag   23700
tcatcaaagg ctggagtttt gaaattccca cgcatatcca ccgcgattga cagttcggta   23760
gatttaccag ccaattgtcc cgcttgccga agtatcatgg ccaaaagggc gctcacgatg   23820
tcgttactgg acaggaaccc tggactcggc ctaccatcag cctggaaaga cgtttgccct   23880
ttgatcaacg tattgcaagc ctccttcaaa tactcgatct taggaccggg gattttcagt   23940
cgccaggtga caagctcggt ggctctcgcc cggacgaagc ccgaccaatt ctttgcaagt   24000
agtgctgccc agtctccgag gccacagtag tgcttgctaa aatccatcct ggaaagaccg   24060
gagctgcttt ctgggacaag acgctcaatc tccgatcgta actgccgatc tggcgacaca   24120
cttgcagaag acatcgccgt cgggtctctg cagcaatcgg ctagaaggcc caagactcgc   24180
gcagcgcctg caccatccat tgcggaatga tgaaacgtca tggcgagaat gatcccatcg   24240
cgcatgacat ttgcttgaaa tcgtaggatc ggccttcgtg gcaacgaaat atccatgtcg   24300
ataggcaatg cgccagccg acttatgatt tcctgctcct cagtgcccgt taggaggcat   24360
tttgattgga tttccttgaa tgactcggcc tggtagtgcc gtatccggag tatagggaac   24420
tggacaagcg actctgaggc ttctggttcg atttgccagg tgtacttcgt ttggctggac   24480
tctgtccgcc gagtcacgtc ccctgcgagg aaggggtgta ccttcaatag cagctcgatg   24540
ccattctcga gaacaccaat gctcttctca ggttgcgtgg tctggaaaaa cagcagaaag   24600
gtgacgttca ttccgagggg attgtggtcg agagaagata aagggtaagc agagcggtcg   24660
ccagttcttc gggcatcgca cattccatct tcacatagac cgtggagtct cacaggtccc   24720
tctttgacct gatctctttg actgactggg agacatactt cctgggtgct catgatttct   24780
gggtgttatc ctattgagtt gagttgtgtc ttgatctttt tttttatttt ttttggattt   24840
ctgaccttgt ttcgcttata ttggactttg cttttctttg tatattgtat tgcattaccg   24900
tacaacaaag catgggattc tctgtgttct gcatgattgt ggagcgtatt ttcctcgatt   24960
tggtatacaa tcaggtcgat ccctggcgga ttccggatct gatgcatgta tacaggtcat   25020
atatctgctt tcctcggtat ttttgagctg aatatcacta tatatgcttt ggagacgatc   25080
aatcgcaaga gagggttagt gattaaatca gttagtctca tccatagtgg gcattagagc   25140
caataaaaga tggtttccac cttgagatgt gatcgccaca agaagatttt gtaaatagta   25200
tgtattttcc aggccctgat ttctatctgc atatttgtca gcttgatcta cggagtacat   25260
cttactgctt ttagatactg acagcagcaa aactccgcgt tgaaggacga gctttgacac   25320
aaggtcaggc acttctctag tacacaaatc ctaatcatcc gacgacatac tactccgtat   25380
gctgtacata gagatccatg tccaattctt gagtctgccc ctctttgatc cacagtccag   25440
ctcagccagg cgcaatctgc atgcattggc atggaagcta ggagctgaca ttggctggaa   25500
ctacgccatc tggggcacaa tgcaagctag gcaactgacc atgtactggg tcagttttga   25560
ttgagtatgc tatacggaag aaagcgacta gtactccgta ggtttgtgta ctacctgcaa   25620
gtggaaagag ataccctagat aggtgacatt agtgtccgaa ccaatgacca atggccctta   25680
tgcacccata tcccttacat ctttcagaaa gagaaaagcc acaagtatat catgtactcc   25740
gtactccgta caacggaatt acttgatctc tatattacct tcttcctgaa gaccgttcct   25800
cgctattgtc agttacacac acaatggatt ccctattgac gagcccgtta tggctcaaaa   25860
ttgcacatga gctagcactt tacctctctt ttattgtgcc aaccgccttt ctcatcataa   25920
caactcaaaa atcatccatt attcgatggg cctggacacc atgtctgctt tatatcctgt   25980
accaattctc tcttcgggta ccctctctgt cgacaagtca attcttgaag ggcgttgcag   26040
```

```
cgggtcaagc aaccgtggct gctttgcaat gccttaatct tcttctgatc acgaagctgg   26100
accaaacgga tctgctacgg gcaaatctat acagtccgtc tgcaggactg ctttctcgcc   26160
ttgctcaatc ctgcgcattg ctggtcaact ccgcggaat cggcacaatc tgggaggtta    26220
gaaacattcc ccagcacgca gcgtttgtcc aaccaaaagg caaggatcaa tcaatgagcc   26280
ggaagcggtt tgtcttgcgg gaaattgcaa tcattgtatg gcagtacctg ctccttgatt   26340
tcatttacga gtcaaccaag ggcacgtcag ccgaggattt gatgcgtctc tttggccctg   26400
gtatggaaat caagtatctc gatgcaacgt tcgaacaatg gatggggcgc ctctccgtgg   26460
gaatattctc ttggcttgta ccttcccgag tctgtcttaa tatcacttcc cgcctgtact   26520
ttctcatctt ggtagtattg ggcatttctt cgcccgagtc ttgtcgaccg ggcttcggca   26580
gagtgcggga tgtatgcacc atccgtggag tctgggggta agtgaactat tccgactgct   26640
ttcattcatt cactaacgcc accacagcaa gttctggcat caatcctttc gttggccact   26700
cacctctgtc ggaaactata tcgcaagaga cgtcctcgga cttgctcatc cctctctttt   26760
ggaacgctac accaatatct tctttacctt tttcacatcc ggcgtattgc accttgtctg   26820
tgatgctatt ctcggcgtcc cgccatctgc gtccggcgcc atgcagttct tctgctcgtt   26880
tccgcttgct attatgattg aggatggggt tcaagaaatc tggcggagag cgacgggcca   26940
aaccaaggac agtgatcgtg cagtaccgtt ctggcagagg ctcgtgggat tctttgggt    27000
ggctgtctgg atgtgtgtca catctccgtt ctacttgtac ccagctgcgc ggcaacatgc   27060
ggagaagaac tggatagtgc cattcagtat agtggaagaa attggccttg gaactgcgca   27120
aaagattttg ctgggttatg gcttgtttgt gtactgggcg gttggtgggg agatttaaat   27180
tcatgtgtcg ggattgttca tcgtggtcaa cactgtttag attgtgatat atattttcac   27240
cgaacacccc agaaacaaaa gatttaagcc ccaattaact accttgaagg gctcatgaga   27300
tttgatcaat gtagcaaccg tcagtatcct aggtcgtgat tcccccagcc agagcgagat   27360
aattttccag acatcatctt atctacatgc aaccaaaaac tccctggcat atattaacag   27420
agcaaaacta gaggagcaaa aaagaaatct caggtttggt ttttaggaat agccgaacgc   27480
gggggtcgaa cccgcagcct taagattaag agtcttacgc tctaccgatt gagctagccc   27540
ggccgggctg ttgaagagag ttgccatata gcgctacata atcctaaagc ggtcagggcc   27600
tgggggggcga acacgctgac ataatgctag cgcgtcgagc ggcgaatcct ctggaaccaa   27660
aattgttagg tggaaggtgg cttcatctac gaatctgggt gttcctcga ttggatctta    27720
tcattgcttc cctgattcgt atgagtcttt aattttctgg ttgcttgact ctgaccgcgg   27780
tcactagatt gcccaccatg tgcgttacta gaacctttcc ccgattcttt gctgcagcta   27840
acactataca gggcaaagct cgtggacgac catcagatcc atactgcctc gttgcataac   27900
ccgattcctt ggcaattgca tacatacgtc tggcctttcc tgatcatctg gcccgtgttc   27960
tttgcctttt acctctctcc cgagcgctat gataccacta ttcagggaca ggagtggacc   28020
tttgtgtttg cggggtctat catcacagtc cagtcgctct tctggctgat gaccaagtgg   28080
aacatcgata ttaacaccct attcacaact actcgatcca aatccatcga cactgcccgg   28140
cttatcaaag tggttccgat caccaatgcc ggctctgccg agatctgtaa cctgattaga   28200
gagcacattg gcccgaagaa gacccttttcg ttcctcttcc agaagcgccg cttcctcttt   28260
taccccgaga ctcgctcctt cgcacccctt tcttacgccc tcgacgccga gccgaagccg   28320
gccctcaaga cttttccagca gagcgagggc ttcacgtcga aggccgagat tgagcgcgtc   28380
```

```
caaaaccact atggtgacaa taccttcgat attcccgttc ccggtttcat tgagctcttc   28440
caggagcatg ccgtcgcgcc gttcttcgtc ttccagatct tctgtgttgg attgtggatg   28500
ttggatgaat actggtacta ctcgctcttc accctcttca tgctcgtgat gtttgagagt   28560
accgttgtgt ggcagcgcca gaggacattg agcgagttcc gtgggatgag catcaagcct   28620
tacgatgtct gggtataccg tgaacggaaa tggcaggaga tcaccagtga taagcttctt   28680
cccggtgatc tcatgtcggt gaaccgcacc aaggaggaca gcggtgttgc ttgtgatatt   28740
cttctggttg aaggcagtgt cattgtcaac gaggctatgc tttctggcga gagcacccct   28800
cttctgaaag actctatcca gctccgtcct ggcgatgact tgattgagcc agatggattg   28860
gataagctct cgtttgtgca tggaggtacc aaagtcctcc aggttactca ccctaatctg   28920
actggcgacg cgggcttgaa gaacttggcc agcaacgtta ccatgcctcc agacaatggt   28980
gccttgggtg tggttgtgaa gaccggtttc gaaaccagcc agggtagcct cgtccgtact   29040
atgatctact cgactgaacg tgtctctgcc aacaatgttg aagctctgct gttcattctc   29100
ttccttttga ttttcgccat tgccgcttcg tggtacgtgt ggcaagaagg tgtgattcgg   29160
gatcgcaaac gctccaagct tctgctcgac tgcgtcctta ttatcaccag tgttgttcct   29220
cccgaattgc ctatgaact cagcttggcc gtcaacacta gtcttgctgc tctgagcaag   29280
tatgccattt tctgcactga gccattccgt atcccctttg ctggtcgtgt tgatatcgct   29340
tgcttcgata agactggtac cctgaccgga gaggatcttg tcgttgatgg tattgctgga   29400
ctcactttgg gtgaggctgg ttcaaaggtc gaagctgatg gtgctcacac cgagttggcc   29460
aattcttctg ctgctggacc cgacaccact ctcgttctcg ccagtgctca tgccttggtg   29520
aaattggatg agggtgaagt cgtcggtgac cccatggaga aggctacttt ggaatggctt   29580
ggctggactc tgggcaagaa cgacactttg tcttccaagg gcaacgctcc cgttgtttct   29640
ggtcgcagcg ttgagtctgt tcaaatcaag agaagattcc agttctcctc ggccctgaag   29700
cgtcagagca ctatcgcgac cattacgacc aatgaccgca atgcttccaa gaagaccaag   29760
tctacttttg tgggtgtcaa gggtgccccc gagaccatca acactatgct ggtcaacaca   29820
cctcccaact acgaggagac ctacaagcac ttcacccgta acggtgctcg tgtgcttgct   29880
cttgcttaca gtacctttc ttcggagacc gagctttccc agagccgtgt gaacaattat   29940
gtccgcgaag agatcgaatc cgaactgatt tttgccggtt ccttgtcct gcagtgcccg   30000 ctgaaggacg atgccatcaa gtctgtccaa atgttaaatg aaagcagtca ccgtgttgtc   30060
atgatcaccg gtgataaccc attgactgct gtccacgtcg cacgcaaggt tgaaattgtt   30120
gaccgtgagg ttctcattct tgatgccccc gaacatgaca actctggaac caagattgtc   30180
tggcgtacca ttgacgataa gctcaacctt gaagtcgacc ccactaagcc tcttgatcct   30240
gaaatcttga agactaagga tatttgtatc actggatatg ccttggcaaa gttcaagggc   30300
cagaaggctc tccctgatct gctccgtcac acctgggttt acgctcgtgt ctctcccaag   30360
cagaaggaag agattctcct tggtcttaaa gatgctggat acaccactct gatgtgcggt   30420
gatggaacca acgatgttgg tgctctgaag caggcccacg tcggtgtcgc gcttctgaac   30480
ggctcgcaag aggatctcac caagatcgct gaacactacc ggaacactaa gatgaaggag   30540
ctgtacgaga agcaggtcag catgatgcaa agatttaacc agcccgcccc tccagtacct   30600
gttctgatcg ctcacctgta tcccccggc cctaccaacc cacactacga gaaagcgatg   30660
gagagagagt cgcagcgcaa gggtgctgcg atcaccgctc ccggcagcac tcccgaagct   30720
attccgacta tcacatcccc tggcgcacag gccctgcagc aatcgaactt gaaccccag   30780
```

```
cagcagaaaa agcagcaggc ccaggcagct gcagctggcc ttgcagacaa gctcacatcg   30840
tctatgatgg aacaggagct ggatgacagc gagcccccca ctatcaagct gggtgatgca   30900
tccgtcgctg ctcccttcac tagcaagttg gccaacgtta ttgctatccc gaatattatc   30960
cgtcaaggtc gttgcaccct ggtcgcgact attcagatgt ataaaatcct cgctttgaac   31020
tgcttgatca gtgcctacag tcttagtgtc atctacctgg atggtatcaa gtttggtgat   31080
ggacaggtca ctatcagcgg tatgctgatg agtgtctgct ccttcaatt tcccgcgcc    31140
aaggtatgtc gtatttccca tgtcgaccaa atgatttgct aatatgttac tgtgtgaagt   31200
ctgtcgaggg tctgtccaag gaacgcccgc aacccaatat tttcaacgtc tacatcattg   31260
gatctgttct tggacagttt gccatccaca ttgcgactct gatctacctt ccaactatg    31320
tctataagca cgagccgtac gtgatgaaaa cttcccctt catttgtcct acttcatagc    31380
taacataatc aacaggagag attctgatat tgatctcgag ggcgagtttg agccttccct   31440
tctgaacagt gccatctacc tcctccagct gattcagcaa atctccacct ctcgattaa    31500
ctaccaaggc cgtcccttcc gtgagtcaat ccgcgagaac aagggcatgt actggggcct   31560
cattgccgcg tccggtgtcg cattctcctg cgccactgaa ttcattcccg agctgaatga   31620
gaagttgcgc ctcgtcccct tcaccaacga atttaaggtg acattgactg tgctgatgat   31680
cttcgactac ggtggctgtt ggttgattga aacgtcctc aagcacctgt tcagtgactt    31740
ccgtcccaag gacattgcca ttcgtcgccc tgaccagctc aagcgggagg cggaacggaa   31800
gttgcaagag caagtcgacg ctgaggccca aaggagctg caaaggaagg tctagaggtt    31860
ggtggtttga agatttgtat ctgtaaacat agagaggagg ttgttgaatt ttagaaatgt   31920
tcaagtggtg tgtgacattt aatacattta ttttttggctt ttattgaagc attcttggaa   31980
actatatgta gaaacaaatt cgtatagttg aatggctcct actctgtact gtccaatcgt   32040
cgtgaggcca ggtattgcct tggtagagaa cagtgtagac tcaaatgtgg cgatcgtccg   32100
atcagcttgt tacgaggtta gggctcgaaa tgatcggccc accataactt cttgtagctc   32160
cttgttgag aggatgcagt ctacccgtta tgtagaccta attatccagg atggtcgaga    32220
atacttctca atacacaggg ttagaccccca gatatatgat atgtcacctc agagaggggc   32280
aaagactggg taattccaaa aaatgtgatt ttgcagaggg tcaaagctat atcggatact   32340
gcttcttttc tctgcctcat agtgaaggaa acactatatt cttcatggta ggcaaagagg   32400
taaaagtgta cgtgccccaa ttcggtagaa ggataggccc tgtttgaaaa ttccacattt   32460
tgaccgatat atctatagaa acatatgaag tagccgcttg gcccttctcc atttgaagct   32520
tcgagctgac gtggacttca aatgcaggat gctttgttcc tttgtactgc catgcaatat   32580
aatgttgcct tgaactcgag attataatgc gaaaacctcg tagagccgat cgcagcccga   32640
gccaacattt ttctataata cataggtaaa cgatctgtga attcagaaag ctcccacatt   32700
gtattataag catgaatcat tcaacgcgag acttcaagct tcatgaaatc cttcaggaac   32760
ccaacagttg aaagaccacc aattccctag atcccactga tttcgattac gacattccgg   32820
attgtagtag ggcatatggc gatgccgggt ttgattgcaa agaatatatt cccatacatt   32880
gcagtaccca cctttgacaa tccaggattc aggtgcgtcg acgccgccgt gattacaact   32940
agtgctggag gcgccgttgt catagaacca tttgcaggag ttaccgtcaa ttgattcggt   33000
gggtagactt cggtctggtc gcaggcattt gaggtcctc gtccagccca cattatgtcc    33060
tttcatttgg atgtagttgc ccttgcagtt cttcttggtg tacatttcca ctgtccatgg   33120
```

```
atggacatat ggcgcatcgc tggttgtggt gcttggtttc gtgttggatg ttttggttga   33180
cttgaccgat gtagttttgc tagtggtggt ggccttggtg gttgtggtgc ttgacgcagc   33240
actggccgat atcgttttat tggatgggga caaggcaagt ctctgaatag tcataaattt   33300
tgcaaaagca ttaaccgcat tagtaggcat ggcagtcttt tttgaggtgg tcgctccaat   33360
ggtgcggttg gtagaagtac agaattccga agtgcttcca cataaccat acgaagagca   33420 ctatgaattt attagatgtt gaagagcagg atttagagcc tcttgactca cacattcatt   33480
agctgcacat ggattcaaag aacccagatc agaccagttg ctagggcgct tgtcccagg   33540 cacccgggg ccacaaacag cattggaaag cgtagctggc atcatgggtt ctccagaact   33600
gaggcatata acagcaccct gcactaaatg gtcacatcca agccattccc aggtttgagc   33660
attgtaggtc tcgatatcag ccaaggcgag agagtgttct tgagcaatcg tggtgcaggt   33720
ttcgcccgcc tggacaacat atttgtgaca agaccatca ctacctgctt gaggtgcacc    33780
tgatattgct gtcggactgg ccaaaaggac gcctatgaga gtcacgaagt tgcttggtcg   33840
gaagcaccac atcatattga ctgatggaga gtagttgctt tgcttgtctt tattttgcaa   33900
ggcaggtttc atctttatct gttcaaagag gaaaacatgt gccaaactgc caaggataga   33960
tgcacgcatg aatatgacat tgccggggag gggcaaatgt ttgtgaaaga actaggatac   34020
tgtgccaggg ccattagcat agtattgaag caaattatag aatggcactg catcaaaatg   34080
tggaatcctc gaattttttc tttgtcttct aacgcctagt gcatgtcttt ccaggttgtc   34140
cttgaaggct ttgtctggtc tcccagaaat ggaaggactc aagggtatgt atacagcttc   34200
taaaacgtaa atgattcacc cgagaaagga attcataatc cgaggaaggt cagcacata   34260 aggctgtctc gaaaccccct gaatgcccaa ggaagaaagg aaattcctac ggctgggtca   34320
gactagcaag aaaacgtcac ttgacttctg agatccactc agatagcaga agaacgtgtt   34380
tggtgatttt cgttctttgt aaatgcatag gaccagatga ttcgaggaat cttcttgtta   34440
gcacccttaa tccaaatctt ctgtagacca agcactcggc tattgatact gtttcgagag   34500
tctgtaagat atgacattac tctgatacag atacgtggaa tggaaacatt gcgggctttc   34560
gaatgacatt gggttgacta acgaaggccc cttcacgcag tgacgaggcc ccaaagttca   34620
aggccaacgc gcaaagcggg accaacatcg aactccccat tctcggggag ctgagggccc   34680
gccttgattt tgacatcttc ccatttgtca aagtcattat tgaacgcctg cgtcatttcc   34740
gaagcattca gaatgcgggc caaccggaag tgacaatcta ggagatcagc acttggcaga   34800
cttcgtacat tgtctgcgtc cttgttgctg aaaaccacct ctatcggaaa aaagaccttg   34860
taatttgaag aaattccttc gaacgtgtga actttgtatt tattgtccac atcctttgaa   34920
atttcggtta gcaaggtaat aaagtaaaat cattccacaa atgggagcgc actcactgtg   34980
ggttcaaagg caagacggaa cgcgccgaag tgttcatgta cccagctagt aagggtgaga   35040
ccgttggata agctgttgat ctcttggtgc ctgaaattca tttcccggat cctgggaaaa   35100
cagcgccaga ggacctccca agctcgtgac gcatttggta tgagatcgtt cttgagcccg   35160
tgagtcattg atcttaatga ggatccgaga acttactcgc cggggatccc agactgcata   35220
tgacaaggga attatgtgtg cgctttctgt attcccgagt ttttcaatat cctctgattt   35280
gcctagactg tcccaccgat cgagatccat gtcaccagtg acaacacagc agtaaccgtc   35340
gcgttttagt aaaccttcct tgaactcccc tgtccgggac ataggctggt ccaaagtgga   35400 attttcttc gcatgggaat cctgccgttc ggttgacgag atagttactg atgggggctt   35460
agaccgagaa cgcactattt cgagtgaacg tataagtcag ggctttgtac tttttttgtta   35520
```

```
acttactacg ggttcttaga ccagtgtaca ggttgcgaaa gtattgataa attccatcat   35580
cgtcttccag gctgatgata tccttcgcaa tggagctttt gccgcgatct gggaggaaat   35640
tcaaaaaagc ttgtaatgat ttttgcagga tgtcttcgcg ttctccacgg ctcttgggtt   35700
tgtaactttc tattcttaag cgtgcggttt caatatcctg cttttgttcg gtttccgatg   35760
cttcagtaga ttgtgaaaac agcgattgtg cgcggggata ggcacgtgct ggaccagaaa   35820
cttcgctctc ttgggtttgc tgtttacgtt tttgagaccg ggtggtgggt cgatctgatt   35880
caggcaattc agaacggcgc cttttaagat tagttttgga tggtggcgac gaggaagttg   35940
gagggatgtt ttggttcggg gcatcggctt gtagtgaagg gggcggtcgc tttgctggtt   36000 tcttttttctt ccccatgatg tctgctagta gtagtatatt tcttgctttc cttttccaat   36060
actgagatgg tagtttcagt ggatgaaaat gagaacaatg ggataattca gtggatggaa   36120
atgagaacaa tgtgatgatg ggggagaaaa gtgatgtggg ggtgtcgggg gatagctccg   36180
agatattcct ccggcagaat cgctccaccg aaaaacagtc cgccggacgg gtcatccccc   36240
ttttggagaa aatgtatttg tagttacaga aaggcattag cccacagaac aagaattcat   36300
ccatatttca ttgttttcca tcaagcaatt actcgtccaa tcgtctctcg gagggtgcag   36360
agaataggct ctctctggaa ggccgctgga aaaagtggga aaaggataca ttctgtggcc   36420
acaggcgtgg gacagggttt ccccctgaca ctgggggaga atgtggaaa tgtggggaa   36480 ctctgcggag acggaagaac aaaaggcggt caactgctgc ctccacgtga tgtcacgtgg   36540
agcttagccg tccagcttgg aagataaccc tagaggaata tgagcatatt ctacggagaa   36600
ctactccgta caacatacgg agtactcata caactctgta gcaacccctg atgtgatctg   36660
tatttgaagt gtggacctga taccgactgc tcctcaaacc ccttaaaccc gtatcgagta   36720
ctccgtaata tgtacaccgt tcactgactc acattgatta atcacattag atctctcgtt   36780
ttcatgtacg tggatcatta tgagttcgag cattgaatat aagctaaaac cataccccct   36840
gaccctaagg ggccttctgg aaagaaaaat cttgtctttt gcaaatcaaa atatatatag   36900
agttgtttac ccgaactgtc gggttatgca tcttcaggcc tgtggagctg tgtcatcatt   36960
ttgttactcc cccttatcta ccgcaggatc gccaaaatgc ctagcgagac tgctacaggt   37020
gactttggtc cagcgccgcc tgggatagac ttgacagaga accaaactgg cgacttgcta   37080
ggagcagtga ttcctgtagc ggtggtcgcg acgactgcgg tgatattgcg gacgattgcg   37140
ccgacgagga tcaaagagat ccgacaaaca gctattgatg actatctcat tgttgcggcg   37200
cttttattct cttggggaac ggcaatatca tgcttcatca gtgagttgac catgaggcca   37260
aagccgatgg gcccagtact cacaacagac tctttaggca ttccatatgg caacggttat   37320
catttgcaat ctgtgacaaa agcagagttt aacactgttt ggaaagtaag gaatccaata   37380
ttaaatgaga tgcctgggat agacgttgac cagacattca gatccttttc gcctatgtca   37440
tgatttacgc tacagccgtt acctgcacca aagcctcgat cgtcttattt tacggccgca   37500
tcttccactt tcgctggtca ctggccatct gcctgtttct ggtcgttgga tattgggttg   37560
ccattattgt cacggttggg atggcctgtc gaccactgcc acatttctgg ttggtctaca   37620
cagatccatc agcccttggt gtctgcattg atattcccac gttctttttc gcaaatggca   37680
ttgctgccat ggcgattgat gtgatcatac tgtgcatgcc gatgccagca atataccagt   37740
ctcagatgca gttgtcgcaa aaggtagcgg tcgtgggtat cctactcttg ggaagtttgt   37800
atgtacctct gcccgggccc tcctacgaga aggactgtag ctaattattc tcagtgtttg   37860
```

```
cgtggcaagt atctgccgga tcatcgcact tcagaatatc accgacggga cagatacgac    37920
gtgggctatc gccccagtct ttatttggtc gtccgtggaa ccatttgttg ggattatttg    37980
cgcatgcctc ccaacatttg ggcctttctt tcggcaatgg cggtccatcg ctcggacgcg    38040
ctcatcaact gatggcagta ccgatccaag ctctgagcta ccatctgaga caacgacctg    38100
gctccgaaga tcccgaacca aaaaacctgc caaggactca atattcagta tcaatgattt    38160
ttgctgtgtc gatgaggtcc aactaatgaa cgatatcaat gccactcggt cgctggggga    38220
cgaggctgcg agtgaccatc aggacgtgga gggaggctgt atcacagtcc aaaaagatgt    38280
ggaagtgaca tgggccaagt acaagtcagg aaaaaaaaat gatctggcct tcaagtatca    38340
taaaggggct tgatcagctt tgcaaatatt tcgacttgac acggactata tttgcgtttt    38400
gtgtatattt aataaaaata gacgccactg gcaatttgta attgataaag gtaagtctta    38460
ttccgtaatc catacccgt actctataca agtactctg tgctccgtac ggagtacacg    38520
gaaacaaacg gggatatagt cgtggcacct ttccgtgtt ggcggacttg cccgtaacgt    38580
aaacactccg cagatccctt ccaacacagt acataatcct gcagcgaaga gcgatctgat    38640
agacgctatg tgccgtcgtg acttgttatg ccaattaacg gtggcagaat tgtggagcaa    38700
tctagcagag gaaagtttcg atgtgcatgc cgagccctaa aaagtcccag tgcggagaat    38760
gtagtaatcg actggacatt ccatgtactt tgcacgctat aacatatttc tatgccatat    38820
accctctgg taatcatgta gatcctcttg cttactgcgt tggctccttt gtatcgtact    38880
ttccgcgtcg cagcattata agaggataga gagaccgcat gagagaatac acaagagaaa    38940
tcactaattc actacctgat cccccaattc actcaacatg tctcacattc acacttccag    39000
attgcaaa                                                             39008
```

<210> SEQ ID NO 267
<211> LENGTH: 556
<212> TYPE: PRT
<213> ORGANISM: Penicillium coprobium PF1169

<400> SEQUENCE: 267

```
Met Glu His Glu Thr Asp Leu Val Ser Phe Ala Phe Ser Gly Pro Ala
1               5                   10                  15

Phe Asp Gln Ser Lys Pro Ile Tyr Ile Asp Ala Arg Asn Pro Ser Arg
            20                  25                  30

Ala Phe Asn Ala Ile Gln Phe Arg Arg Leu Val Arg Ser Leu Ile Ala
        35                  40                  45

Gly Leu Lys Ala Arg Gly Val Glu Arg Gly Asp Cys Val Leu Val Gln
    50                  55                  60

Leu Glu Asn Ser Val Leu His Ser Ala Leu Phe Phe Ala Ile Val Gly
65                  70                  75                  80

Ala Gly Gly Val Tyr Met Gly Phe Asp Val Ala Ser Arg Pro His Glu
                85                  90                  95

Val Ala His Leu Leu Arg Val Ala Glu Pro Arg Leu Ile Ile Thr Ala
            100                 105                 110

Pro Ser Ala Leu Thr Arg Val Leu Glu Val Cys Asn Asn Gln Gly Met
        115                 120                 125

Ser Ser Asn Gln Val Leu Leu Met Asp Glu Lys Ser Ile Glu Ser Val
    130                 135                 140

Val Gln Phe Ala His Gly Gln Ala Glu Gln Thr Glu Asp Leu Asp Thr
145                 150                 155                 160

Gln Thr Val Asp Gln Pro Ile Arg Leu Glu Ser Leu Leu Gln Tyr Gly
```

```
                165                 170                 175
Glu Leu Asp Trp Leu Arg Phe Glu Asp Ser Glu Glu Ser Lys Ile Thr
            180                 185                 190

Pro Ala Ala Met Phe Leu Thr Ser Gly Thr Ser Gly Leu Pro Lys Ala
            195                 200                 205

Ala Ile Arg Thr His His Thr Ile Ile Ser His His Leu Ser Val Tyr
            210                 215                 220

Tyr Glu Val Pro Tyr Pro Val Arg Leu Met Ala Leu Pro Leu Tyr
225                 230                 235                 240

His Ser Phe Gly Asp Phe Trp Gly Asn Ile Phe Pro Ile Arg Tyr Gly
                245                 250                 255

Gln Pro Leu Tyr Ile Ile Pro Arg Phe Glu Ile Thr Ala Leu Leu Asp
            260                 265                 270

Gly Ile Arg Gln His His Ile Thr Glu Thr Tyr Met Val Pro Ala Met
            275                 280                 285

Ile His Ile Leu Asn Arg Ser Ser Leu Asn Val Ala Glu Ser Leu Ser
            290                 295                 300

Ser Leu Arg Tyr Ile Gly Ile Ser Gly Ala Pro Ile Asp Gly Tyr Ser
305                 310                 315                 320

Met Gln Gln Phe Gln Ser Leu Leu Ser Pro Asp Ala Ile Ala Gly Asn
                325                 330                 335

Leu Trp Gly Met Ser Glu Val Gly Val Val Phe Gln Asn Arg Tyr Gly
            340                 345                 350

Ile Gln Pro Gln Phe Gly Ser Val Gly Thr Leu Leu Pro Arg Tyr Glu
            355                 360                 365

Leu Arg Phe Val Asn Pro Asp Thr Gly Glu Asp Val Ala Gly Thr Pro
            370                 375                 380

Asp Ser Pro Gly Glu Leu Tyr Val Arg Gly Pro Gly Leu Leu Leu Ala
385                 390                 395                 400

Tyr Lys Gly Arg Thr Asp Ala Lys Asp Glu Gln Gly Trp Phe Arg Thr
                405                 410                 415

Gly Asp Met Phe His Val Glu Asp Gly Asn Tyr His Val Ile Gly Arg
            420                 425                 430

Thr Lys Asp Leu Ile Lys Val Arg Gly Gln Val Thr Gln Tyr Ser Val
            435                 440                 445

Ala Pro Ala Glu Ile Glu Gly Ile Leu Arg Lys Asp Pro Ser Ile Lys
            450                 455                 460

Asp Ala Ala Val Ile Gly Val Met Leu Pro Asp Gly Ser Ser Glu Val
465                 470                 475                 480

Pro Arg Ala Tyr Val Val Arg Asn Asp Thr Ser Pro Glu Thr Thr Ala
                485                 490                 495

Asp Gln Val Ala Gly Leu Ile Gln Ser Gln Leu Ala Ser Tyr Lys Ala
            500                 505                 510

Leu Asp Gly Gly Val Val Phe Val Asp Ile Pro Arg Ile Gly Ile
            515                 520                 525

Gly Lys His His Arg Ala Lys Leu Ser Gln Leu Asp His Gln Arg Glu
            530                 535                 540

Thr Ile Ala Ser Ile Leu Ala Glu Pro Val Ala Val
545                 550                 555

<210> SEQ ID NO 268
<211> LENGTH: 2447
<212> TYPE: PRT
<213> ORGANISM: Penicillium coprobium PF1169
```

<400> SEQUENCE: 268

Met Lys Ala Thr Glu Pro Val Ala Ile Ile Gly Thr Gly Cys Arg Phe
1               5                   10                  15

Pro Gly Gly Ala Ser Pro Ser Lys Leu Trp Glu Leu Leu Gln Ser
            20                  25                  30

Pro Arg Asp Ile Ala Arg Lys Val Pro Ala Asp Arg Phe Asn Ile Asp
            35                  40                  45

Ala Phe Tyr His Pro Asp Gly Asp His His Gly Thr Thr Asn Val Lys
        50                  55                  60

Glu Ser Tyr Phe Leu Asp Glu Asp Ile Lys Ala Phe Asp Ala Ala Phe
65                  70                  75                  80

Phe Asn Ile Ser Pro Thr Glu Ala Val Ala Met Asp Pro Gln Gln Arg
                85                  90                  95

Leu Leu Leu Glu Thr Val Tyr Glu Ser Leu Asp Ala Ala Gly Leu Arg
            100                 105                 110

Met Asp Ala Leu Gln Arg Ser Lys Thr Gly Val Phe Cys Gly Thr Leu
        115                 120                 125

Arg Asn Asp Tyr Asn Gln Ile Gln Ala Met Asp Pro Gln Ala Phe Pro
130                 135                 140

Ala Tyr Val Val Thr Gly Asn Ser Pro Ser Ile Met Ala Asn Arg Ile
145                 150                 155                 160

Ser Tyr Tyr Phe Asp Trp Gln Gly Pro Ser Met Ala Val Asp Thr Gly
                165                 170                 175

Cys Ser Ser Ser Leu Leu Ala Val His Leu Gly Val Glu Ala Leu Gln
            180                 185                 190

Asn Asp Asp Cys Ser Met Ala Val Ala Val Gly Ser Asn Leu Ile Leu
        195                 200                 205

Ser Pro Asn Ala Tyr Ile Ala Asp Ser Lys Thr Arg Met Leu Ser Pro
210                 215                 220

Thr Gly Arg Ser Arg Met Trp Asp Ser Lys Ala Asp Gly Tyr Gly Arg
225                 230                 235                 240

Gly Glu Gly Val Ala Ser Val Val Leu Lys Arg Leu Gln Asp Ala Ile
                245                 250                 255

Asn Asp Gly Asp Pro Ile Glu Cys Val Ile Arg Ala Ser Gly Ala Asn
            260                 265                 270

Ser Asp Gly Arg Thr Met Gly Ile Thr Met Pro Asn Pro Lys Ala Gln
        275                 280                 285

Gln Ser Leu Ile Leu Ala Thr Tyr Ala Arg Ala Gly Leu Ser Pro Gln
290                 295                 300

Asn Asn Pro Glu Asp Arg Cys Gln Tyr Phe Glu Ala His Gly Thr Gly
305                 310                 315                 320

Thr Gln Ala Gly Asp Pro Gln Glu Ala Ala Ile Asn Ser Ser Phe
                325                 330                 335

Phe Gly Pro Glu Ser Val Pro Asp Ser Thr Asp Arg Leu Tyr Val Gly
            340                 345                 350

Ser Ile Lys Thr Ile Ile Gly His Thr Glu Ala Thr Ala Gly Leu Ala
        355                 360                 365

Gly Leu Ile Lys Ala Ser Ser Leu Gln His Gly Met Ile Ala Pro
370                 375                 380

Asn Leu Leu Met Gln His Leu Asn Pro Lys Ile Lys Pro Phe Ala Ala
385                 390                 395                 400

Lys Leu Ser Val Pro Thr Glu Cys Ile Pro Trp Pro Ala Val Pro Asp

-continued

```
                405                 410                 415
Gly Cys Pro Arg Arg Ala Ser Val Asn Ser Phe Gly Phe Gly Gly Ala
                    420                 425                 430

Asn Val His Val Val Leu Glu Ser Tyr Thr Arg Ser Glu Leu Ser Pro
                    435                 440                 445

Ser Asn Asn Ile Pro Ser Ser Leu Pro Phe Val Phe Ser Ala Ala Ser
                    450                 455                 460

Glu Arg Thr Leu Thr Cys Val Met Glu Ser Tyr Ala Thr Phe Leu Gln
465                 470                 475                 480

Glu His Ala Thr Val Ser Leu Val Gly Leu Ala Leu Ser Leu Trp Asp
                    485                 490                 495

Arg Arg Ser Thr His Arg His Arg Leu Thr Leu Met Ala His Ser Ile
                    500                 505                 510

Gln Glu Leu Lys Asp Gln Ile Asn Thr Glu Ile Ser Arg Arg Val Thr
                    515                 520                 525

Gly Lys Pro Ala Ser Val Val Ser Arg Ser Asn Thr Arg Pro Arg Arg
                    530                 535                 540

Val Met Gly Ile Phe Thr Gly Gln Gly Val Gln Trp Pro Gln Met Gly
545                 550                 555                 560

Leu Asp Leu Ile Glu Ala Ser Pro Ser Ile Arg Lys Trp Ile Met Asn
                    565                 570                 575

Leu Glu Glu Ala Leu Asp Glu Leu Pro Leu Asp Leu Arg Pro Gln Phe
                    580                 585                 590

Ser Leu Leu Asp Glu Leu Ser Gln Pro Ala Ser Ser Ser Arg Val Asn
                    595                 600                 605

Glu Gly Leu Leu Ser Leu Pro Leu Arg Thr Ala Leu Gln Ile Met Gln
                    610                 615                 620

Val Asn Met Leu Arg Ala Val Gly Ile Glu Leu Thr Ile Val Val Gly
625                 630                 635                 640

His Ser Ser Gly Glu Ile Val Ala Ala Tyr Ala Ala Gly Val Leu Thr
                    645                 650                 655

Ala Ser Asp Ala Ile Arg Ile Ala Tyr Leu Arg Gly Met Thr Ile Asp
                    660                 665                 670

Lys Ser Arg Asp Pro Thr Gly Arg Met Met Ala Val Asn Leu Thr Trp
                    675                 680                 685

Gln Gln Ala Gln Asn Ile Cys Ala Leu Glu Ala Tyr Ser Gly Arg Ile
                    690                 695                 700

Ser Val Ala Ala Ala Asn Ser Pro Ser Ser Val Thr Leu Ser Gly Asp
705                 710                 715                 720

Ala Glu Cys Leu Arg Glu Leu Glu Trp Leu Leu Lys Ser Leu Gly Leu
                    725                 730                 735

Thr Pro Arg Met Leu Arg Val Asp Thr Ala Tyr His Ser Pro His Met
                    740                 745                 750

Lys Pro Cys Ala Asp Pro Tyr Arg Asp Ala Met Lys Ala Tyr Pro Val
                    755                 760                 765

Ala Leu Ser Ala Ser Ala Ser Arg Trp Tyr Ser Ser Val Tyr Pro Gly
                    770                 775                 780

Glu Val Met Thr Gly Tyr Asp Gln Gln Glu Leu Thr Gly Glu Tyr Trp
785                 790                 795                 800

Val Glu Asn Met Leu Arg Pro Val Gln Phe Ser Gln Ala Leu Glu Ala
                    805                 810                 815

Ala Ala Arg Asp Ala Gly Pro Pro Asp Leu Ile Ile Glu Ile Gly Pro
                    820                 825                 830
```

-continued

His Pro Thr Leu Arg Gly Pro Val Leu Gln Thr Leu Ser Lys Met His
       835                 840                 845

Ser Ala His Ser Ala Ile Pro Tyr Leu Ala Leu Ala Glu Arg Gly Lys
850                 855                 860

Pro Gly Leu Asp Thr Trp Ala Thr Ala Leu Gly Ser Ser Trp Ala His
865                 870                 875                 880

Leu Gly Pro Asn Val Val Arg Leu Thr Asp Tyr Val Ser Leu Phe Asp
               885                 890                 895

Pro Asn His Trp Pro Val Leu Val Glu Ser Leu Pro Phe Tyr Pro Phe
               900                 905                 910

Asp His Thr Gln Thr Tyr Trp Thr Gln Ser Arg Met Ser Ser Asn His
               915                 920                 925

Asn His Arg Ala Thr Ser Pro Asn Ala Leu Leu Gly Ser Leu Ser Pro
               930                 935                 940

Glu Thr Gly Ala Glu Lys Phe Arg Trp Arg Asn Tyr Leu Arg Pro Glu
945                 950                 955                 960

Glu Leu Pro Trp Leu Ala Asp Arg Arg Ala Asp Ser Gly Ser Val Phe
               965                 970                 975

Pro Glu Thr Gly Tyr Ile Ser Met Ala Leu Gly Ala Gly Met Ile Met
               980                 985                 990

Ala Gln Thr Gln Gly Leu Arg Leu Leu Asn Val Lys Asp Leu Thr Ile
               995                 1000                1005

His Thr Gln Leu Pro Ile Gln Asn Asp Pro Ile Gly Thr Glu Val
       1010                1015                1020

Leu Val Thr Val Gly Ser Ile His Ser His Asp Gly Ala Ile Thr
       1025                1030                1035

Ala Trp Phe Cys Cys Glu Ala Val Val Ser Gly Glu Leu Val Gln
       1040                1045                1050

Cys Ala Thr Ala Lys Met Ile Met His Pro Gly Asp Ser Asp Arg
       1055                1060                1065

Ala Leu Leu Pro Pro Gln Gly Gln Leu Pro Gln Ala Leu Glu Pro
       1070                1075                1080

Val Asp Ser Thr Glu Phe Tyr Asp Ser Leu Arg Arg Ala Asp Tyr
       1085                1090                1095

His Cys Thr Gly Pro Phe Ser Thr Leu Thr Gly Leu Arg Lys Arg
       1100                1105                1110

Arg Asp Leu Ala Thr Gly Ser Val Pro Val Pro Ser Asn Asp Ser
       1115                1120                1125

Asp Glu Pro Met Ala Leu His Pro Ala Ile Leu Asp Leu Gly Val
       1130                1135                1140

Gln Thr Met Ile Ala Ala Ile Gly Gly Leu Glu Glu Thr Leu Leu
       1145                1150                1155

Thr Gly Pro Phe Leu Ser Arg Asn Val Asp Ser Thr Trp Ile Asn
       1160                1165                1170

Pro Val Leu Cys Ala Ser Asp Trp Gln Gly Lys Glu Leu Thr Val
       1175                1180                1185

Ala Ser Tyr Leu Thr Cys Val Asn Gly Asp Arg Ile Arg Gly Asp
       1190                1195                1200

Ile Asp Ile Phe Thr Met Asn Gly Glu Lys Ala Val Gln Leu Glu
       1205                1210                1215

Gly Val Ser Leu Ile Cys Gln Pro Ser Gly Thr Ala Pro Asn Asn
       1220                1225                1230

```
Leu Gln Val Leu Ser Gln Thr Ala Trp Gly Pro Leu Glu Pro Thr
1235                1240                1245

Leu Lys Lys Gly Ser Arg Lys Leu Pro Ala Thr Met Leu Gln Leu
1250                1255                1260

His Ser Leu Arg Glu Glu Leu Ala Leu Leu Tyr Leu Lys Gln Ala
1265                1270                1275

Arg Asn Gly Leu Thr Asp Leu Glu Arg Ser Gly Leu Asp Phe Asp
1280                1285                1290

Gly Ala Arg Leu Leu Ala Trp Met Asn Gln Cys Ile Ala Asn Ala
1295                1300                1305

Ser Gln Glu Pro Asp Pro Val Gly Glu Ser Glu Cys Leu Asp Gln
1310                1315                1320

Lys Ile Glu Asp Phe Thr Ala Gly Val Ser Pro Ser Leu Leu Asn
1325                1330                1335

Asp Pro Gly Leu Thr Ala Ile Ala Ala Val Gly Gln Arg Leu Pro
1340                1345                1350

Arg Val Leu Arg Asp Ser Gly Leu Gln Ile Glu Ala Trp Pro Ala
1355                1360                1365

Ile Asp Glu Glu Ser Gln Tyr Leu Lys Glu Asp Leu Gln Val Leu
1370                1375                1380

Asp Leu Glu Asp Glu Leu Val Ser Val Val Ser Gln Ala Cys Phe
1385                1390                1395

Arg Phe Pro Gln Met Asn Ile Leu Gln Ile Gly Gln Phe Gly Gly
1400                1405                1410

His Val His Ser Gly Leu Lys Lys Met Gly Arg Thr Tyr Arg Ser
1415                1420                1425

Phe Thr Tyr Ala Gly Leu Ser Val Ser Gly Leu Gln Ala Ile Glu
1430                1435                1440

Glu Asp Leu Glu Gln Pro Gly Glu Val Ser His Lys Thr Leu Asp
1445                1450                1455

Ile Asn Glu Asp Pro Val Glu Gln Gly Cys Arg Glu Gln Phe Tyr
1460                1465                1470

Asp Met Val Leu Ile Thr Ala Ala Val Phe Leu Gln Glu Val Ala
1475                1480                1485

Val Ala His Val Arg Arg Leu Leu Lys Pro Gly Gly Phe Leu Val
1490                1495                1500

Leu Leu Val Arg Thr Asn Pro Ser Thr Thr Tyr Leu Asn Leu Leu
1505                1510                1515

Phe Gly Pro Pro Met Arg Cys Thr Glu Thr Gly Lys Gly Tyr Cys
1520                1525                1530

Ser Gly Glu Pro Ile Thr Thr Arg Arg Asp Trp Val Glu Leu Leu
1535                1540                1545

Ser Asn Gly Gly Phe Tyr Gly Leu Asp Ser Phe Asp Ala Ser Gln
1550                1555                1560

Glu Ser Glu Ser Leu Gly Asp Phe Ser Leu Leu Leu Cys Arg Thr
1565                1570                1575

Pro Asp Ser Pro Ala Glu Pro Gln Ser Arg Gly Asp Leu Leu Leu
1580                1585                1590

Leu Gly Gly Asp Ala Glu Glu Ala Asp Cys Leu Thr Ser Glu Leu
1595                1600                1605

Phe Glu Leu Val Gln Asp Asp Phe Val Lys Val Ala His Ala Pro
1610                1615                1620

Asp Leu Asp Leu Ile Glu Asp Arg Asp Leu Ser Lys Leu Thr Val
```

-continued

```
            1625                1630                1635

Leu Tyr Leu Val Asp Asp Arg Asp Leu Thr Asn Ala Thr Leu Ser
        1640                1645                1650

Glu Leu Cys Arg Leu Met Thr Val Ser Lys Arg Met Leu Val Val
        1655                1660                1665

Thr Cys Glu Lys Val Asp His Pro Asp Ala Gly Leu Val Lys Gly
        1670                1675                1680

Leu Leu Ser Thr Phe Leu Ala Ser Glu Arg Ser Ser Ser Leu Leu
        1685                1690                1695

Gln Leu Leu His Ile Thr Asp Pro Val Gly Val Thr Thr Glu Ile
        1700                1705                1710

Leu Ala Thr Ala Leu Gly His Phe Val Gln Ala Ser Ala Ala Gln
        1715                1720                1725

Glu Asn Pro His Ser Cys Gly Leu Thr Asn Ile Glu Pro Glu Ile
        1730                1735                1740

Gln Tyr Asp Gly Ser Met Phe Arg Val Pro Arg Gln Tyr His Asp
        1745                1750                1755

His Ala Thr Gly Leu Arg His Leu Ala Arg Arg Gln Lys Val Thr
        1760                1765                1770

Asp Cys Val Asp Leu Asp Lys Gly Val Val Gln Ile Leu Pro Ala
        1775                1780                1785

Thr Thr Asp Lys Thr Cys Glu Gly Phe Arg Leu Leu Ser Met Ala
        1790                1795                1800

Asp Pro Pro Ile Thr Ala Ser Tyr Gly Pro Thr Leu His Leu Arg
        1805                1810                1815

Val Arg His Ser Ser Ile Ala Ala Val Arg Val Ala Gly Ala Ile
        1820                1825                1830

Phe Leu Arg Leu Val Ile Gly Leu Asp Val Lys Ser Asn Lys Arg
        1835                1840                1845

Met Ile Ala Leu Ser Ser His Ile Ala Ser His Val Ile Val Pro
        1850                1855                1860

Asp Ser Trp Ala Trp Ser Val Pro Asp Thr Val Leu Glu Ala His
        1865                1870                1875

Glu Gln Ser Tyr Leu Arg Ala Thr Ala Ala Leu Leu Ala Gly
        1880                1885                1890

Tyr Leu Val Glu Gln Val Pro Gln Ser Gly Thr Leu Val Val His
        1895                1900                1905

Glu Ala Asp Gly Val Leu Gln Ser Val Phe His Gln Met Leu Thr
        1910                1915                1920

Arg Arg Asp Gly Lys Val Ile Phe Ser Thr Ser Lys Ser Asn Pro
        1925                1930                1935

Asp Lys Glu Arg Pro Met Leu Leu Leu His Glu His Ser Thr Ala
        1940                1945                1950

Arg Gln Leu Ser Gln Val Leu Pro Ser Asp Val Ser Ala Ile Ala
        1955                1960                1965

Ile Leu His Arg Arg Gly Gln Gly Val Tyr Asp Arg Met Leu Ser
        1970                1975                1980

Leu Leu Pro Asp Asn Ala Thr Arg Ile His Leu Gln Asp Phe Tyr
        1985                1990                1995

Leu Thr Ser Ala Ser Thr Gly Pro Ile Asn Ala Asp Asp Ser Ser
        2000                2005                2010

Leu Ile Ala Lys Ala Phe Leu Thr Ala Cys Leu Val Ala Tyr Thr
        2015                2020                2025
```

-continued

Gly Arg Glu Gly Leu Pro Pro Asn Ser Val Asp Ser Leu Pro Ile
2030                2035                2040

Ser Arg Ile Ser Glu Tyr Pro Ile Leu Asp Ser Gln Asp Ala Val
2045                2050                2055

Val Asp Trp Asp Ser Thr Thr Pro Val Leu Ala Gln Ile Pro Thr
2060                2065                2070

Ala Gly Ser Gln Val Gln Leu Ser Glu Lys Lys Thr Tyr Ile Leu
2075                2080                2085

Val Gly Leu Gly Ser Glu Leu Ala His Ala Ile Cys Leu Trp Leu
2090                2095                2100

Ala Thr His Gly Ala Lys Trp Ile Leu Leu Ala Gly Ser Arg Leu
2105                2110                2115

Asp Ser Asp Ala Trp Trp Leu Glu Glu Val Ser Arg Arg Gly Thr
2120                2125                2130

Arg Ile Ala Val Ser Lys Ile Asn Leu Ile Asp Gly Ile Ser Ala
2135                2140                2145

Thr Ser Leu His Gln Thr Ile Pro Tyr Ala Phe Pro Pro Val Val
2150                2155                2160

Gly Gly Val Leu Ile Gln Pro Pro Leu Pro Asp Cys Ser Leu
2165                2170                2175

Ser Gln Leu Thr Ile Asp Ser Leu Arg Asn His Leu His Pro Val
2180                2185                2190

Leu Lys Gly Leu Gln Gln Leu Asp Glu Leu Tyr Lys Thr Pro Thr
2195                2200                2205

Leu Asp Phe Trp Val Leu Ile Gly Ser Ile Ala Gly Val Leu Gly
2210                2215                2220

His Ala Asp Gln Ala Met Thr Ala Ala Met Ser Glu Lys Met Ala
2225                2230                2235

Leu Leu Val Arg His Arg Arg Ala Gln Gly Arg Pro Ala Ser Leu
2240                2245                2250

Val His Leu Gly Glu Ile His Gly Ile Ser Ser Pro Ser Pro Ser
2255                2260                2265

Gln Pro Leu Trp Cys Gly Pro Val Ala Val Ser Gln Arg Asp Val
2270                2275                2280

Asp Glu Ile Leu Ala Glu Ala Ile Leu Cys Gly Arg Ser Asp Ser
2285                2290                2295

Asn Ser Asn Ala Glu Leu Ile Gly Gly Leu Arg His Gln Ser Leu
2300                2305                2310

Lys Cys Gly Tyr Gly Glu Cys Pro Ile Pro Lys Leu Trp Pro Phe
2315                2320                2325

Tyr Ser Tyr Thr Ala Thr Ala Ser Gln Asp Gln Ile Leu Ala Leu
2330                2335                2340

Ile Glu Thr Arg Ser Thr Lys Asp Leu Val Thr Ala Ala Thr Ser
2345                2350                2355

Leu Glu Glu Lys Ala Glu Ala Val Val Arg Pro Leu Met Glu Lys
2360                2365                2370

Ile Arg Ala Ser Leu Asn Leu Ala Glu Asp Ala Pro Leu Ser Ala
2375                2380                2385

Asp Thr Leu Ile Pro Glu Leu Gly Ile Asp Ser Leu Ile Ala Ile
2390                2395                2400

Gly Leu Ser Gln Trp Phe Thr Lys Glu Leu Ser Val Asp Ile Gly
2405                2410                2415

```
Val Ile Leu Ile Leu Ser Gly Val Ser Val Gly Glu Leu Ala His
    2420                2425                2430

Ala Ala Ala Ser Lys Leu Cys Asn Val Ser Val Gly Lys Pro
    2435                2440                2445

<210> SEQ ID NO 269
<211> LENGTH: 509
<212> TYPE: PRT
<213> ORGANISM: Penicillium coprobium PF1169

<400> SEQUENCE: 269

Met Asp Asn Met Asp Asn Met Asn Asn Thr Pro Leu Gly Phe Asn Trp
1               5                   10                  15

Ala Trp Ala Val Ile Ile Ser Phe Leu Gly Leu Leu Thr Phe Ser Phe
                20                  25                  30

Val Ser Pro His Leu Phe Pro Ser Arg Leu Thr Val Ile Asn Gly Gly
            35                  40                  45

Arg Ala Trp Asp Ile Phe Arg Thr Lys Ala Lys Lys Arg Phe Arg Ser
        50                  55                  60

Asp Ala Ala Arg Leu Ile Lys Asn Gly Phe Glu Ser Pro Asp Ala
65                  70                  75                  80

Phe Arg Ile Ile Thr Asp Asn Gly Pro Leu Leu Val Leu Ser Pro Gln
                85                  90                  95

Tyr Ala Arg Glu Val Arg Ser Asp Asp Arg Leu Ser Leu Asp His Phe
            100                 105                 110

Ile Ala Ser Glu Phe His Pro Asn Ile Pro Gly Phe Glu Pro Phe Lys
        115                 120                 125

Leu Ile Leu Asp Pro Lys Asn Pro Leu Asn Thr Ile Leu Lys Ser Asn
    130                 135                 140

Leu Thr Gln Ala Leu Glu Asp Leu Ser Ala Glu Val Thr Glu Ala Leu
145                 150                 155                 160

Ser Ala Thr Cys Thr Asp Asp Pro Glu Trp His Glu Val Ser Val Ser
                165                 170                 175

Gln Thr Ala Leu Lys Ile Ile Ala Gln Met Ala Ser Lys Ala Phe Ile
            180                 185                 190

Gly Gln Glu Arg Cys Arg Asp Ala Lys Trp His Asn Ile Ile Ile Thr
        195                 200                 205

Tyr Thr His Asn Val Tyr Gly Ala Ala Gln Ala Leu His Phe Trp Pro
    210                 215                 220

Ser Phe Leu Arg Pro Ile Val Ala Gln Phe Leu Pro Ala Cys Arg Thr
225                 230                 235                 240

Leu Gln Ala Gln Ile Ala Glu Ala Arg Glu Ile Leu Glu Pro Leu Val
                245                 250                 255

Ala Gln Arg Arg Ala Glu Arg Ala Thr Arg Ala Ala Gln Glu Lys Pro
            260                 265                 270

His Pro Ser Gly Gly Asp Ile Ile Asp Trp Leu Glu Gln Phe Tyr Gly
        275                 280                 285

Asp Gln Pro Tyr Asp Pro Val Ala Ala Gln Leu Leu Leu Ser Phe Ala
    290                 295                 300

Ala Ile His Gly Thr Ser Asn Leu Leu Ala Gln Ala Leu Ile Asp Leu
305                 310                 315                 320

Cys Gly Gln Pro Glu Leu Val Gln Asp Leu Arg Glu Glu Ala Val Ser
                325                 330                 335

Val Leu Gly Lys Glu Gly Trp Thr Arg Ala Ala Leu Tyr Gln Leu Lys
            340                 345                 350
```

```
Leu Met Asp Ser Ala Leu Lys Glu Ser Gln Arg Leu Ala Pro Asn Arg
            355                 360                 365

Leu Leu Ser Met Gly Arg Ile Ala Gln Gly Asp Met Asp Leu Ser Asp
    370                 375                 380

Gly Leu Arg Ile His Arg Gly Thr Thr Leu Met Val Ser Ala His Asn
385                 390                 395                 400

Met Trp Asp Pro Glu Ile Tyr Pro Asp Pro Arg Lys Tyr Asp Gly Tyr
                405                 410                 415

Arg Phe His Lys Leu Arg Gln Thr Ser Gly Gln Glu Gly Gln His Gln
            420                 425                 430

Leu Val Ser Ser Thr Pro Asp His Met Gly Phe Gly Tyr Gly Lys His
            435                 440                 445

Ala Cys Pro Gly Arg Phe Phe Ala Ala Ala Gln Ile Lys Val Ala Leu
            450                 455                 460

Cys Asn Ile Leu Leu Lys Tyr Asp Ile Glu Tyr Arg Gly Gly Lys Ser
465                 470                 475                 480

Pro Gly Val Trp Gly Gln Gly Ile His Leu Phe Pro Asp Pro Thr Ser
                485                 490                 495

Arg Ile His Val Arg Arg Lys Glu Glu Ile Asn Leu
            500                 505

<210> SEQ ID NO 270
<211> LENGTH: 505
<212> TYPE: PRT
<213> ORGANISM: Penicillium coprobium PF1169

<400> SEQUENCE: 270

Met Ile Glu Leu Lys Asp Ala Ser Met Gly Ala Val Leu Leu Thr Cys
1               5                   10                  15

Val Leu Val Leu Ala Gly Leu Tyr Leu Ile Arg Leu Thr Leu Ser Ser
                20                  25                  30

Asp Gln Leu Asp Lys Phe Pro Ser Ile Asn Pro Arg Lys Pro Trp Glu
            35                  40                  45

Ile Val Asn Val Phe Ala Gln Arg Arg Phe Gln Gln Asp Gly Pro Arg
50                  55                  60

Tyr Leu Glu Ala Gly Tyr Ala Lys Ser Pro Ile Phe Ser Val Val Thr
65                  70                  75                  80

Asp Leu Gly Pro Lys Leu Val Val Ser Gly Ala Phe Ile Glu Glu Phe
                85                  90                  95

Lys Asp Glu Lys Leu Leu Asp His Tyr Arg Ser Met Ile Glu Asp Phe
            100                 105                 110

Met Ala Glu Val Pro Gly Phe Glu Ser Met Phe Leu Gly Asn Leu His
            115                 120                 125

Asn Thr Val Leu Arg Asp Val Ile Ser Val Ile Thr Arg Glu Leu Glu
130                 135                 140

Gln Leu Leu Ala Pro Leu Ser Asp Glu Val Ser Ala Ala Leu Val Asp
145                 150                 155                 160

Thr Trp Thr Asp Ser Pro Asp Trp His Glu Val Ala Leu Leu Pro Ser
                165                 170                 175

Met Leu Gly Leu Ile Ala Lys Val Ser Ser Leu Val Phe Val Gly Glu
            180                 185                 190

Pro Leu Cys Arg His Pro Val Trp Leu Glu Thr Val Ile Asn Phe Thr
            195                 200                 205

Leu Ile Arg His Asn Ala Ile Leu Ala Leu His Gln Cys Pro Ala Val
```

```
            210                 215                 220
Leu Arg Pro Val Leu His Trp Val Leu Pro Pro Cys Gln Lys Leu Arg
225                 230                 235                 240

Arg Glu Ile Arg Thr Ala Arg Thr Leu Ile Asp Ser Ala Leu Glu Lys
                245                 250                 255

Ser Arg Lys Asn Pro Gln Thr Glu Lys Phe Ser Ser Val Ala Trp Val
            260                 265                 270

Asp Ala Phe Ala Lys Gly Asn Lys Tyr Asn Ala Ala Met Val Gln Leu
        275                 280                 285

Arg Leu Ala Asn Ala Ser Ile His Ser Ser Ala Asp Leu Leu Val Lys
    290                 295                 300

Ile Leu Ile Asn Leu Cys Glu Gln Pro Glu Leu Ile Arg Asp Leu Arg
305                 310                 315                 320

Asp Glu Ile Ile Ser Val Leu Gly Glu Asn Gly Trp Arg Ser Ser Thr
                325                 330                 335

Leu Asn Gln Leu Lys Leu Leu Asp Ser Val Leu Lys Glu Ser Gln Arg
            340                 345                 350

Leu His Pro Val Thr Thr Gly Ala Phe Ser Arg Phe Thr Arg Gln Asp
        355                 360                 365

Ile Lys Leu Thr Asn Gly Thr Glu Ile Pro Ser Gly Thr Pro Ile Met
    370                 375                 380

Val Thr Asn Asp Val Ala Gly Asp Ala Ser Ile Tyr Asp Asp Pro Asp
385                 390                 395                 400

Val Phe Asp Gly Tyr Arg Tyr Phe Arg Met Arg Glu Gly Ala Asp Lys
                405                 410                 415

Ala Arg Ala Pro Phe Thr Thr Thr Gly Gln Asn His Leu Gly Phe Gly
            420                 425                 430

Tyr Gly Lys Tyr Ala Cys Pro Gly Arg Phe Phe Ala Ala Thr Glu Ile
        435                 440                 445

Lys Ile Ala Leu Cys His Met Leu Leu Lys Tyr Glu Trp Arg Leu Val
    450                 455                 460

Lys Asp Arg Pro His Gly Ile Val Thr Ser Gly Phe Ala Ala Phe Arg
465                 470                 475                 480

Asp Pro Arg Ala Ser Ile Glu Val Arg Arg Ala Val Ala Gly Glu
                485                 490                 495

Glu Leu Glu Val Leu Thr Gly Lys Lys
            500                 505

<210> SEQ ID NO 271
<211> LENGTH: 241
<212> TYPE: PRT
<213> ORGANISM: Penicillium coprobium PF1169

<400> SEQUENCE: 271

Met Asp Gly Trp Ser Asp Ile Ser Ser Ala Pro Ala Gly Tyr Lys Asp
1               5                   10                  15

Val Val Trp Ile Ala Asp Arg Ala Leu Leu Ala Gln Gly Leu Gly Trp
                20                  25                  30

Ser Ile Asn Tyr Leu Ala Met Ile Tyr Gln Ser Arg Lys Asp Arg Thr
            35                  40                  45

Tyr Gly Met Ala Ile Leu Pro Leu Cys Cys Asn Phe Ala Trp Glu Phe
        50                  55                  60

Val Tyr Thr Val Ile Tyr Pro Ser Gln Asn Pro Phe Glu Arg Ala Val
65                  70                  75                  80
```

```
Leu Thr Thr Trp Met Val Leu Asn Leu Tyr Leu Met Tyr Thr Thr Ile
                 85                  90                  95

Lys Phe Ala Pro Asn Glu Trp Gln His Ala Pro Leu Val Gln Arg Ile
            100                 105                 110

Leu Pro Val Ile Phe Pro Val Ala Ile Ala Ala Phe Thr Ala Gly His
            115                 120                 125

Leu Ala Leu Ala Ala Thr Val Gly Val Ala Lys Ala Val Asn Trp Ser
130                 135                 140

Ala Phe Leu Cys Phe Glu Leu Leu Thr Ala Gly Ala Val Cys Gln Leu
145                 150                 155                 160

Met Ser Arg Gly Ser Ser Arg Gly Ala Ser Tyr Thr Ile Trp Val Ser
                165                 170                 175

Arg Phe Leu Gly Ser Tyr Ile Gly Ser Ile Phe Met His Val Arg Glu
            180                 185                 190

Thr His Trp Pro Gln Glu Phe Asp Trp Ile Ser Tyr Pro Phe Val Ala
            195                 200                 205

Trp His Gly Ile Met Cys Phe Ser Leu Asp Ile Ser Tyr Val Gly Leu
            210                 215                 220

Leu Trp Tyr Ile Arg Arg Gln Glu Arg Gln Gly Gln Leu Lys Lys Ala
225                 230                 235                 240

Met
```

<210> SEQ ID NO 272
<211> LENGTH: 464
<212> TYPE: PRT
<213> ORGANISM: Penicillium coprobium PF1169

<400> SEQUENCE: 272

```
Met Lys Val Ile Ile Val Gly Gly Ser Ile Ala Gly Leu Ala Leu Ala
1               5                   10                  15

His Cys Leu Asp Lys Ala Asn Ile Asp Tyr Val Ile Leu Glu Lys Lys
            20                  25                  30

Lys Glu Ile Ala Pro Gln Glu Gly Ala Ser Ile Gly Ile Met Pro Asn
        35                  40                  45

Gly Gly Arg Ile Leu Glu Gln Leu Gly Leu Tyr Asp Gln Ile Glu Glu
    50                  55                  60

Leu Ile Glu Pro Leu Val Arg Ala His Val Thr Tyr Pro Asp Gly Phe
65                  70                  75                  80

Asn Tyr Thr Ser Arg Tyr Pro Ala Leu Ile Gln Gln Arg Phe Gly Tyr
                85                  90                  95

Pro Leu Ala Phe Leu Asp Arg Gln Lys Leu Leu Gln Ile Leu Ala Thr
            100                 105                 110

Gln Pro Val Gln Ser Ser Arg Val Lys Leu Asp His Lys Val Glu Ser
            115                 120                 125

Ile Glu Val Ser Pro Cys Gly Val Thr Val Ile Thr Ser Asn Gly His
        130                 135                 140

Thr Tyr Gln Gly Asp Leu Val Val Gly Ala Asp Gly Val His Ser Arg
145                 150                 155                 160

Val Arg Ala Glu Met Trp Arg Leu Ala Asp Ala Ser Gln Gly Asn Val
                165                 170                 175

Cys Gly Asn Gly Asp Lys Ala Phe Thr Ile Asn Tyr Ala Cys Ile Phe
            180                 185                 190

Gly Ile Ser Ser His Val Asp Gln Leu Asp Pro Gly Glu Gln Ile Thr
            195                 200                 205
```

```
Cys Tyr Asn Asp Gly Trp Ser Ile Leu Ser Val Ile Gly Gln Asn Gly
    210                 215                 220

Arg Ile Tyr Trp Phe Leu Phe Ile Lys Leu Glu Lys Glu Phe Val Tyr
225                 230                 235                 240

Asp Gly Ser His Lys Thr Gln Leu His Phe Ser Arg Glu Asp Ala Arg
            245                 250                 255

Ala His Cys Glu Arg Leu Ala Gln Glu Pro Leu Trp Lys Asp Val Thr
        260                 265                 270

Phe Gly Gln Val Trp Ala Arg Cys Glu Val Phe Gln Met Thr Pro Leu
    275                 280                 285

Glu Glu Gly Val Leu Gly Lys Trp His Trp Arg Asn Ile Ile Cys Ile
290                 295                 300

Gly Asp Ser Met His Lys Phe Ala Pro His Ile Gly Gln Gly Ala Asn
305                 310                 315                 320

Cys Ala Ile Glu Asp Ala Ala Gln Leu Ser Asn Ser Leu His Thr Trp
            325                 330                 335

Leu Ser Gly Ser Gly Lys Glu His Gln Leu Lys Thr Asp Asp Leu Thr
        340                 345                 350

Glu Ile Leu Ala Gln Phe Ala Gln Thr Arg Leu Gln Arg Leu Gly Pro
    355                 360                 365

Thr Ala Met Ala Ala Arg Ser Ala Met Arg Leu His Ala Arg Glu Gly
370                 375                 380

Leu Lys Asn Trp Ile Leu Gly Arg Tyr Phe Leu Pro Tyr Ala Gly Asp
385                 390                 395                 400

Lys Pro Ala Asp Trp Ala Ser Arg Gly Ile Ala Gly Gly Asn Thr Leu
            405                 410                 415

Asp Phe Val Glu Pro Pro Thr Arg Ala Gly Pro Gly Trp Ile Gln Phe
        420                 425                 430

Ser Gln Ser Gly Lys Arg Thr Ser Phe Pro Met Ala Val Ala Gly Leu
    435                 440                 445

Cys Leu Val Ser Ile Val Ala Arg Ile Met Tyr Leu Lys Leu Val Ala
450                 455                 460

<210> SEQ ID NO 273
<211> LENGTH: 317
<212> TYPE: PRT
<213> ORGANISM: Penicillium coprobium PF1169

<400> SEQUENCE: 273

Met Ala Gly Ser Gln Ser Thr Ala Gln Leu Ala Arg Leu Leu Ile Asp
1               5                   10                  15

Ile Ser Arg Phe Asp Lys Tyr Asn Cys Leu Phe Ala Ile Phe Pro Gly
            20                  25                  30

Val Trp Ser Ile Phe Leu Ala Ala Ser Arg His Ala Asp Gly Asp
        35                  40                  45

Pro Val Pro Leu Asp Phe Val Leu Gly Arg Ala Gly Leu Ala Phe Met
    50                  55                  60

Tyr Thr Tyr Met Leu Ser Gly Ala Gly Met Val Trp Asn Asp Trp Ile
65                  70                  75                  80

Asp Arg Asp Ile Asp Ala Gln Val Ala Arg Thr Lys Asn Arg Pro Leu
            85                  90                  95

Ala Ser Gly Arg Leu Ser Thr Arg Ala Ala Leu Ile Trp Met Leu Val
        100                 105                 110

Gln Tyr Ala Ala Ser Val Trp Leu Met Asp Arg Met Val Ser Gly Gln
    115                 120                 125
```

```
Asp Val Trp Thr Tyr Met Leu Pro Leu Thr Gly Ile Ile Leu Tyr
            130                 135                 140

Pro Phe Gly Lys Arg Pro Thr Ser Arg Lys Leu Gly Val Tyr Pro Gln
145                 150                 155                 160

Tyr Ile Leu Gly Ala Ser Ala Leu Thr Ile Leu Pro Ala Trp Ala
                165                 170                 175

Ser Val Tyr Thr Gly Arg Ile Ser Leu Lys Asp Leu Gly Met Arg Cys
                180                 185                 190

Leu Pro Leu Cys Leu Phe Leu Phe Leu Trp Thr Ile Tyr Phe Asn Thr
                195                 200                 205

Ala Tyr Ser Tyr Gln Asp Ile Lys Asp Asp Cys Lys Leu Asn Val Asn
            210                 215                 220

Ser Ser Tyr Val Leu Ala Gly Ser His Val Arg Gly Met Leu Leu Leu
225                 230                 235                 240

Gln Ala Ile Ala Val Leu Val Ile Pro Trp Ile Leu Tyr Thr Ser
                245                 250                 255

Ala Ser Thr Trp Leu Trp Val Ser Trp Leu Gly Val Trp Thr Ala Ser
                260                 265                 270

Leu Gly Glu Gln Leu Tyr Leu Phe Asp Val Lys Asp Pro Ser Ser Gly
            275                 280                 285

Gly Lys Val His Arg Arg Asn Phe Ala Leu Gly Ile Trp Asn Val Leu
            290                 295                 300

Ala Cys Phe Val Glu Leu Leu Tyr Ala Ser Gly Ser Leu
305                 310                 315

<210> SEQ ID NO 274
<211> LENGTH: 522
<212> TYPE: PRT
<213> ORGANISM: Penicillium coprobium PF1169

<400> SEQUENCE: 274

Met Ser Thr Gln Glu Val Cys Leu Pro Val Ser Gln Arg Asp Gln Val
1               5                   10                  15

Lys Glu Gly Pro Val Arg Leu His Gly Leu Cys Glu Asp Gly Met Cys
                20                  25                  30

Asp Ala Arg Arg Thr Gly Asp Arg Ser Ala Tyr Pro Leu Ser Ser Leu
            35                  40                  45

Asp His Asn Pro Leu Gly Met Asn Val Thr Phe Leu Leu Phe Phe Gln
        50                  55                  60

Thr Thr Gln Pro Glu Lys Ser Ile Gly Val Leu Glu Asn Gly Ile Glu
65                  70                  75                  80

Leu Leu Leu Lys Val His Pro Phe Leu Ala Gly Asp Val Thr Arg Arg
                85                  90                  95

Thr Glu Ser Ser Gln Thr Lys Tyr Thr Trp Gln Ile Glu Pro Glu Ala
            100                 105                 110

Ser Glu Ser Leu Val Gln Phe Pro Ile Leu Arg Ile Arg His Tyr Gln
        115                 120                 125

Ala Glu Ser Phe Lys Glu Ile Gln Ser Lys Cys Leu Leu Thr Gly Thr
130                 135                 140

Glu Glu Gln Glu Ile Ile Ser Arg Leu Ala Pro Leu Pro Ile Asp Met
145                 150                 155                 160

Asp Ile Ser Leu Pro Arg Arg Pro Ile Leu Arg Phe Gln Ala Asn Val
                165                 170                 175

Met Arg Asp Gly Ile Ile Leu Ala Met Thr Phe His His Ser Ala Met
```

```
            180                 185                 190
Asp Gly Ala Gly Ala Arg Val Leu Gly Leu Leu Ala Asp Cys Cys
        195                 200                 205
Arg Asp Pro Thr Ala Met Ser Ser Ala Ser Val Ser Pro Asp Arg Gln
210                 215                 220
Leu Arg Ser Glu Ile Glu Arg Leu Val Pro Glu Ser Ser Ser Gly Leu
225                 230                 235                 240
Ser Arg Met Asp Phe Ser Lys His Tyr Cys Gly Leu Gly Asp Trp Ala
                245                 250                 255
Ala Leu Leu Ala Lys Asn Trp Ser Gly Phe Val Arg Ala Arg Ala Thr
            260                 265                 270
Glu Leu Val Thr Trp Arg Leu Lys Ile Pro Gly Pro Lys Ile Glu Tyr
        275                 280                 285
Leu Lys Glu Ala Cys Asn Thr Leu Ile Lys Gly Gln Thr Ser Phe Gln
290                 295                 300
Ala Asp Gly Arg Pro Ser Pro Gly Phe Leu Ser Ser Asn Asp Ile Val
305                 310                 315                 320
Ser Ala Leu Leu Ala Met Ile Leu Arg Gln Ala Gly Gln Leu Ala Gly
                325                 330                 335
Lys Ser Thr Glu Leu Ser Ile Ala Val Asp Met Arg Gly Asn Phe Lys
            340                 345                 350
Thr Pro Ala Phe Asp Asp Tyr Leu Gly Asn Met Val Leu Leu Thr Tyr
        355                 360                 365
Thr Pro Ile Gln Ala Gly Arg Asn Glu Ala Leu Val Asp Gly Thr Asp
370                 375                 380
Pro Ser Val Glu Leu Arg Gln Glu Cys Leu Glu Asp Leu Thr Gln Ile
385                 390                 395                 400
Ala Ala Arg Ile Arg Gln Ser Leu Leu Ala Val Asp Ala Glu Tyr Ile
                405                 410                 415
Gln Asp Ala Leu Ser His Leu His Ser Gln Pro Asp Trp Ala Asp Ile
            420                 425                 430
Gly Phe Arg Gly Val Pro Ile Pro Leu Ser Ser Phe Arg Asn Phe Glu
        435                 440                 445
Ile Phe Gly Leu Asp Phe Gly Glu Ser Leu Gly Ala Gln Pro Arg Gly
        450                 455                 460
Phe Gln Leu His Leu Pro Val Leu Gly Gly Met Cys Phe Ile Leu Pro
465                 470                 475                 480
Lys Gly Gln Asp Asp Val Ala Ser Thr Glu Pro Trp Asp Leu His Leu
                485                 490                 495
Thr Leu Asn Arg Asp Asp Gln Leu Leu Leu Lys Asp Pro Leu Phe
            500                 505                 510
Cys Trp Ala Ile Gly Ala Gln Ala Lys Glu
        515                 520

<210> SEQ ID NO 275
<211> LENGTH: 434
<212> TYPE: PRT
<213> ORGANISM: Penicillium coprobium PF1169

<400> SEQUENCE: 275

Met Asp Ser Leu Leu Thr Ser Pro Leu Trp Leu Lys Ile Ala His Glu
1               5                   10                  15
Leu Ala Leu Tyr Leu Ser Phe Ile Val Pro Thr Ala Phe Leu Ile Ile
            20                  25                  30
```

Thr Thr Gln Lys Ser Ser Ile Ile Arg Trp Ala Trp Thr Pro Cys Leu
            35                  40                  45

Leu Tyr Ile Leu Tyr Gln Phe Ser Leu Arg Val Pro Ser Leu Ser Thr
 50                  55                  60

Ser Gln Phe Leu Lys Gly Val Ala Ala Gly Gln Ala Thr Val Ala Ala
 65                  70                  75                  80

Leu Gln Cys Leu Asn Leu Leu Ile Thr Lys Leu Asp Gln Thr Asp
                 85                  90                  95

Leu Leu Arg Ala Asn Leu Tyr Ser Pro Ser Ala Gly Leu Leu Ser Arg
            100                 105                 110

Leu Ala Gln Ser Cys Ala Leu Leu Val Asn Phe Arg Gly Ile Gly Thr
            115                 120                 125

Ile Trp Glu Val Arg Asn Ile Pro Gln His Ala Ala Phe Val Gln Pro
            130                 135                 140

Lys Gly Lys Asp Gln Ser Met Ser Arg Lys Arg Phe Val Leu Arg Glu
145                 150                 155                 160

Ile Ala Ile Ile Val Trp Gln Tyr Leu Leu Asp Phe Ile Tyr Glu
                165                 170                 175

Ser Thr Lys Gly Thr Ser Ala Glu Asp Leu Met Arg Leu Phe Gly Pro
            180                 185                 190

Gly Met Glu Ile Lys Tyr Leu Asp Ala Thr Phe Glu Gln Trp Met Gly
            195                 200                 205

Arg Leu Ser Val Gly Ile Phe Ser Trp Leu Val Pro Ser Arg Val Cys
            210                 215                 220

Leu Asn Ile Thr Ser Arg Leu Tyr Phe Leu Ile Leu Val Val Leu Gly
225                 230                 235                 240

Ile Ser Ser Pro Glu Ser Cys Arg Pro Gly Phe Gly Arg Val Arg Asp
                245                 250                 255

Val Cys Thr Ile Arg Gly Val Trp Gly Lys Phe Trp His Gln Ser Phe
            260                 265                 270

Arg Trp Pro Leu Thr Ser Val Gly Asn Tyr Ile Ala Arg Asp Val Leu
            275                 280                 285

Gly Leu Ala His Pro Ser Leu Leu Glu Arg Tyr Thr Asn Ile Phe Phe
            290                 295                 300

Thr Phe Phe Thr Ser Gly Val Leu His Leu Val Cys Asp Ala Ile Leu
305                 310                 315                 320

Gly Val Pro Pro Ser Ala Ser Gly Ala Met Gln Phe Phe Cys Ser Phe
                325                 330                 335

Pro Leu Ala Ile Met Ile Glu Asp Gly Val Gln Glu Ile Trp Arg Arg
            340                 345                 350

Ala Thr Gly Gln Thr Lys Asp Ser Asp Arg Ala Val Pro Phe Trp Gln
            355                 360                 365

Arg Leu Val Gly Tyr Leu Trp Val Ala Val Trp Met Cys Val Thr Ser
            370                 375                 380

Pro Phe Tyr Leu Tyr Pro Ala Ala Arg Gln His Ala Glu Lys Asn Trp
385                 390                 395                 400

Ile Val Pro Phe Ser Ile Val Glu Glu Ile Gly Leu Gly Thr Ala Gln
                405                 410                 415

Lys Ile Leu Leu Gly Tyr Gly Leu Phe Val Tyr Trp Ala Val Gly Gly
            420                 425                 430

Glu Ile

<210> SEQ ID NO 276

<211> LENGTH: 1299
<212> TYPE: PRT
<213> ORGANISM: Penicillium coprobium PF1169

<400> SEQUENCE: 276

```
Met Leu Tyr Arg Ala Lys Leu Val Asp Asp His Gln Ile His Thr Ala
1               5                   10                  15

Ser Leu His Asn Pro Ile Pro Trp Gln Leu His Thr Tyr Val Trp Pro
            20                  25                  30

Phe Leu Ile Ile Trp Pro Val Phe Phe Ala Phe Tyr Leu Ser Pro Glu
        35                  40                  45

Arg Tyr Asp Thr Tyr Ile Gln Gly Gln Glu Trp Thr Phe Val Phe Ala
    50                  55                  60

Gly Ser Ile Ile Thr Val Gln Ser Leu Phe Trp Leu Met Thr Lys Trp
65                  70                  75                  80

Asn Ile Asp Ile Asn Thr Leu Phe Thr Thr Arg Ser Lys Ser Ile
                85                  90                  95

Asp Thr Ala Arg Leu Ile Lys Val Val Pro Ile Thr Asn Ala Gly Ser
            100                 105                 110

Ala Glu Ile Cys Asn Leu Ile Arg Glu His Ile Gly Pro Lys Lys Thr
        115                 120                 125

Leu Ser Phe Leu Phe Gln Lys Arg Arg Phe Leu Phe Tyr Pro Glu Thr
    130                 135                 140

Arg Ser Phe Ala Pro Leu Ser Tyr Ala Leu Asp Ala Glu Pro Lys Pro
145                 150                 155                 160

Ala Leu Lys Thr Phe Gln Gln Ser Glu Gly Phe Thr Ser Lys Ala Glu
                165                 170                 175

Ile Glu Arg Val Gln Asn His Tyr Gly Asp Asn Thr Phe Asp Ile Pro
            180                 185                 190

Val Pro Gly Phe Ile Glu Leu Phe Gln Glu His Ala Val Ala Pro Phe
        195                 200                 205

Phe Val Phe Gln Ile Phe Cys Val Gly Leu Trp Met Leu Asp Glu Tyr
    210                 215                 220

Trp Tyr Tyr Ser Leu Phe Thr Leu Phe Met Leu Val Met Phe Glu Ser
225                 230                 235                 240

Thr Val Val Trp Gln Arg Gln Arg Thr Leu Ser Glu Phe Arg Gly Met
                245                 250                 255

Ser Ile Lys Pro Tyr Asp Val Trp Val Tyr Arg Glu Arg Lys Trp Gln
            260                 265                 270

Glu Ile Thr Ser Asp Lys Leu Leu Pro Gly Asp Leu Met Ser Val Asn
        275                 280                 285

Arg Thr Lys Glu Asp Ser Gly Val Ala Cys Asp Ile Leu Leu Val Glu
    290                 295                 300

Gly Ser Val Ile Val Asn Glu Ala Met Leu Ser Gly Glu Ser Thr Pro
305                 310                 315                 320

Leu Leu Lys Asp Ser Ile Gln Leu Arg Pro Gly Asp Asp Leu Ile Glu
                325                 330                 335

Pro Asp Gly Leu Asp Lys Leu Ser Phe Val His Gly Thr Lys Val
            340                 345                 350

Leu Gln Val Thr His Pro Asn Leu Thr Gly Asp Ala Gly Leu Lys Asn
        355                 360                 365

Leu Ala Ser Asn Val Thr Met Pro Pro Asp Asn Gly Ala Leu Gly Val
    370                 375                 380

Val Val Lys Thr Gly Phe Glu Thr Ser Gln Gly Ser Leu Val Arg Thr
```

```
              385                 390                 395                 400
        Met Ile Tyr Ser Thr Glu Arg Val Ser Ala Asn Asn Val Glu Ala Leu
                            405                 410                 415

Leu Phe Ile Leu Phe Leu Leu Ile Phe Ala Ile Ala Ala Ser Trp Tyr
                            420                 425                 430

Val Trp Gln Glu Gly Val Ile Arg Asp Arg Lys Arg Ser Lys Leu Leu
                            435                 440                 445

Leu Asp Cys Val Leu Ile Ile Thr Ser Val Pro Pro Glu Leu Pro
                            450                 455                 460

Met Glu Leu Ser Leu Ala Val Asn Thr Ser Leu Ala Ala Leu Ser Lys
        465                 470                 475                 480

Tyr Ala Ile Phe Cys Thr Glu Pro Phe Arg Ile Pro Phe Ala Gly Arg
                            485                 490                 495

Val Asp Ile Ala Cys Phe Asp Lys Thr Gly Thr Leu Thr Gly Glu Asp
                            500                 505                 510

Leu Val Val Asp Gly Ile Ala Gly Leu Thr Leu Gly Glu Ala Gly Ser
                            515                 520                 525

Lys Val Glu Ala Asp Gly Ala His Thr Glu Leu Ala Asn Ser Ser Ala
        530                 535                 540

Ala Gly Pro Asp Thr Thr Leu Val Leu Ala Ser Ala His Ala Leu Val
        545                 550                 555                 560

Lys Leu Asp Glu Gly Glu Val Val Gly Asp Pro Met Glu Lys Ala Thr
                            565                 570                 575

Leu Glu Trp Leu Gly Trp Thr Leu Gly Lys Asn Asp Thr Leu Ser Ser
                            580                 585                 590

Lys Gly Asn Ala Pro Val Val Ser Gly Arg Ser Val Glu Ser Val Gln
                            595                 600                 605

Ile Lys Arg Arg Phe Gln Phe Ser Ser Ala Leu Lys Arg Gln Ser Thr
                            610                 615                 620

Ile Ala Thr Ile Thr Thr Asn Asp Arg Asn Ala Ser Lys Lys Thr Lys
        625                 630                 635                 640

Ser Thr Phe Val Gly Val Lys Gly Ala Pro Glu Thr Ile Asn Thr Met
                            645                 650                 655

Leu Val Asn Thr Pro Pro Asn Tyr Glu Glu Thr Tyr Lys His Phe Thr
                            660                 665                 670

Arg Asn Gly Ala Arg Val Leu Ala Leu Ala Tyr Lys Tyr Leu Ser Ser
                            675                 680                 685

Glu Thr Glu Leu Ser Gln Ser Arg Val Asn Asn Tyr Val Arg Glu Glu
                            690                 695                 700

Ile Glu Ser Glu Leu Ile Phe Ala Gly Phe Leu Val Leu Gln Cys Pro
        705                 710                 715                 720

Leu Lys Asp Asp Ala Ile Lys Ser Val Gln Met Leu Asn Glu Ser Ser
                            725                 730                 735

His Arg Val Val Met Ile Thr Gly Asp Asn Pro Leu Thr Ala Val His
                            740                 745                 750

Val Ala Arg Lys Val Glu Ile Val Asp Arg Glu Val Leu Ile Leu Asp
                            755                 760                 765

Ala Pro Glu His Asp Asn Ser Gly Thr Lys Ile Val Trp Arg Thr Ile
        770                 775                 780

Asp Asp Lys Leu Asn Leu Glu Val Asp Pro Thr Lys Pro Leu Asp Pro
        785                 790                 795                 800

Glu Ile Leu Lys Thr Lys Asp Ile Cys Ile Thr Gly Tyr Ala Leu Ala
                            805                 810                 815
```

Lys Phe Lys Gly Gln Lys Ala Leu Pro Asp Leu Leu Arg His Thr Trp
            820                 825                 830

Val Tyr Ala Arg Val Ser Pro Lys Gln Lys Glu Glu Ile Leu Leu Gly
            835                 840                 845

Leu Lys Asp Ala Gly Tyr Thr Thr Leu Met Cys Gly Asp Gly Thr Asn
850                 855                 860

Asp Val Gly Ala Leu Lys Gln Ala His Val Gly Val Ala Leu Leu Asn
865                 870                 875                 880

Gly Ser Gln Glu Asp Leu Thr Lys Ile Ala Glu His Tyr Arg Asn Thr
            885                 890                 895

Lys Met Lys Glu Leu Tyr Glu Lys Gln Val Ser Met Met Gln Arg Phe
            900                 905                 910

Asn Gln Pro Ala Pro Pro Val Pro Val Leu Ile Ala His Leu Tyr Pro
            915                 920                 925

Pro Gly Pro Thr Asn Pro His Tyr Glu Lys Ala Met Glu Arg Glu Ser
        930                 935                 940

Gln Arg Lys Gly Ala Ala Ile Thr Ala Pro Gly Ser Thr Pro Glu Ala
945                 950                 955                 960

Ile Pro Thr Ile Thr Ser Pro Gly Ala Gln Ala Leu Gln Gln Ser Asn
            965                 970                 975

Leu Asn Pro Gln Gln Gln Lys Lys Gln Gln Ala Gln Ala Ala Ala Ala
            980                 985                 990

Gly Leu Ala Asp Lys Leu Thr Ser  Ser Met Met Glu Gln  Glu Leu Asp
        995                 1000                1005

Asp Ser  Glu Pro Pro Thr Ile  Lys Leu Gly Asp Ala  Ser Val Ala
    1010                1015                 1020

Ala Pro  Phe Thr Ser Lys Leu  Ala Asn Val Ile Ala  Ile Pro Asn
    1025                1030                 1035

Ile Ile  Arg Gln Gly Arg Cys  Thr Leu Val Ala Thr  Ile Gln Met
    1040                1045                 1050

Tyr Lys  Ile Leu Ala Leu Asn  Cys Leu Ile Ser Ala  Tyr Ser Leu
    1055                1060                 1065

Ser Val  Ile Tyr Leu Asp Gly  Ile Lys Phe Gly Asp  Gly Gln Val
    1070                1075                 1080

Thr Ile  Ser Gly Met Leu Met  Ser Val Cys Phe Leu  Ser Ile Ser
    1085                1090                 1095

Arg Ala  Lys Ser Val Glu Gly  Leu Ser Lys Glu Arg  Pro Gln Pro
    1100                1105                 1110

Asn Ile  Phe Asn Val Tyr Ile  Ile Gly Ser Val Leu  Gly Gln Phe
    1115                1120                 1125

Ala Ile  His Ile Ala Thr Leu  Ile Tyr Leu Ser Asn  Tyr Val Tyr
    1130                1135                 1140

Lys His  Glu Pro Arg Asp Ser  Asp Ile Asp Leu Glu  Gly Glu Phe
    1145                1150                 1155

Glu Pro  Ser Leu Leu Asn Ser  Ala Ile Tyr Leu Leu  Gln Leu Ile
    1160                1165                 1170

Gln Gln  Ile Ser Thr Phe Ser  Ile Asn Tyr Gln Gly  Arg Pro Phe
    1175                1180                 1185

Arg Glu  Ser Ile Arg Glu Asn  Lys Gly Met Tyr Trp  Gly Leu Ile
    1190                1195                 1200

Ala Ala  Ser Gly Val Ala Phe  Ser Cys Ala Thr Glu  Phe Ile Pro
    1205                1210                 1215

| | | | | | | | | | | |
|---|---|---|---|---|---|---|---|---|---|---|
| Glu | Leu | Asn | Glu | Lys | Leu | Arg | Leu | Val | Pro | Phe | Thr | | Asn | Glu | Phe |
| | 1220 | | | | 1225 | | | | | 1230 | |

Lys Val Thr Leu Thr Val Leu Met Ile Phe Asp Tyr Gly Gly Cys
    1235                1240                1245

Trp Leu Ile Glu Asn Val Leu Lys His Leu Phe Ser Asp Phe Arg
    1250                1255                1260

Pro Lys Asp Ile Ala Ile Arg Arg Pro Asp Gln Leu Lys Arg Glu
    1265                1270                1275

Ala Glu Arg Lys Leu Gln Glu Gln Val Asp Ala Glu Ala Gln Lys
    1280                1285                1290

Glu Leu Gln Arg Lys Val
    1295

```
<210> SEQ ID NO 277
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 277
atgatcgagc tcaaagatgc                                              20

<210> SEQ ID NO 278
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 278
cttctttcca gtcaatacct                                              20

<210> SEQ ID NO 279
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 279
atggattccc tattgacgag                                              20

<210> SEQ ID NO 280
<211> LENGTH: 20
<212> TYPE: DNA
<213> ORGANISM: Artificial Sequence
<220> FEATURE:
<223> OTHER INFORMATION: a primer sequence for PCR

<400> SEQUENCE: 280
ttaaatctcc ccaccaaccg                                              20

<210> SEQ ID NO 281
<211> LENGTH: 12
<212> TYPE: DNA
<213> ORGANISM: Artificial Sequence
<220> FEATURE:
<223> OTHER INFORMATION: a primer sequence for PCR

<400> SEQUENCE: 281
cccaagcttg gg                                                      12
```

<210> SEQ ID NO 282
<211> LENGTH: 33
<212> TYPE: DNA
<213> ORGANISM: Artificial Sequence
<220> FEATURE:
<223> OTHER INFORMATION: a primer sequence for PCR

<400> SEQUENCE: 282
agcttgcggc cgcgtacgct taaggcggcc gcg                         33

<210> SEQ ID NO 283
<211> LENGTH: 33
<212> TYPE: DNA
<213> ORGANISM: Artificial Sequence
<220> FEATURE:
<223> OTHER INFORMATION: a primer sequence for PCR

<400> SEQUENCE: 283
aattcgcggc cgccttaagc gtacgcggcc gca                         33

<210> SEQ ID NO 284
<211> LENGTH: 8465
<212> TYPE: DNA
<213> ORGANISM: Penicillium coprobium PF1169

<400> SEQUENCE: 284

| | | |
|---|---|---|
| gcggccgcga attcttgaag acgaaagggc ctcgtgatac gcctatttt ataggttaat | 60 |
| gtcatgataa taatggtttc ttagacgtca ggtggcactt ttcggggaaa tgtgcgcgga | 120 |
| accccattt gtttatttt ctaaatacat tcaaatatgt atccgctcat gagacaataa | 180 |
| ccctgataaa tgcttcaata atattgaaaa aggaagagta tgagtattca acatttccgt | 240 |
| gtcgcccta ttcccttt tgcggcattt tgccttcctg tttttgctca cccagaaacg | 300 |
| ctggtgaaag taaaagatgc tgaagatcag ttgggtgcac gagtgggtta catcgaactg | 360 |
| gatctcaaca gcggtaagat ccttgagagt tttcgccccg aagaacgttt tccaatgatg | 420 |
| agcactttta aagttctgct atgtggcgcg gtattatccc gtgttgacgc cgggcaagag | 480 |
| caactcggtc gccgcataca ctattctcag aatgacttgg ttgagtactc accagtcaca | 540 |
| gaaaagcatc ttacggatgg catgacagta agagaattat gcagtgctgc cataaccatg | 600 |
| agtgataaca ctgcggccaa cttacttctg acaacgatcg aggaccgaa ggagctaacc | 660 |
| gcttttttgc acaacatggg ggatcatgta actcgccttg atcgttggga accggagctg | 720 |
| aatgaagcca taccaaacga cgagcgtgac accacgatgc ctgcagcaat ggcaacaacg | 780 |
| ttgcgcaaac tattaactgg cgaactactt actctagctt cccggcaaca attaatagac | 840 |
| tggatggagg cggataaagt tgcaggacca cttctgcgct cggcccttcc ggctggctgg | 900 |
| tttattgctg ataaatctgg agccggtgag cgtgggtctc gcggtatcat tgcagcactg | 960 |
| gggccagatg gtaagccctc ccgtatcgta gttatctaca cgacggggag tcaggcaact | 1020 |
| atggatgaac gaaatagaca gatcgctgag ataggtgcct cactgattaa gcattggtaa | 1080 |
| ctgtcagacc aagtttactc atatatactt tagattgatt taaaacttca tttttaattt | 1140 |
| aaaaggatct aggtgaagat cctttttgat aatctcatga ccaaaatccc ttaacgtgag | 1200 |
| ttttcgttcc actgagcgtc agaccccgta gaaaagatca aggatcttc ttgagatcct | 1260 |
| ttttttctgc gcgtaatctg ctgcttgcaa acaaaaaaac caccgctacc agcggtggtt | 1320 |
| tgtttgccgg atcaagagct accaactctt tttccgaagg taactggctt cagcagagcg | 1380 |
| cagataccaa atactgtcct tctagtgtag ccgtagttag gccaccactt caagaactct | 1440 |

```
gtagcaccgc ctacatacct cgctctgcta atcctgttac cagtggctgc tgccagtggc    1500
gataagtcgt gtcttaccgg gttggactca agacgatagt taccggataa ggcgcagcgg    1560
tcgggctgaa cgggggggttc gtgcacacag cccagcttgg agcgaacgac ctacaccgaa    1620
ctgagatacc tacagcgtga gctatgagaa agcgccacgc ttcccgaagg gagaaaggcg    1680
gacaggtatc cggtaagcgg cagggtcgga acaggagagc gcacgaggga gcttccaggg    1740
ggaaacgcct ggtatcttta tagtcctgtc gggtttcgcc acctctgact tgagcgtcga    1800
tttttgtgat gctcgtcagg ggggcggagc ctatggaaaa acgccagcaa cgcggccttt    1860
ttacggttcc tggccttttg ctggcctttt gctcacatgt tctttcctgc gttatcccct    1920
gattctgtgg ataaccgtat taccgccttt gagtgagctg ataccgctcg ccgcagccga    1980
acgaccgagc gcagcgagtc agtgagcgag gaagcggaag agcgctgact ccgcgtttc    2040 cagactttac gaaacacgga aaccgaagac cattcatgtt gttgctcagg tcgcagacgt    2100
tttgcagcag cagtcgcttc acgttcgctc gcgtatcggt gattcattct gctaaccagt    2160
aaggcaaccc cgccagccta gccgggtcct caacgacagg agcacgatca tgcgcacccg    2220
tcagatccag acatgataag atacattgat gagtttggac aaaccacaac tagaatgcag    2280
tgaaaaaaat gctttatttg tgaaattgt gatgctattg ctttatttgt aaccattata    2340
agctgcaata aacaagttaa caacaacaat tgcattcatt ttatgtttca ggttcagggg    2400
gaggtgtggg aggttttta aagcaagtaa acctctaca aatgtggtat ggctgattat    2460
gatctctagt caaggcacta tacatcaaat attccttatt aacccctta caaattaaaa    2520 agctaaaggt acacaatttt tgagcatagt tattaatagc agacactcta tgcctgtgtg    2580
gagtaagaaa aaacagtatg ttatgattat aactgttatg cctacttata aggttacag    2640 aatattttc cataatttc ttgtatagca gtgcagcttt ttcctttgtg gtgtaaatag    2700
caaagcaagc aagagttcta ttactaaaca cagcatgact caaaaaactt agcaattctg    2760
aaggaaagtc cttggggtct tctacctttc tcttctttt tggaggagta gaatgttgag    2820
agtcagcagt agcctcatca tcactagatg gcatttcttc tgagcaaaac aggttttcct    2880
cattaaaggc attccaccac tgctcccatt catcagttcc ataggttgga atctaaaata    2940
cacaaacaat tagaatcagt agtttaacac attatacact taaaaatttt atatttacct    3000
tagagcttta aatctctgta ggtagttgt ccaattatgt cacaccacag aagtaaggtt    3060
ccttcacaaa gatccggacc aaagcggcca tcgtgcctcc ccactcctgc agttcggggg    3120
catggatgcg cggatagccg ctgctggttt cctggatgcc gacggatttg cactgccggt    3180
agaactccgc gaggtcgtcc agcctcaggc agcagctgaa ccaactcgcg aggggatcga    3240 gccctagaa agaaggatta cctctaaaca agtgtacctg tgcattctgg gtaaacgact    3300
cataggagag ttgtaaaaaa gtttcggccg gcgtattggg tgttacggag cattcactag    3360
gcaaccatgg ttactattgt atacccatct tagtaggaat gattttcgag gtttatacct    3420
acgatgaatg tgtgtcctgt aggcttgaga gttcaaggaa gaaacagtgc aattatcttt    3480
gcgaacccag gggctggtga cggaatttc atagtcaagc tatcagagta agaagagga    3540 gcatgtcaaa gtacaattag agacaaatat atagtcgcgt ggagccaaga gcggattcct    3600
cagtctcgta ggtctcttga cgaccgttga tctgcttgat ctcgtctccc gaaaatgaaa    3660
atagactctg ctaagctatt cttctgcttc gccggagcct gaaggggcgta ctagggttgc    3720 gaggtccaat gcattaatgc attgcagatg agctgtatct ggaagaggta aacccgaaac    3780
gcgttttatt cttgttgaca tggagctatt aaatcactag aaggcactct ttgctgcttg    3840
```

```
gacaaatgaa cgtatcttat cgagatcctg aacaccattt gtctcaactc cggagctgac    3900
atcgacacca acgatcttat atccagattc gtcaagctgt ttgatgattt cagtaacgtt    3960
aagtggatcg atccgctacc gtacgtccca caggagccgg gccagctccc cgatgtcgtc    4020 gacaccgag agatcgaggg gcacttcctc caggacgtcg aagtcgtgga ggaaggtgaa     4080
ccggagcatg tcctcggcga aggtgtcggt cacctgccat tccgccccctt cgagcaccgc   4140 ggcgagcagt ccgcggtcgg cgcggaatgc gttgaggtgc aattggacga ggctgtaccg    4200
ggggtcgccc gcgtatacgt cggtgaaatc gatcagaccg gtcaccgacg cgttccccgc    4260
atcgacgaaa aggttggtgc catgcagatc gccgtgcacg aatacgggtt cgacgccgtc    4320
gagcagtgcg tcgacggggg gcaggaagtc atcgaccgcg tcgagcagtc gtggggagag    4380 gtaacccccat tccggtggt cctcggcggt ggccgtgcgg cgttcctcga gcagttcggc    4440
gaagaccggg gaatccggtc gcagcgctcc cgtgccggtc agcggaacgg aatgcagccg    4500
gcgcagtacc gcgccgaacc gccgggccag cgccagttgc gtcggccggt ccgcgcgcgc    4560
cgtcgcctcc cgccacgtcg ccccgggggc ggcggccatc accaggtacg gccacggcca    4620
gccgtcgccg ccggagaaca gctcgccgcg ccccaacagc ggtgggaccg gcagcccttg    4680
gcctgccagc acctcgtagg cctcggcttc cgaggcgtag ttctccgggc cgcaccagtg    4740
ctcgccgtag agcttgacga ccgcgccggt gtcggcgatc aggacggggt tggtgctctc    4800
ccccgggacc cgtaaggccc ccggggcggg gaggccgacc gcggccagcg cccgccggcc    4860
ccagggctcc cagaattcca ggtcgttccg gagtttcgcg taggtttcgt ccaatgtaat    4920
ttccatcggc tgggcggggt atttagcggg catatcgatg cttgggtaga ataggtaagt    4980
cagattgaat ctgaaataaa gggaggaagg gcgaacttaa gaaggtatga ccgggtcgtt    5040
cacttacctt gcttgacaaa cgcaccaagt tatcgtgcac caagcagcag atgataataa    5100
tgtcctcgtt cctgtctgct aataagagtc acacttcgag cgccgccgct actgctacaa    5160
gtggggctga tctgaccagt tgcctaaatg aaccatcttg tcaaacgaca caaattttgt    5220
gctcaccgcc tggacgacta aaccaaaata ggcattcatt gttgacctcc actagctcca    5280
gccaagccca aaaagtgctc cttcaatatc atcttctgtc gacctctaat ccaacgcgct    5340
ttcgtcggct tcaggcatac ggaggtttca gcactccgtc cgcttgctca ttacatttgt    5400
ttacttagaa tgatatagct gtgctgccaa tggctcccgt tccggaagcc tatttcccgt    5460
ccctggacaa gtgcttctcc ggggacgttc agcttttgta tgggcgcatt cgctatacat    5520
tgatggtctg ctgctgattt tgctatactt ctaggtcttg gaagagagtc tttctttacg    5580
cttgcgatcc cgaaagcatc accgatgaat cccgggtttt cgagtcgttt ttgtcacatc    5640
ctgatagcat cgaggtgctt ctgaaccgcg gcagcgtctt tcctacgcca tcccctaaga    5700
caaaatccga gtttgatagg agaacagcag cgatccatgc ggagaccatt gcacaagcct    5760
cgtatgacct gaaggaaatc aaagccgatg ctctttggtt gagcgaaaag gctgggattg    5820
atgaaatcaa cgcgcttcgg atcacggtct tggaatggca aacccgtcct gcttcacgtc    5880
tccttggccg actcgctgat gaggaagcca ctagcttgaa acgggcagcc ggagtcgata    5940
cttttcgggt gtcacttgcc gggccgagtt tcgctgacat cctcaacgcc agacccggtg    6000
atggaaacag tgcagccgag tttgtttcgg agaagaatag acgcctgcga ctccgggaac    6060
tatatctgtc tgaacgaagc catatcgtca agacagcccg caaacttctc gccttatctt    6120
tgaacagcga cggtcatgat aacgcgcctc ggccacagcc aggtaggccg aataacttgc    6180
```

```
acaaattggg agtgtccatc ttcgaaacga agatcactgg gaacaactgg catgaattct    6240
ctagcctcca aaaaagcctc ctcactactt ctggaatagc tcagaggccg aggcggcctc    6300
ggcctctgca taaataaaaa aaattagtca gccatggggc ggagaatggg cggaactggg    6360
cggagttagg ggcgggatgg gcggagttag gggcgggact atggttgctg actaattgag    6420
atgcatgctt tgcatacttc tgcctgctgg ggagcctggg gactttccac acctggttgc    6480
tgactaattg agatgcatgc tttgcatact tctgcctgct ggggagcctg ggacttttcc    6540
acaccctaac tgacacacat tccacagccg gatctgcagg acccaacgct gcccgagatg    6600
cgccgcgtgc ggctgctgga gatggcggac gcgatggata tgttctgcca agggttggtt    6660
tgcgcattca cagttctccg caagaattga ttggctccaa ttcttggagt ggtgaatccg    6720
ttagcgaggt gccgccggct tccattcagg tcgaggtggc ccggctccat gcaccgcgac    6780
gcaacgcggg gaggcagaca aggtataggg cggcgcctac aatccatgcc aacccgttcc    6840
atgtgctcgc cgaggcggca taaatcgccg tgacgatcag cggtccaatg atcgaagtta    6900
ggctggtaag agccgcgagc gatccttgaa gctgtccctg atggtcgtca tctacctgcc    6960
tggacagcat ggcctgcaac gcgggcatcc cgatgccgcc ggaagcgaga agaatcataa    7020
tggggaaggc catccagcct cgcgtcgcga acgccagcaa gacgtagccc agcgcgtcgg    7080
ccgccatgcc ggcgataatg gcctgcttct cgccgaaacg tttggtggcg ggaccagtga    7140
cgaaggcttg agcgagggcg tgcaagattc cgaataccgc aagcgacagg ccgatcatcg    7200
tcgcgctcca gcgaaagcgg tcctcgccga aaatgaccca gagcgctgcc ggcacctgtc    7260
ctacgagttg catgataaag aagacagtca taagtgcggc gacgatagtc atgcccgcg    7320
cccaccggaa ggagctgact gggttgaagg ctctcaaggg catcggtcga ggaactttcg    7380
gcggctttgc tgtgcgacag gctcacgtct aaaaggaaat aaatcatggg tcataaaatt    7440
atcacgttgt ccggcgcggc gacggatgtt ctgtatgcgc tgttttttccg tggcgcgttg    7500
ctgtctggtg atctgccttc taaatctggc acagccgaat gcgcgagct tggttttgct    7560
gaaaccagac acacagcaac tgaataccag aaagaaaatc actttacctt tctgacatca    7620
gaagggcaga aatttgccgt tgaacacctg gtcaatacgc gttttggtga gcagcaatat    7680
tgcgcttcga tgacgcttgg cgttgagatt gatacctctg ctgcacaaaa ggcaatcgac    7740
gagctggacc agcgcattcg tgacaccgtc tccttcgaac ttattcgcaa tggagtgtca    7800
ttcatcaagg acgccgctat cgcaaatggt gctatccacg cagcggcaat cgaaacacct    7860
cagccggtga ccaatatcta caacatcagc cttggtatcc agcgtgatga gccagcgcag    7920
aacaaggtaa ccgtcagtgc cgataagttc aaagttaaac ctggtgttga taccaacatt    7980
gaaacgttga tcgaaaacgc gctgaaaaac gctgctgaat gtgcggcgct ggatgtcaca    8040
aagcaaatgg cagcagacaa gaaagcgatg gatgaactgg cttcctatgt ccgcacggcc    8100
atcatgatga atgtttccc cggtggtgtt atctggcagc agtgccgtcg atagtatgca    8160
attgataatt attatcattt gcgggtcctt tccggcgatc cgccttgtta cggggcggcg    8220
acctcgcggg ttttcgctat ttatgaaaat tttccggttt aaggcgtttc cgttcttctt    8280
cgtcataact taatgttttt atttaaaata ccctctgaaa agaaaggaaa cgacaggtgc    8340
tgaaagcgag cttttttggcc tctgtcgttt cctttctctg tttttgtccg tggaatgaac    8400
aatggaagtc aacaaaaagc agagcttatc gatgataagc ggtcaaacat gagaattcgc    8460
ggccg                                                               8465
```

<210> SEQ ID NO 285
<211> LENGTH: 25059
<212> TYPE: DNA
<213> ORGANISM: Penicillium coprobium PF1169

<400> SEQUENCE: 285

| | | | | | |
|---|---|---|---|---|---|
| cgtacgtgtt | tactcaattc | tgatatagca | tacgtatgac | taactttggt ctgggtaata | 60 |
| gccttcaatc | tcatcgagat | tctctgtttg | atagctccat | tcgaatggtg gctttcgcgg | 120 |
| gagacttacg | ccaaggtgaa | tgacattgta | atggccgtga | tatattctcc gctgcttgtc | 180 |
| gttgcagcct | gggttgagac | ccgtcaggcg | cataagattc | gatggaatcg ccgtcatggc | 240 |
| gaagaagacg | atgactgcgc | tcaggaatgg | gagcatgtgg | ccaaggaggt caattttgat | 300 |
| cttgacgata | cctggaaaca | gcacgtaatt | gagtccacgc | cggatatcaa ggttgatagt | 360 |
| tgtacatatg | aactccgaga | gctgagggag | caggttaaaa | tgttgacggg gatggtgaag | 420 |
| gaattgactc | aggagatgga | aaagaaggcg | gatggagcaa | gctaggaagt cctgttgaat | 480 |
| tgtacagcaa | gaatactaca | ctgagcatgg | gacatcgcaa | aggtgatttg ctactgcagt | 540 |
| ttcaccaata | ttacattgcg | aaaactgtat | attctcttaa | tgtctaatag cagcaatcag | 600 |
| cccagtggca | cggaggaaag | tcaccgtcct | gtaaggcaaa | tacttgtgct tcaaatgaat | 660 |
| tttgactatt | tttcatgcga | taactggcaa | agggcagggg | gagaaaaaat gatcattatt | 720 |
| caacccaagc | aaactgtcca | gaaagtgaca | tgcccacttt | gcaagtaaag aagatatgtg | 780 |
| acaatctaac | agtctcaggt | agacattcgc | tcttcattaa | aatccatgcg ttgctcgccg | 840 |
| tagcccaatt | cgaagcactg | gcaacccac | atcgagacct | taaaatcggg tgatcatcac | 900 |
| acagcaacag | gctcagcaag | aatggaggca | atcgtctccc | tttgatgatc cagctgtgag | 960 |
| agcttcgctc | gatggtgctt | gccaataccct | atccgaggaa | tgtcatccac aaatacaaca | 1020 |
| cctccatcta | gggctttata | gctggccagt | tggctttgaa | tcagacctgc cacttgatcg | 1080 |
| gccgtcgtct | ccggggacgt | atcattgcgg | acgacataag | ctcgaggaac ctcgctgctg | 1140 |
| ccatctggga | gcatgactcc | gatcacggct | gcgtccttga | tactcgggtc cttgcgtagg | 1200 |
| atcccttcaa | tctctgcggg | agcgacggag | tatctaaatc | aagcacgata tgttagtcta | 1260 |
| tcatctgctg | catcggatgt | catatggaga | ggaaagaaag | cgaaggatgt gaaggatgaa | 1320 |
| gcctagagga | ctgggtaact | tgccctcgaa | cttttgatgag | atctttggtc cgtccgatga | 1380 |
| catggtagtt | tccgtcttcc | acatggaaca | tgtctccagt | ccggaaccat ccttgctcat | 1440 |
| ctttggcatc | agttcgtcct | ttgtatgcta | gaaggagtcc | cggtccacgg acatacaact | 1500 |
| ctccagggga | gtcggtgtc | ccggcgacat | cttcgcccgt | gtcgggattg acaaagcgca | 1560 |
| gctcatatct | gggcaaaaga | gtccctacac | tgccaaattg | tggttgtatc ccgtagcgat | 1620 |
| tctgaaaaac | cactccaacc | tcagacatgc | cccacagatt | tcccgctata gcgtccggtg | 1680 |
| atagcaggct | ctggaattgc | tgcatagagt | acccgtctat | gggagcaccc gaaataccga | 1740 |
| tatagcgcag | agaagacaag | ctctcggcta | cattcaagga | ggacctattg agaatgtgga | 1800 |
| tcatggcagg | aaccatgtac | gtttccgtga | tgtggtgctg | gcggatgccg tcgagcaaag | 1860 |
| cggtgatttc | gaagcgcggg | ataatgtaca | gaggctggcc | gtaccgaatg gggaagatgt | 1920 |
| tgccccagaa | gtcgccaaaa | gaatggtaca | gtggcagtgc | catcaaacga acgacggggt | 1980 |
| atggcacttc | atagtagacg | ctcagatggt | gggaaatgat | cgtgtggtgg gttcgaattg | 2040 |
| cggctttggg | gagaccgctg | gtgccactgg | ttaggaacat | agccgccggc gtgatcttgc | 2100 |
| tctcctcgct | atcttcgaaa | cgaagccaat | ccaactcgcc | atactggagc agactctcca | 2160 |

```
ggcggatagg ttggtccact gtctgggtgt cgagatcctc cgtctgctcc gcctggccat   2220
gtgcaaattg gactacactt tcgatagact tctcatccat cagaaggact tggtttgagg   2280
acattccttg attattgcaa acttccagga ctctggtcag cgcactcgga gcagtaataa   2340
tcaaccgagg ctcggcgaca cgaagcagat gagccacttc atgggggcga ctagcgacat   2400 caaacccat atacactccg cccgcaccaa cgatggcaaa gaaagagca gagtgtagaa   2460 cctaggctga tgttagcagc atatcattgt tatggggtag tgtgattaca ctgttctcca   2520
gttgcacgag tacacaatcg cctcgttcca caccccgggc tttgaggccc gcaatgagtg   2580
atcgcaccag ccgtcggaat tggatggcat tgaaagcacg cgaagggttg cgggcatcaa   2640
tatagatggg cttagattgg tcaaaggcag gaccactaaa agcaaagctg actaggtctg   2700
tctcgtgctc catatcgatg cttatattgt acagttctcg tgtgctattg acatgcagaa   2760
cttgatgcag gatttgtgct cactttaagt agtagtacat ggaatgctca gacctcccat   2820
atcactttga tcgacactgc acgggacaag tatcatgcag aagactattg agaagaatgc   2880
cacgccacca attcgtatta tactaatcta gcctaagcca atacatgtaa agagtactat   2940
ttaggaccca cactgtcatt gcagagcttt gaagcagctg catgcgctaa ttcacccaca   3000
gatacgccac taagaatcaa aattaccccg atgtcgacgc tcagctcttt cgtaaaccat   3060
tgactcagcc caatggcgat aagcgagtca atcccgagct caggaatcag cgtgtcagca   3120
gagagcggtg catcctcggc caagttcaag ctggcccgaa ttttctccat tagtggtctc   3180
acgactgctt cggcttttc ttccaagctt gtcgctgcag tgacaagatc tttggtcgac   3240
cgggtctcaa tcaatgcaag tatttgatct tgagacgccg tggccgtata ggagtagaat   3300
ggccataact tcggtatcgg gcactcgcca tagccacact tcaaactctg tgtcggagt   3360 cccccgatta actcagcgtt ggaattggaa tctgagcgcc cgcagaggat tgcctcggcg   3420
agtatctcgt cgacatcccg ctgggataca gctaccgggc cacaccaaag aggctgactg   3480
ggagaaggac tagaaatgcc gtggatctcg cccagatgta ctagacttgc tggtctgccc   3540
tgggctcgac ggtggcggac cagcagggcc atttctcgg acatcgctgc agtcattgcc   3600
tggtccgcat ggcctaacac tcctgcaata gatccgatga gcacccaaaa gtccagagtt   3660
ggggtcttgt agagctcatc tagctgctgc agccccttca agaccggatg cagatggttc   3720
cggagggaat ctatcgtgag ctgggacaag gaacagtcag gtagaggcgg aggctgaatt   3780
agaactcctc ccactaccgg ggggaacgca tagggaatag tttgatgcaa actggtggca   3840
gaaatgccat cgatcaggtt tctggcattg attagcttgt gcatttgaat tcatgggtac   3900
gtaagtaact tacattttcg agaccgctat gcgcgttccc cgtcgagaaa cttcttccaa   3960
ccaccacgca tctgagtcaa gtctagagcc agcaaggagg atccattttg ccccgtgtgt   4020
tgctagccaa agacagatag catgggctag ttcactgcct agacctacaa gtatgtaggt   4080 tttttctct gacagctgca cctgggaacc agcagtcggt atctgggcga gcaccggagt   4140
tgtagagtcc caatctacca cggcatcctg ggagtcaagg attgggtact cggaaatcct   4200
gctgattggt aacgagtcca cagaatttgg tgggagcccc tcgcggccgg tgtacgccac   4260
taagcaggcg gttaggaaag ccttggctat gagtgacgaa tcatccgcgt tgatcggccc   4320
tgtcgatgca gaggtaaggt agaaatcctg caaatggatt cgtgtcgcgt tgtcaggcaa   4380
gagcgatagc atgcgatcat agacaccctg tccacgacga tgtagaatcg ctatggccga   4440
cacatctgag ggaagtacct gagacaattg ccgcgcagtg ctatgctcgt gcaaaagcaa   4500
catcggtctt tctttgtctg ggttgctttt gctagtgctg aagataacct taccatcccg   4560
```

```
ccgggtcagc atttggtgga aaacagactg aaggacccca tcagcctcgt gcactacaag    4620
cgtgcctgat tgtgggactt gttcgaccag gtatcctgcc aacagagcag ccgctgtggc    4680
gcggagataa gactgctcgt gggcttccaa caccgtgtct ggcactgacc acgcccagga    4740
gtctggaacg ataacatgag atgcaatgtg ggacgacaga gcgatcattc tcttgttgct    4800
cttaacgtcc agccctatga ccagccgcag aaatatggcc cctgcaaccc gcacggctgc    4860
tatactggaa tgtcgaactc gcagatgaag ggttgggcca taacttgcgg ttatcggcgg    4920
atcagccatc gaaagaaggc ggaacccttc acaagtcttg tcggtcgtag caggaaggat    4980
ttgtacaact cccttgtcga ggtccacgca gtctgtcact ttttgccgcc tggctagatg    5040
gcgcagccca gtagcatggt cgtgatattg ccgaggaaca cggaacatag agccgtcgta    5100
ttgaatttcg ggctcgatgt tggtgagtcc gcacgaatga ggattttctt gagctgcact    5160
agcttgaaca aagtgtccaa gagctgtcgc caatatttcc gttgtaactc caaccggatc    5220
tgtgatatgt agcagttgta gcagagaaga cgatcgttca gaagccagga aggtggaaag    5280
gagacctttc accagtccgg catcagggtg gtcgaccttc tcacaggtca ccactaacat    5340
tcgcttactg actgtcatca gtctgcacaa ctcgctcaag gtagcgtttg tcagatctcg    5400
atcatcgacg aggtacagaa cagtcaattt agataaatcg cgatcttcaa tgagatctag    5460
gtctggcgca tgagcaacct tgacgaagtc atcctgtacc aattcaaaaa gctctgaggt    5520
aagacaatct gcctcctcag cgtcaccgcc aagcaacagc aggtctccgc ggctctgtgg    5580
ttccgcagga ctgtctggag tgcgacagag aaggagtgaa aagtccccaa ggctttcact    5640
ctcttgggac gcatcgaacg aatccaagcc atagaatccg ccgttagaca gtagctcaac    5700
ccagtccctc ctggtagtaa ttggctcacc agagcagtag cctttcccgg tctctgtgca    5760
tctcattgga ggaccgaata gaagattcaa atatgtagtg ctgggattcg ttcgtactag    5820
taggaccaag aatccaccag gcttgagcaa gcgacgaaca tgagccaccg cgacctcttg    5880
cagaaatacc gcggctgtga tcagcaccat atcgtagaat tgctcgcggc agccctgctc    5940
gacaggatcc tcattgatgt ccaacgtttt gtgcgacacc tcgccaggtt gctcaaggtc    6000
ttcctcaatc gcttgtaggc cagaaacgga gagtccagca taagtaaatg accgataagt    6060
ccgacccatc ttcttcagtc cagagtgaac atggcctcca aattggccga tctgaaggat    6120
attcatttgt ggaaagcgga acacgcctg gctgacgaca gatacgagct cgtcttctag    6180
atccaagact tgcaagtcct ccttcagata ttgactttcc tcatcgatgg ccggccaggc    6240
ctctatttga agaccagaat cacgcagaac gcgaggtagc cgctggccta ccgcagcaat    6300
ggccgtgaga ccagggtcat tcaagagtga cgggctcact ccagctgtga agtcctcaat    6360
cttctggtcc aagcactcgg attccccgac agggtctggc tcttggctag catttgcaat    6420
gcattggttc atccatgcaa gcagacgagc accatcgaaa tccaatccgc ttcgctccaa    6480
gtccgtcagt ccattgcgag cctgcttgag atacagtagc gcaagctcct ctcggagaga    6540
gtgtagctgt agcatggtag ctggcaactt ccgtgatccc ttcttcagag tgggctcaag    6600
cggtccccac gcggtctggg aaagaacctg caagttgttt ggtgcagttc cagatggctg    6660
gcatatgaga gaaacacctt cgagctggac agccttttcc ccattcatgg tgaagatgtc    6720
aatatcaccg cgaattcgat ctccattaac gcaggtcaga tagcttgcta ccgtcaattc    6780
cttgccttgc caatctgaag cacataacac cggatttatc caggtactgt caacatttct    6840
cgataagaat ggtcccgtca gcagcgtctc ttcaagccca ccaattgcag caatcattgt    6900
```

```
ttgaacacca aggtccaaaa tagccgggtg aagagccatg ggctcatccg aatcatttga     6960
gggaacgggc acactcccag tggctagatc acgccttttg cggagtcccg tcaaggtaga     7020
gaatgggcca gtacagtggt agtcagcgcg gcgcaggctg tcatagaatt cagtgctgtc     7080
cacgggctcc aaggcctgag gtagctgtcc ctgtggggt aggagagcac ggtcagaatc      7140
ccctggatgc atgatcatct tggctgttgc acactgaacg agctctccgg atacaacagc     7200
ttcgcagcag aaccaagcag taatggctcc atcatgcgag tgaatactac ccacggtgac     7260
aagcacttca gtgccgatgg gatcattctg aatcgggagc tgagtgtgga tggtcaagtc     7320
cttgacattc aacaagcgta ggccttgtgt ctgtgccatt atcatacctg cctccagtgc     7380
catcgatatg tatcctgtct cagggaagac agatcccgaa tcggcacgac ggtcggccaa     7440
ccagggcagc tcctctggtc gtagatagtt tcgccaacgg aacttttctg ctccggtctc     7500
tggactgaga gaaccgagaa gtgcgttagg agatgtagca cgatggttat ggttcgaaga     7560
cattcgcgac tgtgtccagt atgtctgagt atggtcgaag gggtagaatg gtagcgattc     7620
taccaacaca ggccaatgat ttggatcaaa gagtgagaca tagtctgtga ggcggacgac     7680
atttgggccg aggtgtgccc aggaagatcc tagggccgtt gcccatgtat cgaggccggg     7740 cttttcctcgc tcagcaagag caaggtaagg aattgccgag tgggccgagt gcatttttgga   7800 gagggtctgt aggacaggcc ctctcagtgt cggatggggc ccgatctcaa tgatgagatc     7860
tggtggccca gcgtctcgtg ccgcggcctc tagggcttgg gaaaactgaa caggacgcag     7920
catattctca acccagtact cccctgtcaa ttcctgctgg tcatacccag tcatgacctc     7980
ccctgggtag acactcgagt accagcgcga ggcagaagct gacagggcga caggatacgc     8040
tttcattgcg tcacgatatg gatctgcaca aggcttcata tgcggagagt gatatgcggt     8100
gtccactcga agcatacgcg gagtgaggcc caggctcttc agcagccact ccagctcccg     8160
caggcactct gcgtcgccgg ataacgtgac gctggatggc gagttggcgg cagcaacgct     8220
tatacgtccg gagtaggctt ctaaagcaca gatattctgc gcctgctgcc atgtcaaatt     8280
cacggccatc atccgacctg tcggatcgcg tgacttatca atggtcatcc ccctaaggta     8340
cgcgatgcgg attgcatccg aggccgtcag cacacccgca gcataggctg ctacaatctc     8400
gccggaagag tgaccgacca caatggtaag ctcaatccct accgcacgga gcatgttgac     8460
ttgcatgatt tgcaacgctg tccgtagggg gagagaaagg aggccctcgt ttacgcgcga     8520
ggacgatgcc ggctgtgaca actcgtcgag aagagaaaac tgtggacgaa ggtctagtgg     8580
aagctcatcc aaagcttcct ccagattcat aatccatttt cgaattgagg gacttgcctc     8640
aatcagatca agtcccattt gtggccattg gactccttgg cccgtgaaga tgcccatgac     8700
gcgtctgggc cgagtgttgg atctggagac gacagaggct ggtttacccg tgacccttcg     8760
acttatttct gtattgatct ggtctttcaa ctcttgtatt gagtgtgcca ttagcgtcaa     8820
ccggtggcga tgagtggaac gtcgatccca caaagagagc gccagaccaa cgagactgac     8880
tgttgcgtgt tcctggagga atgttgcgta tgattccatc acacaagtga gggtccgctc     8940
agacgcagca gaaaagacaa agggcagact ggagggtatg ttgttggacg gactgagctc     9000
cgagcgagtg tagcttttcta ggacgacatg cacattggca cccccgaatc caaaggagtt    9060
caccgaggct cgacgaggac agccatctgg gactgcaggc cacgggatgc attctgtggg     9120
gacagaaagc ttggcggcaa acggtttaat ttttggattg agatgctgca tcaggagatt     9180
aggagcaatc atcccgtgtt gcagcgagag ggatgccttg atcaatcccg ctagtccagc     9240
agtggcctct gtatgtccaa ttattgtctt aattgaccca acatacagcc gatcggtcga     9300
```

```
atctggaacg gattcgggcc caaagaagct tgagttgatt gcggctgctt cctgcggatc    9360
tccggcctgg gttcccgtgc catgagcctc gaagtactgg caccgatctt ccgggttgtt    9420
ttgaggagag agccccgcgc gtgcataggt tgcgaggatc aatgattgtt gtgcctttgg    9480
attaggcatc gtgatcccca tagttcgccc atccgagttt gccctgagg cacggatcac    9540 gcattcgata ggatctccat cattaatcgc gtcctgcaga cgttttagta caaccgaagc    9600
cacaccctcg ccacgtccgt agccgtcggc cttgctgtcc cacattctac tccggccggt    9660
aggggacagc atccgtgttt tagaatccgc aatataggca ttgggagaca ggatcaggtt    9720
gcttcctact gccactgcca tggaacagtc atcgttctgc agagcctcga ctcccagatg    9780
aacagccaag agactcgaag aacatccggt gtcaacggcc atagaaggac cttgccagtc    9840
aaagtagtaa gagatacgat tggccatgat tgacggtgag tttcccgtaa ccacatacgc    9900
ggggaacgcc tgaggatcca tggcctggat ttgattgtaa tcgttgcgaa gtgtaccgca    9960
gaacaccccg gtctttgagc gctgcagcgc atccatccgt aacccggccg catcgagcga   10020
ttcgtacacg gtctctagga gcaatcgctg ttgtggatcc attgctaccg cttcagttgg   10080
cgagatattg aagaaggccg catcaaaggc tttgatgtcc tcgtccaaga agtatgactc   10140
tttgacgttt gttgtgccat ggtggtctcc atctggatga taaaaggcat ctatattgaa   10200
tctgtcggcc ggaactttgc gcgcgatatc ccgagggctt tgaagaagct cccacagttt   10260
cgaaggagag gaagcgccac cgggaaagcg gcatcctgta ccaataatag caacaggctc   10320
tgttgctttc attgtgagat tataagagag gtgtaaaacc tgagatcaaa ataatttgca   10380
gttgggtggc tgtagctcta ctgagagtac gttcatagat ataagcaatg cagtgttgcc   10440
ttacttactt ccacgatctt gtcagcatat ctatcgaacg aatagcaaaa ctggacctat   10500
agagcaattt ccggccatcg atagatcatt ggatagctgt cctatttggg aagtatgatc   10560
tacaatttat gcagccacaa actatacaaa gtggtccatc gccagatttg gcgatgagca   10620
gcggtgtgga atagtgactt tgatgaacat gtcaggtcct gcatctacat gtgcaggtgt   10680
ccaaggatgc tccttgcgcg aagaagtgga gtagggacat tcagctacct ccttatcttt   10740
tcccttcttt taatgctcac tctgtgcata ataatagtgg cgaatatcga agcatcgaaa   10800
tccaacgaca ttgagacaac atggataaca tggacaacat gaacaacaca cctttaggtt   10860
tcaactgggc ctgggcagtc atcatctctt tcctgggtct gctgactttt tcctttgtct   10920
cgccacacct ctttccttca agattgacgg tgattaatgg tggaagagcc tgggatatct   10980
ttcgtaccaa ggccaaaaag cgatttcgct cggacgcagc acgtcttata aagaacggct   11040
tcgaggaggt gagtatggaa aaactgcatc atttaggata aagtgctaaa cgttccttct   11100
tactccagtc tcctgatgcc tttgcattta tcacggataa cggtccttg ctggtcttgt    11160 cacctcaata cgctcgtgag gttcgcagcg atgatagact cagccttgac catttcattg   11220
cctcggtttg tcttgcttca tgtccaacgt ttttctagtt ggcgtcgcta agcttctact   11280
gtttaggaat ttcaccccaa catcccaggt ttcgagccgt tcaaattgat cttggatcca   11340
aagaacccgt tgaacacgat cctcaagtcc aatctcacac aagcactggg tactgacatc   11400
gtcctctccg ctcttatgca gcccattaca tagctaacat tgtttacctg atagcttat    11460 ctgacagagg acttgtctgc ggaggtaaca gaggcactat ctgcaacctg taccgatgac   11520
cctggtaagc tataaaacat ggttttccaa aggttctggt atcaatacta actttctttc   11580
ttctcttaat caaagagtgg cacgaggtca gcgttagtca aacggctctc aaaattatcg   11640
```

```
cacaaatggc gtccaaagcc ttcattggac aagaaagatg ccgggatgcc aagtggcata    11700
acattatcat cacgtacacg cacaacgtct atggagcagc acaggcactc cacttttggc    11760
ccagtttcct acgacccata gtggcacagt ttttgccagc atgccgaact tgcaggctc     11820
agattgctga agcgcgagag atcttggagc cattggtagc ccagagacga gccgagagag    11880
ccacccgagc cgctcaggag aagcctcatc cgtctggtgg ggatatcatt gactggctgg    11940
aacagtttta tggggaccaa ccgtatgatc ccgtggccgc acagctactg ctctcatttg    12000
ctgctatcca tggaacttcc aatctcctgg cgcaagcgct catagatctc tgtggccaac    12060
cggagctagt acaggatctc cgggaagaag ctgtgtccgt gctgggtaaa gagggatgga    12120
ccagggccgc cttgtaccaa ctcaaactaa tggacagcgc cctgaaagaa agccagcggt    12180
tggcgccaaa cagattgtgt gagtgggccc ttcctcttgc cccccaattt gaccattcaa    12240
ctggccatta gagactaatt caggtgtgct tttacagtat cgatgggacg cattgcgcaa    12300
ggcgatatgg acctgtctga tggtctccgt atccaccggg gcacgaccct catggtgtct    12360
gcccacaaca tgtgggatcc tgaaatctac cctgatcccc gaaaatacga tggctaccga    12420
ttccataagt tgcgacaaac atcagggcaa gagggccagc accaactcgt atcctcgacg    12480
ccggatcaca tgggattcgg atacggaaag catgcttgcc cggacggtt tttcgccgca    12540
gcccagatca agttgcatt gtgcaatatc ctcctcaagt atgatattga atacaggggt    12600
ggcaagtccc caggtgtgtg gggtcaggc atacatctgt ttcccgatcc gacgtctagg    12660
atccacgtcc gtcgtcggaa agaggagatt aacttgtgat actattgtct aactatgcgg    12720
atgtggttga atgcaaggac tctctctctc tctctgtctg attgatattt gagttttcta    12780
tggtgatcga gcaagatttt tgcaatgtgg agcccatgca tgctcatgag gcctattggg    12840
ccgatctctt cgagatcgtg atcgagagca aatttgagaa cctcagacct tgtttatttg    12900
aaagtagcag atgaacaata gaattgtttt tacttttgga atggttccac aataatccta    12960
gtctagattt aagataccaa tattgaagtg ttatgtttgc atgtatcttc agctgctcca    13020
cccgcgtgga gtgattatta gcttattagc gccttctcat taatacgccc tccagttcca    13080
gcctctcaaa agtaatatgc tggaatgata gaggtaattg gctaatggcc tcaaggcaac    13140
cctgcagata gtgaagcaaa agcaataaat attcaatatt cacacataat ttgacatacg    13200
gagtactccg tactccgttt aagatcgggc atagtattgg atgatgttag aatatatctt    13260
ggcaaggtga catatacaat gtactccgta tgttgtacag tgtcaatggc tttgtggagc    13320
tgaagatgcg gtgatttctt ttcctgatgc atcatcaagt ccggaaaatt gatgaaaatc    13380
tacgagtacc tcgagggatg aacttccctg cacagatcat gacatacata taaactattg    13440
atccacttgc attagcggga gtctagcaag agcaagtcta tgtattccct acatggtcga    13500
ggaggtaagt tcgggctgaa aaatacgatg cagcatacac tacccttaca actagctgtt    13560
taatcagaaa aagcaaatag aaattagggc acaatttact ctttactgcc aaccccccgt    13620
cgtaacccct gctgctagca ttgattggct gtcagtcgta caacgaagaa acgacactgt    13680
ctgtgattat attctattcc atcacaaacg tagcccggag tgcccttccc agagtccttg    13740
tcttgtacac cgtgcttgtc ttagcatttt cattatgatc gagctcaaag atgcttcgat    13800
gggggctgta ttgctgacat gcgtccttgt gcttgcaggc ctatatctca ttcgattgac    13860
gttatcaagc gaccaattgg acaagttttc tagcatcaat cctcggaagc cctgggaaat    13920
cgtcaatgtc ttcgcccaaa gaagatttca acaggatggc cctaggtatc tggaagctgg    13980
gtatgcaaag gtgtgttcca taagcaactg ctccaaaagg cgaataaggc tgaaagttac    14040
```

```
tacagtcccc catctttagc gtggtcaccg acctggggcc aaaattagtg gtttcgggtg   14100
cattcatcga ggaattcaag gatgaaaagc tgttggacca ttatcggtca atgatcgagg   14160
tttgtacgac gttagtgatt atgaaagagc aagcgcttac ttgtgcaagg acttcatggc   14220
agaggtacct ggttttgagt cgatgttcct ggggaatcta cacaatacgg tacttcgcga   14280
tgtgatttct gtcatcactc gcgaactagg taaatattct ttccttttga ctgtccggtt   14340
atccgctgag ttctaatttt atagaacaac tgctagcacc tctctcggat gaagtatcag   14400
cggctctggt agatacttgg acggactcac caggtgggtc aaagcacact tcccaataga   14460
aatcaggagg aaataaaaac taatatcaat atagactggc atgaggtagc actgcttcca   14520
agcatgctgg gcttgatcgc aaaggtttca tctctcgtct tcgtgggtga accgttgtgc   14580
cgccacccag tctggttgga gacagtgatc aacttcaccc tcattcgaca caacgcaatc   14640
ttagccctcc accagtgccc tgctgtactt cggcccgtcc ttcactgggt tcttccacca   14700
tgccagaaac tccgacgaga gatcagaact gcacggacac tgatcgactc tgctctggaa   14760
aaatcaagaa agaatccgca gaccgagaaa ttttccagcg ttgcctgggt tgatgctttt   14820
gccaaaggca acaagtataa tgcagccatg gtgcagttaa gactggcaaa tcgtccatc    14880 cactccagcg ccgatctcct ggtcaagatt cttatcaatc tatgcgagca gccagaattg   14940
attcgggacc tccgggacga gattatctct gttcttgggg agaatggatg gcgatcctcg   15000
acactgaacc aattaaagct ccttgatagt gttctgaagg agagccagcg gttgcatcca   15060
gtcacaaccg gtatgcatcg tcggctgttc aaactgcgtg cccagtgcat atgctgacca   15120
tttactttag gagcattttc gcgctttact cggcaagata tcaagttgac caatggcact   15180
gagattcctt caggaacacc cattatggtc actaatgatg tcgccgggga tgccagtatc   15240
tatgatgatc ccgatgtctt cgatgggtat cggtacttca gaatgcgtga aggagccgat   15300
aaggcccggg caccattcac aacgacgggc caaaatcacc ttgggtttgg gtacgggaag   15360
tatgcttgtc ctggtcgatt ctttgctgct accgagatta agatagcgct ctgccatatg   15420
ttgttgaagt atgaatggag gctagtaaag gacaggccgc atgggatagt tacaagcggg   15480
ttcgcagcat tccgtgaccc acgagcaagc atagaagtcc gcagacgcgc ggtggcggga   15540
gaagagctcg aggtattgac tggaaagaag tgatctaggg aaaattacga actcatagta   15600
tgagcaacca tacccaaaac aaagagactt accaacccca tcatcaaggt agactgggga   15660
ttttgactat gtcgatgtaa atcggtcaac agccttatta ggatatataa attatacgct   15720
tctcaggctt taaagcatca cccagcacga taatttctct ggattattgc aaaaccaaga   15780
aattctctga tccacagctg tatactccgt actccgttca tcatcttaca gtcatgcaga   15840
gggtgaaagg ggtcagtgtg tgacggtatt tcggtatctc gcctcgtaat ttgacagatc   15900
cagcgttaaa cccagcccaa gacttgagta gactatattt attctctttg atatccatct   15960
cagcatcaag ttttgacgt tgtattacta tcctcgtttg gaattctcct cccaggtctt    16020
gcttcattgc ttatagcatt ctaccaaaaa cgtcactgtc atggacgggt ggtcagacat   16080
atcatcagcg cctgccggat acaaggatgt tgttggata gcagatcggg ctctgctagc   16140
ccaaggattg ggatggtcaa tcaactacct ggccatgata taccaatcgc gcaaagaccg   16200
cacatacggc atggccattt tgccactatg ttgcaacttt gcgtgggaat tcgtctacac   16260
tgtcatctat ccttctcaaa atcccttcga gagagctgtc ctcacaacat ggatggtcct   16320
gaacctctac ctcatgtaca ctaccatcaa attcgctccc aacgaatggc agcacgcccc   16380
```

```
gctcgtccag cgaattcttc cagtgatatt ccctgtggca atcgcggcat ttacggcggg    16440
gcatctcgcc ttggctgcga cagtgggagt ggccaaggca gtcaactgga gcgcctttct    16500
gtgctttgag ctattgactg ccggtgccgt gtgccagctc atgagtcggg gatctagcag    16560
aggggcgtcg tatacaatct ggtatgttct ttttgccttg tggatcttgc ttgggtttat    16620
tggctaatgt gaattgtggt tggcagggtc tcaagatttc tgggctcgta tatcggtagt    16680
atctttatgc atgttcgaga gacccactgg ccgcaggagt ttgactggat cagctaccct    16740
ttcgtggcgt ggcatggcat catgtgcttc tcgctggata tttcttatgt gggcttactg    16800
tggtacattc gtcggcagga gcgccagggc caattgaaga aagctatgtg atcgacagga    16860
ccatgcatga tggaggtccg cactaacctc aactgtactt tgtacaggtc tgagtgctat    16920
atgacgatag tcacaaaaca gagttggagg ttatttgcgc acattgacta aaaatgggag    16980
agctgatgga tatatgcaag ggggatcagg tctcgatctg atcgtgccga tcgacaagaa    17040
caatgctttg tctgggcggg tccaattgtc tagcctagaa gtctaaattt caattttctt    17100
cggacttttt acatagtaac tactgcctag gactcgggat atgaagtata atggcgagaa    17160
atggctggct gcaggggaca tacaggtgat aatttgccct cgatctggca gctagttacg    17220
tcaatatctt gttagtaaac accagttgta gatcttgcg tatatatgaa actcaaaagc    17280
atttgtgtct actccgtaat taccttccca accccctccag tgccattgaa accatgaagg    17340
tcatcattgt cggagggtcc atcgcgggtc tcgcctcgc ccattgcttg acaaggcca    17400 acattgacta tgtcattcta gaaaagaaga aagaaattgc ccccaggaa ggtgcttcca    17460 ttggtatcat gcctaatggt ggtcggatcc tggaacagct tgggttatac gaccagatcg    17520
aggagctgat cgagcctttg gtgagggcgc atgtaactta ccccgacggc ttcaactata    17580
caagtcgata ccctgcactc atacagcagc ggtgcgtcaa tataagcttt ctactttctg    17640
atttgaaact aatgcgagag gtcttaggtt tggctatcca cttgcattct tggatcgaca    17700
gaagttactg caaattctgg caactcagcc ggtccaatcc agccgagtga aactagacca    17760
caaggttgag agcattgagg tctccccatg tggcgtcacg gtgataacaa gcaacggaca    17820
cacctatcag ggcgatcttg tcgtcggggc tgatggagtg catagtcggg tacgagcgga    17880
gatgtggcga ctggcagatg cctcgcaggg gaacgtatgt ggaaatggag acaaaggtaa    17940
cattattcct actgttttgt cctatcctcg cttttttttt tcttggccaa gtgttttgac    18000
tttgagctgg aaagctaata tattgattta tagcatttac gatcaactat gcctgcatct    18060
ttggaatttc gtcacacgtc gatcaattgg accctggcga gcaaataacc tgttacaatg    18120
atgggtggag tatccttagt gtgatcggac agaatggcag gatctactgg ttcctcttta    18180
tcaagctgga aaaagaattc gtttatgatg gatcacacaa aacccagctc cactttagcc    18240
gtgaagacgc ccgagctcat tgcgagaggc tggcgcagga gcctctctgg aaagatgtga    18300
catttggtca ggtctgggct cgatgtgagg tcttcaaat gacacccttg aagaagggg    18360 tgcttggcaa atggcactgg agaaacatta tctgcatcgg agacagcatg cataaggtca    18420
gcagctcatt atcactcctg gcttactgac ttttgtaatt aattgacatt ctcatgcagt    18480
tcgcaccgca tattggacag ggtgctaatt gcgctatcga ggatgcagct cagctcagca    18540
atagtttgca cacttggctg agcggatctg gaaaggagca tcaactaaaa accgatgatt    18600
tgacagagat tctggctcaa tttgcacaaa ctcgcctcca gaggctaggt ccgacggcca    18660
tggccgctcg atctgctatg cgtctgcatg cgcgggaagg gctcaaaaac tggatactgg    18720
gacgctactt cttgccctac gctggtgaca agccggccga ctgggcctcc cgaggaatcg    18780
```

```
caggtgggaa tactttggac ttcgtagagc ctcccacgcg ggctggtcct ggctggattc   18840
agttcagcca gtcgggtaaa aggacttcgt ttcccatggc agtggcaggt ctgtgcctag   18900
tgagcattgt ggcccgaatc atgtatttga aattagttgc atagagaggc ccaccatatc   18960
tggagtactt catacagagt gttttatggg acaatataaa ctttagggca atttagcgct   19020
ttgatataga tcatctgcat actagtaagg caaccctgaa ggtgatcgac acgatctgca   19080
aaaatcaata tcgtgcttcg ttacggagta ttgttttcta catgtcatag tgcgcgctgc   19140
cccagtgggg ctatgcagaa agtgatttcg atgtattgct acttacagtg atgtggtcca   19200
gcatgtcagc cattgctcta gtgcgtgcgt gtactgacca catcgcggcc attgccattt   19260
atctagggtc ctgtcgcctc aaaagcttgt ggtcacaaat cgtttgatcc ttcgagatca   19320
tactgaattt ttgttcaatc tgtcatcatg gctggctctc agtctacggc gcagttggct   19380
cgccttctca ttgatatctc ccgatttgac aaatacaact gtttatttgc tatattccct   19440
ggaggtacgg agtagtgcag accacttcaa cattatacca ccgcgctcac aatttcatat   19500
agtctggtct atcttccttg cagcagcctc acgacacgct gatggcgacc ccgtccctct   19560
ggactttgta ttgggccgcg caggactggc cttcatgtac acgtatatgc tgagcggcgc   19620
aggaatggta tggaacgact ggatcgaccg cgatatcgat gcccaggtgg cccgtaccaa   19680
gaatcggccc ctcgcctccg gtcggctttc caccagagct gccctcattt ggatgcttgt   19740
ccagtacgca gcctcggtct ggctgatgga ccgcatggtg agcgggcagg atgtgtacgt   19800
cttttttcct cctcgtaccc caaacaatta ttctgttgat tgaaaactga ccctaatcat   19860
tctccagatg gacatacatg cttcctctca caaccgggat tatcttgtat cccttcggca   19920
agcgaccgac aagtcgcaag ctgggcgtct atccgcaata catcctcggt gcaagcagcg   19980
cccttactat cctcccagcc tgggcctccg tctacacagg ccgtatatct ttgaaggatc   20040
tgggtatgcg gtgtctcccg cttttgtctct tcctgtttct gtggaccatc tacttcaaca   20100
ccgcctacag ctatcaggat attaaggatg actgtaagct gaatgtgaat tcgtcgtacg   20160
tcctcgcggg gagccatgtg cgtggaatgc ttctgttaca ggctattgct gtggtgctgg   20220
tgatcccctg gattctctac accagcgcct ccacttggcc ctgggtctca tggctggggg   20280
tatggacggc atctctcggc gagcagcttt atctctttga tgtgaaggat ccgagtagcg   20340
gtggaaaggt tcatcggcgg aatttcgcac tggggatttg gaatgtgctg gcctgctttg   20400
ttgagctgct atatgcttca ggctctctgt gaatgatgtt aatacgatgt ggtccggatg   20460
agacttgggg agtagagtct gagaggctta aatgggtaa atggtgcgat gttggcacag   20520
tgtgaactat tcataaatct ttgctacgaa gttgggcttc acctttcaat tgagaagttg   20580
ttactggaat ttttcgacac tcaaaattcg aagagacttg tattattaga gggatatagc   20640
ctatgtcttc caattggtgt agaatcccaa ctacgagacc gcttcagaac gttggagcac   20700
aaggatagaa agttcaccta ttcgaaattc tctactgtcg tacatatgct atgtacatgt   20760
tactcctttg cttgcgcacc tatagcccag caaaacaagg gatcctttgc taacaggagc   20820
tgatcatcac ggttcagagt cagatgcaaa tcccacggct ccgtactcgc cacatcatcc   20880 tgacccttg gaaggataaa gcacatcccc cctaagacag gcaaatgtag ttggaacct   20940 cgaggttgcg ctccaaggct ctccccaaag tccagtccga agatttcaaa attcctaaag   21000
ctgctcagag ggataggaac tccccgaaat ccgatatccg cccagtcagg ctgcgagtgg   21060
agatgggata gagcgtcttg aatatattct gcgtcaaccg ccaaaagact ctggcgtata   21120
```

```
cgagctgcaa tttgtgtgag atcctccaga cactcctggc gcaattccac cgaaggatct   21180
gtgccatcaa ctagggcctc gtttctccca gcttgaattg gcgtatatgt caatagcacc   21240
atgtttccca gatagtcatc aaaggctgga gttttgaaat tcccacgcat atccaccgcg   21300
attgacagtt cggtagattt accagccaat tgtcccgctt gccgaagtat catggccaaa   21360
agggcgctca cgatgtcgtt actggacagg aaccctggac tcggcctacc atcagcctgg   21420
aaagacgttt gcccttttgat caacgtattg caagcctcct tcaaatactc gatcttagga   21480
ccggggattt tcagtcgcca ggtgacaagc tcggtggctc tcgcccggac gaagcccgac   21540
caattctttg caagtagtgc tgcccagtct ccgaggccac agtagtgctt gctaaaatcc   21600
atcctggaaa gaccggagct gctttctggg acaagacgct caatctccga tcgtaactgc   21660
cgatctggcg acacacttgc agaagacatc gccgtcgggt ctctgcagca atcggctaga   21720
aggcccaaga ctcgcgcagc gcctgcacca tccattgcgg aatgatgaaa cgtcatggcg   21780
agaatgatcc catcgcgcat gacatttgct tgaaatcgta ggatcggcct tcgtggcaac   21840
gaaatatcca tgtcgatagg caatggcgcc agccgactta tgatttcctg ctcctcagtg   21900
cccgttagga ggcattttga ttggatttcc ttgaatgact cggcctggta gtgccgtatc   21960
cggagtatag ggaactggac aagcgactct gaggcttctg gttcgatttg ccaggtgtac   22020
ttcgtttggc tggactctgt ccgccgagtc acgtcccctg cgaggaaggg gtgtaccttc   22080
aatagcagct cgatgccatt ctcgagaaca ccaatgctct tctcaggttg cgtggtctgg   22140
aaaaacagca gaaaggtgac gttcattccg aggggattgt ggtcgagaga agataaaggg   22200
taagcagagc ggtcgccagt tcttcgggca tcgcacattc catcttcaca tagaccgtgg   22260
agtctcacag gtccctcttt gacctgatct ctttgactga ctgggagaca tacttcctgg   22320
gtgctcatga tttctgggtg ttatcctatt gagttgagtt gtgtcttgat cttttttttt   22380
attttttttg gatttctgac cttgtttcgc ttatattgga cttttgctttt ctttgtatat   22440
tgtattgcat taccgtacaa caaagcatgg gattctctgt gttctgcatg attgtgggagc   22500
gtattttcct cgatttggta tacaatcagg tcgatccctg gcggattccg gatctgatgc   22560
atgtatacag gtcatatatc tgcttttcctc ggtattttttg agctgaatat cactatatat   22620
gctttggaga cgatcaatcg caagagaggg ttagtgatta aatcagttag tctcatccat   22680
agtgggcatt agagccaata aaagatggtt tccaccttga gatgtgatcg ccacaagaag   22740
attttgtaaa tagtatgtat tttccaggcc ctgatttcta tctgcatatt tgtcagcttg   22800
atctacggag tacatcttac tgcttttaga tactgacagc agcaaaactc cgcgttgaag   22860
gacgagcttt gacacaaggt caggcacttc tctagtacac aaatcctaat catccgacga   22920
catactactc cgtatgctgt acatagagat ccatgtccaa ttcttgagtc tgcccctctt   22980
tgatccacag tccagctcag ccaggcgcaa tctgcatgca ttggcatgga agctaggagc   23040
tgacattggc tggaactacg ccatctgggg cacaatgcaa gctaggcaac tgaccatgta   23100
ctgggtcagt tttgattgag tatgctatac ggaagaaagc gactagtact ccgtaggttt   23160
gtgtactacc tgcaagtgga aagagatacc tagataggtg acattagtgt ccgaaccaat   23220
gaccaatggc cctcatgcac ccatatccct tacatctttc agaaagagaa agccacaag   23280
tatatcatgt actccgtact ccgtacaacg gaattacttg atctctatat taccttcttc   23340
ctgaagaccg tttctcgcta ttgtcagtta cacacacaat ggattcccta ttgacgagcc   23400
cgttatggct caaaattgca catgagctag cactttacct ctcttttatt gtgccaaccg   23460
cctttctcat cataacaact caaaaatcat ccattattcg atgggcctgg acaccatgtc   23520
```

```
tgctttatat cctgtaccaa ttctctcttc gggtaccctc tctgtcgaca agtcaattct   23580
tgaagggcgt tgcagcgggt caagcaaccg tggctgcttt gcaatgcctt aatcttcttc   23640
tgatcacgaa gctggaccaa acggatctgc tacgggcaaa tctatacagt ccgtctgcag   23700
gactgctttc tcgccttgct caatcctgcg cattgctggt caacttccgc ggaatcggca   23760
caatctggga ggttagaaac attccccagc acgcagcgtt tgtccaacca aaaggcaagg   23820
atcaatcaat gagccggaag cggtttgtct tgcgggaaat tgcaatcatt gtatggcagt   23880
acctgctcct tgatttcatt tacgagtcaa ccaagggcac gtcagccgag gatttgatgc   23940
gtctctttgg ccctggtatg gaaatcaagt atctcgatgc aacgttcgaa caatggatgg   24000
ggcgcctctc cgtgggaata ttctcttggc ttgtaccttc ccgagtctgt cttaatatca   24060
cttcccgcct gtactttctc atcttggtag tattgggcat ttcttcgccc gagtcttgtc   24120
gaccgggctt cggcagagtg cgggatgtat gcaccatccg tggagtctgg gggtaagtga   24180
actattccga ctgctttcat tcattcacta acgccaccac agcaagttct ggcatcaatc   24240
ctttcgttgg ccactcacct ctgtcggaaa ctatatcgca agagacgtcc tcggacttgc   24300
tcatccctct cttttggaac gctacaccaa tatcttcttt accttttttca catccggcgt   24360 attgcaccttt gtctgtgatg ctattctcgg cgtcccgcca tctgcgtccg gcgccatgca   24420
gttcttctgc tcgtttccgc ttgctattat gattgaggat ggggttcaag aaatctggcg   24480
gagagcgacg ggccaaacca aggacagtga tcgtgcagta ccgttctggc agaggctcgt   24540
gggatatctt tgggtggctg tctggatgtg tgtcacatct ccgttctact tgtacccagc   24600
tgcgcggcaa catgcggaga agaactggat agtgccattc agtatagtgg aagaaattgg   24660
ccttggaact gcgcaaaaga ttttgctggg ttatggcttg tttgtgtact gggcggttgg   24720
tggggagatt taaattcatg tgtcgggatt gttcatcgtg gtcaacactg tttagattgt   24780
gatatatatt ttcaccgaac accccagaaa caaaagattt aagccccaat taactacctt   24840
gaagggctca tgagatttga tcaatgtagc aaccgtcagt atcctaggtc gtgattcccc   24900
cagccagagc gagataattt tccagacatc atcttatcta catgcaacca aaaactccct   24960
ggcatatatt aacagagcaa aactagagga gcaaaaaaga aatctcaggt ttggttttta   25020
ggaatagccg aacgcggggg tcgaacccgc agccttaag                          25059
```